US011572543B2

(12) United States Patent
Bauer et al.

(10) Patent No.: US 11,572,543 B2
(45) Date of Patent: Feb. 7, 2023

(54) TARGETING BCL11A ENHANCER FUNCTIONAL REGIONS FOR FETAL HEMOGLOBIN REINDUCTION

(71) Applicants: The Children's Medical Center Corporation, Boston, MA (US); The Broad Institute, Inc., Cambridge, MA (US); Massachusetts Institute of Technology, Cambridge, MA (US)

(72) Inventors: Daniel E. Bauer, Cambridge, MA (US); Stuart H. Orkin, Brookline, MA (US); Neville Sanjana, New York, NY (US); Ophir Shalem, Albany, CA (US); Feng Zhang, Cambridge, MA (US)

(73) Assignees: THE CHILDREN'S MEDICAL CENTER. CORPORATION, Boston, MA (US); THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 160 days.

(21) Appl. No.: 15/572,523

(22) PCT Filed: May 6, 2016

(86) PCT No.: PCT/US2016/031224
§ 371 (c)(1),
(2) Date: Nov. 8, 2017

(87) PCT Pub. No.: WO2016/182917
PCT Pub. Date: Nov. 17, 2016

(65) Prior Publication Data
US 2018/0171297 A1    Jun. 21, 2018

Related U.S. Application Data

(60) Provisional application No. 62/158,882, filed on May 8, 2015.

(51) Int. Cl.
| | |
|---|---|
| C12N 5/078 | (2010.01) |
| C12N 15/10 | (2006.01) |
| C12N 9/22 | (2006.01) |
| C12N 15/11 | (2006.01) |
| C12N 15/86 | (2006.01) |

(52) U.S. Cl.
CPC .......... *C12N 5/0641* (2013.01); *C12N 9/22* (2013.01); *C12N 15/102* (2013.01); *C12N 15/11* (2013.01); *C12N 15/86* (2013.01); *C12N 2310/20* (2017.05); *C12N 2510/00* (2013.01); *C12N 2740/15041* (2013.01)

(58) Field of Classification Search
None
See application file for complete search history.

(56) References Cited

U.S. PATENT DOCUMENTS

| | | |
|---|---|---|
| 5,460,964 A | 10/1995 | McGlave et al. |
| 5,635,387 A | 6/1997 | Fei et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,759,793 A | 6/1998 | Schwartz et al. |
| 5,928,638 A | 7/1999 | Uchida et al. |
| 6,682,907 B1 | 1/2004 | Charneau et al. |
| 8,383,604 B2 | 2/2013 | Orkin et al. |
| 9,228,185 B2 | 1/2016 | Orkin et al. |
| 9,822,355 B2 | 11/2017 | Orkin et al. |
| 9,885,041 B2 | 2/2018 | Orkin et al. |
| 10,287,588 B2 | 5/2019 | Milsom et al. |
| 10,662,429 B2 | 5/2020 | Milsom et al. |
| 2004/0259247 A1 | 12/2004 | Tuschl et al. |
| 2005/0227917 A1 | 10/2005 | Williams et al. |
| 2008/0051431 A1 | 2/2008 | Verhelle et al. |
| 2010/0273213 A1 | 10/2010 | Mineno et al. |
| 2011/0182867 A1 | 7/2011 | Orkin et al. |
| 2011/0294114 A1 | 12/2011 | Van Der Loo et al. |
| 2013/0004471 A1 | 1/2013 | Denaro et al. |
| 2013/0179999 A1 | 7/2013 | Hannon et al. |

(Continued)

FOREIGN PATENT DOCUMENTS

| | | |
|---|---|---|
| EP | 1752536 A1 | 2/2007 |
| EP | 2334794 B1 | 11/2016 |

(Continued)

OTHER PUBLICATIONS

UCSC Genome Browser of Human Assembly, hg19. Feb. 2009. 1 Page.*
Bauer et al., "HbF-Associated Genetic Variation Marks an Erythroid Regulatory Element Essential for BCL11A Transcription and Subsequent Stage-Specific Globin Expression." Blood 120:828 (2012).
Hancarova et al. "A patient with de novo 0.45 Mb deletion of 2p16.1: The role of BCL11A, PAPOLG, REL, and FLJ16341 in the 2p15-p16.1 microdeletion syndrome." American Journal of Medical Genetics Part A 161(4):865-870 (2013).
Hendel et al., "Chemically modified guide RNAs enhance CRISPR-Cas genome editing in human primary cells." Nature Biotechnology 33(9):985-989 (2015).

(Continued)

Primary Examiner — James D Schultz
Assistant Examiner — Kimberly A Aron
(74) Attorney, Agent, or Firm — Nixon Peabody LLP; David S. Resnick; Jeanne Jodoin

(57) ABSTRACT

Provided herein are nucleic acid molecules that target the BCL11A enhancer functional regions, compositions comprising the nucleic acid molecules and methods for increasing fetal hemoglobin levels in a cell by disrupting BCL11A expression at the genomic level. Also provided herein are methods and compositions relating to the treatment of hemoglobinopathies by reinduction of fetal hemoglobin levels. In particular, the nucleic acid molecules target the +62, +58, and/or +55 enhancer functional regions.

7 Claims, 24 Drawing Sheets
Specification includes a Sequence Listing.

(56) References Cited

U.S. PATENT DOCUMENTS

| | | | |
|---|---|---|---|
| 2014/0018410 | A1 | 1/2014 | Novobrantseva et al. |
| 2014/0068797 | A1* | 3/2014 | Doudna ............... A61K 38/465 800/18 |
| 2015/0056705 | A1* | 2/2015 | Conway ............... C07K 14/805 435/468 |
| 2015/0132269 | A1 | 5/2015 | Orkin et al. |
| 2015/0133528 | A1 | 5/2015 | Krieg et al. |
| 2015/0232882 | A1 | 8/2015 | Zheng et al. |
| 2017/0173184 | A1 | 6/2017 | Gaspar et al. |
| 2017/0218372 | A1 | 8/2017 | Milsom et al. |
| 2018/0119138 | A1 | 5/2018 | Bauer et al. |
| 2018/0119175 | A1 | 5/2018 | Conway et al. |

FOREIGN PATENT DOCUMENTS

| | | | | |
|---|---|---|---|---|
| EP | 2334794 | B8 | 4/2017 | |
| JP | 2006507841 | A | 3/2006 | |
| WO | 2004054512 | A2 | 7/2004 | |
| WO | 2009/007685 | A2 | 1/2009 | |
| WO | 2010/030963 | A2 | 3/2010 | |
| WO | 2011/072086 | A1 | 6/2011 | |
| WO | 2011133889 | A2 | 10/2011 | |
| WO | 2012/073047 | A2 | 6/2012 | |
| WO | 2012079046 | A2 | 6/2012 | |
| WO | 2013049615 | A1 | 4/2013 | |
| WO | WO-2013126794 | A1* | 8/2013 | ............... C12N 9/22 |
| WO | 2013176772 | A1 | 11/2013 | |
| WO | 2014/085593 | A1 | 6/2014 | |
| WO | 2014093965 | A1 | 6/2014 | |
| WO | 2015/065964 | A1 | 5/2015 | |
| WO | 2015148863 | A2 | 10/2015 | |
| WO | 2015164739 | A1 | 10/2015 | |
| WO | 2015164750 | A2 | 10/2015 | |
| WO | 2015164759 | A2 | 10/2015 | |
| WO | 2015183667 | A1 | 12/2015 | |
| WO | 2016094304 | A2 | 6/2016 | |
| WO | 2016/182893 | A1 | 11/2016 | |
| WO | 2016183448 | A1 | 11/2016 | |
| WO | 2017040529 | A1 | 3/2017 | |
| WO | 2017139576 | A1 | 8/2017 | |
| WO | 2018218135 | A1 | 11/2018 | |

OTHER PUBLICATIONS

Liu et al., "Functional studies of BCL11A: characterization of the conserved BCL11A-XL splice variant and its interaction with BCL6 in nuclear paraspeckles of germinal center B cells." Molecular Cancer 5(18):1-6 (2006).
Papayannopoulou et al., "Erythroid progenitors circulating in the blood of adult individuals produce fetal hemoglobin in culture." Science 199(4335):1349-1350 (1978).
Pauling et al., "Sickle cell anemia a molecular disease." Science 110(2865):543-548 (1949).
Pembrey et al., "Fetal haemoglobin production and the sickle gene in the oases of Eastern Saudi Arabia." British journal of haematology 40(3):415-429 (1978).
Perrine "Fetal globin induction—can it cure beta thalassemia?" American Society of Hematology Education Program Book pp. 38-44 (2005).
Platt et al., "Mortality in sickle cell disease. Life expectancy and risk factors for early death." New England Journal of Medicine 330(23):1639-1644 (1994).
Purton et al., "All-trans retinoic acid enhances the long-term repopulating activity of cultured hematopoietic stem cells." Blood 95(2):470-477 (2000).
Renella et al. "Hematopoietic SIN lentiviral micro RNA-mediated silencing of BCL11A: pre-clinical evidence for a sickle cell disease gene-therapy trial." 120(21):Abstract 753 (2012).
Ridley et al., "Erythropoietin: A Review" J Natl Med Assoc., 86(2):129-135 (1994).
Rodriguez et al., "A bioavailability and pharmacokinetic study of oral and intravenous hydroxyurea." Blood 9 (5):1533-1541 (1998).
Rosenblum et al., "Peripheral blood erythroid progenitors from patients with sickle cell anemia: HPLC separation of hemoglobins and the effect of a HbF switching factor." Progress in Clinical and Biological Research 191:397-410 (1985).
Saiki et al., "Human EVI9, a homologue of the mouse myeloid leukemia gene, is expressed in the hematopoietic progenitors and down-regulated during myeloid differentiation of HL60 cells." Genomics 70(3):387-391 (2000).
Sankaran et al., "Developmental and species-divergent globin switching are driven by BCL11A." Nature 460 (7259):1093-1097 (2009).
Sankaran et al., "Human fetal hemoglobin expression is regulated by the developmental stage-specific repressor BCL11A." Science 322(5909):1839-1843 (2008).
Sankaran et al., "Targeted therapeutic strategies for fetal hemoglobin induction." American Society of Hematology Education Program Book 2011(1):459-465 (2011).
Satterwhite et al., "The BCL11 gene family: involvement of BCL11A in lymphoid malignancies." Blood, 98 (12):3413-3420 (2001).
Schopman et al. "Optimization of shRNA inhibitors by variation of the terminal loop sequence." Antiviral Research 86(2):204-211 (2010).
Sebastiani et al., "BCL11A enhancer haplotypes and fetal hemoglobin in sickle cell anemia." Blood Cells, Molecules, and Diseases 54(3):224-230 (2015).
Sedgewick et al., "BCL11A is a major HbF quantitative trait locus in three different populations with β-hemoglobinopathies." Blood Cells, Molecules, and Diseases 41(3):255-258 (2008).
Shen et al., "Modifcation of globin gene expression by RNA targeting strategies." Experimental Hematology, 35 (8):1209-1218 (2007).
Takeuchi et al., "Redesign of extensive protein—DNA interfaces of meganucleases using iterative cycles of in vitro compartmentalization." PNAS 111(11):4061-4066 (2014).
Terasawa et al., "Synthetic pre-miRNA-based shRNA as potent RNAi triggers." Journal of Nucleic Acids (2011).
Thein "Genetic modifiers of the beta-haemoglobinopathies." British Journal of Hematology, 141(3):357-366 (2008).
Thein et al., "Discovering the genetics underlying foetal haemoglobin production in adults." British Journal of Haematology 145(4):455-467 (2009).
Thompson "Structure, Function, and Molecular Defects of Factor IX." Blood 67(3):565-72 (1986).
Uda et al., "Genome-wide association study shows BCL11A associated with persistent fetal hemoglobin and amelioration of the phenotype of β-thalassemia." PNAS 105(5):1620-1625 (2008).
Wang et al. "Genetic screens in human cells using the CRISPR/Cas9 system." Science 343(6166):80-84 (2013).
Wang et al. "Supplementary Material: Genetic screens in human cells using the CRISPR/Cas9 system." Science 343 (6166):80-84 (2013).
Wang et al., "In Vivo Delivery Systems for Therapeutic Genome Editing" International Journal of Molecular Sciences 17(5):1-19 (2016).
Wang et al., "Selection of hyperfunctional siRNAs with improved potency and specificity." Nucleic Acids Research 37 (22):e152 (2009).
White et al., "Factor VIII Gene and Hemophili A." Blood 73(1):1-12 (1989).
World Health Organization. "Sickle-cell anaemia. Report A59/9. Provisional agenda item 11.4." 59th World Health Assembly. www.who.int/gb/ebwha/pdf_files/WHA59/A59_9-en.pdf (2006).
Xu et al., "Correction of sickle cell disease in adult mice by interference with fetal hemoglobin silencing", Science 334 (6058):993-996 (2011).
Xu et al., "Reactivation of silenced human HbF in adult mice by inactivation of BCL11A." Blood 116:Abstract 643 (2010).
Xu et al., "Transcriptional silencing of beta-globin by BCL11A involvs long-range interactions and cooperation with SOX6." Genes and Development 24(8):783-798 (2010).

(56) References Cited

OTHER PUBLICATIONS

Yin et al., "Bcl11a Causes p21 Cip1 Down-Regulation and Transplantable Leukemia in Nf1-Deficient Mice." Blood 110 (11):2657-2657 (2007) [Abstract Only].
Chabchoub et al., "The facial dysmorphy in the newly recognised microdeletion 2p15-p16.1 refined to a 570 kb region in 2p15" Journal of Medical Genetics 45(3):189-192 (2008).
Kirschner et al., "Genomic mapping of chromosomal region 2p15-p21 (D2S378-D2S391): integration of Genemap'98 within a framework of yeast and bacterial artificial chromosomes" Genomics 62(1):21-33 (1999).
Taymans et al., "Radiation hybrid mapping of chromosomal region 2p15-p16: integration of expressed and polymorphic sequences maps at the Carney complex (CNC) and Doyne honeycomb retinal dystrophy (DHRD) loci." Genomics 56(3):344-349 (1999).
Akinsheye et al., "Fetal hemoglobin in sickle cell anemia." Blood 118(1):19-27 (2011).
Amaya et al., "Mi2β-mediated silencing of the fetal γ-globin gene in adult erythroid cells." Blood 121(17):3493-501 (2013).
Amendah et al., "Sickle cell disease-related pediatric medical expenditures in the U.S." American Journal of Preventive Medicine 38(4 Suppl):S550-S556 (2010).
Atweh et al., "Pharmacological induction of fetal hemoglobin in sickle cell disease and beta-thalassemia." Seminars in Hematology 38(4):367-73 (2001).
Bauer et al., "An Erythroid Enhancer of BCL11A Subject to Genetic Variation Determines Fetal Hemoglobin Level." Science 342(6155):253-257 (2013).
Bauer et al., "Hemoglobin switching's surprise: the versatile transcription factor BCL11A is a master repressor of fetal hemoglobin" Current Opinion in Genetics & Development 33:62-70 (2015).
Bauer et al., "Reawakening fetal hemoglobin: prospects for new therapies for the B-globin disorders." Blood 120 (15):2945-2953 (2012).
Bauer et al., "Supplementary Material: An Erythroid Enhancer of BCL11A Subject to Genetic Variation Determines Fetal Hemoglobin Level." Science 342(6155):253-257 (2013).
Bjurström et al. "Reactivating fetal hemoglobin expression in human adult erythroblasts through BCL11A knockdown using targeted endonucleases." Molecular Therapy—Nucleic Acids 5:e351 (2016).
Boettcher et al., "Choosing the right tool for the job: RNAi, TALEN, or CRISPR." Molecular Cell 58(4):575-585 (2015).
Bohmer et al., "Identification of fetal nucleated red cells in co-cultures from fetal and adult peripheral blood: differential effects of serum on fetal and adult erythropoiesis." Prenatal Diagnosis 19(7):628-636 (1999).
Bunn "Reversing ontogeny." New Engl. J. Med. 328(2):129-131 (1993).
Canver et al., "BCL11A enhancer dissection by Cas9-mediated in situ saturating mutagenesis." Nature 527 (7577):192-197 (2015).
Cao et al., "Recent advances in B-thalassemias." Pediatric Reports 3(2):65-71 (2011).
Doleman et al., "Sickle cell anemia: targeting the role of fetal hemoglobin in therapy." Clinical Pediatrics 46 (5):386-391 (2007).
Cox et al., "Therapeutic genome editing: prospects and challenges" Nature Medicine 21 (2):121-131 (2015).
Dixit et al., "Hydroxyurea in thalassemia intermedia—a promising therapy." Annals of Hematology 84(7):441-446 (2005).
Doench et al., "Rational design of highly active sgRNAs for CRISPR-Cas9-mediated gene inactivation." Nature Biotechnology 32(12):1262-1267 (2014).
Doench et al., "Supplementary Material: Rational design of highly active sgRNAs for CRISPR-Cas9-mediated gene inactivation." Nature Biotechnology 32(12):1262-1267 (2014).
Examination Search Report, dated May 11, 2018 in corresponding Canadian No. 2737180.
Fenaux "Inhibitors of DNA methylation: beyond myelodysplastic syndromes." Nature Reviews Clinical Oncology 2 (S21):S36-S44 (2005).
Fischer et al., "Pulmonary Passage is a Major Obstacle for Intravenous Stem Cell Delivery: The Pulmonary First-Pass Effect" Stem Cells and Development 18(5):683-91 (2009).
Flanagan et al., "Hydroxycarbamide alters erythroid gene expression in children with sickle cell anaemia." British Journal of Haematology 157(2):240-248 (2012).
GeneCard for BCL11A, retrieved from http://www.genecards.org/cgi-bin/carddisp.pl?gene=BCL11A on Jun. 22, 2012.
Goffin et al., "DNA methyltransferase inhibitors—state of the art." Annals of Oncology 13(11):1699-716 (2002).
Goldberg et al., "Treatment of sickle cell anemia with hydroxyurea and erythropoietin." New England Journal of Medicine 323(6):366-372 (1990).
Hackam "Translating animal research into clinical benefit" BMJ 334:163-68 (2007).
Harding et al., "Large animal models for stem cell therapy", Stem Cell Research & Therapy 4(23):1-9 (2013).
Hebbel et al., "The HDAC inhibitors trichostatin A and suberoylanilide hydroxamic acid exhibit multiple modalities of benefit for the vascular pathobiology of sickle transgenic mice." Blood 115(12):2483-2490 (2010).
Higgs et al., "Genetic complexity in sickle cell disease." PNAS 105(33):11595-11596 (2008).
Ho et al., "In vitro induction of fetal hemoglobin in human erythroid progenitor cells." Experimental Hematology 31 (7):586-591 (2003).
Hsieh et al., "Allogeneic hematopoietic stem-cell transplantation for sickle cell disease." New England Journal of Medicine 361(24):2309-2317 (2009).
Jane et al., "Understanding fetal globin gene expression: a step towards effective HbF reactivation in haemoglobinopathies." British Journal of Haematology 102(2):415-423 (1998).
Kauf et al., "The cost of health care for children and adults with sickle cell disease." American Journal of Hematology 84(6):323-327 (2009).
Koshy et al., "2-deoxy 5-azacytidine and fetal hemoglobin induction in sickle cell anemia." Blood 96(7):2379-2384 (2000).
Labie "Le contrôle en trans de la production d'hémoglobine fœtale: une recherche qui dure depuis 20 ans." Hématologie 14(2):165-166 (2008).
Lettre et al., "DNA polymorphisms at the BCL11A, HBS1L-MYB, and beta-globin loci associate with fetal hemoglobin levels and pain crises in sickle cell disease." PNAS 105(33):11869-11874 (2008).
Liu et al., "Bcl11a is essential for normal lymphoid development." Nature Immunology 4(6):525-532 (2003).
Lulli et al., "MicroRNA-486-3p regulates γ-globin expression in human erythroid cells by directly modulating BCL11A." PLoS One 8(4):e60436 (2013).
Makala et al., "Fetal Hemoglobin Induction to Treat b-Hemoglobinopathies: From Bench to Bedside" J Hematol Transfus 2(2):1-2 (2014).
Martin-Subero et al., "Recurrent involvement of the REL and BCL11A loci in classical Hodgkin lymphoma." Blood 99(4):1474-1477 (2002).
Matsuda et al., "Transcription factors LRF and BCL11A independently repress expression of fetal hemoglobin" Science 351(6270):285-289 (2016).
Menzel et al., "A QTL influencing F cell production maps to a gene encoding a zinc-finger protein on chromosome 2p15." Nature Genetics 39(10):1197-1199 (2007).
Migliaccio et al., "Influence of recombinant hematopoietins and of fetal bovine serum on the globin synthetic pattern of human BFUe." Blood 76(6):1150-1157 (1990).
Moffat et al., "A lentiviral RNAi library for human and mouse genes applied to an arrayed viral high-content screen." Cell 124(6):1283-1298 (2006).
Nemudryi et al., "TALEN and CRISPR/Cas Genome Editing Systems: Tools of Discovery" Acta Naturae, 6(3):19-40 (2014).
Neven et al., "A Mendelian predisposition to B-cell lymphoma caused by IL-10R deficiency," Blood 3713-3722 (2013).
Orkin et al., "Recent advances in globin research using genome-wide association studies and gene editing." Annals of the New York Academy of Sciences 1368 (1):5-10 (2016).

(56) References Cited

OTHER PUBLICATIONS

GenBank Accession No. NM_022893.4. "*Homo sapiens* BAF chromatin remodeling complex subunit BCL11A (BCL11A), transcript variant 1, mRNA." https://www.ncbi.nim.nih.gov/nuccore/NM_022893.4 (2019).
Bofill-De Ros et al. "Guidelines for the optimal design of miRNA-based shRNAs." Methods 103: 157-166 (2016).
Guda et al. "miRNA-embedded shRNAs for lineage-specific BCL11A knockdown and hemoglobin F induction." Molecular Therapy 23(9): 1465-1474 (2015).
Roggenkamp et al. "Tuning CRISPR-Cas9 gene drives in *Saccharomyces cerevisiae*." G3: Genes, Genomes, Genetics 8(3): 999-1018 (2018).
Win et al. "A modular and extensible RNA-based gene-regulatory platform for engineering cellular function." Proceedings of the National Academy of Sciences 104(36): 14283-14288 (2007).
Knowles et al. "Palmitate diet-induced loss of cardiac caveolin-3: a novel mechanism for lipid-induced contractile dysfunction." PLoS One 8(4): e61369 pp. 1-11 (2013).
Esrick et al. "Post-transcriptional genetic silencing of BCL11A to treat sickle cell disease." New England Journal of Medicine 384(3): 205-215 (2021).
Yin et al. "BCL11A: a potential diagnostic biomarker and therapeutic target in human diseases." Bioscience Reports 39(11): 1-13 (2019).
Boden et al. "Enhanced gene silencing of HIV-1 specific siRNA using microRNA designed hairpins." Nucleic Acids Research 32(3): 1154-1158 (2004).
Brendel et al. "Lineage-specific BCL11A knockdown circumvents toxicities and reverses sickle phenotype." The Journal of Clinical Investigation 126(10): 3668-3878 (2016).
Brendel et al. "Optimization of Bcl11a Knockdown by miRNA scaffold embedded shrnas leading to enhanced induction of fetal hemoglobin in erythroid cells for the treatment of beta-hemoglobinopathies." Blood 124(21): 2150-2150 (2014).
Calloni et al. "Scaffolds for artificial miRNA expression in animal cells." Human Gene Therapy Methods 26(5): 162-174 (2015).
Cante-Barrett et al. "Lentiviral gene transfer into human and murine hematopoietic stem cells: size matters." BMC Research Notes 9(1): 1-6 (2016).
Cavazzana-Calvo et al. "Transfusion independence and HMGA2 activation after gene therapy of human β-thalassaemia." Nature 467(7313): 318-322 (2010).
Clever et al. "RNA secondary structure and binding sites for gag gene products in the 5'packaging signal of human immunodeficiency virus type 1." Journal of Virology 69(4): 2101-2109 (1995).
Cullen et al. "Regulatory pathways governing HIV-1 replication." Cell 58(3): 423-426 (1989).
Cullen. "Human immunodeficiency virus as a prototypic complex retrovirus." Journal of Virology 65(3): 1053-1056 (1991).
Database GenBank [Online] Mar. 3, 2015, Anonymous: "TPA: *Homo sapiens* microRNA hsa-mir-144 precursor", XP55876619, Database accession No. LM608500.
Extended European Search Report dated Jan. 12, 2021, for European Application No. 18775163.1, 11 pages.
Ginn et al. "Gene therapy clinical trials worldwide to 2012—an update." The Journal of Gene Medicine 15(2): 65-77 (2013).
Huang et al. "Role of the hepatitis B virus posttranscriptional regulatory element in export of intronless transcripts." Molecular and Cellular Biology 15(7): 3864-3869 (1995).
Imren et al. "Permanent and panerythroid correction of murine β thalassemia by multiple lentiviral integration in hematopoietic stem cells." Proceedings of the National Academy of Sciences 99(22): 14380-14385 (2002).
International Search Report and Written Opinion dated Jun. 25, 2018, for International Application No. PCT/US2018/025165, 10 pages.
Kitowski, "A Lentiviral Vector Conferring Coregulated, Erythroid-Specific Expression of [gamma]-Globin and shRNA Sequences to BCL11A for the Treatment of Sickle Cell Disease," Jan. 1, 2006, 105 pages.
Kutner et al. "Production, concentration and titration of pseudotyped HIV-1-based lentiviral vectors." Nature Protocols 4(4): 495-505 (2009).
Kutner et al. "Simplified production and concentration of HIV-1-based lentiviral vectors using HYPERFlask vessels and anion exchange membrane chromatography." BMC Biotechnology 9(1): 1-7 (2009).
Landau et al. "Packaging system for rapid production of murine leukemia virus vectors with variable tropism." Journal of Virology 66(8): 5110-5113 (1992).
Liu et al. "HnRNP L binds a cis-acting RNA sequence element that enables intron-dependent gene expression." Genes & Development 9(14): 1766-1780 (1995).
Luc et al. "Bcl11a deficiency leads to hematopoietic stem cell defects with an aging-like phenotype." Cell Reports 16 (12): 3181-3194 (2016).
Mahajan et al. "Control of beta globin genes." Journal of Cellular Biochemistry 102(4): 801-810 (2007).
Malik et al. "Successful Correction of the Human Cooley's Anemia β-Thalassemia Major Phenotype Using a Lentiviral Vector Flanked by the Chicken Hypersensitive Site 4 Chromatin Insulator." Annals of the New York Academy of Sciences 1054(1): 238-249 (2005).
May et al. "Therapeutic haemoglobin synthesis in β-thalassaemic mice expressing lentivirus-encoded human β-globin." Nature 406(6791): 82-86 (2000).
Naldini. "Gene therapy returns to centre stage." Nature 526(7573): 351-360 (2015).
Negre et al. "Preclinical Evaluation of a Novel Lentiviral Vector Driving Lineage-Specific BCL11A Knockdown, β-Globin Induction and Simultaneous Repression of β-Globin for the Potential Treatment of Sickle Cell Disease." Blood 130(Supplement 1): 3557-3557 (2017).
Pawliuk et al. "Correction of sickle cell disease in transgenic mouse models by gene therapy." Science 294(5550): 2368-2371 (2001).
Pawliuk et al. "Correction of sickle cell disease in transgenic mouse models by gene therapy." Science 294(5550): 2368-2371 (2001) [Supplemental Material].
Rasmussen et al. "The miR-144/451 locus is required for erythroid homeostasis." Journal of Experimental Medicine 207(7): 1351-1358 (2010).
Soneoka et al. "A transient three-plasmid expression system for the production of high titer retroviral vectors." Nucleic Acids Research 23(4): 628-633 (1995).
Wang et al. "A 'suicide' CRISPR-Cas9 system to promote gene deletion and restoration by electroporation in Cryptococcus neoformans." Scientific Reports 6(1): 1-13 (2016).
Wu et al. "Highly efficient therapeutic gene editing of human hematopoietic stem cells." Nature Medicine 25(5): 776-783 (2019).
Yu et al. "Bcl11a is essential for lymphoid development and negatively regulates p53." Journal of Experimental Medicine 209(13): 2467-2483 (2012).
Zennou et al. "HIV-1 genome nuclear import is mediated by a central DNA flap." Cell 101(2): 173-185 (2000).
Zufferey at al. "Woodchuck hepatitis virus posttranscriptional regulatory elememt enhances expression of transgenes delivered by retroviral vectors." Journal of Virology 73(4): 2886-2892 (1999).
Johari et al. "Integrated cell and process engineering for improved transient production of a "difficult-to-express"fusion protein by CHO cells." Biotechnology and Bioengineering 112(12): 2527-2542 (2015).

* cited by examiner

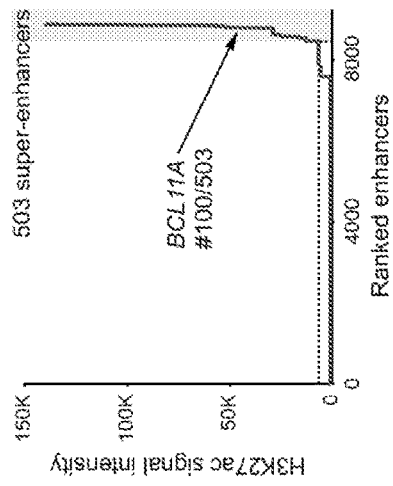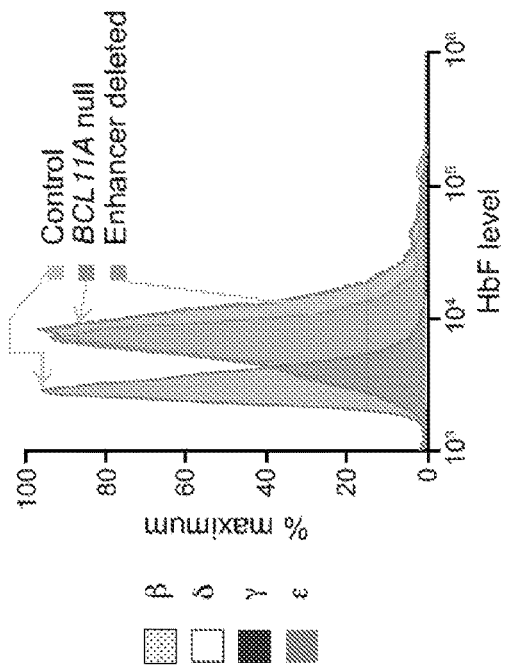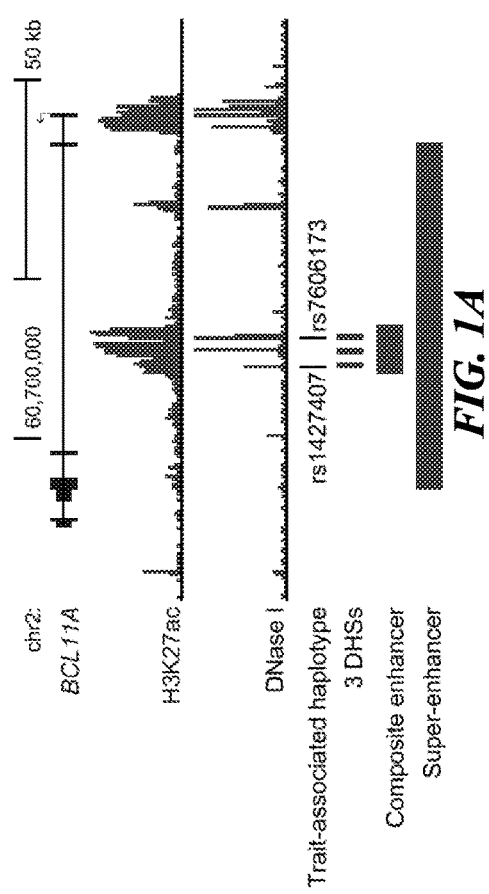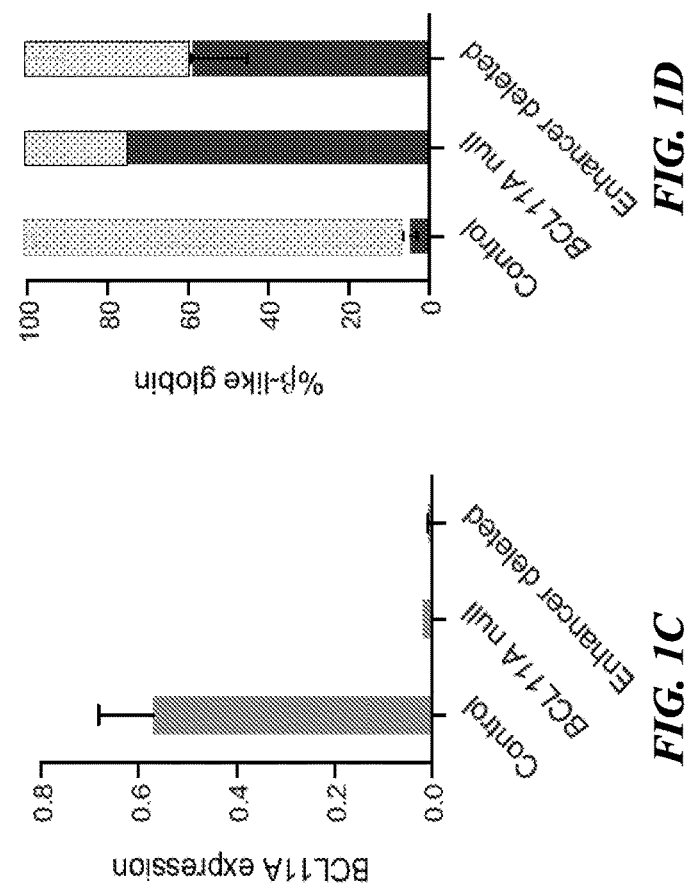
FIG. 1A
FIG. 1B
FIG. 1C
FIG. 1D
FIG. 1E

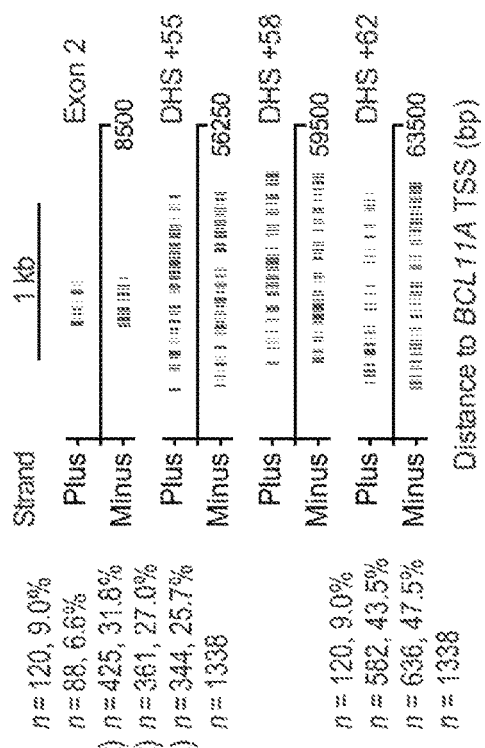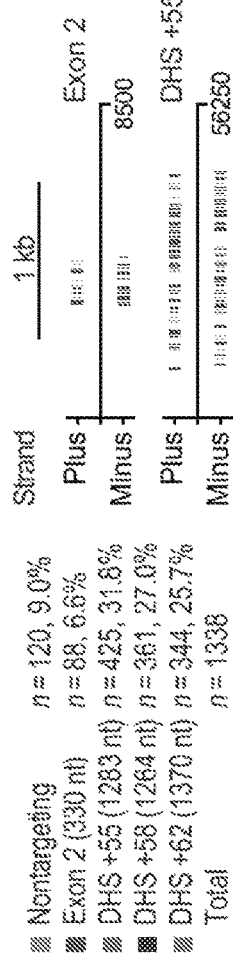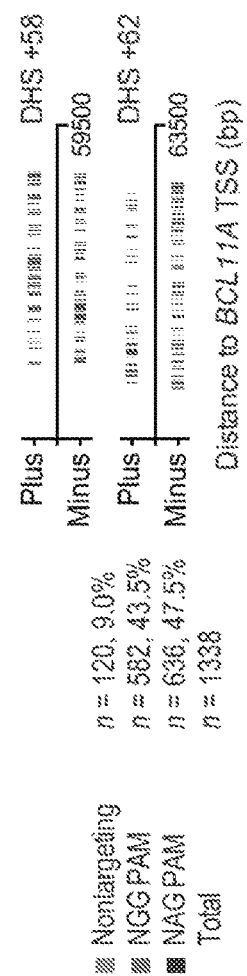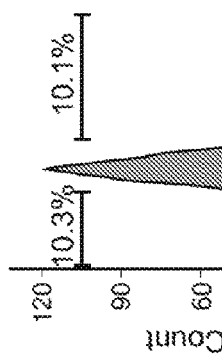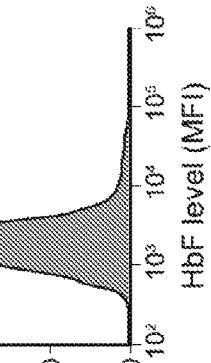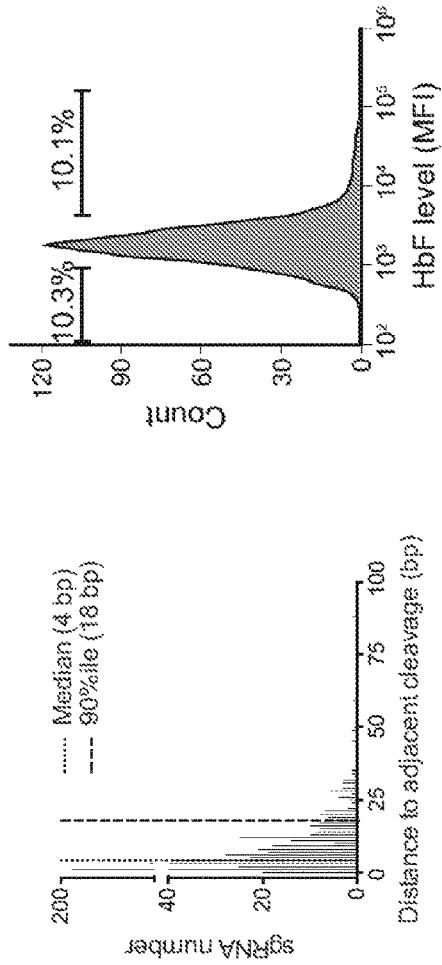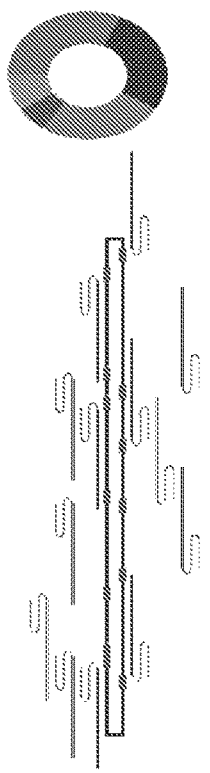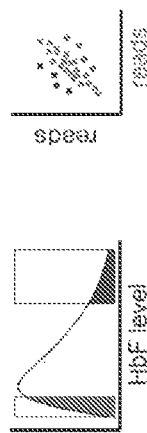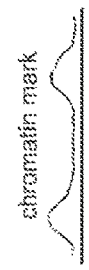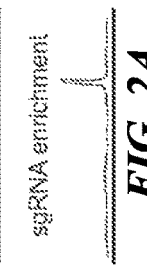
FIG. 2A
FIG. 2B
FIG. 2C
FIG. 2D
FIG. 2E

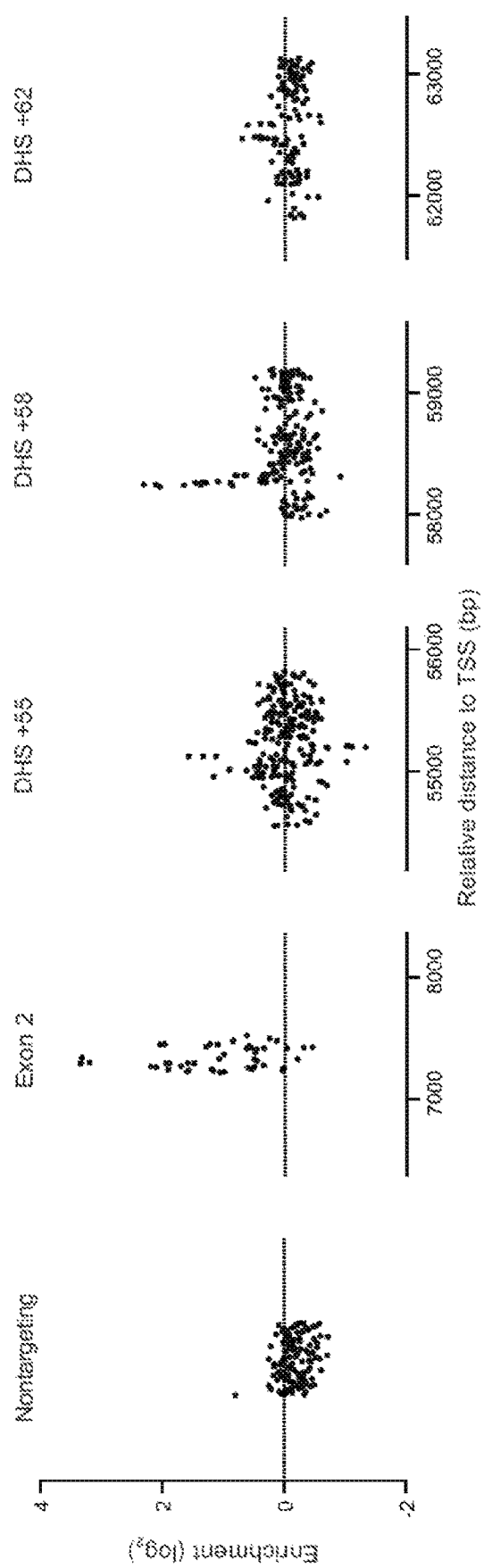
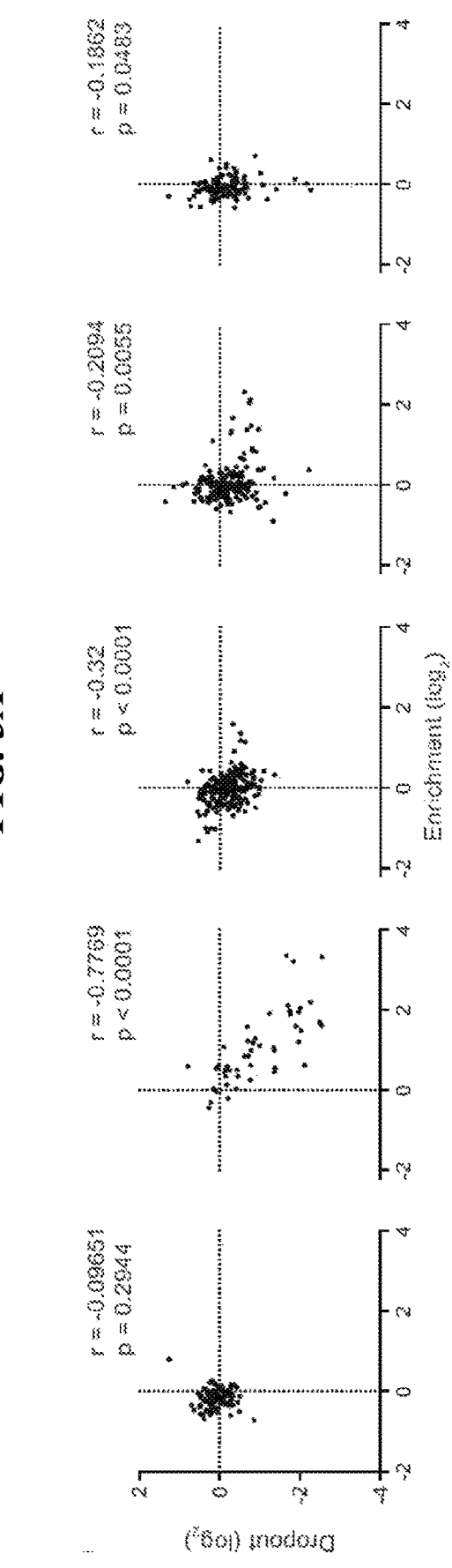
FIG. 3A
FIG. 3B

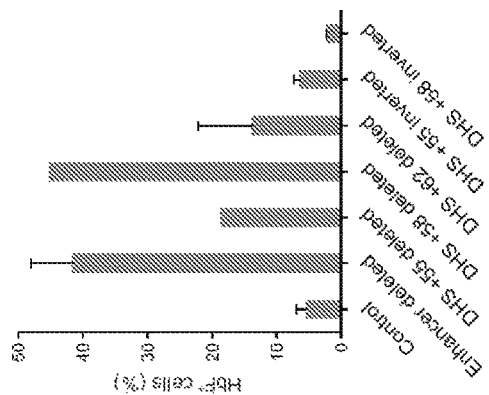
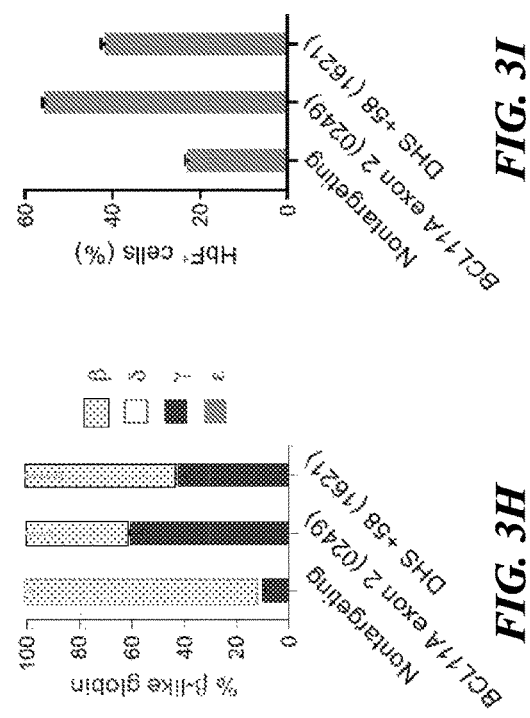
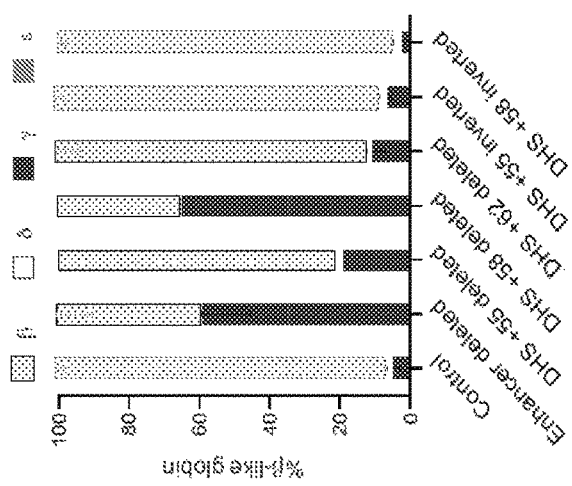
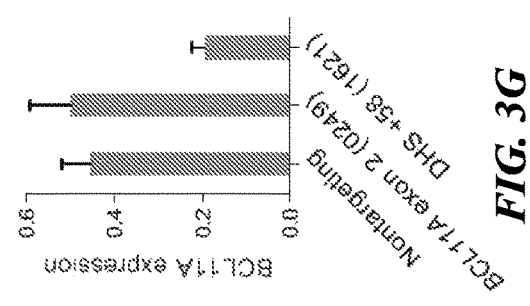
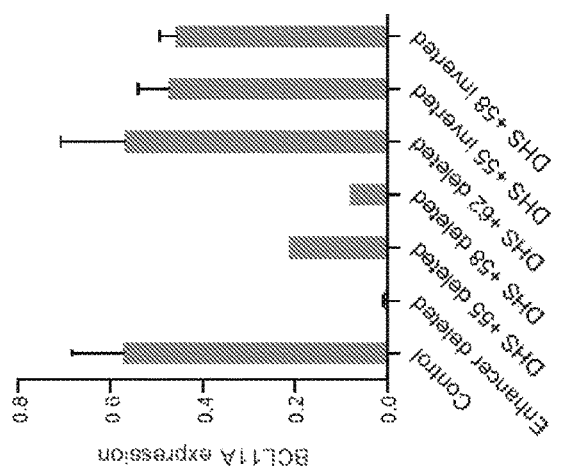
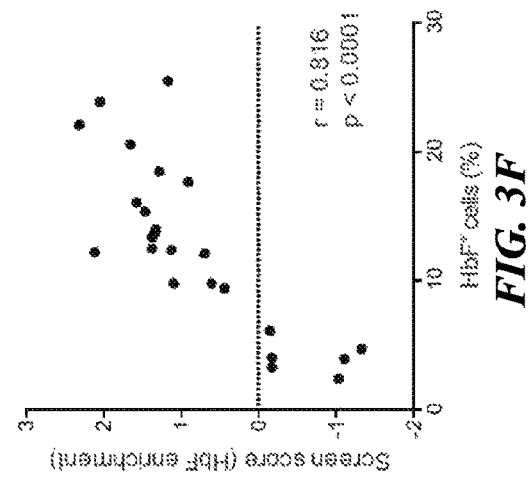

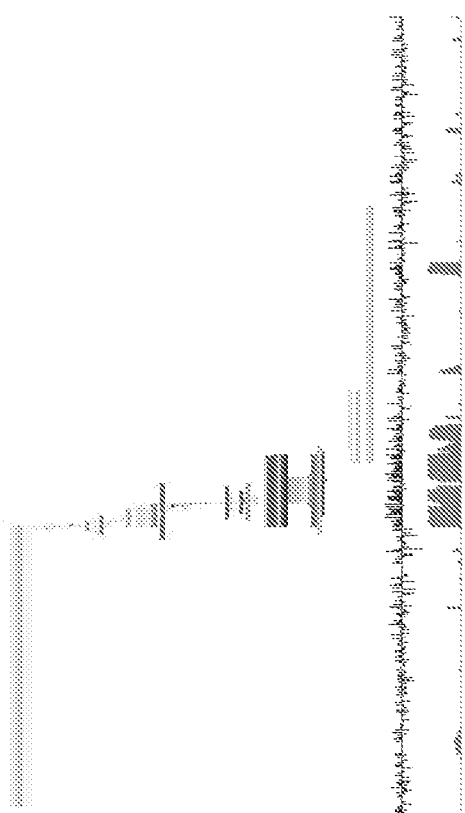
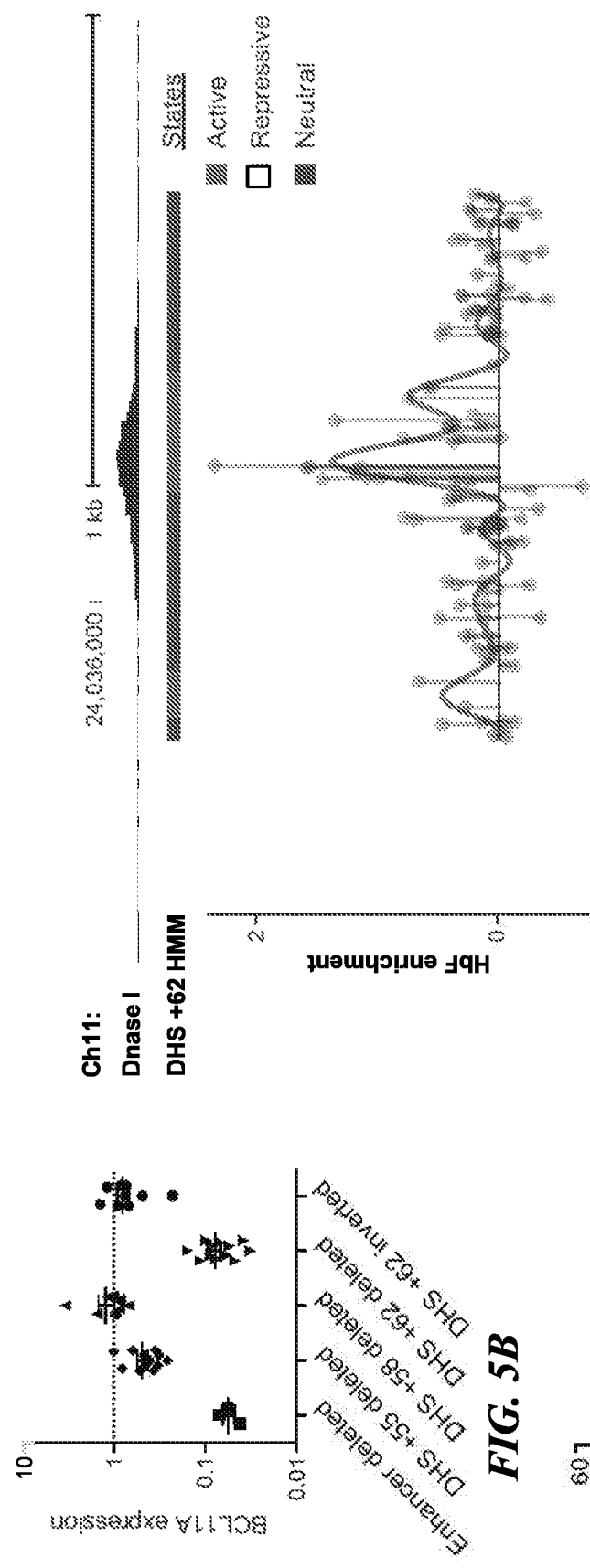
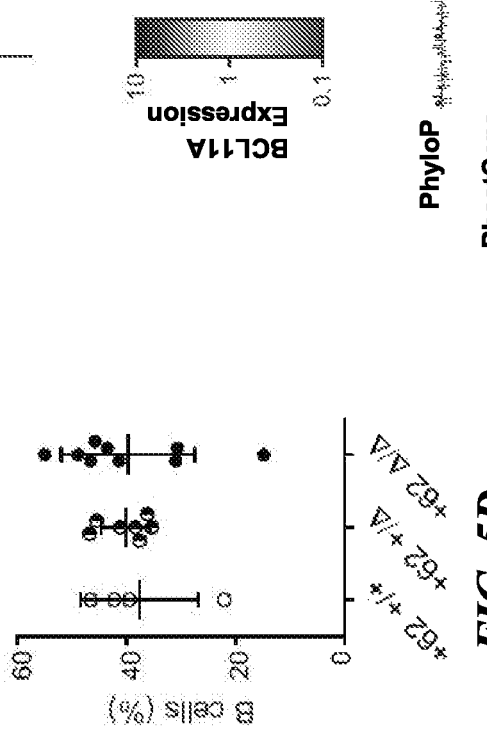
FIG. 5C
FIG. 5B
FIG. 5D

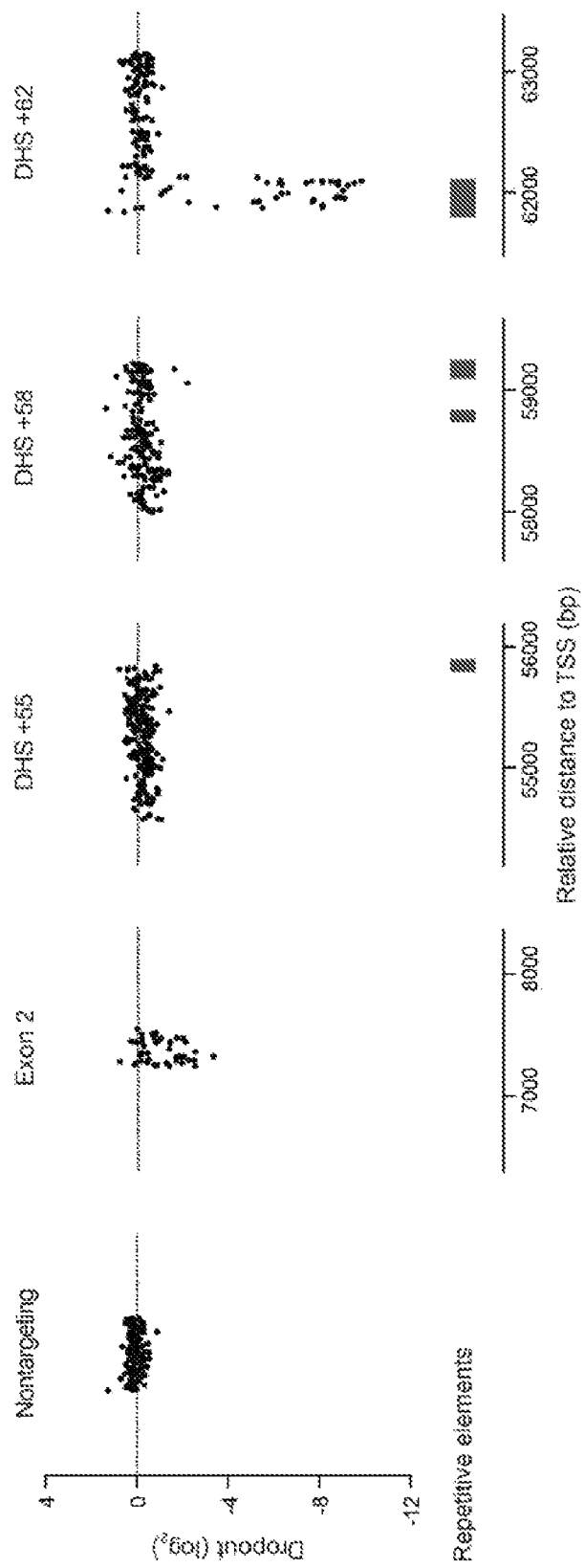
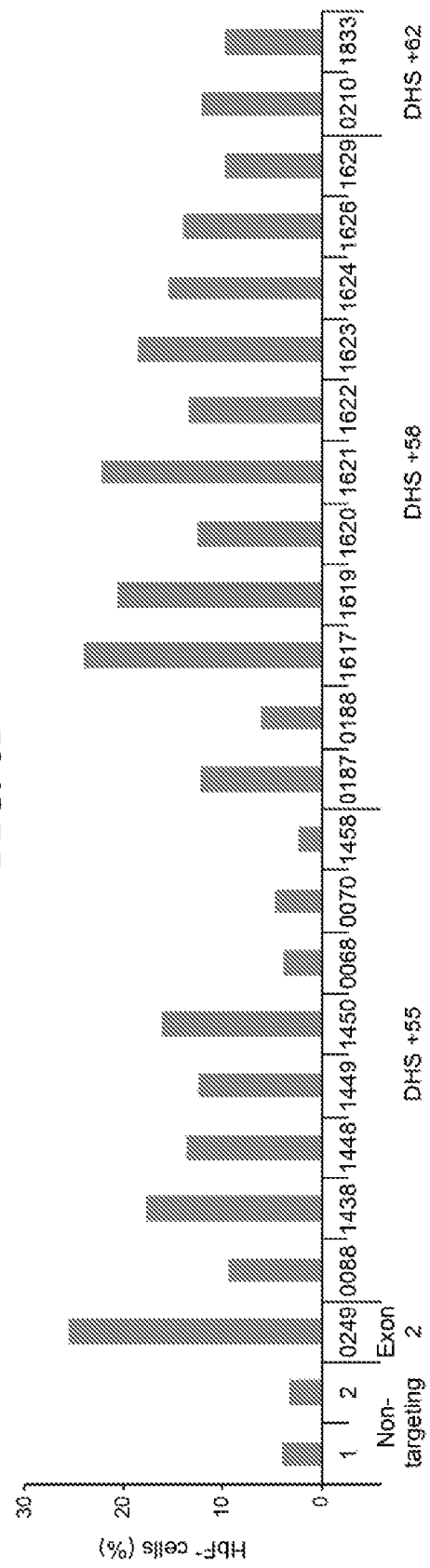
FIG. 6F
FIG. 7A

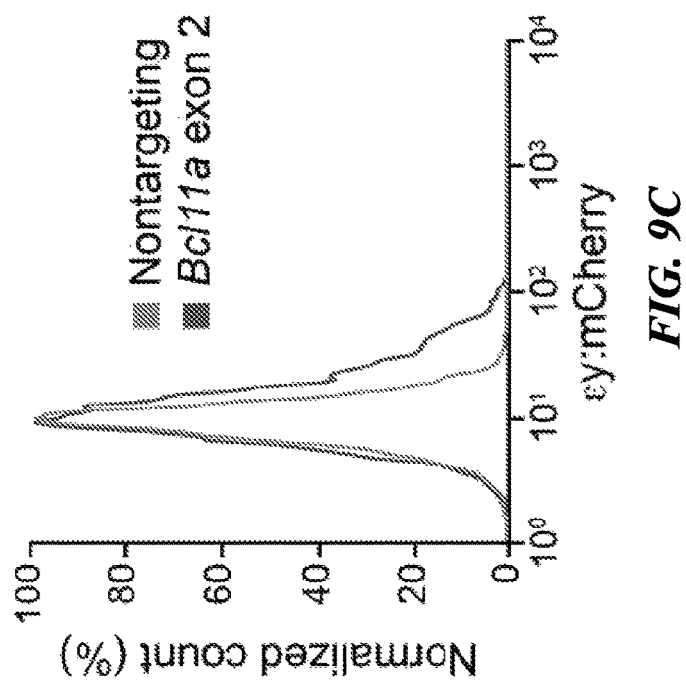
FIG. 9A
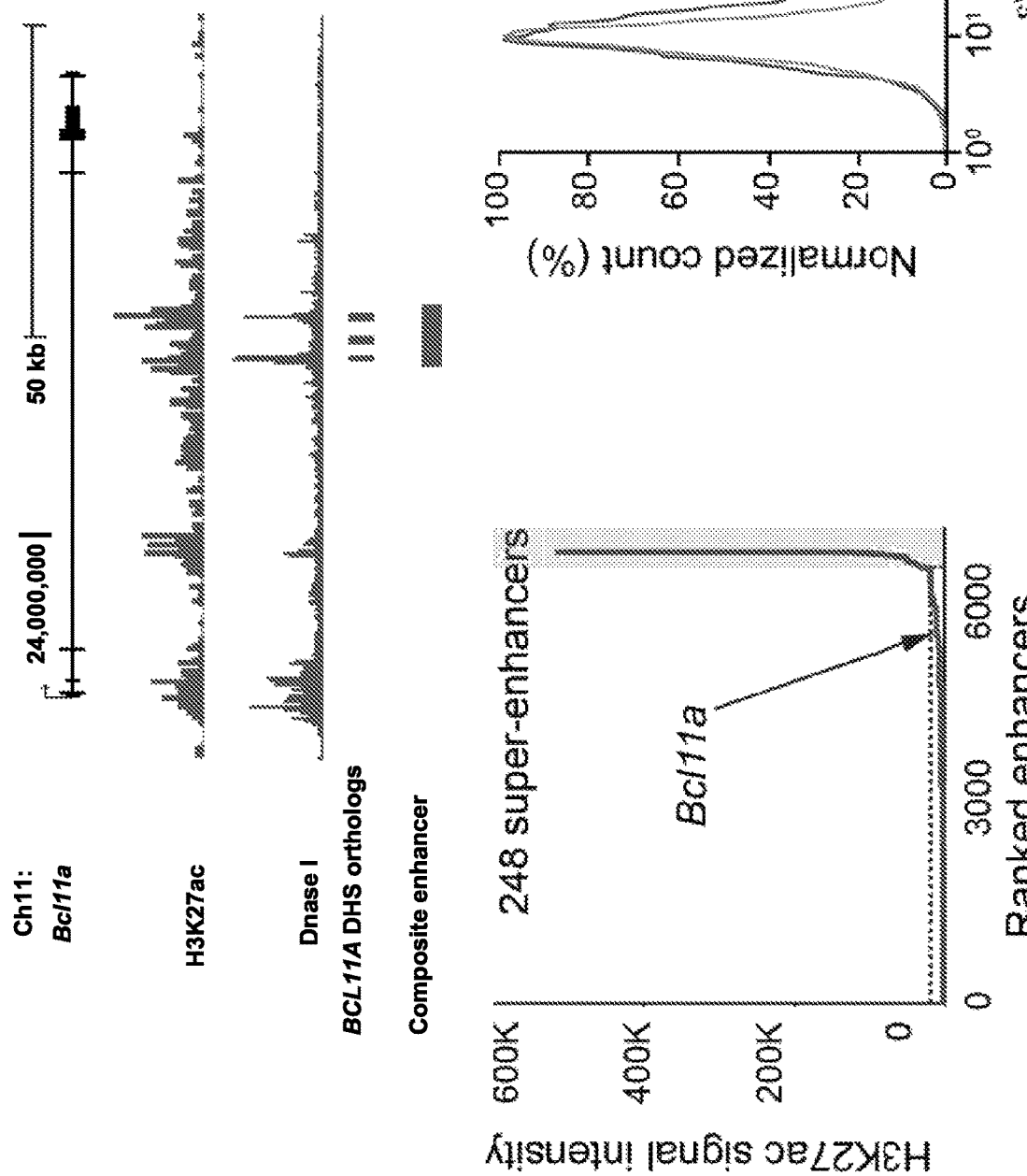
FIG. 9B
FIG. 9C

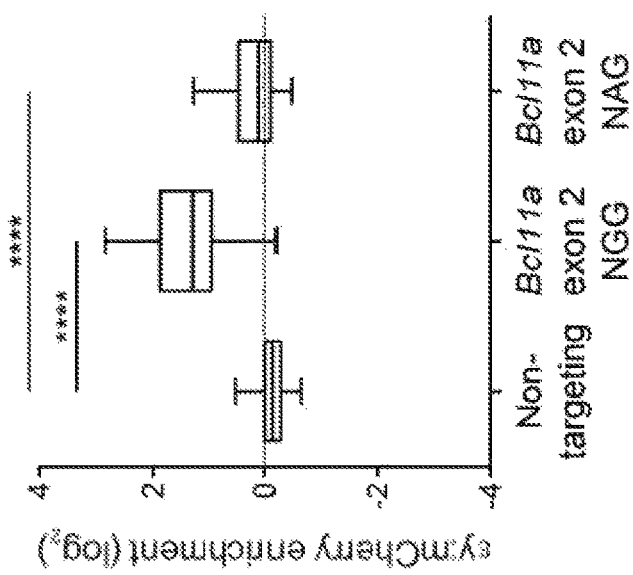
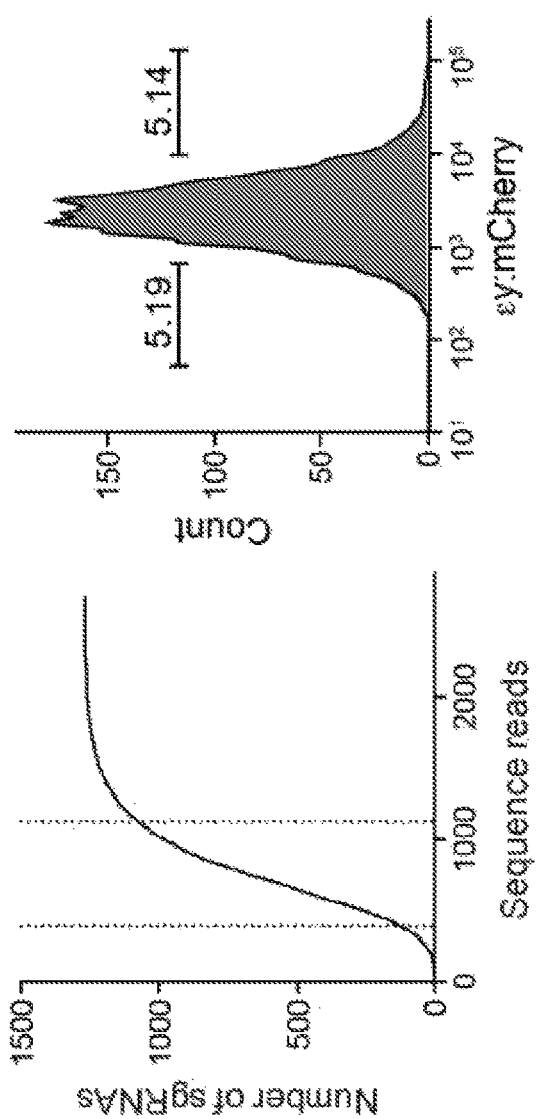
FIG. 9K
FIG. 9J
FIG. 9I

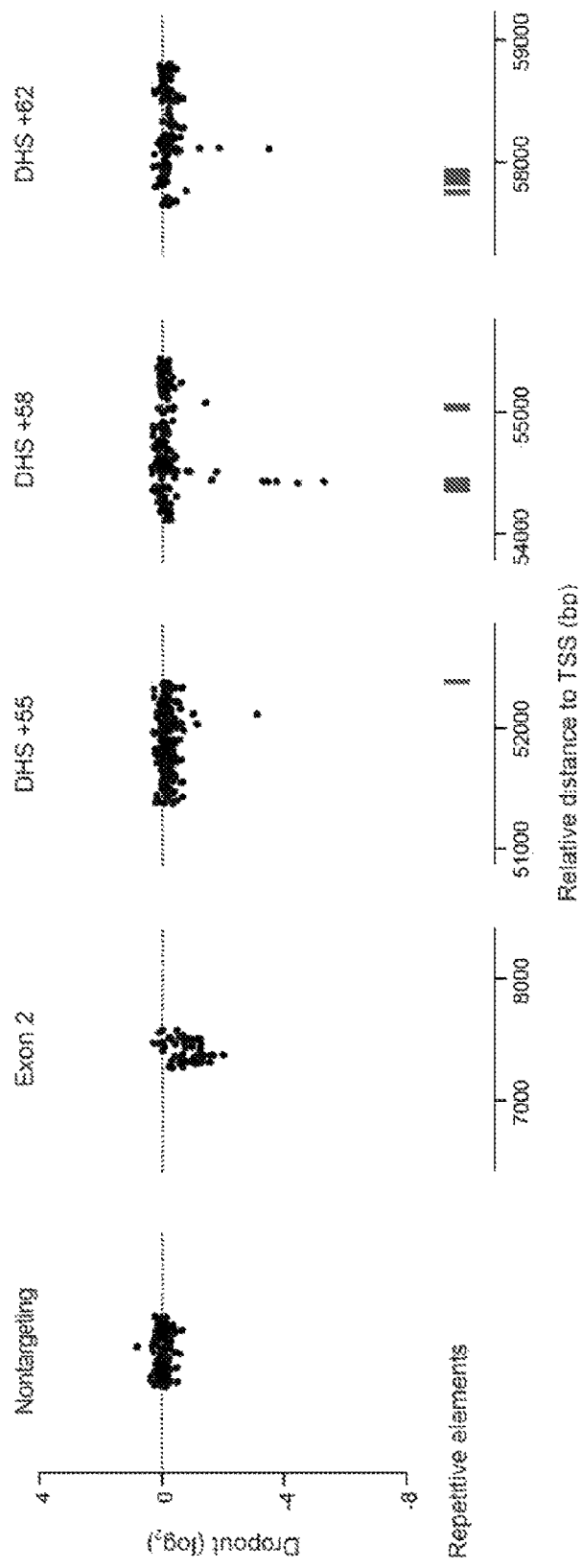
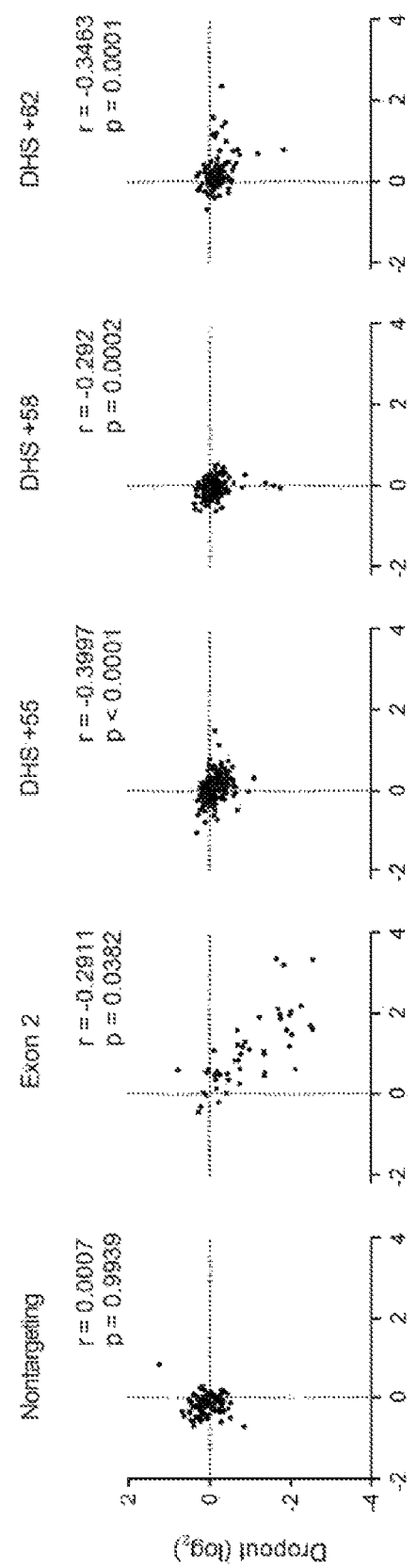
FIG. 10C
FIG. 10D

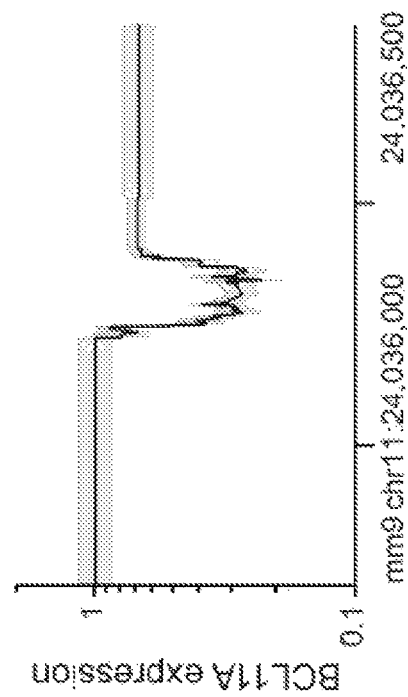
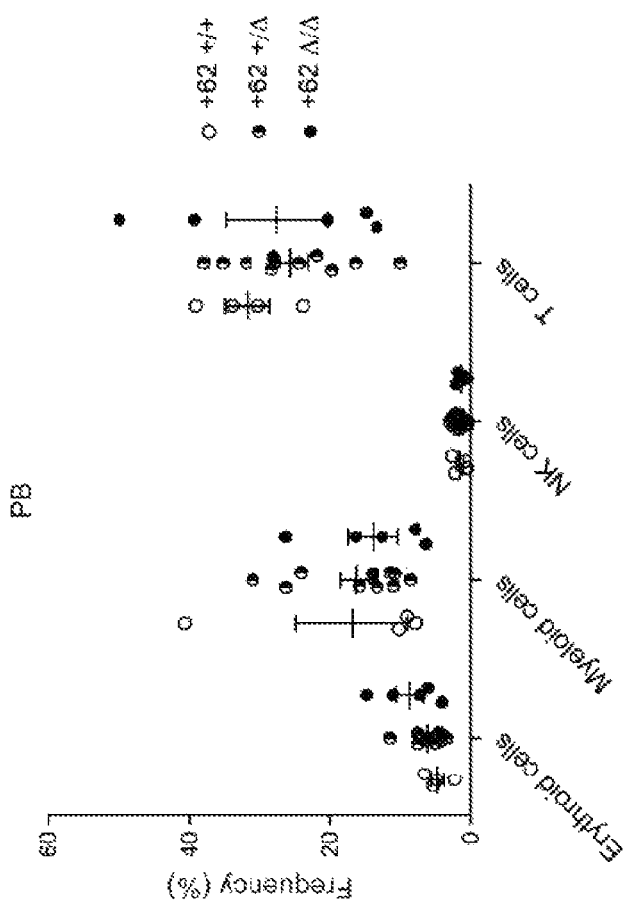
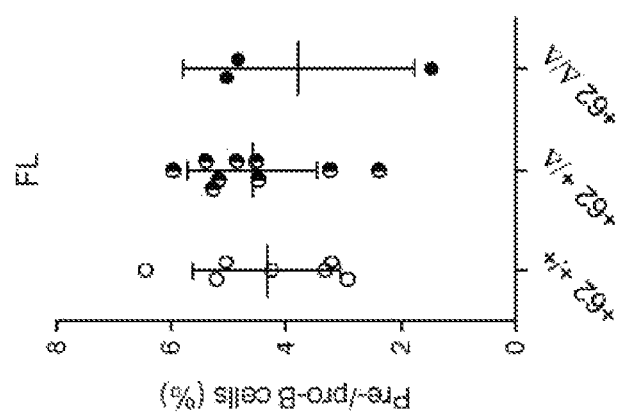
FIG. 11A  FIG. 11B  FIG. 11C  FIG. 11D

SEQUENCE LISTING

<160> NUMBER OF SEQ ID NOS: 262

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 1
tctgaggagc tagagacttg ngg                                           23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

```
<220> FEATURE:
<221> NAME/KEY: modified_base
<222> LOCATION: (21)..(21)
<223> OTHER INFORMATION: a, c, t, g, unknown or other

<400> SEQUENCE: 2
agcaaatagg cttagtgtgc ngg                                              23

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 3
ggctaaataa tgaatgtccc nggrc                                            25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 4
tcccttccta gaattggcct ngg                                              23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 5
ttcccttcct agaattggcc ngg                                              23

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 6
gaatgtccca ggccaattct nggrc                                            25

<210> SEQ ID NO 7
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 7
cccacttccc ttcctagaat ngg                                          23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 8
cctggtacca ggaaggcaat ngg                                          23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 9
tcctggtacc aggaaggcaa ngg                                          23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 10
gcatcatcct ggtaccagga ngg                                          23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

```
<400> SEQUENCE: 11
cattgcatca tcctggtacc ngg                                          23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 12
ctccaagcat tgcatcatcc ngg                                          23

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 13
taccaggatg atgcaatgct nggrc                                        25

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 14
gggtgtgccc tgagaaggtg ngg                                          23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 15
agggtgtgcc ctgagaaggt ngg                                          23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 16
tcacagggtg tgccctgaga ngg                                   23

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 17
ggcacaccct gtgatcttgt nggrc                                 25

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 18
agcacacaag atgcacaccc ngg                                   23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 19
tgtgcttggt cggcactgat nggrc                                 25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 20
gtgcttggtc ggcactgata nggrc                                 25
```

-continued

```
<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 21
tgcttggtcg gcactgatag nggrc                                              25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 22
gggtcgcggt agggagttgt nggrc                                              25

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 23
gccaacagtg ataaccagca ngg                                                23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 24
tgccaacagt gataaccagc ngg                                                23

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

-continued

<400> SEQUENCE: 25
gccctgctgg ttatcactgt nggrc                                         25

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 26
agcagccctg ggcacagaag ngg                                           23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 27
cctctatgta gacgggtgtg ngg                                           23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 28
ggaagggcct ctatgtagac ngg                                           23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 29
ggaggtgtgg agggataac ngg                                            23

<210> SEQ ID NO 30
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 30
ctggcagacc ctcaagagca ngg                                            23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 31
cccatggagg tggggagatg ngg                                            23

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 32
gtcatcctcg gccaatgaag nggrc                                          25

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 33
aagtgagcca ggtgatagaa ngg                                            23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 34
tgaaaccaag cttcctctgc ngg                                            23
```

```
<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 35
agggagaaat gagacaaaag nggrc                                              25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 36
aagaggccac tgagtccttt nggrc                                              25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 37
ctaacagttg cttttatcac nggrc                                              25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 38
ttgcttttat cacaggctcc nggrc                                              25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
```

<223> OTHER INFORMATION: a, c, t, g, unknown or other

<400> SEQUENCE: 39
ttttatcaca ggctccagga nggrc                                        25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 40
tttatcacag gctccaggaa nggrc                                        25

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 41
atcagaggcc aaaccttcc ngg                                           23

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 42
cacaggctcc aggaagggtt nggrc                                        25

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 43 cacgcccca ccctaatcag ngg                                           23

<210> SEQ ID NO 44
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 44
gaagggtttg gcctctgatt nggrc                                              25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 45
aagggtttgg cctctgatta nggrc                                              25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 46
ggtttggcct ctgattaggg nggrc                                              25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 47
gtttggcctc tgattagggt nggrc                                              25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 48
tttggcctct gattagggtg nggrc                                              25
```

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 49
ttggcctctg attagggtgg nggrc                                          25

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 50
tctgattagg gtgggggcgt nggrc                                          25

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 51
attagggtgg gggcgtgggt nggrc                                          25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 52
tgggtggggt agaagaggac nggrc                                          25

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 53
gcaaacggcc accgatggag ngg                                              23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 54
cctgggcaaa cggccaccga ngg                                              23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 55
aagaggcccc cctgggcaaa ngg                                              23

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 56
ccatcggtgg ccgtttgccc nggrc                                            25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 57
catcggtggc cgtttgccca nggrc                                            25

<210> SEQ ID NO 58
<211> LENGTH: 25
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 58
atcggtggcc gtttgcccag nggrc                                          25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 59
tcggtggccg tttgcccagg nggrc                                          25

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 60
cggtggccgt ttgcccaggg nggrc                                          25

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 61
cttccgaaag aggccccct ngg                                             23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 62

```
ccttccgaaa gaggcccccc ngg                                          23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 63 tcaggggag gcaagtcagt ngg                                           23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 64
agggaaaagg gagaggaaaa ngg                                          23

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 65
tgtaactaat aaataccagg nggrc                                        25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 66
ccagctgaag aaagaacatt nggrc                                        25

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (21)..(21)
<223> OTHER INFORMATION: a, c, t, g, unknown or other

<400> SEQUENCE: 67
ccatctccct aatctccaat ngg                                          23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 68
tggggagaga agagtggaaa ngg                                          23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 69
ggagtatggg gagagaagag ngg                                          23

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 70
acaacctcct tgtttacaga nggrc                                        25

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 71
gagatttact cttgttgccc nggrc                                        25

<210> SEQ ID NO 72
<211> LENGTH: 25

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 72
ttgcccgggc tggaatgcaa nggrc                                       25

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 73
ggagatcgct tgaacctggg ngg                                         23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 74
ctcagctact cgggaggctg ngg                                         23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 75
tgtaatctca gctactcggg ngg                                         23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 76
```
gcctgtaatc tcagctactc ngg                                              23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 77
tgcctgtaat ctcagctact ngg                                              23

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 78
caggcatgta ttaccatgcc nggrc                                            25

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 79
caggaggatc acctgaggtc ngg                                              23

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 80
ctcaggtgat cctcctgccc nggrc                                            25

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (21)..(21)
<223> OTHER INFORMATION: a, c, t, g, unknown or other

<400> SEQUENCE: 81
cccagcactt tgggaggccg ngg                                            23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 82
tcccagcact ttgggaggcc ngg                                            23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 83
atcccagcac tttgggaggc ngg                                            23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 84
acctgtaatc ccagcacttt ngg                                            23

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 85
gccccggcct cccaaagtgc nggrc                                          25

<210> SEQ ID NO 86
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 86
ccccggcctc ccaaagtgct nggrc                                           25

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 87
atttgctctt ctccagggtg nggrc                                           25

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 88
taaacagcca ccccacaccc ngg                                             23

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 89
tttgctcttc tccagggtgt nggrc                                           25

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

```
<400> SEQUENCE: 90
ctcttctcca gggtgtgggg nggrc                                              25

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 91
tgtggggtgg ctgtttaaag nggrc                                              25

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 92
gggtggctgt ttaaagaggg nggrc                                              25

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 93
agttcaagta gatatcagaa nggrc                                              25

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 94
tatcagaagg gaactgtttg nggrc                                              25

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 95
aagaatggct tcaagaggct nggrc                                              25

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 96
tctgtaagaa tggcttcaag nggrc                                              25

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 97
acagatgatg aaccagacca ngg                                                23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 98
tgaaccagac cacggcccgt ngg                                                23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 99
gaaccagacc acggcccgtt ngg                                                23

```
<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 100
ggcccgttgg gagctccaga ngg                                              23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 101
gcccgttggg agctccagaa ngg                                              23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 102
cccgttggga gctccagaag ngg                                              23

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 103
ctggagctcc caacgggccg nggrc                                            25

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

<400> SEQUENCE: 104
ccccttctgg agctcccaac nggrc                                            25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 105 tcccttctg gagctcccaa nggrc                                             25

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 106
gatcatgacc tcctcacctg ngg                                              23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 107
atcatgacct cctcacctgt ngg                                              23

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 108
aggaggtcat gatcccttc nggrc                                             25

<210> SEQ ID NO 109
<211> LENGTH: 25
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 109
ggcactgccc acaggtgagg nggrc                                           25

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 110
gtgccagatg aacttcccat ngg                                             23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 111
tgccagatga acttcccatt ngg                                             23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 112
gccagatgaa cttcccattg ngg                                             23

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 113
tctggcactg cccacaggtg nggrc                                           25
```

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 114
ccagatgaac ttcccattgg ngg                                             23

<210> SEQ ID NO 115
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 115
gttcatctgg cactgcccac nggrc                                           25

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 116
cccccaatgg gaagttcatc nggrc                                           25

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 117
aaataagaat gtcccccaat nggrc                                           25

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)

<223> OTHER INFORMATION: a, c, t, g, unknown or other

<400> SEQUENCE: 118
aaaataagaa tgtcccccaa nggrc                                         25

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 119
cacaaacgga aacaatgcaa ngg                                           23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 120
cctctgctta gaaaaagctg ngg                                           23

<210> SEQ ID NO 121
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 121
ccacagcttt ttctaagcag nggrc                                         25

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 122
tcgattggtg aaggggaagg nggrc                                         25

<210> SEQ ID NO 123
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 123
atctcgattg gtgaagggga nggrc                                               25

<210> SEQ ID NO 124
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 124
tttcatctcg attggtgaag nggrc                                               25

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 125
gaaaaaagca tccaatcccg ngg                                                 23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 126
aaaagcatcc aatcccgtgg ngg                                                 23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 127
gcatccaatc ccgtggaggt ngg                                                 23
```

```
<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 128
tcccgtggag gttggcatcc ngg                                          23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 129
tggcatccag gtcacgccag ngg                                          23

<210> SEQ ID NO 130
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 130
gatgccaacc tccacgggat nggrc                                        25

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 131
acctggatgc caacctccac nggrc                                        25

<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (21)..(21)
<223> OTHER INFORMATION: a, c, t, g, unknown or other

<400> SEQUENCE: 132
gacctggatg ccaacctcca nggrc                                         25

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 133
cgtcatcctc tggcgtgacc nggrc                                         25

<210> SEQ ID NO 134
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 134
gataaacaat cgtcatcctc nggrc                                         25

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 135
ctgctatgtg ttcctgtttg nggrc                                         25

<210> SEQ ID NO 136
<211> LENGTH: 265
<212> TYPE: DNA
<213> ORGANISM: Homo sapiens

<400> SEQUENCE: 136
gacactgaag gctgggcaca gccttgggga ccgctcacag gacatgcagc agtgtgtgcc    60
gacaactccc taccgcgacc cctatcagtg ccgaccaagc acacaagatg cacacccagg   120
ctgggctgga cagaggggtc ccacaagatc acagggtgtg ccctgagaag gtggggagct   180
cacagcctcc aagcattgca tcatcctggt accaggaagg caatgggctg ccccataccc   240
acttcccttc ctagaattgg cctgg                                        265

<210> SEQ ID NO 137
<211> LENGTH: 229
```

```
<212> TYPE: DNA
<213> ORGANISM: Homo sapiens

<400> SEQUENCE: 137
ttcattccca ttgagaaata aatccaatt ctccatcacc aagagagcct tccgaaagag    60 gccccctgg gcaaacggcc accgatggag aggtctgcca gtcctcttct accccaccca   120
cgcccccacc ctaatcagag gccaaaccct tcctggagcc tgtgataaaa gcaactgtta  180
gcttgcacta gactagcttc aaagttgtat tgaccctggt gtgttatgt              229

<210> SEQ ID NO 138
<211> LENGTH: 145
<212> TYPE: DNA
<213> ORGANISM: Homo sapiens

<400> SEQUENCE: 138
atttcccttc tgatatctac ttgaactttc agataaaaaa aaaaaagcaa gttgcagtaa   60
catgttatgc tacacaaaga ttagcatgaa tatccaccct ctttaaacag ccaccccaca  120
ccctggagaa gagcaaatgt gaagt                                        145

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ggcgtgggtg gggtagaaga gga                                           23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gggggcgtgg gtggggtaga aga                                           23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tcagaggcca aaccttcct gga                                            23

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
caaacccttc ctggagcctg tga                                           23
```

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
caccagggtc aatacaactt tga                                              23

<210> SEQ ID NO 144
<211> LENGTH: 9
<212> TYPE: PRT
<213> ORGANISM: Unknown
<220> FEATURE:
<223> OTHER INFORMATION: Description of Unknown:
      "LAGLIDADG" family motif peptide

<400> SEQUENCE: 144

Leu Ala Gly Leu Ile Asp Ala Asp Gly
1               5

<210> SEQ ID NO 145
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ggccggccgg atccggcgca acaaacttct ctctgctgaa acaagccgga gatgtcgaag      60
agaatcctgg accgatggtg agcaagggcg agga                                  94

<210> SEQ ID NO 146
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ggccggccga attcttactt gtacagctcg tcca                                  34

<210> SEQ ID NO 147
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ggccggcccg tacgcgtacg gccaccatgg atagcactga gaacgtcatc aagcccctt       58

<210> SEQ ID NO 148
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ggccggccac gcgtctactg gaacaggtgg tggcgggcct                40

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cgtaacttga aagtatttcg atttcttggc                          30

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ggccggccgc tcgagggagg gcctatttcc                          30

<210> SEQ ID NO 151
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ccggccggcc cgggttgtgg atgaatactg ccattt                   36

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ggaggcttgg taggtttaag aa                                  22

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ccaattccca ctcctttcaa                                     20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tggaaaggag aacggcccgg                                     20

```
<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tgaacaccct cgttaaaggc                                                  20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
aacactagcc cacatgccaa                                                  20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gcccacagag gcacggttaa                                                  20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
aggcacggtt aatggtggcg                                                  20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cacaggaagc catggtcctt                                                  20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gcactgacgt aggtagtgac                                                  20
```

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ataggatatg gcactgacgt                                              20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cattatcttc tctggtctcg                                              20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
atactgggga acacattgta                                              20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tgagcacatt cttacgccta                                              20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ctaggcgtaa gaatgtgctc                                              20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166 gaaccccta taaactagtc                                               20

```
<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggcaaaccag actagtttat                                                    20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168 cagggagaa ctcggcatga                                                     20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gatggagttg gttgaccgta                                                    20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ggtaggaccc aacactacgc                                                    20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
atgcctaggg tgttttgacg                                                    20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tgaaccagac cacggcccgt                                                    20

<210> SEQ ID NO 173
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gcatccaatc ccgtggaggt                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
cactggcttc ctgttcttgt                                              20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aaggttttca aggcaaataa                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gtaatggagc ccgcatgctg                                              20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gccagtgtac aggcaagtac                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tcgctgcctt cagttctgct                                              20

<210> SEQ ID NO 179
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ttatggaact caggaactgc                                            20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gatgcctttt tcatctcgat                                            20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
attccttgag tgtcatatat                                            20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tctggaatca ctatgtatat                                            20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
tgctccgagc ttgtgaacta                                            20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tatcacaggc tccaggaagg                                            20

<210> SEQ ID NO 185
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 185
tagtttgctt cccccaatga                                                     20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gccaggaaat tggtggtaga                                                     20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgctccgagc ttgtgaacta                                                     20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tatcacaggc tccaggaagg                                                     20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gtgggcagtt acgttttcgt                                                     20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gccaggaaat tggtggtaga                                                     20

<210> SEQ ID NO 191
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 191
ggtcagggtg ttgcagagat                                                     20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
cacaccctgt gatcttgtgg                                                     20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
gacttaaact gccgctcctg                                                     20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gggcctcagg ctctttatct                                                     20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cccagagctc agtgagatga                                                     20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gggaaagggc ctgataactt                                                     20

<210> SEQ ID NO 197
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 197
gaacagagac cactactggc aat                                              23

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ctcagaaaaa tgacagcacc a                                                21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tttgaaagta ccagcacagc a                                                21

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ccctctggca tcaaaatgag                                                  20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
aacagaccca tgtgctaggc                                                  20

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tgctgaattc ctgtaaagtg agg                                              23

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
gaggtgacca gggtgtgagt                                        20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aagaagaggc cctggacatt                                        20

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
catcttaagg caagaatcac t                                      21

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ccagtcaatc caaaccctgt                                        20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
tattaatgcc cagccagctc                                        20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
gtggtccaga cctagccaag                                        20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 209
tttgagcagg agggaatttg                                              20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ataggtggtt gggcttctcc                                              20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ggagtggctg ttgaaagagg                                              20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
cactcaagga atgcaagcaa                                              20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tacttggtgg ctttcccaac                                              20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
agatggtcct ctgcatccac                                              20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 215
gacttaaact gccgctcctg                                              20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
aggcatccaa agggaagaat                                              20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
acttcagcct ccagcactgt                                              20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ccactggagt ggaaccaagt                                              20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
gggatcagag gtgaacagga                                              20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
tggactttgc actggaatca                                              20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
```

```
ttgtttacag aggggcaacc                                              20
```

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222

```
ggggaagggg tattgaattg                                              20
```

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223

```
aacagaccca tgtgctaggc                                              20
```

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224

```
gaacctggga ggcagaagat                                              20
```

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225

```
tgtgtggact gccttttctg                                              20
```

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226

```
tgtggagctc tggaatgatg                                              20
```

<210> SEQ ID NO 227
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
ggtagtgtgg gggtggagt                                          19

<210> SEQ ID NO 228
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
tcagcctgtt ccctcagtg                                          19

<210> SEQ ID NO 229
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ggtagtgtgg gggtggagt                                          19

<210> SEQ ID NO 230
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
tcagcctgtt ccctcagtg                                          19

<210> SEQ ID NO 231
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ggtagtgtgg gggtggagt                                          19

<210> SEQ ID NO 232
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tcagcctgtt ccctcagtg                                          19

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ggtagtgtgg gggtggagt                                          19

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
agatggtcct ctgcatccac                                              20

<210> SEQ ID NO 235
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
ggtagtgtgg gggtggagt                                               19

<210> SEQ ID NO 236
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
tcagcctgtt ccctcagtg                                               19

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tacttggtgg cttcccaac                                               20

<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
tcagcctgtt ccctcagtg                                               19

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
atgcttggtt gtcgccttat                                              20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
cactcaagga atgcaagcaa                                              20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
acccagaaga ctgtggatgg                                              20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ttcagctcag ggatgacctt                                              20

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ctgaggagaa gtctgccgtt a                                            21

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
agcatcagga gtggacagat                                              20

<210> SEQ ID NO 245
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tggatgatct caagggcac                                               19

```
<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tcagtggtat ctggaggaca                                               20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gcaagaaggt gctgacttcc                                               20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
accatcacgt tacccaggag                                               20

<210> SEQ ID NO 249
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gaggagaaga ctgctgtcaa tg                                            22

<210> SEQ ID NO 250
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
agggtagacc accagtaatc tg                                            22

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
aaccccagca cttaagcaaa                                               20

<210> SEQ ID NO 252
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ggaggtcatg atccccttct                                                  20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tggtgaaggt cggtgtgaac                                                  20

<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ccatgtagtt gaggtcaatg aagg                                             24

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tttaacgatg gcctgaatca ctt                                              23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
cagcacaatc acgatcatat tgc                                              23

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tggcctgtgg agtaaggtca a                                                21

<210> SEQ ID NO 258
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gaagcagagg acaagttccc a                                              21

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tggacaacct caaggagacc                                                20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
acctctgggg tgaattcctt                                                20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
aaccccagca cttaagcaaa                                                20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
acaggtgaga aggtcgtggt                                                20
```

TARGETING BCL11A ENHANCER FUNCTIONAL REGIONS FOR FETAL HEMOGLOBIN REINDUCTION

CROSS-REFERENCE TO RELATED APPLICATIONS

This application is a 35 U.S.C. § 371 National Phase Entry Application of International Application No. PCT/US2016/031224 filed May 6, 2016, which designates the U.S., and which claims benefit under 35 U.S.C. § 119(e) of the U.S. provisional application No. 62/158,882 filed May 8, 2015, the contents of each of which are incorporated herein by reference in their entirety.

This application claims benefit under 35 U.S.C. § 119(e) of the U.S. provisional application No. 62/158,882 filed May 8, 2015, the contents of which is/are incorporated herein by reference in its entirety.

GOVERNMENT SUPPORT

This invention was made with government support under Grant nos. DK093705, DK097768, HL032262, HL032259, MH100706, MH110049, and HG008171, awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 5, 2016, is named 701039-084941-PCT_SL.txt and is 73,650 bytes in size.

BACKGROUND

Normal adult hemoglobin comprises four globin proteins, two of which are alpha ($\alpha$) proteins and two of which are beta ($\beta$) proteins. During mammalian fetal development, particularly in humans, the fetus produces fetal hemoglobin, which comprises two gamma ($\gamma$)-globin proteins instead of the two $\beta$-globin proteins. During the neonatal period, a globin switch occurs, referred to as the "fetal switch", at which point, erythroid precursors switch from making predominantly $\gamma$-globin to making predominantly $\beta$-globin. The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth until HbA becomes predominant. This switch results primarily from decreased transcription of the gamma-globin genes and increased transcription of beta-globin genes. On average, the blood of a normal adult contains less than 1% HbF, though residual HbF levels have a variance of over 20 fold in healthy adults and are genetically controlled.

Hemoglobinopathies encompass a number of anemias of genetic origin in which there is a decreased production and/or increased destruction (hemolysis) of red blood cells (RBCs). These also include genetic defects that result in the production of abnormal hemoglobins with a concomitant impaired ability to maintain oxygen concentration. Some such disorders involve the failure to produce normal $\beta$-globin in sufficient amounts, while others involve the failure to produce normal $\beta$-globin entirely. These disorders associated with the $\beta$-globin protein are referred to generally as $\beta$-hemoglobinopathies. For example, $\beta$-thalassemias result from a partial or complete defect in the expression of the $\beta$-globin gene, leading to deficient or absent HbA. Sickle cell anemia results from a point mutation in the $\beta$-globin structural gene, leading to the production of an abnormal (sickle) hemoglobin (HbS). HbS is prone to polymerization, particularly under deoxygenated conditions. HbS RBCs are more fragile than normal RBCs and undergo hemolysis more readily, leading eventually to anemia.

Recently, the search for treatment aimed at reduction of globin chain imbalance or predisposition to hemoglobin polymerization in patients with $\beta$-hemoglobinopathies has focused on the pharmacologic manipulation of fetal hemoglobin ($\alpha 2\gamma 2$; HbF). The therapeutic potential of such approaches is indicated by observations of the mild phenotype of individuals with co-inheritance of both homozygous $\beta$-thalassemia and hereditary persistence of fetal hemoglobin (HPFH), as well as by those patients with homozygous $\beta$-thalassemia who synthesize no adult hemoglobin, but in whom a reduced requirement for transfusions is observed in the presence of increased concentrations of fetal hemoglobin. Furthermore, it has been observed that certain populations of adult patients with $\beta$ chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease. It is now accepted that hemoglobin disorders, such as sickle cell anemia and the $\beta$-thalassemias, are ameliorated by increased HbF production.

The switch from fetal hemoglobin to adult hemoglobin ($\alpha 2\gamma 2$; HbA) usually proceeds within six months after parturition. However, in the majority of patients with $\beta$-hemoglobinopathies, the upstream $\gamma$ globin genes are intact and fully functional, so that if these genes become reactivated, functional hemoglobin synthesis could be maintained during adulthood, and thus ameliorate disease severity. Unfortunately, the in vivo molecular mechanisms underlying the globin switch are not well understood.

Evidence supporting the feasibility of reactivation of fetal hemoglobin production comes from experiments in which it was shown that peripheral blood, containing clonogenic cells, when given the appropriate combination of growth factors, produce erythroid colonies and bursts in semisolid culture. Individual cells in such colonies can accumulate fetal hemoglobin (HbF), adult hemoglobin (HbA) or a combination of both. In cultures from adult blood, nucleated red cells accumulate either HbA (F−A+) only, or a combination of HbF and HbA (F+A+). Importantly, individual colonies contain both F+ and F− cells, indicating that both types are progeny from the same circulating stem cells. Thus, during the early stages of development in culture, cells execute an option, through currently unknown mechanisms, whether or not to express HbF. The proportion of adult F+ cells developing in culture does not appear to be preprogrammed in vivo, but appears to depend on culture conditions: A shift into the combined HbF and HbA expression pathway can, for example, be achieved in vitro by high serum concentrations, due to the activity of an unidentified compound that can be absorbed on activated charcoal.

A distal regulatory region upstream of the BCL11A gene that can regulate expression of the BCL11A protein was recently discovered. The BCL11A protein acts as a stage specific regulator of fetal hemoglobin expression by repressing $\gamma$-globin induction. This upstream distal regulatory region mapped to the human chromosome 2 at location 60,716,189-60,728,612 in the human genomic DNA according to UCSC Genome Browser hg 19 human genome assembly. Noticeably, this upstream distal regulatory region consistently contains three DNAse 1-hypersensitive sites (DHS)+62, +58, and +55. Identification of specific functional regions within this ~12 kb molecules that play a role in the globin switch is important for the development of novel therapeutic strategies that interfere with adult hemoglobin and induce fetal hemoglobin synthesis. Such functional regions would provide new targets for the development of therapeutic interventions for a variety of hemoglobinopathies in which reactivation of fetal hemoglobin synthesis would significantly ameliorate disease severity and morbidity.

SUMMARY

Embodiments described herein are based in part to the discovery of defined functional regions within the BCL11A ~12 kb enhancer region that regulate expression of the BCL11A protein. These functional regions are mapped to the previously identified three DNAse 1-hypersensitive sites (DHS)+62, +58, and +55. Specifically, the functional regions are found at location 60725424 to 60725688 (+55 functional region); at location 60722238 to 60722466 (+58 functional region); and at location 60718042 to 60718186 (+62 functional region) of the human chromosome 2. Genome editing disruption at these regions were functionally verified for expression of the BCL11A mRNA, expression of the BCL11A protein, and ultimately for the enrichment of fetal hemoglobin (HbF) produced. Small single guide RNA (sgRNA) sequences were design to target these functional regions using the CRISPR/Cas9 technology and the disruption results in at least a greater than or equal normalized HbF enrichment of 0.259. In particular, targeting and disrupting the +58 functional region produced super HbF enrichment whereas targeting and disrupting the +55 or +62 functional regions produced moderate HbF enrichments. Therefore, targeting these three +62, +58, and +55 functional regions, alone or in combination, using specifically designed sgRNA and CRISPR technology, can provide therapeutic strategies that interfere with adult hemoglobin and induce fetal hemoglobin synthesis.

Provided herein are nucleic acid molecules that target the three BCL11A enhancer functional regions, these three +62, +58, and +55, compositions comprising the nucleic acid molecules, and methods for increasing fetal hemoglobin levels in a cell by disrupting BCL11A expression at the genomic level. Also provided herein are methods and compositions relating to the treatment of hemoglobinopathies by reinduction of fetal hemoglobin levels. In particular, the nucleic acid molecules target the +62, +58, and/or the +55 enhancer functional regions.

Accordingly, in one embodiment, provided herein is a nucleic acid molecule comprising a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612.

In one embodiment, provided herein is a nucleic acid molecule consisting essentially of a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612.

In one embodiment, this disclosure provides a vector comprising a nucleic acid sequence which is: (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60,716,189 to 60,728,612.

In one embodiment, this disclosure provides a vector consisting essentially a nucleic acid sequence which is: (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60,716,189 to 60,728,612.

In some embodiments, this disclosure provides compositions comprising the nucleic acid molecules described supra and/or the vectors described supra. In one embodiment, the compositions are use in in vitro methods for producing an engineered cell (e.g. transfection with the nucleic acid and/or or vector described, or genetic modification described herein) so that the cell has reduced or decreased mRNA or protein expression of BCL11A compared to a similar cell that had not gone through the engineered process.

In one embodiment, this disclosure provides a method of increasing fetal hemoglobin levels in a cell, the method comprising the steps of: contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), and/or at location 60722238 to 60722466 (+58 functional region), and/or at location 60718042 to 60718186 (+62 functional region), causing at least one genetic modification therein, whereby fetal hemoglobin expression is increased in said cell, or its progeny, relative to said cell prior to said contacting, and wherein the human chromosome 2 is that according to UCSC Genome Browser hg 19 human genome assembly. In one embodiment, the method is an in vitro or ex vivo method.

In one embodiment, this disclosure provides an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein. In one embodiment, the isolated genetic engineered human cell has reduced or decreased mRNA or protein expression of BCL11A compared to a control cell that has no one genetic modification on chromosome 2 location 60,716,189-60,728,612.

In one embodiment, this disclosure provides a method for producing an isolated genetic engineered human cell having at least one genetic modification comprising contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), and/or at location 60722238 to 60722466 (+58 functional region), and/or at location 60718042 to 60718186 (+62 functional region), causing at least one genetic modification therein, wherein the human chromosome 2 is that according to UCSC Genome Browser hg 19 human genome assembly.

In one embodiment, this disclosure provides a method for producing a progenitor cell having decreased BCL11A mRNA or protein expression, the method comprising contacting an isolated progenitor cell with a nucleic acid molecule described herein or a vector described herein.

In one embodiment, this disclosure provides a method for producing a progenitor cell having decreased BCL11A mRNA or BCL11A protein expression, the method comprising contacting an isolated progenitor cell with an agent that binds the human BCL11A enhancer functional regions located on chromosome 2 at location 60725424 to 60725688 (+55 functional region), and/or at location 60722238 to 60722466 (+58 functional region), and/or at location 60718042 to 60718186 (+62 functional region), where the agent binds to (a) the plus or minus strand of the human chromosome 2 at location 60725424 to 60725688 (+55 functional region); (b) the plus or minus strand of the human chromosome 2 at location 60722238 to 60722466 (+58 functional region); or (c) the plus or minus strand of the human chromosome 2 at location 60718042 to 60718186 (+62 functional region); wherein the human chromosome 2 is that according to UCSC Genome Browser hg 19 human genome assembly, thereby reducing the mRNA or protein expression of BCL11A.

In one embodiment, this disclosure provides a method for increasing fetal hemoglobin levels in a mammal in need thereof, the method comprising the steps of contacting an isolated hematopoietic progenitor cell in said mammal with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region), causing at least one genetic modification therein, whereby fetal hemoglobin expression is increased in said mammal, relative to expression prior to said contacting, and wherein the human chromosome 2 is that according to UCSC Genome Browser hg 19 human genome assembly.

In one embodiment, this disclosure provides a method for increasing fetal hemoglobin levels in a mammal in need thereof, the method comprising transplanting an isolated genetic engineered human cell described herein or a composition described herein into the mammal.

Another aspect described herein relates to a use of an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein for the purpose of increasing the fetal hemoglobin levels in a mammal.

Another aspect described herein relates to a use of an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein for the treatment a hemoglobinopathy in a mammal.

Another aspect described herein relates to a use of an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein for the manufacturer of medicament for the treatment a hemoglobinopathy in a mammal whereby the fetal hemoglobin levels in a mammal is increased.

Another aspect described herein is a composition comprising isolated genetic engineered human cells having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein. In one embodiment, the composition further comprises a pharmaceutically acceptable carrier.

Another aspect described herein relates to a use of a composition comprising isolated genetic engineered human cells having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein for the purpose of increasing the fetal hemoglobin levels in a mammal.

Another aspect described herein relates to a use of a composition comprising isolated genetic engineered human cells having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein for the treatment a hemoglobinopathy in a mammal.

Another aspect described herein relates to a use of a composition comprising isolated genetic engineered human cells having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein for the manufacturer of medicament for the treatment a hemoglobinopathy in a mammal whereby the fetal hemoglobin levels in a mammal is increased.

Another aspect described herein is a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein. In one embodiment, the composition further comprises a pharmaceutically acceptable carrier.

Another aspect described herein relates to a use of a composition a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein for the purpose of increasing the fetal hemoglobin levels in a mammal.

Another aspect described herein relates to a use of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein for the treatment a hemoglobinopathy in a mammal.

Another aspect described herein relates to a use of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein for the manufacturer of medicament for the treatment a hemoglobinopathy in a mammal whereby the fetal hemoglobin levels in a mammal is increased.

In one embodiment, provided herein is a use of a nucleic acid molecule comprising a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612, for increasing the fetal hemoglobin in a mammal or for the treatment of a hemoglobinopathy in the mammal or for reducing the mRNA or expression of BCL11A, wherein the mRNA or protein expression of BCL11A is reduced.

In one embodiment, provided herein is a use of an effective amount of a composition comprising a nucleic acid molecule described herein or a vector described herein, together with at least a DNA-targeting endonuclease or a vector carrying the coding sequence of a DNA-targeting endonuclease for increasing the fetal hemoglobin in a mammal or for the treatment of a hemoglobinopathy in the mammal or for reducing the mRNA or expression of BCL11A, whereby the DNA-targeting endonuclease cleaves the genomic DNA of a human cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein.

In one embodiment, provided herein is a use of an effective amount of a composition comprising a nucleic acid molecule described herein or a vector described herein, together with at least a DNA-targeting enzyme or a vector carrying the coding sequence of a DNA-targeting enzyme for increasing the fetal hemoglobin in a mammal or for the treatment of a hemoglobinopathy in the mammal or for reducing the mRNA or expression of BCL11A, wherein the DNA-targeting enzyme produces at least one epigenetic modification in the genomic DNA of a human cell on chromosome 2, thereby affecting the mRNA or expression of BCL11A. In one embodiment, the at least one epigenetic modification is at location 60725424 to 60725688 (+55 functional region), and/or at location 60722238 to 60722466 (+58 functional region), and/or at location 60718042 to 60718186 (+62 functional region). In another embodiment, the effect of the one epigenetic modification is reducing the mRNA or protein expression of BCL11A. In one embodiment, the at least one epigenetic modification in the genomic DNA of the cell on chromosome 2 indirectly or directly affects the location 60725424 to 60725688 (+55 functional region), at location 60722238 to 60722466 (+58 functional region), and/or at location 60718042 to 60718186 (+62 functional region) of chromosome 2.

In one embodiment, provided herein is a use of any isolated cells described herein for increasing the fetal hemoglobin in a mammal or for the treatment of a hemoglobinopathy in the mammal.

In one embodiment, provided herein is a use of a composition comprising isolated genetic engineered human cells for increasing the fetal hemoglobin in a mammal or for the treatment of a hemoglobinopathy in the mammal, wherein the cells have at least one genetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) made by the process of contacting the cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) causing at least one genetic modification therein.

In one embodiment, provided herein is a use of a composition comprising isolated genetic engineered human cells for increasing the fetal hemoglobin in a mammal or for the treatment of a hemoglobinopathy in the mammal, wherein the cells have at least one epigenetic modification on chromosome 2. In one embodiment, the at least one epigenetic modification on chromosome 2 is at location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly). In another embodiment, at least one epigenetic modification on chromosome 2 is made by the process of contacting the cells with an effective amount of a composition comprising a nucleic acid molecule described herein or a vector described herein, together with at least a DNA-targeting enzyme or a vector carrying the coding sequence of a DNA-targeting enzyme whereby the DNA-targeting enzyme produces at least one epigenetic modification in the genomic DNA of the cell on chromosome 2 which affects the location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) causing therein.

In one embodiment, provided herein is a use of any isolated cells described herein or any one of the compositions described herein for the manufacture of a medicament for increasing the fetal hemoglobin in a mammal in need thereof or for the treatment of a hemoglobinopathy in a mammal.

Another aspect described herein is a method of increasing fetal hemoglobin levels in a cell, the method comprising the steps of: contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in said cell, or its progeny, relative to the cell prior to the contacting.

Another aspect described herein is a method for increasing fetal hemoglobin levels in a mammal in need thereof, the method comprising the steps of contacting an isolated hematopoietic progenitor cell in said mammal with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in said mammal, relative to expression prior to said contacting.

Another aspect described herein is a method for increasing fetal hemoglobin levels in a mammal in need thereof, the method comprising transplanting an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) into the mammal.

In one embodiment, this disclosure provides a method for increasing fetal hemoglobin levels in a mammal in need thereof, the method comprising the steps of providing an isolated population of hematopoietic progenitor cells or hematopoietic stem cells from the mammal in ex vivo, and contacting the population of hematopoietic progenitor or stem cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of isolating a population of hematopoietic progenitor cells or hematopoietic stem cells from the mammal, and contacting in ex vivo the population of hematopoietic progenitor or stem cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of (a) providing isolating a population of hematopoietic progenitor cells or hematopoietic stem cells from the mammal and (b) deleting/adding/substituting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of isolating a population of hematopoietic progenitor cells or hematopoietic stem cells from the mammal and ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method of treatment of a hemoglobinopathy in a mammal comprising the steps of: (a) providing hematopoietic progenitor cells or hematopoietic stem cells or iPSCs; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal comprising the steps of: (a) isolating hematopoietic progenitor cells or hematopoietic stem cells from the mammal; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal comprising the steps of: (a) providing hematopoietic progenitor cells or hematopoietic stem cells or iPSCs; (b) ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal comprising the steps of: (a) isolating hematopoietic progenitor cells or hematopoietic stem cells from the mammal; (b) ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal (e.g. a human) comprising introducing a composition described herein comprising isolated genetic engineered cells having at least one genetic modification on chromosome 2 location 60725424 to 60725688 (+55 functional region), and/or at location 60722238 to 60722466 (+58 functional region), and/or at location 60718042 to 60718186 (+62 functional region) whereby fetal hemoglobin expression is increased in the mammal.

In one embodiment, this disclosure provides a method of treatment of a hemoglobinopathy in a mammal (e.g. a human) comprising increasing fetal hemoglobin expression in the mammal by method described herein.

In one embodiment, this disclosure provides a composition comprising isolated genetic engineered human cells described herein.

In one embodiment of this aspect and all other aspects described herein, the nucleic acid sequence is excludes the entire BCL11A enhancer functional regions.

In one embodiment of this aspect and all other aspects described herein, the nucleic acid sequence is excludes the entire SEQ. ID. NOS: 136, 137, and/or 138 identified in Table 8.

In one embodiment of this aspect and all other aspects described herein, the nucleic acid sequence is short and is greater than or equal to 13 base pair (bp). In other embodiments, the nucleic acid sequence is short and is greater than or equal to 15 bp, is greater than or equal to 16 bp, is greater than or equal to 17 bp, is greater than or equal to 18 bp, is greater than or equal to 19 bp, is greater than or equal to 20 bp, is greater than or equal to 21 bp, is greater than or equal to 22 bp, is greater than or equal to 23 bp, is greater than or equal to 24 bp, is greater than or equal to 25 bp, is greater than or equal to 26 bp, is greater than or equal to 27 bp, or is greater than or equal to 28 bp.

In one embodiment of this aspect and all other aspects described herein, the nucleic acid sequence is about 13-30 bp. In other embodiments, the nucleic acid sequence is about 13-20 bp, 13-21 bp, 13-22 bp, 13-23 bp, 13-24 bp, 13-25 bp, 13-26 bp, 13-27 bp, 13-28 bp, 13-29 bp, 14-20 bp, 14-21 bp, 14-22 bp, 14-23 bp, 14-24 bp, 14-25 bp, 14-26 bp, 14-27 bp, 14-28 bp, 14-29 bp, 15-20 bp, 15-21 bp, 15-22 bp, 15-23 bp, 15-24 bp, 15-25 bp, 15-26 bp, 15-27 bp, 15-28 bp, 15-29 bp, 16-20 bp, 16-21 bp, 16-22 bp, 16-23 bp, 16-24 bp, 16-25 bp, 16-26 bp, 16-27 bp, 16-28 bp, 16-29 bp, 17-20 bp, 17-21 bp, 17-22 bp, 17-23 bp, 17-24 bp, 17-25 bp, 17-26 bp, 17-27 bp, 17-28 bp, 17-29 bp, 18-20 bp, 18-21 bp, 18-22 bp, 18-23 bp, 18-24 bp, 18-25 bp, 18-26 bp, 18-27 bp, 18-28 bp, 18-29 bp, 19-21 bp, 19-22 bp, 19-23 bp, 19-24 bp, 19-25 bp, 19-26 bp, 19-27 bp, 19-28 bp, 19-29 bp, 20-22 bp, 20-23 bp, 20-24 bp, 20-25 bp, 20-26 bp, 20-27 bp, 20-28 bp, 20-29 bp, 21-23 bp, 21-24 bp, 21-25 bp, 21-26 bp, 21-27 bp, 21-28 bp, 21-29 bp, 22-24 bp, 22-25 bp, 22-26 bp, 22-27 bp, 22-28 bp, 22-29 bp, 23-25 bp, 23-26 bp, 23-27 bp, 23-28 bp, 23-29 bp, 24-26 bp, 24-27 bp, 24-28 bp, 24-29 bp, 25-27 bp, 25-28 bp, 25-29 bp, 26-28 bp, 26-29 bp, 27-29 bp, 14-30 bp, 15-30 bp, 16-30 bp, 17-30 bp, 18-30 bp, 19-30 bp, 20-30 bp, 21-30 bp, 22-30 bp, 23-30 bp, 24-30 bp, 25-30 bp, 26-30 bp, 27-30 bp, or 28-30 bp.

In one embodiment of this aspect and all other aspects described herein, the nucleic acid sequence is about 20 bp. In other embodiments, the nucleic acid sequence is about 13 bp, is about 14 bp, is about 15 bp, is about 16 bp, is about 17 bp, is about 18 bp, is about 19 bp, is about 20 bp, is about 21 bp, is about 22 bp, is about 23 bp, is about 24 bp, is about 25 bp, is about 26 bp, is about 27 bp, is about 28 bp, is about 29 bp, or is about 30 bp.

In one embodiment of this aspect and all other aspects described herein, the nucleic acid sequence comprises a sequence selected from the group consisting of SEQ ID NOS: 1-94.

In one embodiment of this aspect and all other aspects described herein, the nucleic acid sequence consists essentially of a sequence selected from the group consisting of SEQ ID NOS: 1-94.

In one embodiment of this aspect and all other aspects described herein, the nucleic acid sequence is a sequence selected from the group consisting of SEQ ID NOS: 1-94.

In one embodiment of this aspect and all other aspects described herein, the nucleic acid sequence consists of a sequence selected from the group consisting of SEQ ID NOS: 1-94.

In one embodiment of this aspect and all other aspects described herein, the nucleic acid sequence further comprising a trans-activating CRISPR RNA (tracrRNA) sequence.

In one embodiment of this aspect and all other aspects described herein, the nucleic acid molecule is a single guide RNA (sgRNA).

In one embodiment of this aspect and all other aspects described herein, the nucleic acid molecule comprises a vector.

In one embodiment of this aspect and all other aspects described herein, the vector is a viral vector, such as a lentiviral vector.

In one embodiment of this aspect and all other aspects described herein, the vector is a sgRNA expression vector.

In one embodiment of this aspect and all other aspects described herein, the method further comprising contacting the same isolated progenitor cell with at least a DNA-targeting endonuclease or a vector carrying the coding sequence of a DNA-targeting endonuclease.

In one embodiment of this aspect and all other aspects described herein, the at least a DNA-targeting endonuclease is a Cas (CRISPR-associated) protein.

In one embodiment of this aspect and all other aspects described herein, the Cas protein is Cas9.

In one embodiment of this aspect and all other aspects described herein, the isolated progenitor cell or isolated cell is a hematopoietic progenitor cell or a hematopoietic stem cell.

In one embodiment of this aspect and all other aspects described herein, the hematopoietic progenitor is a cell of the erythroid lineage.

In one embodiment of this aspect and all other aspects described herein, the isolated progenitor cell or isolated cell is an induced pluripotent stem cell.

In one embodiment of this aspect and all other aspects described herein, the isolated progenitor cell or isolated cell is contacted ex vivo or in vitro.

In one embodiment of this aspect and all other aspects described herein, the contacted progenitor cell or contacted cell acquires at least one genetic modification.

In one embodiment of this aspect and all other aspects described herein, the at least one genetic modification is a deletion, insertion or substitution of the nucleic acid sequence.

In one embodiment of this aspect and all other aspects described herein, the least one genetic modification is located between chromosome 2 location 60725424 to 60725688 (+55 functional region), at location 60722238 to 60722466 (+58 functional region), and/or at location 60718042 to 60718186 (+62 functional region).

In one embodiment of this aspect and all other aspects described herein, the contacted progenitor cell or contacted cell acquires at least one epigenetic modification in the BCL11A enhancer functional region.

In one embodiment of this aspect and all other aspects described herein, the at least one epigenetic modification is selected from the group consisting of alteration of DNA methylation, histone tail modification, histone subunit composition and nucleosome positioning.

In one embodiment of this aspect and all other aspects described herein, the at least one epigenetic modification is located between chromosome 2 location 60725424 to 60725688 (+55 functional region), at location 60722238 to 60722466 (+58 functional region), and/or at location 60718042 to 60718186 (+62 functional region).

In one embodiment of this aspect and all other aspects described herein, the isolated cell or isolated population of cells is/are human cell(s).

In one embodiment of this aspect and all other aspects described herein, the isolated cell or isolated population of cells is/are progenitor cell(s).

In one embodiment of this aspect and all other aspects described herein, the human cell is a hematopoietic progenitor cell.

In one embodiment of this aspect and all other aspects described herein, the human cell is an induced pluripotent stem cell.

In one embodiment of this aspect and all other aspects described herein, the induced pluripotent stem cell is hematopoietic progenitor cell.

In one embodiment of this aspect and all other aspects described herein, the hematopoietic progenitor is a cell of the erythroid lineage.

In one embodiment of this aspect and all other aspects described herein, the hematopoietic progenitor cell or isolated is contacted ex vivo or in vitro or in vivo.

In one embodiment of this aspect and all other aspects described herein, the at least one genetic modification is a deletion.

In another embodiment of this aspect and all other aspects described herein, the nucleic acid molecule consists essentially of one or more of the sequences described in Table 7 or SEQ ID NOS: 1-94.

In further embodiment of any treatment method, the method comprises chemotherapy and/or radiation therapy to remove or reduced the endogenous hematopoietic progenitor or stem cells in the mammal.

In one embodiment of any method, the contacted cells having at least one genetic modification can be cryopreserved and stored until the cells are needed for administration into a mammal.

In one embodiment of any described method, the hematopoietic progenitor or stem cells or isolated cells can be substituted with an iPSCs described herein.

In one embodiment of any described method, the hematopoietic progenitor or stem cells or iPSCs or isolated cells are autologous to the mammal, meaning the cells are derived from the same mammal. In another of the embodiments of the described method, the hematopoietic progenitor or stem cells or iPSCs or isolated cells are non-autologous to the mammal, meaning the cells are not derived from the same mammal, but another mammal of the same species. For example, the mammal is a human.

In one embodiment of any treatment method, the method further comprises selecting a mammal in need of increased fetal hemoglobin expression.

In one embodiment of any treatment method, the method further comprises selecting a mammal in need of treatment of a hemoglobinopathy.

In any embodiment of any treatment method described, the hemoglobinopathy is α-hemoglobinopathy.

In any embodiment of any treatment method described, the hemoglobinopathy is β-thalassemia.

In any embodiment of any treatment method described, the hemoglobinopathy is sickle cell anemia.

BRIEF DESCRIPTION OF DRAWINGS

FIGS. 1A-1E show the human erythroid enhancer requirement for BCL11A expression and HbF repression.

FIG. 1A shows a schematic representation of the human BCL11A locus (transcription from right to left) with erythroid chromatin marks and trait-associated haplotype denoted.

FIG. 1B shows the ranked enhancers in primary human adult erythroid precursors by H3K27ac signal intensity, with super-enhancers shaded.

FIGS. 1C-1E show that the deletion of the human composite BCL11A enhancer in HUDEP-2 cells demonstrates the necessity of the enhancer for BCL11A expression normalize to GAPDH, repression of γ-globin mRNA, and repression of HbF. Error bars reflect standard error of the mean (SEM).

FIGS. 2A-2H show the representative data from a tiled pooled in situ CRISPR-Cas9 BCL11A enhancer screen.

FIG. 2A is a schematic diagram of the workflow of CRISPR-Cas9 enhancer screen showing library synthesis, delivery, and analysis.

FIG. 2B shows the sgRNA library composition by target sequences and PAM restriction.

FIG. 2C shows the distribution of NGG PAM sgRNAs mapped to genomic cleavage position.

FIG. 2D shows the distance to adjacent genomic cleavage position for NGG PAM sgRNAs.

FIG. 2E shows the HbF sorting of library transduced cells.

FIG. 2F shows the effect of the control sgRNAs on HbF enrichment. Boxes demonstrate 25th, median, and 75th percentiles and whiskers minimum and maximum values. **** P<0.0001, ns non-significant.

FIG. 2G shows the sgRNA representation in plasmid pool and cells at the conclusion of experiment (left), and in HbF-high and HbF-low pools (right), with dotted lines at x=y and x=8y.

FIG. 2H shows the quantile-quantile plots of sgRNA enrichment scores.

FIGS. 3A-3I show the functional mapping of the human BCL11A enhancer.

FIG. 3A shows the mapping sgRNA enrichment scores relative to genomic cleavage positions. Non-targeting sgRNAs pseudo-mapped with 5 bp spacing.

FIG. 3B shows the correlation between dropout and enrichment scores.

FIGS. 3C-3E shows that BCL11A expression normalized to GAPDH, β-like globin expression, and HbF+ fraction in HUDEP-2 cells with deletion or inversion of individual DHSs.

FIG. 3F shows the correlation between HbF enrichment score from pooled sgRNA screen and HbF+ fraction by arrayed validation of individual sgRNAs in HUDEP-2 cells.

FIG. 3G-3I shows the BCL11A expression normalized to GAPDH, β-like globin expression, and HbF+ fraction in HUDEP-2 cells from primary human erythroid precursors transduced with Cas9 and individual sgRNAs. Error bars represent SEM. A filtered of the human library targeting sgRNA enrichment score for enrichment of >0.259 and for NGG RC & NGG sgRNA gave the 135 targeting sequences shown in Table 7. These are the sgRNA targeting the +62, +58, and +55 functional regions in the BCL11A enhancer as well as a set of sgRNA that target the exon 2 of BCL11A.

FIGS. 5A-5F show the functional sequence requirement at the mouse BCL11A erythroid enhancer for in vivo hemoglobin switching.

FIG. 5A shows the mapping sgRNA εy:mCherry enrichment scores to genomic cleavage positions. Non-targeting sgRNAs pseudo-mapped with 5 bp spacing.

FIG. 5B shows the BCL11A expression in mouse erythroid clones with deletion or inversion of individual DHSs normalized to controls set as 1.

FIG. 5C shows the HMM segmentation of active functional states at +62 ortholog. Enrichment scores shown as gray lines and circles; curve graph therein is the smoothed enrichment score. DNase I sequencing from mouse fetal liver erythroid precursors[42]. BCL11A expression determined by RT-qPCR displayed as a heat-map in 108 hemizygous+62 ortholog deletion clones listed from top to bottom by genomic position of deletion midpoint. PhyloP (scale from −3.3 to 2.1) and PhastCons (from 0 to 1) estimates of evolutionary conservation among 30 vertebrates.

FIG. 5D shows the transgenic human globin expression in mouse E16.5 chimeric β-YAC/+62 deleted fetal livers.

FIGS. 5E-5F show the BCL11A expression, B cell number, and transgenic human n-like globin expression in β-YAC/+62 deleted mice. * P<0.05 Error bars represent SEM.

FIGS. 6A-6F collectively show the representative data from a tiled pooled in situ CRISPR-Cas9 BCL11A enhancer screen. Distribution of NAG PAM sgRNAs mapped to genomic cleavage position. The vertical lines represent sgRNA cleavage sites for sgRNAs mapped to plus and minus strands. Distance to adjacent genomic cleavage position for NAG PAM sgRNAs. Deep sequencing the lentiviral plasmid library demonstrated that 1,337 of 1,338 sgRNAs (99.9%) were successfully cloned. The representation of sgRNAs within the library showed a relatively narrow distribution, with a median of 718 and the 10% and 90% percentiles ranging from 337 to 1,205 normalized reads as indicated by the vertical dotted lines. HbF distribution in HUDEP-2 cells transduced with Cas9 and individual sgRNAs, either non-targeting or targeting BCL11A exon 2. Enrichment scores of NGG sgRNAs between six biological replicates. Mapping sgRNA dropout scores of NGG sgRNAs relative to genomic cleavage positions and repetitive elements. Non-targeting sgRNAs pseudo-mapped with 5 bp spacing.

FIGS. 7A-7B show the validation of the select sgRNAs identified in the described enhancer screen.

FIG. 7A shows the HbF+ fraction in HUDEP-2 cells transduced in arrayed format with 24 sgRNAs from all 5 mapping categories with enrichment scores ranging from the highest to the lowest in the screen.

FIG. 7B shows the β-like globin gene expression normalized to reference gene (GAPDH) in primary human erythroid precursors transduced with Cas9 and individual sgRNAs. Erythroid differentiation of primary human erythroid precursors evaluated by CD71 and CD235a surface markers, enucleation frequency (CD235a+ Hoescht33342−), and morphology by May-Grünwald-Giemsa staining.

FIGS. 8A-8B show the functional assessment of enhancer sequences.

FIG. 8A shows the topology of the Hidden Markov model (HMM) used to infer the three functional enhancer states (Active, Repressive, and Neutral) and based on Gaussian emission of sgRNA enrichment scores. All possible transitions between states are allowed.

FIG. 8B shows the frequency distribution of indels from HUDEP-2 cells exposed to Cas9 and individual sgRNAs, sorted into HbF-high and -low pools, and subjected to deep sequencing of the target site. Indels calculated on a per nucleotide basis throughout an amplicon surrounding the sgRNA-1617 and −1621 cleavage sites (dotted lines). An indel enrichment ratio was calculated by dividing normalized indel frequencies in high-HbF by low-HbF pool.

FIGS. 9A-9K show the representative data from a tiled pooled in situ CRISPR-Cas9 BCL11A enhancer screen.

FIG. 9A shows a schematic representation of the mouse BCL11A locus (transcription from left to right) with erythroid chromatin marks and regions of primary sequence homology to the human DHSs displayed.

FIG. 9B shows the ranked enhancers in mouse fetal liver erythroid precursors by H3K27ac signal intensity, with super-enhancers shaded.

FIG. 9C shows the mCherry expression upon exposure to Cas9 and an individual sgRNA targeting Bcl11a exon 2 in MEL εy:mCherry reporter cells.

FIG. 9D shows a representative strategy to knock-in by homology-directed repair the fluorescent protein mCherry into the mouse embryonic globin Hbb-y locus (encoding the εy embryonic globin chain).

FIG. 9E shows the sgRNA library composition by target sequence and PAM restriction.

FIG. 9F-9G show the distribution of NGG (upper left) and NAG (upper right) PAM sgRNAs mapped to genomic cleavage position. The vertical lines represent sgRNA cleavage sites for sgRNAs mapped to plus and minus strands. Distance to adjacent genomic cleavage position for NGG (lower left) and NAG (lower right) PAM sgRNAs.

FIG. 9I shows that deep sequencing the lentiviral plasmid library demonstrated that 1,271 of 1,271 sgRNAs (100%) were successfully cloned. The representation of sgRNAs within the library showed a relatively narrow distribution, with a median of 735 and the 10% and 90% percentiles ranging from 393 to 1,240 normalized reads as indicated by the vertical dotted lines.

FIG. 9J shows the εy:mCherry sort of library transduced cells.

FIG. 9K shows the control sgRNA enrichment. Boxes demonstrate 25th, median, and 75th percentiles and whiskers minimum and maximum values. **** P<0.0001.

FIGS. 10A-10D show the BCL11A enhancer screen analyses.

FIG. 10A shows the sgRNA representation in plasmid pool and cells at conclusion of experiment (left), and in εy:mCherry-high and εy:mCherry-low pools (right), with dotted lines at x=y and x=8y.

FIG. 10B shows the quantile-quantile plots of sgRNA enrichment scores.

FIG. 10C shows the mapping sgRNA dropout scores of NGG sgRNAs relative to genomic cleavage positions and repetitive elements. Non-targeting sgRNAs pseudo-mapped with 5 bp spacing.

FIG. 10D shows the correlation between dropout and enrichment scores.

FIGS. 11A-11D show the Requirement of BCL11A erythroid enhancer during murine ontogeny.

FIG. 11A shows the BCL11A expression determined by RT-qPCR in 108 hemizygous+62 ortholog deletion clones. Per nucleotide mean effect size was calculated as the mean fold change BCL11A expression of all clones in which that nucleotide was deleted. Gray shading represents one standard deviation.

FIG. 11B shows the schema for analysis of transgenic human β-like globin (β-YAC) gene expression during development in chimeric fetal liver. Right panel shows data from control β-YAC chimeric fetal liver demonstrating that γ-globin repression occurs by E16.5.

FIG. 11C shows the progeny of heterozygous BCL11A +62 ortholog deletion intercrosses as compared to expected Mendelian ratio.

FIG. 11D shows the BCL11A expression relative to GAPDH in mouse E16.5 brain from various genotypes. Fraction of fetal liver comprised of B cell progenitors at E16.5 from various genotypes. Peripheral blood analysis from 4 week old mice to examine the frequency of various circulating hematopoietic lineages in BCL11A +62 ortholog deletion wild-type, heterozygous, and homozygous mice.

BRIEF LISTING OF TABLES

Figure 2F:
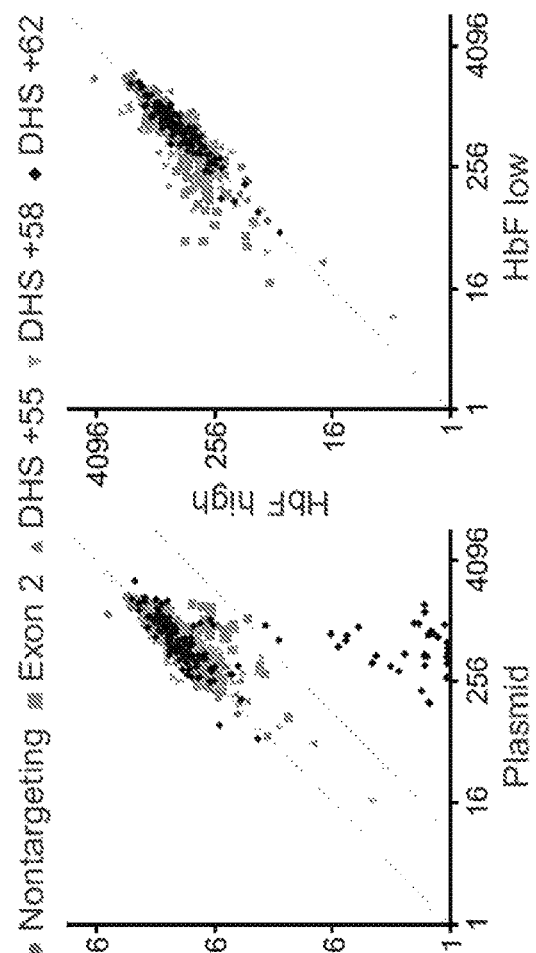

Table 1. sgRNA Sequences.
Table 2. Oligonucleotide primers for Deletion Clone Screening.
Table 3. Oligonucleotide primers for Inversion Clone Screening.
Table 4. Oligonucleotide primers for Mouse +62 Deletion Analysis.
Table 5. RT qPCR Oligonucleotides.
Table 6. Location of BCL11A enhancer region for targeting to achieve BCL11A knockdown.
Table 7. sgRNA sequences that produced HFb enrichment over 0259.
Table 8. Sequences of the BCL11A enhancer +62, +58, and +55 functional regions.
Table 9: NGA restricted sgRNA sequences that produced HbF enrichment over 0.259.

DETAILED DESCRIPTION

The methods and compositions described herein relate, in part, to the discovery of more defined functional regions within the BCL11A ~12 kb enhancer region that regulate expression of the BCL11A protein. The functional regions are location 60725424 to 60725688 (+55 functional region), location 60722238 to 60722466 (+58 functional region), and location 60718042 to 60718186 (+62 functional region) on the human chromosome 2 according to UCSC Genome Browser hg 19 human genome assembly. The BCL11A protein acts as a stage specific regulator of fetal hemoglobin expression by repressing γ-globin induction.

Genome editing disruption at these regions were functionally verified for expression of the BCL11A mRNA, expression of the BCL11A protein, and ultimately for the enrichment of fetal hemoglobin (HbF) produced. Small single guide RNA (sgRNA) sequences were design to target these functional regions using the CRISPR/Cas9 technology to reduced BCL11A expression and increase HbF expression. The sgRNA sequences showing disruptions that are at least a greater than or equal normalized HbF enrichment of 0.259 are shown in Table 7 and are identified as SEQ ID NOS: 1-94.

In particular, targeting and disrupting the +58 functional region produced super HbF enrichment whereas targeting and disrupting the +55 or +62 functional regions produced moderate HbF enrichments. Therefore, targeting these three +62, +58, and +55 functional regions, alone or in combination, using specifically designed sgRNA and CRISPR technology, can provide therapeutic strategies that interfere with adult hemoglobin and induce fetal hemoglobin synthesis.

Provided herein are nucleic acid molecules that target the three BCL11A enhancer functional regions, these three +62, +58, and +55, compositions comprising the nucleic acid molecules, and methods for increasing fetal hemoglobin levels in a cell by disrupting BCL11A expression at the genomic level. Also provided herein are methods and compositions relating to the treatment of hemoglobinopathies by reinduction of fetal hemoglobin levels. In particular, the nucleic acid molecules target the +62, +58, and/or the +55 enhancer functional regions.

Accordingly, the methods and compositions provided herein are novel methods for the regulation of γ-globin expression in eythroid cells. More specifically, these activities can be harnessed in methods for the treatment of β-hemoglobinopathies by induction of γ-globin via inhibition of the BCL11A gene product.

The disclosure described herein, in one embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Accordingly, in one embodiment, provided herein is a nucleic acid molecule comprising a nucleic acid sequence that is (a) complementary to the plus or minus strand of the human chromosome 2 at location 60725424 to 60725688 (+55 functional region); (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612.

Additionally, small single guide RNA (sgRNA) sequences were design to target BCL11A coding exon 2 using the CRISPR/Cas9 technology also showed effective disruption of BCL11A expression. The sgRNA sequences showing disruptions that are at least a greater than or equal normalized HbF enrichment of 0.259 are shown in Table 7 and are identified as SEQ ID NOS: 95-135.

In one embodiment, provided herein is a nucleic acid molecule comprising a nucleic acid sequence that is complementary to the plus or minus strand of the human BCL11A exon 2, wherein the nucleic acid sequence excludes the entire human BCL11A exon 2 sequence. In one embodiment, the nucleic acid sequence comprises SEQ ID NOS: 94-135.

In one embodiment, provided herein is a nucleic acid molecule consisting essentially of a nucleic acid sequence that is complementary to the plus or minus strand of the human BCL11A exon 2, wherein the nucleic acid sequence excludes the entire human BCL11A exon 2 sequence. In one embodiment, the nucleic acid sequence consisting essentially SEQ ID NOS: 94-135.

In one embodiment, provided herein is a nucleic acid molecule consisting of a nucleic acid sequence that is complementary to the plus or minus strand of the human BCL11A exon 2, wherein the nucleic acid sequence excludes the entire human BCL11A exon 2 sequence. In one embodiment, the nucleic acid sequence consists of SEQ ID NOS: 94-135.

In one embodiment, provided herein is a nucleic acid molecule consisting essentially of a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612.

In one embodiment, this disclosure provides a vector comprising a nucleic acid sequence which is: (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60,716,189 to 60,728, 612.

In one embodiment, this disclosure provides a vector consisting essentially a nucleic acid sequence which is: (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60,716,189 to 60,728,612.

In one embodiment, this disclosure provides a vector comprising a nucleic acid sequence that is complementary to the plus or minus strand of the human BCL11A exon 2, wherein the nucleic acid sequence excludes the entire human BCL11A exon 2 sequence.

One aspect described herein relates to a method for producing an isolated genetic engineered human cell having at least one genetic modification comprising contacting the cell with an effective amount of a composition comprising a nucleic acid molecule described herein or a vector comprising the nucleic acid molecule described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) (according to UCSC Genome Browser hg 19 human genome assembly) causing at least one genetic modification therein.

Another aspect provided herein relates to a method of increasing fetal hemoglobin levels in an isolated cell, the method comprising decreasing the BCL11A mRNA or protein expression in the cell. In one aspect, the decrease of BCL11A mRNA or protein expression is achieved by causing at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly). In another aspect, the decrease of BCL11A mRNA or protein expression is achieved by causing at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) that results in an epigenetic modification of the genetic function at chromosome 2 location 60725424 to 60725688 (+55 functional region), at location 60722238 to 60722466 (+58 functional region), and/or at location 60718042 to 60718186 (+62 functional region). In this aspect, the BCL11A enhancer activity located within this chromosome 2 location 60725424 to 60725688 (+55 functional region), at location 60722238 to 60722466 (+58 functional region), and/or at location 60718042 to 60718186 (+62 functional region) is reduced.

By decrease in this aspect, the enhancer activity in enhancing BCL11A mRNA or protein expression in the cell is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein. By decrease of the BCL11A mRNA or protein expression in the cell means that protein expression is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein.

Another aspect provided herein relates to a method of increasing fetal hemoglobin levels in an isolated cell, the method comprising providing an isolated human cell or progenitor cell and decreasing the BCL11A mRNA or protein expression in the cell.

Another aspect provided herein relates to an ex vivo or in vitro method of increasing fetal hemoglobin levels in an isolated cell, the method comprising providing an isolated human cell or progenitor cell and decreasing the BCL11A mRNA or protein expression in the cell.

Another aspect provided herein relates to an ex vivo or in vitro method for producing a progenitor cell having decreased BCL11A mRNA or protein expression, the method comprising contacting an isolated progenitor cell with a nucleic acid molecule comprising or consisting essentially of a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612, thereby reducing the mRNA or protein expression of BCL11A.

Another aspect provided herein relates to an ex vivo or in vitro method for producing an isolated genetic engineered human cell having at least one genetic modification comprising contacting an isolated cell with an effective amount of a nucleic acid molecule comprising or consisting essentially of a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612, causing at least one genetic modification therein.

Another aspect provided herein relates to an ex vivo or in vitro method for producing a progenitor cell having decreased BCL11A mRNA or protein expression, the method comprising contacting an isolated progenitor cell with a vector comprising a nucleic acid molecule comprising or consisting essentially of a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612, thereby reducing the mRNA or protein expression of BCL11A.

Another aspect provided herein relates to an ex vivo or in vitro method for producing an isolated genetic engineered human cell having at least one genetic modification comprising contacting an isolated cell with an effective amount of a vector comprising a nucleic acid molecule comprising or consisting essentially of a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612, causing at least one genetic modification therein.

Another aspect provided herein relates to an ex vivo or in vitro method for producing an isolated genetic engineered human cell having at least one genetic modification comprising contacting an isolated cell with an effective amount of a composition comprising a nucleic acid described herein.

Another aspect provided herein relates to an ex vivo or in vitro method for producing an isolated genetic engineered human cell having at least one genetic modification comprising contacting an isolated cell with an effective amount of a composition comprising a vector described herein.

In some embodiments of any of the ex vivo or in vitro methods described herein, the isolated progenitor cell or isolated cell is a hematopoietic progenitor cell.

In some embodiments of any of the ex vivo or in vitro methods described herein, the hematopoietic progenitor is a cell of the erythroid lineage.

In some embodiments of any of the ex vivo or in vitro methods described herein, wherein the isolated progenitor cell or isolated cell is an induced pluripotent stem cell.

Another aspect described herein relates to a method for increasing fetal hemoglobin levels in a mammal in need thereof, the method comprising decreasing the BCL11A mRNA or protein expression in a hematopoietic progenitor cell in the mammal. In one aspect, the decrease of BCL11A mRNA or protein expression is achieved by causing at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly). In another aspect, the decrease of BCL11A mRNA or protein expression is achieved by causing at least one epigenetic modification at the genomic DNA of the cell on chromosome 2. In another aspect, the decrease of BCL11A mRNA or protein expression is achieved by causing at least one epigenetic modification at the genomic DNA of the cell on chromosome 2 location 60725424 to 60725688 (+55 functional region), at location 60722238 to 60722466 (+58 functional region), and/or at location 60718042 to 60718186 (+62 functional region).

Another aspect provided herein relates to a method for increasing fetal hemoglobin levels in a mammal in need thereof, the method comprising transplanting a genetic engineered human cell as described herein into the mammal.

In one embodiment, provided herein is a nucleic acid molecule comprising a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612.

In one embodiment, provided herein is a nucleic acid molecule consisting essentially of a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612.

In one embodiment, this disclosure provides a vector comprising a nucleic acid sequence which is: (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60,716,189 to 60,728,612.

In one embodiment, this disclosure provides a vector consisting essentially a nucleic acid sequence which is: (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60,716,189 to 60,728,612.

In one embodiment, this disclosure provides a method of increasing fetal hemoglobin levels in a cell, the method comprising the steps of: contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), and/or at location 60722238 to 60722466 (+58 functional region), and/or at location 60718042 to 60718186 (+62 functional region), causing at least one genetic modification therein, whereby fetal hemoglobin expression is increased in said cell, or its progeny, relative to said cell prior to said contacting, and wherein the human chromosome 2 is that according to UCSC Genome Browser hg 19 human genome assembly.

In one embodiment, this disclosure provides an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein. In one embodiment, the isolated genetic engineered human cell has reduced or decreased mRNA or protein expression of BCL11A compared to a control cell that has no one genetic modification on chromosome 2 location 60,716,189-60,728,612.

In one embodiment, this disclosure provides a method for producing an isolated genetic engineered human cell having at least one genetic modification comprising contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), and/or at location 60722238 to 60722466 (+58 functional region), and/or at location 60718042 to 60718186 (+62 functional region), causing at least one genetic modification therein, wherein the human chromosome 2 is that according to UCSC Genome Browser hg 19 human genome assembly.

In one embodiment, this disclosure provides a method for producing a progenitor cell having decreased BCL11A mRNA or protein expression, the method comprising contacting an isolated progenitor cell with a nucleic acid molecule described herein or a vector described herein.

In one embodiment, this disclosure provides a method for producing a progenitor cell having decreased BCL11A mRNA or BCL11A protein expression, the method comprising contacting an isolated progenitor cell with an agent that binds the human BCL11A enhancer functional regions located on chromosome 2 at location 60725424 to 60725688 (+55 functional region), and/or at location 60722238 to 60722466 (+58 functional region), and/or at location 60718042 to 60718186 (+62 functional region), where the agent binds to (a) the plus or minus strand of the human chromosome 2 at location 60725424 to 60725688 (+55 functional region); (b) the plus or minus strand of the human chromosome 2 at location 60722238 to 60722466 (+58 functional region); or (c) the plus or minus strand of the human chromosome 2 at location 60718042 to 60718186 (+62 functional region); wherein the human chromosome 2 is that according to UCSC Genome Browser hg 19 human genome assembly, thereby reducing the mRNA or protein expression of BCL11A.

In one embodiment, this disclosure provides a method for increasing fetal hemoglobin levels in a mammal in need thereof, the method comprising the steps of contacting an isolated hematopoietic progenitor cell in said mammal with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region), causing at least one genetic modification therein, whereby fetal hemoglobin expression is increased in said mammal, relative to expression prior to said contacting, and wherein the human chromosome 2 is that according to UCSC Genome Browser hg 19 human genome assembly.

In one embodiment, this disclosure provides a method for increasing fetal hemoglobin levels in a mammal in need thereof, the method comprising transplanting an isolated genetic engineered human cell described herein or a composition described herein into the mammal.

Another aspect described herein is a composition comprising isolated genetic engineered human cells having at least one genetic modification on chromosome 2 location 60725424 to 60725688 (+55 functional region), and/or at location 60722238 to 60722466 (+58 functional region), and/or at location 60718042 to 60718186 (+62 functional region) according to a method described herein. In one embodiment, the composition further comprises a pharmaceutically acceptable carrier.

Another aspect described herein is a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein. In one embodiment, the composition further comprises a pharmaceutically acceptable carrier.

Another aspect described herein is a method of increasing fetal hemoglobin levels in a cell, the method comprising the steps of: contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in said cell, or its progeny, relative to the cell prior to the contacting.

Another aspect described herein is a method for increasing fetal hemoglobin levels in a mammal in need thereof, the method comprising the steps of contacting an isolated hematopoietic progenitor cell in said mammal with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in said mammal, relative to expression prior to said contacting.

Another aspect described herein is a method for increasing fetal hemoglobin levels in a mammal in need thereof, the method comprising transplanting an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) into the mammal.

In one embodiment, this disclosure provides a method for increasing fetal hemoglobin levels in a mammal in need thereof, the method comprising the steps of providing an isolated population of hematopoietic progenitor cells or hematopoietic stem cells from the mammal in ex vivo, and contacting the population of hematopoietic progenitor or stem cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of isolating a population of hematopoietic progenitor cells or hematopoietic stem cells from the mammal, and contacting in ex vivo the population of hematopoietic progenitor or stem cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of (a) providing isolating a population of hematopoietic progenitor cells or hematopoietic stem cells from the mammal and (b) deleting/adding/substituting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of isolating a population of hematopoietic progenitor cells or hematopoietic stem cells from the mammal and ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method of treatment of a hemoglobinopathy in a mammal comprising the steps of: (a) providing hematopoietic progenitor cells or hematopoietic stem cells or iPSCs; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal comprising the steps of: (a) isolating hematopoietic progenitor cells or hematopoietic stem cells from the mammal; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cell of step (b) into the mammal.

In one embodiment, this disclosure provides a method of treatment of a hemoglobinopathy in a mammal comprising the steps of: (a) providing hematopoietic progenitor cells or hematopoietic stem cells or iPSCs; (b) ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal comprising the steps of: (a) isolating hematopoietic progenitor cells or hematopoietic stem cells from the mammal; (b) ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal (e.g. a human) comprising introducing a composition described herein comprising isolated genetic engineered cells having at least one genetic modification on chromosome 2 location 60725424 to 60725688 (+55 functional region), at location 60722238 to 60722466 (+58 functional region), and/or at location 60718042 to 60718186 (+62 functional region) whereby fetal hemoglobin expression is increased in the mammal.

In one embodiment, this disclosure provides a method of treatment of a hemoglobinopathy in a mammal (e.g. a human) comprising increasing fetal hemoglobin expression in the mammal by method described herein.

In one embodiment, this disclosure provides a composition comprising isolated genetic engineered human cells described herein.

In one embodiment of this aspect and all other aspects described herein, the method further comprises selecting a mammal in need of increasing fetal hemoglobin levels therein.

In one embodiment of this aspect and all other aspects described herein, the nucleic acid sequence is excludes the entire BCL11A enhancer functional regions.

In one embodiment of this aspect and all other aspects described herein, the nucleic acid sequence is excludes the entire SEQ. ID. NOS: 136, 137, and/or 138 identified in Table 8.

In one embodiment of this aspect and all other aspects described herein, the nucleic acid sequence is short and is greater than or equal to 13 base pair (bp). In other embodiments, the nucleic acid sequence is short and is greater than or equal to 15 bp, is greater than or equal to 16 bp, is greater than or equal to 17 bp, is greater than or equal to 18 bp, is greater than or equal to 19 bp, is greater than or equal to 20 bp, is greater than or equal to 21 bp, is greater than or equal to 22 bp, is greater than or equal to 23 bp, is greater than or equal to 24 bp, is greater than or equal to 25 bp, is greater than or equal to 26 bp, is greater than or equal to 27 bp, or is greater than or equal to 28 bp.

In one embodiment of this aspect and all other aspects described herein, the nucleic acid sequence is about 13-30 bp. In other embodiments, the nucleic acid sequence is about 13-20 bp, 13-21 bp, 13-22 bp, 13-23 bp, 13-24 bp, 13-25 bp, 13-26 bp, 13-27 bp, 13-28 bp, 13-29 bp, 14-20 bp, 14-21 bp, 14-22 bp, 14-23 bp, 14-24 bp, 14-25 bp, 14-26 bp, 14-27 bp, 14-28 bp, 14-29 bp, 15-20 bp, 15-21 bp, 15-22 bp, 15-23 bp, 15-24 bp, 15-25 bp, 15-26 bp, 15-27 bp, 15-28 bp, 15-29 bp, 16-20 bp, 16-21 bp, 16-22 bp, 16-23 bp, 16-24 bp, 16-25 bp, 16-26 bp, 16-27 bp, 16-28 bp, 16-29 bp, 17-20 bp, 17-21 bp, 17-22 bp, 17-23 bp, 17-24 bp, 17-25 bp, 17-26 bp, 17-27 bp, 17-28 bp, 17-29 bp, 18-20 bp, 18-21 bp, 18-22 bp, 18-23 bp, 18-24 bp, 18-25 bp, 18-26 bp, 18-27 bp, 18-28 bp, 18-29 bp, 19-21 bp, 19-22 bp, 19-23 bp, 19-24 bp, 19-25 bp, 19-26 bp, 19-27 bp, 19-28 bp, 19-29 bp, 20-22 bp, 20-23 bp, 20-24 bp, 20-25 bp, 20-26 bp, 20-27 bp, 20-28 bp, 20-29 bp, 21-23 bp, 21-24 bp, 21-25 bp, 21-26 bp, 21-27 bp, 21-28 bp, 21-29 bp, 22-24 bp, 22-25 bp, 22-26 bp, 22-27 bp, 22-28 bp, 22-29 bp, 23-25 bp, 23-26 bp, 23-27 bp, 23-28 bp, 23-29 bp, 24-26 bp, 24-27 bp, 24-28 bp, 24-29 bp, 25-27 bp, 25-28 bp, 25-29 bp, 26-28 bp, 26-29 bp, 27-29 bp, 14-30 bp, 15-30 bp, 16-30 bp, 17-30 bp, 18-30 bp, 19-30 bp, 20-30 bp, 21-30 bp, 22-30 bp, 23-30 bp, 24-30 bp, 25-30 bp, 26-30 bp, 27-30 bp, or 28-30 bp.

In one embodiment of this aspect and all other aspects described herein, the nucleic acid sequence is about 20 bp. In other embodiments, the nucleic acid sequence is about 13 bp, is about 14 bp, is about 15 bp, is about 16 bp, is about 17 bp, is about 18 bp, is about 19 bp, is about 20 bp, is about 21 bp, is about 22 bp, is about 23 bp, is about 24 bp, is about 25 bp, is about 26 bp, is about 27 bp, is about 28 bp, is about 29 bp, or is about 30 bp.

In one embodiment of this aspect and all other aspects described herein, the nucleic acid sequence comprises a sequence selected from the group consisting of SEQ ID NOS: 1-94.

In one embodiment of this aspect and all other aspects described herein, the nucleic acid sequence consists essentially of a sequence selected from the group consisting of SEQ ID NOS: 1-94.

In one embodiment of this aspect and all other aspects described herein, the nucleic acid sequence is a sequence selected from the group consisting of SEQ ID NOS: 1-94.

In one embodiment of this aspect and all other aspects described herein, the nucleic acid sequence consists of a sequence selected from the group consisting of SEQ ID NOS: 1-94.

In one embodiment of this aspect and all other aspects described herein, the nucleic acid sequence further comprising a trans-activating CRISPR RNA (tracrRNA) sequence.

In one embodiment of this aspect and all other aspects described herein, the nucleic acid molecule is a single guide RNA (sgRNA).

In one embodiment of this aspect and all other aspects described herein, the nucleic acid molecule comprises a vector.

In one embodiment of this aspect and all other aspects described herein, the vector is a viral vector, such as a lentiviral vector.

In one embodiment of this aspect and all other aspects described herein, the vector is a sgRNA expression vector.

In one embodiment of this aspect and all other aspects described herein, the method further comprising contacting the same isolated progenitor cell with at least a DNA-targeting endonuclease or a vector carrying the coding sequence of a DNA-targeting endonuclease.

In one embodiment of this aspect and all other aspects described herein, the at least a DNA-targeting endonuclease is a Cas (CRISPR-associated) protein.

In one embodiment of this aspect and all other aspects described herein, the Cas protein is Cas9.

In one embodiment of this aspect and all other aspects described herein, the method further comprises providing an isolated cell or an isolated progenitor cell or an isolated population of cells which can be progenitor cell or hematopoietic progenitor cell.

In one embodiment of this aspect and all other aspects described herein, the isolated cell is an isolated progenitor cell.

In one embodiment of this aspect and all other aspects described herein, the isolated progenitor cell is an isolated human cell.

In one embodiment of this aspect and all other aspects described herein, the isolated human cell is a hematopoietic progenitor cell or a hematopoietic stem cell. In other embodiment, the isolated human cell is an embryonic stem cell, a somatic stem cell, a progenitor cell, or a bone marrow cell.

In one embodiment of this aspect and all other aspects described herein, the method described herein comprises contacting an embryonic stem cell, a somatic stem cell, a progenitor cell, a bone marrow cell, a hematopoietic stem cell, or a hematopoietic progenitor cell with an effective amount of a composition described herein or an effective amount of at least isolated nucleic acid molecule described herein.

In another embodiment of this aspect and all other aspects described herein, the hematopoietic cell is a cell of the erythroid lineage. Methods of isolating hematopoietic progenitor cell are well known in the art, e.g., by flow cytometric purification of CD34+ or CD133+ cells, microbeads conjugated with antibodies against CD34 or CD133, markers of hematopoietic progenitor cell. Commercial kits are also available, e.g., MACS® Technology CD34 MicroBead Kit, human, and CD34 MultiSort Kit, human, and STEMCELL™ Technology EasySep™ Mouse Hematopoietic Progenitor Cell Enrichment Kit.

In another embodiment of this aspect and all other aspects described herein, the hematopoietic stem cells, hematopoietic progenitor cells, embryonic stem cells, somatic stem cells, or progenitor cells are collected from peripheral blood, cord blood, chorionic villi, amniotic fluid, placental blood, or bone marrow.

In another embodiment of this aspect and all other aspects described herein, the human cell is an induced pluripotent stem cell (iPSC).

In another embodiment of this aspect and all other aspects described herein, the contacting of any cell described herein can be ex vivo or in vitro or in vivo.

In some embodiments of any of the methods or compositions described herein, the isolated progenitor cell or isolated cell is a hematopoietic progenitor cell.

In some embodiments of any of the methods or compositions described herein, the hematopoietic progenitor is a cell of the erythroid lineage.

In some embodiments of any of the methods or compositions described herein, wherein the isolated progenitor cell or isolated cell is an induced pluripotent stem cell.

In another embodiment of this aspect and all other aspects described herein, the contacting of any cell described herein comprises contacting with an agent that binds the genomic DNA of the cell on chromosome 2 and produces an epigenetic modification in the genome of the cell on chromosome 2, thereby reducing the mRNA or protein expression of BCL11A. In one embodiment, the epigenetic modification is on chromosome 2 location 60,716,189-60,728,612 (according to UCSC Genome Browser hg 19 human genome assembly).

In one embodiment of this aspect and all other aspects described herein, the at least one epigenetic modification in the genomic DNA of the cell on chromosome 2 indirectly or directly affects the location 60725424 to 60725688 (+55 functional region), and/or at location 60722238 to 60722466 (+58 functional region), and/or at location 60718042 to 60718186 (+62 functional region) of chromosome 2.

As used herein, "indirectly affecting the location 60725424 to 60725688 (+55 functional region), at location 60722238 to 60722466 (+58 functional region), and/or at location 60718042 to 60718186 (+62 functional region) of chromosome 2" refers to long distance effects of epigenetic modification in the genomic DNA of the cell on chromosome 2 the location 60725424 to 60725688 (+55 functional region), at location 60722238 to 60722466 (+58 functional region), and/or at location 60718042 to 60718186 (+62 functional region) of chromosome 2.

In another embodiment of this aspect and all other aspects described herein, the contacting of any cell described herein comprises contact with an agent that binds the genomic DNA of the cell on chromosome 2 location 60725424 to 60725688 (+55 functional region), at location 60722238 to 60722466 (+58 functional region), and/or at location 60718042 to 60718186 (+62 functional region) (according to UCSC Genome Browser hg 19 human genome assembly), and produces an epigenetic modification on chromosome 2, thereby reducing the mRNA or protein expression of BCL11A.

In another embodiment of this aspect and all other aspects described herein, the contacting of any cell described herein comprises contact with an effective amount of a composition comprising at least a DNA-targeting enzyme or a vector carrying the coding sequence of a DNA-targeting enzyme whereby the DNA-targeting enzyme produces an epigenetic modification on chromosome 2, thereby reducing the mRNA or protein expression of BCL11A.

In another embodiment of this aspect and all other aspects described herein, the contacting of any cell described herein comprises contact with an effective amount of a composition comprising at least a DNA-targeting enzyme or a vector carrying the coding sequence of a DNA-targeting enzyme whereby the DNA-targeting enzyme produces an epigenetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) thereby reducing the mRNA or protein expression of BCL11A. In one aspect, fetal hemoglobin expression is increased in the mammal, relative to expression prior to the contacting.

In another embodiment of this aspect and all other aspects described herein, the hematopoietic progenitor cell, the isolated human cell, or isolated cell is contacted ex vivo or in vitro.

In another embodiment of this aspect and all other aspects described herein, the at least one genetic modification is a deletion. In another embodiment of this aspect and all other aspects described herein, the at least one epigenetic modification.

In another embodiment of this aspect and all other aspects described herein, the deletion comprises one or more of the DNAse 1-hypersensitive sites (DHS)+62, +58, and +55 as described herein in the Examples section. In another embodiment of this aspect and all other aspects described herein, the deletion consists essentially of one or more of the DNAse 1-hypersensitive sites (DHS)+62, +58, and +55 as described herein in the Examples section. In another embodiment, the deletion consists of one or more of the DNAse 1-hypersensitive sites (DHS)+62, +58, and +55 as described herein in the Examples section.

In another embodiment of this aspect and all other aspects described herein, the epigenetic modification comprises or affects one or more of the DNAse 1-hypersensitive sites (DHS)+62, +58, and +55 as described herein in the Examples section. As used herein, the phrase "affects one or more of the DNAse 1-hypersensitive sites" means natural function of these DNAse 1-hypersensitive sites (DHS)+62, +58, and +55 are reduce, for example, access to transcription factors or DNA degradation enzymes such as DNase I. In general, DNase I hypersensitive sites (DHSs) are regions of chromatin which are sensitive to cleavage by the DNase I enzyme. In these specific regions of the genome, chromatin has lost its condensed structure, exposing the DNA, and making it accessible. This raises the availability of DNA to degradation by enzymes, like DNase I. These accessible chromatin zones are functionally related to transcriptional activity, since this remodeled state is necessary for the binding of proteins such as transcription factors. Accordingly, the epigenetic modification contemplated herein results in reduced access to DNA degradation enzymes that is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that is not treated in any method disclosed herein.

In another embodiment of this aspect and all other aspects described herein, the epigenetic modification is from 60,716,189 to 60,728,612, from 60,716,189 to 60,723,870, from 60,722,992 to 60,728,612, from 60,717,236 to 60,719,036, from 60,722,006 to 60,723,058, from 60,724,917 to 60,726,282, from 60,616,396 to 60,618,032, from 60,623,536 to 60,624,989, from 60,626,565 to 60,628,177, from 60,717,236 to 60,719,036, from 60,721,212 to 60,722,958, from 60,724,780 to 60,726,471, from 60,739,075 to 60,740,154, from 60,748,003 to 60,749,009, from 60,826,438 to 60,827,601, or from 60,831,589 to 60,833,556.

In another embodiment of this aspect and all other aspects described herein, the deletion removes the entire region between chromosome 2 location 60725424 to 60725688 (+55 functional region), at location 60722238 to 60722466 (+58 functional region), and/or at location 60718042 to 60718186 (+62 functional region) removes a portion of the region resulting in disruption of one or more DNAse 1-hypersensitive sites (DHS). As used herein, the term "disruption" refers to a decrease in erythroid transcription of BCL11A in a cell comprising a disruption of one or more DNAse −1 hypersensitive sites by at least 10% (e.g., at least 20%, at least 30%, at least 40%, at least 50%, at least 60%, at least 70%, at least 80%, at least 90%, at least 95%, at least 99% or even 100% (i.e., no detectable erythroid transcription)) compared to a cell not having such a disruption. In one embodiment, the disruption comprises an inability of a modified DNAse-1hypersensitive site to bind to its native transcription factors (e.g., GATA1 and TAL1).

In another embodiment of this aspect and all other aspects described herein, the epigenetic modification that interferes with the establishment and/or maintenance of the epigenetic signature at the enhancer region on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) thereby leading to reduced mRNA or protein expression of BCL11A, and increasing fetal hemoglobin expression in the mammal.

In one embodiment of this aspect and all other aspects described herein, the epigenetic modification that interferes with the establishment and/or maintenance of the epigenetic signature at the enhancer region on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) includes but is not limited to epigenetic modifications that affects DNase I sensitivity, epigenetic modifications that affects histone modifications, epigenetic modifications that affects GATA1/TAL1 binding, and epigenetic modifications that affects long-range promoter interaction of the promoter of BCL11A.

For example, an epigenetic modification that interferes with the establishment and/or maintenance of the epigenetic signature at the enhancer region on chromosome 2 location functional regions described include but is not limited to at least one deletion within chromosome 2 location 60,716,189-60,728,612 such that the overall function of this region is affected whereby the mRNA and expression of BCL11A is reduced or decreased. For example, the deletion is at the DNaseI sensitivity regions chromosome 2 location 60,716,189-60,728,612, e.g., +62, +58, and +55. The deletion could be at +62 or +58 or +55 or combination thereof. For examples, at +62 and +58, +58 and +55, +62 and +55, or at all three +62, +58, and +55.

As another example, an epigenetic modification that interferes with the establishment and/or maintenance of the epigenetic signature at the enhancer region on chromosome 2 location +55, +58 and +62 functional regions include but is not limited to changes in the histone modifications on chromosome 2 that is not at location functional regions or changes in the histone modifications on chromosome 2 at location functional regions, or both histone modifications on chromosome 2 not at location 60,716,189-60,728,612 as well as at location 60,716,189-60,728,612 such that the overall function of this region is affected whereby the mRNA and expression of BCL11A is reduced or decreased.

In another embodiment, an epigenetic modification that interferes with the establishment and/or maintenance of the epigenetic signature at the enhancer region on chromosome 2 location 60,716,189-60,728,612 include but is not limited to an insertion of at least one engineered specific-repressor sequence that change the epigenetic features of noncoding elements at chromosome 2, +55, +58 and +62 functional regions, and thus result in repression of target gene expression. The first is specifically focused on epigenetically repressing individual enhancers. In other words, insertion of engineered specific-repressor sequences into chromosome 2 would prospectively interfering with epigenetic modification at the BCL11A erythroid enhancer which eventually leads to reduced BCL11A gene expression.

Any methods known in the art can be used to produce the epigenetic modification contemplated. For example, as described in Mendenhall E. M. et al., Nat. Biotechnol. 8 Sep. 2013, and Maeder M L et al., Nat Biotechnol. 9 Oct. 2013 2013.

In one embodiment of this aspect and all other aspects described herein, the insertion of at least one engineered specific-repressor sequence on any location chromosome 2 results in but is not limited to reduced DNaseI sensitivity regions at chromosome 2 location +55, +58 and +62 functional regions; increased histone modifications on chromosome 2 location 60,716,189-60,728,612 or at the +55, +58 and +62 functional regions; reduced transcription factors binding to the GATA1/TAL1 of the enhancer region on chromosome 2 +55, +58 and +62 functional regions; and reduced or weakened interaction between the chromosome 2 location +55, +58 and +62 functional regions with the BCL11A promoter.

In one embodiment of this aspect and all other aspects described herein, the overall effects of the insertion of at least one engineered specific-repressor sequence on any location chromosome 2 is reduced or decreased mRNA and expression of BCL11A.

In some embodiments, as used in the context of mRNA and expression of BCL11A, interaction between the chromosome 2 location 60,716,189-60,728,612, at the +55, +58 and +62 functional regions, or BCL11A enhancer with the BCL11A promoter, and transcription factors binding to the GATA1/TAL1 of the enhancer region, the term "reduced" or "decreased" refers to at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to the control situation that is in the absence of the epigenetic modification or insertion of engineered sequences disclosed herein. By decrease of the BCL11A mRNA or protein expression in the cell means that protein expression is at least 5% lower is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more compared to a control cell that does not have the epigenetic modification or insertion of engineered sequences disclosed herein.

In one embodiment of this aspect and all other aspects described herein, the insertion of at least one engineered specific-repressor sequence occurs within the DNaseI sensitivity regions of chromosome 2 location 60,716,189-60,728,612, or at the +55, +58 and +62 functional regions. The insertion could be at the 5'end of +62 or +58 or +55 or at the 3'end of +62 or +58 or +55, or between +62 and +58, or between +58 and +55, or between +55 and +62.

In one embodiment of this aspect and all other aspects described herein, the insertion of at least one engineered specific-repressor sequence changes the DNaseI sensitivity regions of chromosome 2 location +55, +58 and +62 functional regions.

In one embodiment of this aspect and all other aspects described herein, the epigenetic modifications changes the DNaseI sensitivity regions of chromosome 2 location 60,716,189-60,728,612 or at the +55, +58 and +62 functional regions.

In one embodiment of this aspect and all other aspects described herein, the epigenetic modifications changes the histone modifications on chromosome 2 location 60,716,189-60,728,612, or at the +55, +58 and +62 functional regions.

In one embodiment of this aspect and all other aspects described herein, the insertion of at least one engineered specific-repressor sequence changes the histone modifications on chromosome 2 location 60,716,189-60,728,612 or at the +55, +58 and +62 functional regions.

In one embodiment of this aspect and all other aspects described herein, the epigenetic modifications changes the GATA1/TAL1 binding of the enhancer region on chromosome +55, +58 and +62 functional regions, such that the overall function of this region is affected whereby the mRNA and expression of BCL11A is reduced or decreased. For example, the binding of transcription factors to the GATA1/TAL1.

In one embodiment of this aspect and all other aspects described herein, the insertion of at least one engineered specific-repressor sequence occurs within the GATA1/TAL1 as described herein. The insertion can be at the 5' end or 3'end of GATA1 or TAD. The insertion can be between GATA1 and TAL1 The insertion changes the GATA1/TAL1 binding of the enhancer region on chromosome 2 +55, +58 and +62 functional regions, such that the overall function of this region is affected whereby the mRNA and expression of BCL11A is reduced or decreased. For example, the binding of transcription factors to the GATA1/TAL1.

In one embodiment of this aspect and all other aspects described herein, the epigenetic modification changes the interaction between the BCL11A enhancer and the BCL11A promoter. In one embodiment, the interaction is reduced or weakened such that the overall function of this region is affected whereby the mRNA and expression of BCL11A is reduced or decreased.

In one embodiment of this aspect and all other aspects described herein, the epigenetic modifications changes the interaction between the chromosome 2 location 60,716,189-60,728,612 and/or the +55, +58 and +62 functional regions with the BCL11A promoter. In one embodiment, the interaction is reduced or weakened such that the overall function of this region is affected whereby the mRNA and expression of BCL11A is reduced or decreased.

Also provided herein in another aspect is an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) made by the process of contacting the cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon 2 causing at least one genetic modification therein.

In another aspect is an isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) for use in increasing fetal hemoglobin levels in a mammal in need thereof, wherein the at least one genetic modification is made by the process of contacting the cell with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon 2 causing at least one genetic modification therein.

In one embodiment of this aspect and all other aspects described herein, the isolated genetic engineered human cell having at least one epigenetic modification at the genomic DNA of the cell on chromosome 2. In another of this aspect and all other aspects described herein, the isolated genetic engineered human cell having at least one epigenetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon2.

In some aspects of any of these isolated genetic engineered human cells having at least one epigenetic modification, the cells are transplanted into a mammal for use in increasing the fetal hemoglobin in the mammal.

In one embodiment of this aspect and all other aspects described herein, the isolated genetic engineered human cell having at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon 2 is transplanted into a mammal for use in increasing the fetal hemoglobin in the mammal.

In one embodiment of this aspect and all other aspects described herein, the isolated genetic engineered human cell having at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon 2 is stored for later use by cryopreservation.

In some aspects of any of those isolated genetic engineered human cells having at least one epigenetic modification, the cells are stored for later use by cryopreservation.

In one embodiment of this aspect and all other aspects described herein, the isolated genetic engineered human cell having at least one genetic modification at the genomic DNA of the cell on chromosome 2 location 60725424 to 60725688 (+55 functional region), and/or at location 60722238 to 60722466 (+58 functional region), and/or at location 60718042 to 60718186 (+62 functional region) or at the BCL11A exon 2 is cryopreserved, thawed and transplanted into mammal for use in increasing the fetal hemoglobin in the mammal.

In some aspects of any of those isolated genetic engineered human cells having at least one epigenetic modification, cryopreserved, thawed and transplanted into mammal for use in increasing the fetal hemoglobin in the mammal.

Another aspect provided herein relates to a composition comprising isolated genetic engineered human cells, wherein the cells have at least one genetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) made by the process of contacting the cells with an effective amount of a composition comprising a nucleic acid molecule or a vector carrying the nucleic acid molecule, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) (according to UCSC Genome Browser hg 19 human genome assembly) causing at least one genetic modification therein.

Another aspect provided herein relates to a composition comprising isolated genetic engineered human cells for use in increasing fetal hemoglobin levels in a mammal in need thereof, wherein the cells have at least one genetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) made by the process of contacting the cells with an effective amount of a composition comprising a nucleic acid molecule or a vector carrying the nucleic acid molecule, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) (according to UCSC Genome Browser hg 19 human genome assembly) causing at least one genetic modification therein.

Another aspect provided herein relates to a composition comprising isolated genetic engineered human cells, wherein the cells have at least one epigenetic modification on chromosome 2. In one embodiment, the at least one epigenetic modification on chromosome 2 is at location 60725424 to 60725688 (+55 functional region), at location 60722238 to 60722466 (+58 functional region), and/or at location 60718042 to 60718186 (+62 functional region) (according to UCSC Genome Browser hg 19 human genome assembly). In another embodiment, at least one epigenetic modification on chromosome 2 is made by the process of contacting the cells with an effective amount of a composition comprising a nucleic acid molecule or a vector carrying the nucleic acid molecule, together with at least a DNA-targeting enzyme or a vector carrying the coding sequence of a DNA-targeting enzyme whereby the DNA-targeting enzyme produces at least one epigenetic modification in the genomic DNA of the cell on chromosome 2 which affects the location 60725424 to 60725688 (+55 functional region), at location 60722238 to 60722466 (+58 functional region), and/or at location 60718042 to 60718186 (+62 functional region) (according to UCSC Genome Browser hg 19 human genome assembly) causing therein.

Another aspect provided herein relates to a composition comprising isolated genetic engineered human cells for use in increasing fetal hemoglobin levels in a mammal in need thereof, wherein the cells have at least one epigenetic modification on chromosome 2. In one embodiment, the at least one epigenetic modification on chromosome 2 is at location 60725424 to 60725688 (+55 functional region), at location 60722238 to 60722466 (+58 functional region), and/or at location 60718042 to 60718186 (+62 functional region) (according to UCSC Genome Browser hg 19 human genome assembly).

In one embodiment of this aspect and all other aspects described herein, the composition causes an increase in fetal hemoglobin mRNA or protein expression in the contact cell.

In one embodiment of this aspect and all other aspects described herein, the cells of any compositions described are autologous, to the mammal who is the recipient of the cells in a transplantation procedure, i.e., the cells of the composition are derived or harvested from the mammal prior to any described modification.

In one embodiment of this aspect and all other aspects described herein, the cells of any compositions described are non-autologous to the mammal who is the recipient of the cells in a transplantation procedure, i.e., the cells of the composition are not derived or harvested from the mammal prior to any described modification.

In one embodiment of this aspect and all other aspects described herein, the cells of any compositions described are at the minimum HLA type matched with to the mammal who is the recipient of the cells in a transplantation procedure.

In one embodiment of this aspect and all other aspects described herein, the cells of any compositions described are isolated progenitor cells prior to any described modification.

In one embodiment of this aspect and all other aspects described herein, the cells of any compositions described are isolated hematopoietic progenitor cells prior to any described modification.

In one embodiment of this aspect and all other aspects described herein, the cells of any compositions described are isolated induced pluripotent stem cells prior to any described modification.

In another embodiment of this aspect and all other aspects described herein, the deletion comprises one or more of the DNAse 1-hypersensitive sites (DHS)+62, +58, and +55 as described herein in the Examples section. In another embodiment of this aspect and all other aspects described herein, the deletion consists essentially of one or more of the DNAse 1-hypersensitive sites (DHS)+62, +58, and +55 as described herein in the Examples section. In another embodiment, the deletion consists of one or more of the DNAse 1-hypersensitive sites (DHS)+62, +58, and +55 as described herein in the Examples section. In one embodiment, as used herein, the term "portion" in the context of genomic deletion is at least 10% to about 100% of the specified region. In other embodiments, the portion deleted is at least 20%, at least 30%, at least 40%, at least 50%, at least 60%, at least 70%, at least 80%, at least 90%, at least 95%, at least 99% or even 100% of the specified region.

In another embodiment of this aspect and all other aspects described herein, the deletion removes the entire region between chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) or removes a portion of the region resulting in disruption of one or more DNAse 1-hypersensitive sites (DHS).

In one embodiment of this aspect and all other aspects described herein, the method further comprises selecting a mammal in need of increasing fetal hemoglobin.

In one embodiment of this aspect and all other aspects described herein, the mammal has been diagnosed with a hemoglobinopathy.

In one embodiment of this aspect and all other aspects described herein, the mammal in need of increasing fetal hemoglobin has been diagnosed with a hemoglobinopathy.

In one embodiment of this aspect and all other aspects described herein, the hemoglobinopathy is a β-hemoglobinopathy.

In one embodiment of this aspect and all other aspects described herein, the hemoglobinopathy is sickle cell disease.

In one embodiment of this aspect and all other aspects described herein, the hemoglobinopathy is β-thalassemia.

In one embodiment of this aspect and all other aspects described herein, the contacted cell, human cell, hematopoietic progenitor cell or its progeny is administered to the mammal.

In one embodiment, this disclosure provides a method for increasing fetal hemoglobin levels in a mammal in need thereof, the method comprising the steps of providing an isolated population of hematopoietic progenitor cells or hematopoietic stem cells from the mammal in ex vivo, and contacting the population of hematopoietic progenitor or stem cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting. In further embodiment of this method, the contacted population of hematopoietic progenitor or stem cells having increased fetal hemoglobin expression is cryopreserved and stored or reintroduced into the mammal. In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs described herein.

In one embodiment, this disclosure provides a method for increasing fetal hemoglobin levels in a mammal in need thereof, the method comprising the steps of isolating a population of hematopoietic progenitor cells or hematopoietic stem cells from the mammal, and contacting in ex vivo the population of hematopoietic progenitor or stem cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting. In further embodiment of this method, the ex vivo contacted population of hematopoietic progenitor or stem cells having increased fetal hemoglobin expression is cryopreserved and stored or reintroduced into the mammal. In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs derived from the mammal. In any embodiment of the method, the method further comprises selecting a mammal in need of increased fetal hemoglobin expression.

In one embodiment, this disclosure provides a method for increasing fetal hemoglobin levels in a mammal in need thereof, the method comprising the steps of providing isolating a population of hematopoietic progenitor cells or hematopoietic stem cells from the mammal and deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in said mammal, relative to expression prior to said contacting. In further embodiment of this method, the population of hematopoietic progenitor or stem cells with deleted genomic DNA and having increased fetal hemoglobin expression is cryopreserved and stored or reintroduced into the mammal. In another embodiment, the population of hematopoietic progenitor or stem cells with deleted genomic DNA and having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs described herein. In any of the embodiment of the described method, the hematopoietic progenitor or stem cells or iPSCs are analogous to the mammal, meaning the cells are derived from the same mammal. In another of the embodiment of the described method, the hematopoietic progenitor or stem cells or iPSCs are non-analogous to the mammal, meaning the cells are not derived from the same mammal, but another mammal of the same species. For example, the mammal is a human. In any embodiment of the method, the method further comprises selecting a mammal in need of increased fetal hemoglobin expression.

In one embodiment, this disclosure provides a method for increasing fetal hemoglobin levels in a mammal in need thereof, the method comprising the steps of isolating a population of hematopoietic progenitor cells or hematopoietic stem cells from the mammal and ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in said mammal, relative to expression prior to said contacting. In further embodiment of this method, the population of hematopoietic progenitor or stem cells with deleted genomic DNA and having increased fetal hemoglobin expression is cryopreserved and stored or reintroduced into the mammal. In another embodiment, the cryopreserved population of hematopoietic progenitor or stem cells having increased fetal hemoglobin expression is thawed and then reintroduced into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells can be substituted with an iPSCs derived from the mammal. In any embodiment of the method, the method further comprises selecting a mammal in need of increased fetal hemoglobin expression.

In one embodiment of any method described, the method further comprises selecting a mammal in need of increased fetal hemoglobin expression. Exemplary mammal in need of increased fetal hemoglobin expression is one that has been diagnosed with a hemoglobinopathy.

In one embodiment, this disclosure provides a method of treatment of a hemoglobinopathy in a mammal comprising the steps of: (a) providing hematopoietic progenitor cells or hematopoietic stem cells or iPSCs; (b) contacting the cells ex vivo or in vitro with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 causing at least one genetic modification therein, whereby fetal hemoglobin expression is increased in said mammal, relative to expression prior to said contacting; and (c) administering the cells of step (b) into the mammal.

In one embodiment of any method, the cells after step (b) can be cryopreserved till they are needed for administration into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells or iPSCs are autologous to the mammal, meaning the cells are derived from the same mammal. In another of the embodiment of the described method, the hematopoietic progenitor or stem cells or iPSCs are non-autologous to the mammal, meaning the cells are not derived from the same mammal, but another mammal of the same species. For example, the mammal is a human.

In one embodiment of any method described, the method further comprises selecting a mammal in need of treatment of a hemoglobinopathy.

In one embodiment, this disclosure provides a method of treatment of a hemoglobinopathy in a mammal comprising the steps of: (a) isolating hematopoietic progenitor cells or hematopoietic stem cells from the mammal; (b) contacting the cells ex vivo or in vitro with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to said contacting; and (c) administering the cells of step (b) into the mammal.

In one embodiment, the cells after step (b) can be cryopreserved till they are needed for administration into the mammal. In any embodiment of the method, the method further comprises selecting a mammal in need of treatment of a hemoglobinopathy.

In one embodiment, this disclosure provides a method of treatment of a hemoglobinopathy in a mammal comprising the cells steps of: (a) providing hematopoietic progenitor cells or hematopoietic stem cells or iPSCs; (b) ex vivo deleting the genomic DNA of the cells on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in said mammal, relative to expression prior to said contacting; and (c) administering the cells of step (b) into the mammal.

In one embodiment, the cells after step (b) can be cryopreserved till they are needed for administration into the mammal. In further embodiment of this method, the method comprises chemotherapy and/or radiation therapy to remove or reduced the endogenous hematopoietic progenitor or stem cells in the mammal. In any of the embodiment of the described method, the hematopoietic progenitor or stem cells or iPSCs are analogous to the mammal, meaning the cells are derived from the same mammal. In another of the embodiments of the described method, the hematopoietic progenitor or stem cells or iPSCs are non-analogous to the mammal, meaning the cells are not derived from the same mammal, but another mammal of the same species. For example, the mammal is a human. In any embodiment of the method, the method further comprises selecting a mammal in need of treatment of a hemoglobinopathy.

In one embodiment, this disclosure provides a method of treatment of a hemoglobinopathy in a mammal comprising the steps of: (a) isolating hematopoietic progenitor cells or hematopoietic stem cells from the mammal; (b) ex vivo deleting the genomic DNA of the cells on chromosome 2 location 60725424 to 60725688 (+55 functional region), and/or at location 60722238 to 60722466 (+58 functional region), and/or at location 60718042 to 60718186 (+62 functional region) causing at least one genetic modification therein, whereby fetal hemoglobin expression is increased in the mammal, relative to expression prior to said contacting; and (c) administering the cells of step (b) into the mammal.

In one embodiment, the cells after step (b) can be cryopreserved till they are needed for administration into the mammal. In further embodiment of this method, the method comprises chemotherapy and/or radiation therapy to remove or reduced the endogenous hematopoietic progenitor or stem cells in the mammal. In any embodiment of the method, the method further comprises selecting a mammal in need of treatment of a hemoglobinopathy.

In one embodiment, this disclosure provides a method of treatment of a hemoglobinopathy in a mammal (e.g. a human) comprising introducing a composition described herein comprising isolated genetic engineered cells having at least one genetic modification on chromosome 2 location 60725424 to 60725688 (+55 functional region), and/or at location 60722238 to 60722466 (+58 functional region), and/or at location 60718042 to 60718186 (+62 functional region) whereby fetal hemoglobin expression is increased in the mammal. In further embodiment of this method, the method comprises chemotherapy and/or radiation therapy to remove or reduced the endogenous hematopoietic progenitor or stem cells in the mammal. In any embodiment of the method, the method further comprises selecting a mammal in need of treatment of a hemoglobinopathy.

In one embodiment, this disclosure provides a method of treatment of a hemoglobinopathy in a mammal (e.g. a human) comprising increasing fetal hemoglobin expression in the mammal by method described herein.

In one aspect of any method, the method further comprises of selecting a subject diagnosed with a hemoglobinopathy or a subject at risk of developing a hemoglobinopathy.

In one aspect of any method, the hemoglobinopathy is sickle cell disease (SCD) or thalassemia (THAL). For example, β-thalassemias.

In one aspect of the method, the method further comprising administering to the subject a therapy comprising oxygen, hydroxyurea, folic acid, or a blood transfusion.

In one aspect, the present specification provides a method of treating, or reducing a risk of developing, a hemoglobinopathy in a subject In any embodiment of any treatment method described, the hemoglobinopathy is a β-hemoglobinopathy.

In any embodiment of any treatment method described, the hemoglobinopathy is β-thalassemia.

In any embodiment of any treatment method described, the hemoglobinopathy is sickle cell anemia.

In one of embodiment of any described method, the hematopoietic progenitor or stem cells or iPSCs are autologous to the mammal, meaning the cells are derived from the same mammal. In another of the embodiment of any described method, the hematopoietic progenitor or stem cells or iPSCs are non-autologous to the mammal, meaning the cells are not derived from the same mammal, but another mammal of the same species. For example, the mammal is a human.

In one of embodiment of any described method, the contacting of any cell described herein can be ex vivo or in vitro or in vivo.

In another embodiment of any described method, the contacting of any cell described herein comprises contact with an agent that binds the genomic DNA of the cell on chromosome 2 and produces an epigenetic modification in the genome of the cell on chromosome 2, thereby reducing the mRNA or protein expression of BCL11A. In one embodiment, the epigenetic modification is on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly).

In another embodiment of any described method, the contacting of any cell described herein comprises contact with an agent that binds the genomic DNA of the cell on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly), and produces an epigenetic modification on chromosome 2, thereby reducing the mRNA or protein expression of BCL11A.

In another embodiment of any described method, the contacting of any cell described herein comprises contact with an effective amount of a composition comprising at least a DNA-targeting enzyme or a vector carrying the coding sequence of a DNA-targeting enzyme whereby the DNA-targeting enzyme produces an epigenetic modification on chromosome 2, thereby reducing the mRNA or protein expression of BCL11A.

In another embodiment of any described method, the contacting of any cell described herein comprises contact with an effective amount of a composition comprising at least a DNA-targeting enzyme or a vector carrying the coding sequence of a DNA-targeting enzyme whereby the DNA-targeting enzyme produces an epigenetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) thereby reducing the mRNA or protein expression of BCL11A. In one aspect, fetal hemoglobin expression is increased in the mammal, relative to expression prior to the contacting.

In another embodiment of any described method, the hematopoietic progenitor cell, the isolated human cell, or isolated cell is contacted ex vivo or in vitro.

In another embodiment of any described method, the at least one genetic modification is a deletion. In another embodiment of this aspect and all other aspects described herein, the at least one epigenetic modification.

In one embodiment, provided herein is a use of an agent that binds the genomic DNA of the cell on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) for increasing the fetal hemoglobin in a mammal or for the treatment of a hemoglobinopathy in the mammal or for reducing the mRNA or expression of BCL11A, wherein the mRNA or protein expression of BCL11A is reduced. In one embodiment, the agent is a nucleic acid molecule comprising a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region).

In one embodiment, provided herein is an agent that binds the genomic DNA of the cell on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) for use in a method for increasing the fetal hemoglobin in a mammal or for the treatment of a hemoglobinopathy in the mammal or for reducing the mRNA or expression of BCL11A, wherein the mRNA or protein expression of BCL11A is reduced. In one embodiment, the agent is a nucleic acid molecule comprising a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region).

In one embodiment, provided herein is a use of an effective amount of a composition comprising a nucleic acid molecule described herein or a vector described herein in a method for increasing the fetal hemoglobin in a cell or in a mammal or for the treatment of a hemoglobinopathy in the mammal or for reducing the mRNA or expression of BCL11A in a cell or in a mammal. In one aspect, the method comprising transplanting the cells with the at least one epigenetic modification into the mammal, the cells had been contacted with the described composition comprising of a nucleic acid described.

In one embodiment, provided herein is a composition comprising a nucleic acid molecule described herein or a vector described herein a use in a method for increasing the fetal hemoglobin in a cell or in a mammal or for the treatment of a hemoglobinopathy in the mammal or for reducing the mRNA or expression of BCL11A in a cell or in a mammal. In one aspect, the method comprising transplanting the cells with the at least one epigenetic modification into the mammal, the cells had been contacted with the described composition comprising of a nucleic acid described.

The nucleic acid molecule comprising a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region). In one embodiment, the composition further comprises at least a DNA-targeting endonuclease or a vector carrying the coding sequence of a DNA-targeting endonuclease for increasing the fetal hemoglobin in a mammal or for the treatment of a hemoglobinopathy in the mammal or for reducing the mRNA or expression of BCL11A, wherein the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) causing at least one genetic modification therein. In one aspect, the method comprising transplanting the cells with the at least one epigenetic modification into the mammal, the cells had been contacted with the described composition comprising of a nucleic acid described.

In one embodiment, provided herein is a use of an effective amount of a composition comprising a nucleic acid molecule described herein or a vector described herein, together with at least a DNA-targeting enzyme or a vector carrying the coding sequence of a DNA-targeting enzyme, the use is in a method for increasing the fetal hemoglobin in cell or a mammal or for the treatment of a hemoglobinopathy in the mammal or for reducing the mRNA or expression of BCL11A in a cell or in a mammal, wherein the DNA-targeting enzyme produces at least one epigenetic modification in the genomic DNA of the cell on chromosome 2, thereby affecting the mRNA or expression of BCL11A. In one embodiment, the at least one epigenetic modification is at location 60725424 to 60725688 (+55 functional region), and/or at location 60722238 to 60722466 (+58 functional region), and/or at location 60718042 to 60718186 (+62 functional region). In another embodiment, the effect of the one epigenetic modification is reducing the mRNA or protein expression of BCL11A. In one aspect, the method comprising transplanting the cells with the at least one epigenetic modification into the mammal.

In one embodiment, provided herein is a use of an effective amount of a composition comprising a nucleic acid molecule described herein or a vector described herein, the use is in a method for increasing the fetal hemoglobin in cell or a mammal or for the treatment of a hemoglobinopathy in the mammal or for reducing the mRNA or expression of BCL11A in a cell or in a mammal, wherein the DNA-targeting enzyme produces at least one epigenetic modification in the genomic DNA of the cell on chromosome 2, thereby affecting the mRNA or expression of BCL11A.

In one embodiment, provided herein is a composition comprising a nucleic acid molecule described herein or a vector described herein, for use in a method for increasing the fetal hemoglobin in cell or a mammal or for the treatment of a hemoglobinopathy in the mammal or for reducing the mRNA or expression of BCL11A in a cell or in a mammal, wherein the DNA-targeting enzyme produces at least one epigenetic modification in the genomic DNA of the cell on chromosome 2, thereby affecting the mRNA or expression of BCL11A.

In one embodiment, provided herein is a composition comprising a nucleic acid molecule described herein or a vector described herein, together with at least a DNA-targeting enzyme or a vector carrying the coding sequence of a DNA-targeting enzyme, for use in a method for increasing the fetal hemoglobin in cell or a mammal or for the treatment of a hemoglobinopathy in the mammal or for reducing the mRNA or expression of BCL11A in a cell or in a mammal, wherein the DNA-targeting enzyme produces at least one epigenetic modification in the genomic DNA of the cell on chromosome 2, thereby affecting the mRNA or expression of BCL11A. In one embodiment, the at least one epigenetic modification is at location 60725424 to 60725688 (+55 functional region), and/or at location 60722238 to 60722466 (+58 functional region), and/or at location 60718042 to 60718186 (+62 functional region). In another embodiment, the effect of the one epigenetic modification is reducing the mRNA or protein expression of BCL11A. In one aspect, the method comprising transplanting the cells with the at least one epigenetic modification into the mammal.

In one embodiment, provided herein is a use of any isolated cells described herein in a method for increasing the fetal hemoglobin in a mammal or for the treatment of a hemoglobinopathy in the mammal. In one aspect, the method comprising transplanting the described isolated engineered cells into the mammal.

In one embodiment, provided herein is a use of a composition comprising isolated genetic engineered human cells for in a method of increasing the fetal hemoglobin in a mammal or for the treatment of a hemoglobinopathy in the mammal, wherein the cells have at least one genetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) made by the process of contacting the cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein. In one aspect, the method comprising transplanting the described composition comprising the described isolated engineered cells into the mammal.

In one embodiment, provided herein is a composition comprising isolated genetic engineered human cells for a use in a method of increasing the fetal hemoglobin in a mammal or for the treatment of a hemoglobinopathy in the mammal, wherein the cells have at least one genetic modification on chromosome 2 location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) made by the process of contacting the cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60,716,189-60,728,612 (according to UCSC Genome Browser hg 19 human genome assembly) causing at least one genetic modification therein. In one aspect, the method comprising transplanting the described composition comprising the described isolated engineered cells into the mammal.

In one embodiment, provided herein is a use of a composition comprising isolated genetic engineered human cells in a method for increasing the fetal hemoglobin in a mammal or for the treatment of a hemoglobinopathy in the mammal, wherein the cells have at least one epigenetic modification on chromosome 2. In one embodiment, the at least one epigenetic modification on chromosome 2 is at location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly). In another embodiment, at least one epigenetic modification on chromosome 2 is made by the process of contacting the cells with an effective amount of a composition comprising a nucleic acid molecule described herein or a vector described herein, together with at least a DNA-targeting enzyme or a vector carrying the coding sequence of a DNA-targeting enzyme whereby the DNA-targeting enzyme produces at least one epigenetic modification in the genomic DNA of the cell on chromosome 2 which affects the location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) causing therein. In one aspect, the method comprising transplanting the described composition of isolated engineered cells into the mammal.

In one embodiment, provided herein is a composition comprising isolated genetic engineered human cells a use of in a method for increasing the fetal hemoglobin in a mammal or for the treatment of a hemoglobinopathy in the mammal, wherein the cells have at least one epigenetic modification on chromosome 2. In one embodiment, the at least one epigenetic modification on chromosome 2 is at location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly). In another embodiment, at least one epigenetic modification on chromosome 2 is made by the process of contacting the cells with an effective amount of a composition comprising a nucleic acid molecule described herein or a vector described herein, together with at least a DNA-targeting enzyme or a vector carrying the coding sequence of a DNA-targeting enzyme whereby the DNA-targeting enzyme produces at least one epigenetic modification in the genomic DNA of the cell on chromosome 2 which affects the location 60725424 to 60725688 (+55 functional region), and/or at location 60722238 to 60722466 (+58 functional region), and/or at location 60718042 to 60718186 (+62 functional region) (according to UCSC Genome Browser hg 19 human genome assembly) causing therein. In one aspect, the method comprising transplanting the described composition of isolated engineered cells into the mammal.

In one embodiment, provided herein is a use of any isolated cells described herein or any one of the compositions described herein for the manufacture of a medicament for use in increasing the fetal hemoglobin in a mammal or for the treatment of a hemoglobinopathy in the mammal.

In one embodiment of use of the composition described herein, the composition causes an increase in fetal hemoglobin mRNA or protein expression in the contact cell.

In one embodiment of use of the composition described herein, the cells of any compositions described are autologous, to the mammal who is the recipient of the cells in a transplantation procedure, i.e., the cells of the composition are derived or harvested from the mammal prior to any described modification.

In one embodiment of use of the composition described herein, the cells of any compositions described are non-autologous to the mammal who is the recipient of the cells in a transplantation procedure, i.e., the cells of the composition are not derived or harvested from the mammal prior to any described modification.

In one embodiment of use of the composition described herein, the cells of any compositions described are at the minimum HLA type matched with to the mammal who is the recipient of the cells in a transplantation procedure.

In one embodiment of use of the composition described herein, the cells of any compositions described are isolated progenitor cells prior to any described modification.

In one embodiment of use of the composition described herein, the cells of any compositions described are isolated hematopoietic progenitor cells prior to any described modification.

In one embodiment of use of the composition described herein, the cells of any compositions described are isolated induced pluripotent stem cells prior to any described modification.

In one embodiment of use of the composition described herein, the cells of any compositions described are cryopreserved prior to use.

In one embodiment of any one method described, the method is used to treat, prevent, or ameliorate a hemoglobinopathy is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease.

In various embodiments of any one method described, the vectors are administered by direct injection to a cell, tissue, or organ of a subject in need of gene therapy, in vivo. In various other embodiments of any one method described, cells are transduced in vitro or ex vivo with vectors of the invention, and optionally expanded ex vivo. The transduced cells are then administered to a subject in need of gene therapy.

In one embodiment of any one method described, the method further comprises selecting a subject in need of the gene therapy described. For example, a subject exhibiting symptoms or cytology of a hemoglobinopathy is selected from the group consisting of hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease. Alternatively, the subject carries a genetic mutation that is associated with a hemoglobinopathy, a genetic mutation described herein. For example, a subject diagnosis of SCD with genotype HbSS, HbS/β0 thalassemia, HbSD, or HbSO, and/or with HbF <10% by electrophoresis.

In one embodiment, this disclosure provides a method of providing a transduced or engineered/genetically modified cell to a subject that comprises administering, e.g., parenterally, one or more cells transduced with a vector contemplated herein into the subject. In one embodiment, the vector is one that carries one or more of the nucleic acid sequences described herein or a nucleic acid molecule comprising a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612. In one embodiment, the nucleic acid molecule comprises a sequence selected from the group consisting of SEQ ID NOS:1-94. In one embodiment, the nucleic acid molecule consist of a sequence selected from the group consisting of SEQ ID NOS:1-94. In one embodiment, the nucleic acid molecule consist essentially of a sequence selected from the group consisting of SEQ ID NOS:1-94.

In a particular embodiment, a method of preventing, ameliorating, or treating a hemoglobinopathy in a subject is provided. The method comprises administering a population of cells comprising engineered/genetically modified hematopoietic stem cells or hematopoietic progenitor cells transduced with a vector contemplated herein. In one embodiment, the nucleic acid molecule comprises a sequence selected from the group consisting of SEQ ID NOS:1-94. In one embodiment, the nucleic acid molecule consist of a sequence selected from the group consisting of SEQ ID NOS:1-94. In one embodiment, the nucleic acid molecule consist essentially of a sequence selected from the group consisting of SEQ ID NOS:1-94.

In particular embodiments of any methods described, a population of engineered/genetically modified cells administered to a subject comprises hematopoietic stem or progenitor cells, proerythroblasts, basophilic erythroblasts, polychromatic erythroblasts, orthochromatic erythroblasts, polychromatic erythrocytes, and erythrocytes (RBCs), or any combination thereof, and any proportion of which may be genetically modified by the vectors contemplated herein.

In some embodiments of any methods described, the population of engineered/genetically modified cells can be culture expanded in vitro or ex vivo prior to implantation/engraftment into a subject or prior to cryopreservation for storage.

In some embodiments of any methods described, the population of engineered/genetically modified cells can be culture expanded in vitro or ex vivo after cryopreservation prior to implantation/engraftment into a subject.

In some embodiments of any methods described, the population of engineered/genetically modified cells can be differentiated in vitro or ex vivo prior to implantation into a subject.

The genetically modified cells may be administered as part of a bone marrow or cord blood transplant in an individual that has or has not undergone bone marrow ablative therapy. In one embodiment, genetically modified cells contemplated herein are administered in a bone marrow transplant to an individual that has undergone chemoablative or radioablative bone marrow therapy.

In one embodiment of any method described, a dose of genetically modified cells is delivered to a subject intravenously. In one embodiment, genetically modified hematopoietic cells are intravenously administered to a subject.

In particular embodiments, patients receive a dose of genetically modified cells, e.g., hematopoietic stem cells, of about $1\times10^5$ cells/kg, about $5\times10^5$ cells/kg, about $1\times10^6$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $5\times10^7$ cells/kg, about $1\times10^8$ cells/kg, or more in one single intravenous dose. In certain embodiments, patients receive a dose of genetically modified cells, e.g., hematopoietic stem cells described herein or genetic engineered cells described herein or progeny thereof, of at least $1\times10^5$ cells/kg, at least $5\times10^5$ cells/kg, at least $1\times10^6$ cells/kg, at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, at least $1\times10^7$ cells/kg, at least $5\times10^7$ cells/kg, at least $1\times10^8$ cells/kg, or more in one single intravenous dose.

In an additional embodiment, patients receive a dose of genetically modified cells, e.g., hematopoietic stem cells, of about $1\times10^5$ cells/kg to about $1\times10^8$ cells/kg, about $1\times10^6$ cells/kg to about $1\times10^8$ cells/kg, about $1\times10^6$ cells/kg to about 9×10⁶ cells/kg, about 2×10⁶ cells/kg to about 8×10⁶ cells/kg, about 2×10⁶ cells/kg to about 8×10⁶ cells/kg, about 2×10⁶ cells/kg to about 5×10⁶ cells/kg, about 3×10⁶ cells/kg to about 5×10⁶ cells/kg, about 3×10⁶ cells/kg to about 4×10⁸ cells/kg, or any intervening dose of cells/kg.

In various embodiments, the methods of the invention provide more robust and safe gene therapy than existing methods and comprise administering a population or dose of cells comprising about 5% transduced/genetically modified cells, about 10% transduced/genetically modified cells, about 15% transduced/genetically modified cells, about 20% transduce/genetically modified d cells, about 25% transduced/genetically modified cells, about 30% transduced/genetically modified cells, about 35% transduced/genetically modified cells, about 40% transduced/genetically modified cells, about 45% transduced/genetically modified cells, or about 50% transduce/genetically modified d cells, to a subject.

In one embodiment, the invention provides genetically modified cells, such as a stem cell, e.g., hematopoietic stem cell, with the potential to expand or increase a population of erythroid cells. In particular embodiments, hematopoietic stem cells are transduced with a vector of the invention and administered to an individual in need of therapy for hemoglobinopathy. Hematopoietic stem cells are the origin of erythroid cells and thus, are preferred. In one embodiment, the vector is one that carries one or more of the nucleic acid sequences described herein or a nucleic acid molecule comprising a nucleic acid sequence that is (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612. In one embodiment, the nucleic acid molecule comprises a sequence selected from the group consisting of SEQ ID NOS:1-94. In one embodiment, the nucleic acid molecule consist of a sequence selected from the group consisting of SEQ ID NOS:1-94. In one embodiment, the nucleic acid molecule consist essentially of a sequence selected from the group consisting of SEQ ID NOS:1-94.

In one embodiment, the genetically modified cells are further transduced with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region).

In one embodiment, the contacted hematopoietic stem cells described herein or genetic engineered cells described herein or the the progeny cells thereof are implanted with prostaglandin E2 and/or antioxidant N-acetyl-L-cysteine (NAC) to promote the engraftments of the respective cells.

In a further embodiment of any methods described herein, the hematopoietic stem cell or hematopoietic progenitor cell being contacted is of the erythroid lineage.

In one embodiment of any methods described herein, the hematopoietic stem cell or hematopoietic progenitor cell is collected from peripheral blood, cord blood, chorionic villi, amniotic fluid, placental blood, or bone marrow.

In a further embodiment of any methods described herein, the recipient subject is treated with chemotherapy and/or radiation prior to implantation of the contacted or transfected cells (ie. the contacted hematopoietic stem cells described herein or genetic engineered cells described herein or the the progeny cells thereof).

In one embodiment, the chemotherapy and/or radiation is to reduce endogenous stem cells to facilitate engraftment of the implanted cells.

In one aspect of any method, the contacted hematopoietic stem cells described herein or genetic engineered cells described herein or the progeny cells thereof are treated ex vivo with prostaglandin E2 and/or antioxidant N-acetyl-L-cysteine (NAC) to promote subsequent engraftment in a recipient subject.

Engraftment analysis was performed 4, 8 and 12 weeks post transplantation in peripheral blood and bone marrow. For example, harvest a sample of blood from these locations and determine the BCL11A expression by any method known in the art.

In one aspect of any one method described herein, the method comprises obtaining a sample or a population of embryonic stem cells, somatic stem cells, progenitor cells, bone marrow cells, hematopoietic stem cells, or hematopoietic progenitor cells from the subject.

In one embodiment of any one method described herein, the cells that is contacted with a nucleic acid molecule describe herein, or a vector describe herein, or a composition describe herein comprising a nucleic acid molecule or a vector is derived from embryonic stem cells, somatic stem cells, progenitor cells, bone marrow cells, hematopoietic stem cells, or hematopoietic progenitor cells.

In one embodiment, the embryonic stem cells, somatic stem cells, progenitor cells, bone marrow cells, hematopoietic stem cells, hematopoietic progenitor cells are isolated from the host subject, transfected, cultured (optional), and transplanted back into the same host, i. e. an autologous cell transplant. In another embodiment, the embryonic stem cells, somatic stem cells, progenitor cells, bone marrow cells, hematopoietic stem cells, or hematopoietic progenitor cells are isolated from a donor who is an HLA-type match with a host (recipient) who is diagnosed with or at risk of developing a hemoglobinopathy. Donor-recipient antigen type-matching is well known in the art. The HLA-types include HLA-A, HLA-B, HLA-C, and HLA-D. These represent the minimum number of cell surface antigen matching required for transplantation. That is the transfected cells are transplanted into a different host, i.e., allogeneic to the recipient host subject. The donor's or subject's embryonic stem cells, somatic stem cells, progenitor cells, bone marrow cells, hematopoietic stem cells, or hematopoietic progenitor cells can be transfected with a vector or nucleic acid comprising the nucleic acid molecule described herein, the transfected cells are culture expanded, and then transplanted into the host subject. In one embodiment, the transplanted cells engrafts in the host subject. The transfected cells can also be cryopreserved after transfected and stored, or cryopreserved after cell expansion and stored.

In one aspect of any method, the embryonic stem cell, somatic stem cell, progenitor cell, bone marrow cell, hematopoietic stem cell, or hematopoietic progenitor cell is autologous or allogeneic to the subject.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the phrase "agent that binds the genomic DNA of the cell on chromosome 2 location 60725424 to 60725688 (+55 functional region), at location 60722238 to 60722466 (+58 functional region), and/or at location 60718042 to 60718186 (+62 functional region)" refers to small molecules, nucleic acids, proteins, peptides or oligonucleotides that can bind to the location within the genomic DNA (e.g., chromosome 2 location 60725424 to 60725688 (+55 functional region), at location 60722238 to 60722466 (+58 functional region), and/or at location 60718042 to 60718186 (+62 functional region)) and represses mRNA or protein expression of BCL11A in a cell by at least 20% compared to the mRNA or protein level of BCL11A in a cell not treated with such an agent. In one embodiment, the agent "interferes with BCL11A interactions with BCL11A binding partners," as that phrase is used herein.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

By "interferes with BCL11A interactions with BCL11A binding partners" is meant that the amount of interaction of BCL11A with the BCL11A binding partner is at least 5% lower in populations treated with a BCL11A inhibitor, than a comparable, control population, wherein no BCL11A inhibitor is present. It is preferred that the amount of interaction of BCL11A with the BCL11A binding partner in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no BCL11A inhibitor is added. At a minimum, BCL11A interaction can be assayed by determining the amount of BCL11A binding to the BCL11A binding partner using techniques standard in the art, including, but not limited to, mass spectrometry, immunoprecipitation, or gel filtration assays. Alternatively, or in addition, BCL11A activity can be assayed by measuring fetal hemoglobin expression at the mRNA or protein level following treatment with a candidate BCL11A inhibitor.

In one embodiment, BCL11A activity is the interaction of BCL11A with its binding partners: GATA-1, FOG-1, components of the NuRD complex, matrin-3, MTA2 and RBBP7. Accordingly, any antibody or fragment thereof, small molecule, chemical or compound that can block this interaction is considered an inhibitor of BCL11A activity.

As used herein, the term "genetic engineered cell" refers to a cell that comprises at least one genetic modification, as that term is used herein.

As used herein, the term "genetic modification" refers to a disruption at the genomic level resulting in a decrease in BCL11A expression or activity in a cell. Exemplary genetic modifications can include deletions, frame shift mutations, point mutations, exon removal, removal of one or more DNAse 1-hypersensitive sites (DHS) (e.g., 2, 3, 4 or more DHS regions), etc.

By "inhibits BCL11A expression" is meant that the amount of expression of BCL11A is at least 5% lower in a cell or cell population treated with a DNA-targeting endonuclease, than a comparable, control cell or cell population, wherein no DNA-targeting endonuclease is present. It is preferred that the percentage of BCL11A expression in a treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no DNA-targeting endonuclease is added.

By "inhibits BCL11A activity" is meant that the amount of functional activity of BCL11A is at least 5% lower in a cell or cell population treated with the methods described herein, than a comparable, control cell or population, wherein no DNA-targeting endonuclease is present. It is preferred that the percentage of BCL11A activity in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no DNA-targeting endonuclease is added. At a minimum, BCL11A activity can be assayed by determining the amount of BCL11A expression at the protein or mRNA levels, using techniques standard in the art. Alternatively, or in addition, BCL11A activity can be determined using a reporter construct, wherein the reporter construct is sensitive to BCL11A activity. The γ-globin locus sequence is recognizable by the nucleic acid-binding motif of the BCL11A construct.

In one embodiment, as used herein, the term "DNA targeting endonuclease" refers to an endonuclease that generates a double-stranded break at a desired position in the genome (e.g., chromosome 2 location 60,716,189-60,728,612) without producing undesired off-target double-stranded breaks. The DNA targeting endonuclease can be a naturally occurring endonuclease (e.g., a bacterial meganuclease) or it can be artificially generated (e.g., engineered meganucleases, TALENs, or ZFNs, among others).

In another embodiment, as used herein, the term "DNA targeting endonuclease" refers to an endonuclease that generates a single-stranded break or a "nick" or break on one strand of the DNA phosphate sugar backbone at a desired position in the genome (e.g., chromosome 2 location 60725424 to 60725688 (+55 functional region), at location 60722238 to 60722466 (+58 functional region), and/or at location 60718042 to 60718186 (+62 functional region)) without producing undesired off-target DNA stranded breaks.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the methods and compositions described herein can include such other forms of expression vectors, such as viral vectors (e.g., replication defective retroviruses, lentiviruses, adenoviruses and adeno-associated viruses), which serve equivalent functions.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the DNA-targeting endonuclease can be delivered by way of a vector comprising a regulatory sequence to direct synthesis of the DNA-targeting endonuclease at specific intervals, or over a specific time period. It will be appreciated by those skilled in the art that the design of the expression vector can depend on such factors as the choice of the target cell, the level of expression desired, and the like.

As used herein the term "cleaves" generally refers to the generation of a double-stranded break in the DNA genome at a desired location.

As used herein, the term "effective amount of a composition comprising at least a DNA-targeting endonuclease" refers to an amount of a DNA-targeting endonuclease that yields sufficient endonuclease activity to generate a double-stranded break in the desired location of the genome. In one embodiment, the effective amount of a DNA-targeting endonuclease generates a double-stranded break at the desired genetic locus in at least 20% of the cells in a population contacted with the composition (e.g., at least 30%, at least 40%, at least 50%, at least 60%, at least 70%, at least 80%, at least 90%, at least 95%, at least 99%, or even 100% of the cells in the population comprise a genetic modification produced by the DNA-targeting endonuclease composition).

As used herein the term "increasing the fetal hemoglobin levels" in a cell indicates that fetal hemoglobin is at least 5% higher in populations treated with an agent that disrupts BCL11A mRNA or protein expression (e.g., a DNA-targeting endonuclease) by binding to genomic DNA at chromosome 2 location 60,716,189-60,728,612, than in a comparable, control population, wherein no agent is present. It is preferred that the percentage of fetal hemoglobin expression in a population treated with such an agent that binds the genomic DNA at chromosome 2 location 60,716,189-60,728,612 is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the agent that binds genomic DNA at chromosome 2 location 60,716,189-60,728,612. In one embodiment, any method known in the art can be used to measure an increase in fetal hemoglobin expression, e. g. Western Blot analysis of fetal γ-globin protein and quantifying mRNA of fetal γ-globin.

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human hematopoietic progenitor cells, e.g., a substantially pure population of human hematopoietic progenitor cells as compared to a heterogeneous population of cells comprising human hematopoietic progenitor cells and cells from which the human hematopoietic progenitor cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of hematopoietic progenitor cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not hematopoietic progenitor cells as defined by the terms herein.

A "subject," as used herein, includes any animal that exhibits a symptom of a monogenic disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy vectors, cell-based therapeutics, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

In one embodiment, as used herein, "prevent," and similar words such as "prevented," "preventing" etc., indicate an approach for preventing, inhibiting, or reducing the likelihood of the occurrence or recurrence of, a disease or condition. In another embodiment, the term refers to delaying the onset or recurrence of a disease or condition or delaying the occurrence or recurrence of the symptoms of a disease or condition. In another embodiment, as used herein, "prevention" and similar words includes reducing the intensity, effect, symptoms and/or burden of a disease or condition prior to onset or recurrence of the disease or condition.

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of hematopoietic progenitor cells so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

As used herein, "prevention" or "preventing," when used in reference to a disease, disorder or symptoms thereof, refers to a reduction in the likelihood that an individual will develop a disease or disorder, e.g., a hemoglobinopathy. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

In connection with contacting a cell with a DNA-targeting endonuclease to decrease BCL11A expression, the phrase "increasing fetal hemoglobin levels in a cell" indicates that fetal hemoglobin in a cell or population of cells is at least 5% higher in the cell or population of cells treated with the DNA-targeting endonuclease, than a comparable, control population, wherein no DNA-targeting endonuclease is present. It is preferred that the fetal hemoglobin expression in a DNA-targeting endonuclease treated cell is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated population. The term "control treated population" is used herein to describe a population of cells that has been treated with identical media, viral induction, nucleic acid sequences, temperature, confluency, flask size, pH, etc., with the exception of the addition of the BCL11A inhibitor.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

Accordingly, in one embodiment, the mammal has been diagnosed with a hemoglobinopathy. In a further embodiment, the hemoglobinopathy is a β-hemoglobinopathy. In one preferred embodiment, the hemoglobinopathy is a sickle cell disease. As used herein, "sickle cell disease" can be sickle cell anemia, sickle-hemoglobin C disease (HbSC), sickle beta-plus-thalassemia (HbS/β+), or sickle beta-zero-thalassaemia (HbS/β0). In another preferred embodiment, the hemoglobinopathy is a β-thalassemia.

As used herein, the term "hemoglobinopathy" means any defect in the structure or function of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term further includes any decrease in the amount or effectiveness of hemoglobin, whether normal or abnormal, caused by external factors such as disease, chemotherapy, toxins, poisons, or the like.

In one embodiment, the term "effective amount", as used herein, refers to the amount of a cell composition that is safe and sufficient to treat, lesson the likelihood of, or delay the development of a hemoglobinopathy. The amount can thus cure or result in amelioration of the symptoms of the hemoglobinopathy, slow the course of hemoglobinopathy disease progression, slow or inhibit a symptom of a hemoglobinopathy, slow or inhibit the establishment of secondary symptoms of a hemoglobinopathy or inhibit the development of a secondary symptom of a hemoglobinopathy. The effective amount for the treatment of the hemoglobinopathy depends on the type of hemoglobinopathy to be treated, the severity of the symptoms, the subject being treated, the age and general condition of the subject, the mode of administration and so forth. Thus, it is not possible or prudent to specify an exact "effective amount". However, for any given case, an appropriate "effective amount" can be determined by one of ordinary skill in the art using only routine experimentation.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Hemoglobinopathies

Fetal hemoglobin (HbF) is a tetramer of two adult α-globin polypeptides and two fetal β-like γ-globin polypeptides. During gestation, the duplicated γ-globin genes constitute the predominant genes transcribed from the β-globin locus. Following birth, γ-globin becomes progressively replaced by adult β-globin, a process referred to as the "fetal switch" (3). The molecular mechanisms underlying this switch have remained largely undefined and have been a subject of intense research. The developmental switch from production of predominantly fetal hemoglobin or HbF (α2γ2) to production of adult hemoglobin or HbA (α2β2) begins at about 28 to 34 weeks of gestation and continues shortly after birth at which point HbA becomes predominant. This switch results primarily from decreased transcription of the gamma-globin genes and increased transcription of beta-globin genes. On average, the blood of a normal adult contains only about 2% HbF, though residual HbF levels have a variance of over 20 fold in healthy adults (Atweh, Semin. Hematol. 38(4):367-73 (2001)).

Hemoglobinopathies encompass a number of anemias of genetic origin in which there is a decreased production and/or increased destruction (hemolysis) of red blood cells (RBCs). These disorders also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders specifically associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickled) hemoglobin (HbS). HbS RBCS are more fragile than normal RBCs and undergo hemolysis more readily, leading eventually to anemia (Atweh, Semin. Hematol. 38(4):367-73 (2001)). Moreover, the presence of a BCL11A genetic variant, HBS1L-MYB variation, ameliorates the clinical severity in beta-thalassemia. This variant has been shown to be associated with HbF levels. It has been shown that there is an odds ratio of 5 for having a less severe form of beta-thalassemia with the high-HbF variant (Galanello S. et al., 2009, Blood, in press).

The search for treatment aimed at reduction of globin chain imbalance in patients with β-hemoglobinopathies has focused on the pharmacologic manipulation of fetal hemoglobin (α2γ2; HbF). The important therapeutic potential of such approaches is indicated by observations of the mild phenotype of individuals with co-inheritance of both homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of fetal hemoglobin. Furthermore, it has been observed that certain populations of adult patients with β chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease (Pembrey, et al., Br. J. Haematol. 40: 415-429 (1978)). It is now accepted that β-hemoglobinopathies, such as sickle cell anemia and the β-thalassemias, are ameliorated by increased HbF production. (Reviewed in Jane and Cunningham Br. J. Haematol. 102: 415-422 (1998) and Bunn, N. Engl. J. Med. 328: 129-131 (1993)).

While the molecular mechanisms controlling the in vivo developmental switch from γ- to β-globin gene expression are currently unknown, there is accumulating evidence that external factors can influence γ-globin gene expression. The first group of compounds discovered having HbF reactivation activity were cytotoxic drugs. The ability to cause de novo synthesis of HbF by pharmacological manipulation was first shown using 5-azacytidine in experimental animals (DeSimone, Proc Natl Acad Sci USA. 79(14):4428-31 (1982)). Subsequent studies confirmed the ability of 5-azacytidine to increase HbF in patients with β-thalassemia and sickle cell disease (Ley, et al., N. Engl. J. Medicine, 307: 1469-1475 (1982), and Ley, et al., Blood 62: 370-380 (1983)). Additional experiments demonstrated that baboons treated with cytotoxic doses of arabinosylcytosine (ara-C) responded with striking elevations of F-reticulocytes (Papayannopoulou et al., Science. 224(4649):617-9 (1984)), and that treatment with hydroxyurea led to induction of γ-globin in monkeys or baboons (Letvin et. al., N Engl J Med. 310(14):869-73 (1984)).

The second group of compounds investigated for the ability to cause HbF reactivation activity was short chain fatty acids. The initial observation in fetal cord blood progenitor cells led to the discovery that γ-aminobutyric acid can act as a fetal hemoglobin inducer (Perrine et al., Biochem Biophys Res Commun. 148(2):694-700 (1987)). Subsequent studies showed that butyrate stimulated globin production in adult baboons (Constantoulakis et al., Blood. December; 72(6):1961-7 (1988)), and it induced γ-globin in erythroid progenitors in adult animals or patients with sickle cell anemia (Perrine et al., Blood. 74(1):454-9 (1989)). Derivatives of short chain fatty acids such as phenylbutyrate (Dover et al., Br J Haematol. 88(3):555-61 (1994)) and valproic acid (Liakopoulou et al., 1: Blood. 186(8):3227-35 (1995)) also have been shown to induce HbF in vivo. Given the large number of short chain fatty acid analogs or derivatives of this family, there are a number of potential compounds of this family more potent than butyrate. Phenylacetic and phenylalkyl acids (Torkelson et al., Blood Cells Mol Dis. 22(2):150-8. (1996)), which were discovered during subsequent studies, were considered potential HbF inducers as they belonged to this family of compounds. Presently, however, the use of butyrate or its analogs in sickle cell anemia and β-thalassemia remains experimental and cannot be recommended for treatment outside of clinical trials.

Clinical trials aimed at reactivation of fetal hemoglobin synthesis in sickle cell anemia and β-thalassemia have included short term and long term administration of such compounds as 5-azacytidine, hydroxyurea, recombinant human erythropoietin, and butyric acid analogs, as well as combinations of these agents. Following these studies, hydroxyurea was used for induction of HbF in humans and later became the first and only drug approved by the Food and Drug Administration (FDA) for the treatment of hemoglobinopathies. However, varying drawbacks have contraindicated the long term use of such agents or therapies, including unwanted side effects and variability in patient responses. For example, while hydroxyurea stimulates HbF production and has been shown to clinically reduce sickling crisis, it is potentially limited by myelotoxicity and the risk of carcinogenesis. Potential long term carcinogenicity would also exist in 5-azacytidine-based therapies. Erythropoietin-based therapies have not proved consistent among a range of patient populations. The short half-lives of butyric acid in vivo have been viewed as a potential obstacle in adapting these compounds for use in therapeutic interventions. Furthermore, very high dosages of butyric acid are necessary for inducing γ-globin gene expression, requiring catheterization for continuous infusion of the compound. Moreover, these high dosages of butyric acid can be associated with neurotoxicity and multiorgan damage (Blau, et al., Blood 81: 529-537 (1993)). While even minimal increases in HbF levels are helpful in sickle cell disease, β-thalassemias require a much higher increase that is not reliably, or safely, achieved by any of the currently used agents (Olivieri, Seminars in Hematology 33: 24-42 (1996)).

Identifying natural regulators of HbF induction and production could provide a means to devise therapeutic interventions that overcome the various drawbacks of the compounds described above. Recent genome-wide association studies have yielded insights into the genetic basis of numerous complex diseases and traits (McCarthy et al., Nat Rev Genet 9, 356 (2008) and Manolio et. al. J Clin Invest 118, 1590 (2008)). However, in the vast majority of instances, the functional link between a genetic association and the underlying pathophysiology remains to be uncovered. The level of fetal hemoglobin (HbF) is inherited as a quantitative trait and clinically important, given its above-mentioned and well-characterized role in ameliorating the severity of the principal β-hemoglobinopathies, sickle cell disease and β-thalassemia (Nathan et. al., Nathan and Oski's hematology of infancy and childhood ed. 6th, pp. 2 v. (xiv, 1864, xli p.) 2003)). Two genome-wide association studies have identified three major loci containing a set of five common single nucleotide polymorphisms (SNPs) that account for ~20% of the variation in HbF levels (Lettre et al., Proc Natl Acad Sci USA (2008); Uda et al., Proc Natl Acad Sci USA 105, 1620 (2008); Menzel et al., Nat Genet 39, 1197 (2007)). Moreover, several of these variants appear to predict the clinical severity of sickle cell disease (Lettre et al., Proc Natl Acad Sci USA (2008)) and at least one of these SNPs may also affect clinical outcome in β-thalassemia (Uda et al., Proc Natl Acad Sci USA 105, 1620 (2008)). The SNP with the largest effect size, explaining over 10% of the variation in HbF, is located in the second intron of a gene on chromosome 2, BCL11A. Whereas BCL11A, a C2H2-type zinc finger transcription factor, has been investigated for its role in lymphocyte development (Liu et al., Nat Immunol 4, 525 (2003) and Liu et al., Mol Cancer 5, 18 (2006)), its role in red blood cell production or globin gene regulation has not been previously assessed.

At the onset of the recombinant DNA era, studies of globin gene structure provided a strong molecular foundation for interrogating the fetal globin switch. Considerable effort has focused on delineating the cis-elements within the β-globin locus necessary for proper regulation of the genes within the β-like globin cluster. These studies relied on naturally occurring mutations and deletions that dramatically influence HbF levels in adults, and have been complemented by generation of transgenic mice harboring portions of the cluster (Nathan et. al., Nathan and Oski's hematology of infancy and childhood ed. 6th, pp. 2 v. (xiv, 1864, xli p.) 2003) and G. Stamatoyannopoulos, Exp Hematol 33, 259 (2005)). Although the precise cis-elements required for globin switching remain ill-defined, findings in transgenic mice have strongly indicated that the γ-globin genes are autonomously silenced in the adult stage, a finding that is most compatible with the absence of fetal-stage specific activators or the presence of a stage-specific repressor. The results of recent genetic association studies provide candidate genes to interrogate for their involvement in control of the γ-globin genes, such as BCL11A.

As used herein, treating or reducing a risk of developing a hemoglobinopathy in a subject means to ameliorate at least one symptom of hemoglobinopathy. In one aspect, the invention features methods of treating, e.g., reducing severity or progression of, a hemoglobinopathy in a subject. In another aspect, the methods can also be used to reduce a risk of developing a hemoglobinopathy in a subject, delaying the onset of symptoms of a hemoglobinopathy in a subject, or increasing the longevity of a subject having a hemoglobinopathy. In one aspect, the methods can include selecting a subject on the basis that they have, or are at risk of developing, a hemoglobinopathy, but do not yet have a hemoglobinopathy, or a subject with an underlying hemoglobinopathy. Selection of a subject can include detecting symptoms of a hemoglobinopathy, a blood test, genetic testing, or clinical recordings. If the results of the test(s) indicate that the subject has a hemoglobinopathy, the methods also include administering the compositions described herein, thereby treating, or reducing the risk of developing, a hemoglobinopathy in the subject. For example, a subject who is diagnosis of SCD with genotype HbSS, HbS/β0 thalassemia, HbSD, or HbSO, and/or HbF <10% by electrophoresis.

As used herein, the term "hemoglobinopathy" refers to a condition involving the presence of an abnormal hemoglobin molecule in the blood. Examples of hemoglobinopathies include, but are not limited to, SCD and THAL. Also included are hemoglobinopathies in which a combination of abnormal hemoglobins is present in the blood (e.g., sickle cell/Hb-C disease). An exemplary example of such a disease includes, but is not limited to, SCD and THAL. SCD and THAL and their symptoms are well-known in the art and are described in further detail below. Subjects can be diagnosed as having a hemoglobinopathy by a health care provider, medical caregiver, physician, nurse, family member, or acquaintance, who recognizes, appreciates, acknowledges, determines, concludes, opines, or decides that the subject has a hemoglobinopathy.

The term "SCD" is defined herein to include any symptomatic anemic condition which results from sickling of red blood cells. Manifestations of SCD include: anemia; pain; and/or organ dysfunction, such as renal failure, retinopathy, acute-chest syndrome, ischemia, priapism, and stroke. As used herein the term "SCD" refers to a variety of clinical problems attendant upon SCD, especially in those subjects who are homozygotes for the sickle cell substitution in HbS. Among the constitutional manifestations referred to herein by use of the term of SCD are delay of growth and development, an increased tendency to develop serious infections, particularly due to pneumococcus, marked impairment of splenic function, preventing effective clearance of circulating bacteria, with recurrent infarcts and eventual destruction of splenic tissue. Also included in the term "SCD" are acute episodes of musculoskeletal pain, which affect primarily the lumbar spine, abdomen, and femoral shaft, and which are similar in mechanism and in severity. In adults, such attacks commonly manifest as mild or moderate bouts of short duration every few weeks or months interspersed with agonizing attacks lasting 5 to 7 days that strike on average about once a year. Among events known to trigger such crises are acidosis, hypoxia, and dehydration, all of which potentiate intracellular polymerization of HbS (J. H. Jandl, Blood: Textbook of Hematology, 2nd Ed., Little, Brown and Company, Boston, 1996, pages 544-545).

As used herein, "THAL" refers to a hereditary disorder characterized by defective production of hemoglobin. In one embodiment, the term encompasses hereditary anemias that occur due to mutations affecting the synthesis of hemoglobins. In other embodiments, the term includes any symptomatic anemia resulting from thalassemic conditions such as severe or β-thalassemia, thalassemia major, thalassemia intermedia, α-thalassemias such as hemoglobin H disease. β-thalassemias are caused by a mutation in the β-globin chain, and can occur in a major or minor form. In the major form of β-thalassemia, children are normal at birth, but develop anemia during the first year of life. The mild form of β-thalassemia produces small red blood cells. Alpha-thalassemias are caused by deletion of a gene or genes from the globin chain.

By the phrase "risk of developing disease" is meant the relative probability that a subject will develop a hemoglobinopathy in the future as compared to a control subject or population (e.g., a healthy subject or population). For example, an individual carrying the genetic mutation associated with SCD, an A to T mutation of the β-globin gene, and whether the individual in heterozygous or homozygous for that mutation increases that individual's risk.

Hematopoietic Progenitor Cells

In one embodiment, the hematopoietic progenitor cell is contacted ex vivo or in vitro. In a specific embodiment, the cell being contacted is a cell of the erythroid lineage. In one embodiment, the cell composition comprises cells having decreased BCL11A expression.

"Hematopoietic progenitor cell" as the term is used herein, refers to cells of a stem cell lineage that give rise to all the blood cell types including the myeloid (monocytes and macrophages, neutrophils, basophils, eosinophils, erythrocytes, megakaryocytes/platelets, dendritic cells), and the lymphoid lineages (T-cells, B-cells, NK-cells). A "cell of the erythroid lineage" indicates that the cell being contacted is a cell that undergoes erythropoiesis such that upon final differentiation it forms an erythrocyte or red blood cell (RBC). Such cells belong to one of three lineages, erythroid, lymphoid, and myeloid, originating from bone marrow hematopoietic progenitor cells. Upon exposure to specific growth factors and other components of the hematopoietic microenvironment, hematopoietic progenitor cells can mature through a series of intermediate differentiation cellular types, all intermediates of the erythroid lineage, into RBCS. Thus, cells of the "erythroid lineage", as the term is used herein, comprise hematopoietic progenitor cells, rubriblasts, prorubricytes, erythroblasts, metarubricytes, reticulocytes, and erythrocytes.

In some embodiment, the hematopoietic progenitor cell has at least one of the cell surface marker characteristic of hematopoietic progenitor cells: CD34+, CD59+, Thy1/CD90+, CD38lo/−, and C-kit/CD117+. Preferably, the hematopoietic progenitor cells have several of these markers.

In some embodiments, the hematopoietic progenitor cells of the erythroid lineage have the cell surface marker characteristic of the erythroid lineage: CD71 and Ter119.

Stem cells, such as hematopoietic progenitor cells, are capable of proliferation and giving rise to more progenitor cells having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a hematopoietic progenitor cell), which in turn can differentiate into other types of precursor cells further down the pathway (such as an erythrocyte precursor), and then to an end-stage differentiated cell, such as an erythrocyte, which plays a characteristic role in a certain tissue type, and may or may not retain the capacity to proliferate further.

Induced Pluripotent Stem Cells

In some embodiments, the genetic engineered human cells described herein are derived from isolated pluripotent stem cells. An advantage of using iPSCs is that the cells can be derived from the same subject to which the progenitor cells are to be administered. That is, a somatic cell can be obtained from a subject, reprogrammed to an induced pluripotent stem cell, and then re-differentiated into a hematopoietic progenitor cell to be administered to the subject (e.g., autologous cells). Since the progenitors are essentially derived from an autologous source, the risk of engraftment rejection or allergic responses is reduced compared to the use of cells from another subject or group of subjects. In some embodiments, the hematopoietic progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Reprogramming methodologies for generating pluripotent cells using defined combinations of transcription factors have been described induced pluripotent stem cells. Yamanaka and Takahashi converted mouse somatic cells to ES cell-like cells with expanded developmental potential by the direct transduction of Oct4, Sox2, Klf4, and c-Myc (Takahashi and Yamanaka, 2006). iPSCs resemble ES cells as they restore the pluripotency-associated transcriptional circuitry and muc of the epigenetic landscape. In addition, mouse iPSCs satisfy all the standard assays for pluripotency: specifically, in vitro differentiation into cell types of the three germ layers, teratoma formation, contribution to chimeras, germline transmission (Maherali and Hochedlinger, 2008), and tetraploid complementation (Woltjen et al., 2009).

Subsequent studies have shown that human iPS cells can be obtained using similar transduction methods (Lowry et al., 2008; Park et al., 2008; Takahashi et al., 2007; Yu et al., 2007b), and the transcription factor trio, OCT4, SOX2, and NANOG, has been established as the core set of transcription factors that govern pluripotency (Jaenisch and Young, 2008). The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (–)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for Reprogramming

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of hematopoietic progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; □□III-tubulin; □-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fth117; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Genome Editing and DNA-Targeting Endonucleases

As used herein, the term "genome editing" refers to a reverse genetics method using artificially engineered nucleases to cut and create specific double-stranded breaks at a desired location(s) in the genome, which are then repaired by cellular endogenous processes such as, homologous recombination (HR), homology directed repair (HDR) and non-homologous end-joining (NHEJ). NHEJ directly joins the DNA ends in a double-stranded break, while HDR utilizes a homologous sequence as a template for regenerating the missing DNA sequence at the break point.

Genome editing cannot be performed using traditional restriction endonucleases since most restriction enzymes recognize a few base pairs on the DNA as their target and the probability is very high that the recognized base pair combination will be found in many locations across the genome resulting in multiple cuts (i.e., not limited to a desired location). To overcome this challenge and create site-specific double-stranded breaks, several distinct classes of nucleases have been discovered and bioengineered to date. These are the meganucleases, Zinc finger nucleases (ZFNs), Cas9/CRISPR system, and transcription-activator like effector nucleases (TALENs).

Meganucleases are commonly grouped into four families: the LAGLIDADG family ("LAGLIDADG" disclosed as SEQ ID NO: 144), the GIY-YIG family, the His-Cys box family and the HNH family. These families are characterized by structural motifs, which affect catalytic activity and recognition sequence. For instance, members of the LAGLIDADG family ("LAGLIDADG" disclosed as SEQ ID NO:

144) are characterized by having either one or two copies of the conserved LAGLIDADG motif (see Chevalier et al. (2001), Nucleic Acids Res. 29(18): 3757-3774). The LAGLIDADG meganucleases ("LAGLIDADG" disclosed as SEQ ID NO: 144) with a single copy of the LAGLI-DADG motif (SEQ ID NO: 144) form homodimers, whereas members with two copies of the LAGLIDADG (SEQ ID NO: 144) are found as monomers. Similarly, the GIY-YIG family members have a GIY-YIG module, which is 70-100 residues long and includes four or five conserved sequence motifs with four invariant residues, two of which are required for activity (see Van Roey et al. (2002), Nature Struct. Biol. 9: 806-811). The His-Cys box meganucleases are characterized by a highly conserved series of histidines and cysteines over a region encompassing several hundred amino acid residues (see Chevalier et al. (2001), Nucleic Acids Res. 29(18): 3757-3774). In the case of the NHN family, the members are defined by motifs containing two pairs of conserved histidines surrounded by asparagine residues (see Chevalier et al. (2001), Nucleic Acids Res. 29(18): 3757-3774). The four families of meganucleases are widely separated from one another with respect to conserved structural elements and, consequently, DNA recognition sequence specificity and catalytic activity.

Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision BioSciences' Directed Nuclease Editor™ genome editing technology.

ZFNs and TALENs restriction endonuclease technology utilizes a non-specific DNA cutting enzyme which is linked to a specific DNA sequence recognizing peptide(s) such as zinc fingers and transcription activator-like effectors (TALEs). Typically an endonuclease whose DNA recognition site and cleaving site are separate from each other is selected and the its cleaving portion is separated and then linked to a sequence recognizing peptide, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically happen in repeats that are 3 bp apart and are found in diverse combinations in a variety of nucleic acid interacting proteins such as transcription factors. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs for use with the methods and compositions described herein can be obtained commercially from e.g., Sangamo Biosciences™ (Richmond, Calif.).

It is contemplated herein that the Cas9/CRISPR system of genome editing be employed with the methods and compositions described herein. Clustered regularly interspaced short palindromic repeats (CRISPR)/CRISPR-associated (Cas) systems is useful for RNA-programmable genome editing (see e.g., Jinek, M. et al. Science (2012) 337(6096): 816-821).

Trans-activating crRNA (tracrRNA) is a small trans-encoded RNA. It was first discovered in the human pathogen *Streptococcus pyogenes*. (see Deltcheva E, et al. (2011). Nature 471 (7340): 602-7). In bacteria and archaea, CRISPR/Cas (clustered, regularly interspaced short palindromic repeats/CRISPR-associated proteins) constitute an RNA-mediated defense system which protects against viruses and plasmids. This defensive pathway has three steps. First a copy of the invading nucleic acid is integrated into the CRISPR locus. Next, CRISPR RNAs (crRNAs) are transcribed from this CRISPR locus. The crRNAs are then incorporated into effector complexes, where the crRNA guides the complex to the invading nucleic acid and the Cas proteins degrade this nucleic acid. (See Terns MP and Terns RM (2011). Curr Opin Microbiol 14 (3): 321-7). There are several pathways of CRISPR activation, one of which requires a tracrRNA which plays a role in the maturation of crRNA. TracrRNA is complementary to and base pairs with a pre-crRNA forming an RNA duplex. This is cleaved by RNase III, an RNA-specific ribonuclease, to form a crRNA/tracrRNA hybrid. This hybrid acts as a guide for the endonuclease Cas9, which cleaves the invading nucleic acid. (see Deltcheva E, et al. supra; Jinek M, et al. (2012), Science 337 (6096): 816-21; and Brouns S J (2012), Science 337 (6096): 808-9).

Alternatively, genome editing can be performed using recombinant adeno-associated virus (rAAV) based genome engineering, which is a genome-editing platform centered around the use of rAAV vectors that enables insertion, deletion or substitution of DNA sequences into the genomes of live mammalian cells. The rAAV genome is a single-stranded deoxyribonucleic acid (ssDNA) molecule, either positive- or negative-sensed, which is about 4.7 kilobase long. These single-stranded DNA viral vectors have high transduction rates and have a unique property of stimulating endogenous homologous recombination in the absence of causing double strand DNA breaks in the genome. One of skill in the art can design a rAAV vector to target a desired genomic locus and perform both gross and/or subtle endogenous gene alterations in a cell, such as a deletion. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Pharmaceutically Acceptable Carriers

The methods of administering human hematopoietic progenitors cells or genetic engineered cells described herein or their progeny to a subject as described herein involve the use of therapeutic compositions comprising hematopoietic progenitor cells. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired.

In general, the hematopoietic progenitor cells described herein or genetic engineered cells described herein or their progeny are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the hematopoietic progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

In some embodiments, the compositions of isolated genetic engineered cells described further comprises a pharmaceutically acceptable carrier. In one embodiment, the pharmaceutically acceptable carrier does not include tissue or cell culture media.

In some embodiments, the compositions of nucleic acid molecules described further comprises a pharmaceutically acceptable carrier. In one embodiment, the pharmaceutically acceptable carrier does not include tissue or cell culture media.

In some embodiments, the compositions of vector comprising the nucleic acid molecules described further comprises a pharmaceutically acceptable carrier. In one embodiment, the pharmaceutically acceptable carrier does not include tissue or cell culture media.

Administration & Efficacy

As used herein, the terms "administering," "introducing" and "transplanting" are used interchangeably in the context of the placement of cells, e.g. hematopoietic progenitor cells, as described herein into a subject, by a method or route which results in at least partial localization of the introduced cells at a desired site, such as a site of injury or repair, such that a desired effect(s) is produced. The cells e.g. hematopoietic progenitor cells, or their differentiated progeny can be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of hematopoietic progenitor cells or engineered cells with reduced BCL11A expression is administered via a systemic route of administration, such as an intraperitoneal or intravenous route.

When provided prophylactically, hematopoietic progenitor cells or engineered cells with reduced BCL11A expression described herein can be administered to a subject in advance of any symptom of a hemoglobinopathy, e.g., prior to the switch from fetal γ-globin to predominantly β-globin. Accordingly, the prophylactic administration of a hematopoietic progenitor cell population serves to prevent a hemoglobinopathy, as disclosed herein.

When provided therapeutically, hematopoietic progenitor cells are provided at (or after) the onset of a symptom or indication of a hemoglobinopathy, e.g., upon the onset of sickle cell disease.

In some embodiments of the aspects described herein, the hematopoietic progenitor cell population or engineered cells with reduced BCL11A expression being administered according to the methods described herein comprises allogeneic hematopoietic progenitor cells obtained from one or more donors. As used herein, "allogeneic" refers to a hematopoietic progenitor cell or biological samples comprising hematopoietic progenitor cells obtained from one or more different donors of the same species, where the genes at one or more loci are not identical. For example, a hematopoietic progenitor cell population or engineered cells with reduced BCL11A expression being administered to a subject can be derived from umbilical cord blood obtained from one more unrelated donor subjects, or from one or more non-identical siblings. In some embodiments, syngeneic hematopoietic progenitor cell populations can be used, such as those obtained from genetically identical animals, or from identical twins. In other embodiments of this aspect, the hematopoietic progenitor cells are autologous cells; that is, the hematopoietic progenitor cells are obtained or isolated from a subject and administered to the same subject, i.e., the donor and recipient are the same.

For use in the various aspects described herein, an effective amount of hematopoietic progenitor cells or engineered cells with reduced BCL11A expression, comprises at least $10^2$ cells, at least $5 \times 10^2$ cells, at least $10^3$ cells, at least $5 \times 10^3$ cells, at least $10^4$ cells, at least $5 \times 10^4$ cells, at least $10^5$ cells, at least $2 \times 10^5$ cells, at least $3 \times 10^5$ cells, at least $4 \times 10^5$ cells, at least $5 \times 10^5$ cells, at least $6 \times 10^5$ hematopoietic progenitor cells, at least $7 \times 10^5$ cells, at least $8 \times 10^5$ cells, at least $9 \times 10^5$ cells, at least $1 \times 10^6$ cells, at least $2 \times 10^6$ cells, at least $3 \times 10^6$ cells, at least $4 \times 10^6$ cells, at least $5 \times 10^6$ cells, at least $6 \times 10^6$ cells, at least $7 \times 10^6$ cells, at least $8 \times 10^6$ cells, at least $9 \times 10^6$ cells, or multiples thereof. The hematopoietic progenitor cells or engineered cells with reduced BCL11A expression can be derived from one or more donors, or can be obtained from an autologous source. In some embodiments of the aspects described herein, the hematopoietic progenitor cells are expanded in culture prior to administration to a subject in need thereof.

In one embodiment, the term "effective amount" as used herein refers to the amount of a population of human hematopoietic progenitor cells or their progeny needed to alleviate at least one or more symptom of a hemoglobinopathy, and relates to a sufficient amount of a composition to provide the desired effect, e.g., treat a subject having a hemoglobinopathy. The term "therapeutically effective amount" therefore refers to an amount of hematopoietic progenitor cells, or genetic engineered cells described herein or their progeny or a composition comprising hematopoietic progenitor cells, or genetic engineered cells described herein or their progeny that is sufficient to promote a particular effect when administered to a typical subject, such as one who has or is at risk for a hemoglobinopathy. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

As used herein, "administered" refers to the delivery of a hematopoietic stem cell composition as described herein into a subject by a method or route which results in at least partial localization of the cell composition at a desired site. A cell composition can be administered by any appropriate route which results in effective treatment in the subject, i.e. administration results in delivery to a desired location in the subject where at least a portion of the composition delivered, i.e. at least $1 \times 10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. For the delivery of cells, administration by injection or infusion is generally preferred.

In one embodiment, the cells as described herein are administered systemically. The phrases "systemic administration," "administered systemically", "peripheral administration" and "administered peripherally" as used herein refer to the administration of a population of hematopoietic progenitor cells other than directly into a target site, tissue, or organ, such that it enters, instead, the subject's circulatory system and, thus, is subject to metabolism and other like processes.

The efficacy of a treatment comprising a composition as described herein for the treatment of a hemoglobinopathy can be determined by the skilled clinician. However, a treatment is considered "effective treatment," as the term is used herein, if any one or all of the signs or symptoms of, as but one example, levels of fetal β-globin are altered in a beneficial manner, other clinically accepted symptoms or markers of disease are improved or ameliorated, e.g., by at least 10% following treatment with an inhibitor. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of sepsis; or (2) relieving the disease, e.g., causing regression of symptoms; and (3) preventing or reducing the likelihood of the development of infection or sepsis.

The treatment according to the present invention ameliorates one or more symptoms associated with a β-globin disorder by increasing the amount of fetal hemoglobin in the individual. Symptoms typically associated with a hemoglobinopathy, include for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

In one embodiment, the hematopoietic progenitor cell is contacted ex vivo or in vitro with a DNA targeting endonuclease, and the cell or its progeny is administered to the mammal (e.g., human). In a further embodiment, the hematopoietic progenitor cell is a cell of the erythroid lineage. In one embodiment, a composition comprising a hematopoietic progenitor cell that was previously contacted with a DNA-targeting endonuclease and a pharmaceutically acceptable carrier and is administered to a mammal.

In one embodiment, any method known in the art can be used to measure an increase in fetal hemoglobin expression, e.g., Western Blot analysis of fetal hemoglobin protein and quantifying mRNA of fetal γ-globin.

In one embodiment, the hematopoietic progenitor cell is contacted with a DNA-targeting endonuclease in vitro, or ex vivo. In one embodiment, the cell is of human origin (e.g., an autologous or heterologous cell). In one embodiment, the composition causes an increase in fetal hemoglobin expression.

The present invention can be defined in any of the following numbered sub-paragraphs:

[1] A nucleic acid molecule comprising a nucleic acid sequence that is: (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60,716,189 to 60,728,612.

[2] The nucleic acid molecule of sub-paragraph 1, wherein the nucleic acid sequence is excludes the entire BCL11A enhancer functional regions.

[3] The nucleic acid molecule of sub-paragraph 1, wherein the nucleic acid sequence is excludes the entire SEQ. ID. NOS: 136, 137 and 138.

[4] The nucleic acid molecule of sub-paragraph 1, wherein the nucleic acid sequence is short and is greater than or equal to 13 base pair (bp).

[5] The nucleic acid molecule of sub-paragraph 1, wherein the nucleic acid sequence is about 13-30 bp.

[6] The nucleic acid molecule of sub-paragraph 1, wherein the nucleic acid sequence is about 20 bp.

[7] The nucleic acid molecule of sub-paragraph 1, wherein the nucleic acid sequence is selected from the group consisting of SEQ ID NOS: 1-94.

[8] The nucleic acid molecule of sub-paragraph 1, wherein the nucleic acid sequence further comprising a trans-activating CRISPR RNA (tracrRNA) sequence.

[9] The nucleic acid molecule of sub-paragraph 1, wherein the nucleic acid molecule is a single guide RNA (sgRNA).

[10] The nucleic acid molecule of sub-paragraph 1, wherein the nucleic acid molecule comprises a vector.

[11] The nucleic acid molecule of sub-paragraph 10, wherein the vector is a sgRNA expression vector.

[12] A vector comprising a nucleic acid sequence which is: (a) complementary to the plus or minus strand of the human chromosome 2 at location 60725424 to 60725688 (+55 functional region); or (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid acid sequence excludes the entire human chromosome 2 and also excludes the genomic DNA sequence on the human chromosome 2 from location 60,716,189 to 60,728,612.

[13] The vector of sub-paragraph 12, wherein the nucleic acid sequence is excludes the entire BCL11A enhancer functional regions.

[14] The vector of sub-paragraph 12, wherein the nucleic acid sequence is excludes the entire SEQ. ID. NOS: 136, 137 and 138.

[15] The vector of sub-paragraph 12, wherein the nucleic acid sequence is short and is greater than or equal to 13 base pair (bp).

[16] The vector of sub-paragraph 12, wherein the nucleic acid sequence is about 13-30 base pair (bp).

[17] The vector of sub-paragraph 12, wherein the nucleic acid sequence is about 20 bp.

[18] The vector of sub-paragraph 12, wherein the nucleic acid sequence is selected from the group consisting of SEQ ID NOS: 1-94.

[19] The vector of sub-paragraph 12, wherein the nucleic acid sequence further comprising a trans-activating CRISPR RNA (tracrRNA) sequence.

[20] The vector of claim 12, wherein the vector is a sgRNA expression vector.

[21] A method for producing a progenitor cell having decreased BCL11A mRNA or protein expression, the method comprising contacting an isolated progenitor cell with a nucleic acid molecule of any one of sub-paragraphs 1-11 or a vector of any one of sub-paragraphs 12-20.

[22] A method for producing a progenitor cell having decreased BCL11A mRNA or BCL11A protein expression, the method comprising contacting an isolated progenitor cell with an agent that binds the human BCL11A enhancer functional regions located on chromosome 2 at location 60725424 to 60725688 (+55 functional region), at location 60722238 to 60722466 (+58 functional region), and/or at location 60718042 to 60718186 (+62 functional region), where the agent binds: (a) to the plus or minus strand of the human chromosome 2 at location 60725424 to 60725688 (+55 functional region); or (b) to the plus or minus strand of the human chromosome 2 at location 60722238 to 60722466 (+58 functional region); or (c) to the plus or minus strand of the human chromosome 2 at location 60718042 to 60718186 (+62 functional region); wherein the human chromosome 2 is that according to UCSC Genome Browser hg 19 human genome assembly, thereby reducing the mRNA or protein expression of BCL11A.

[23] The method of sub-paragraph 21 or 22, further comprising contacting the same isolated progenitor cell with at least a DNA-targeting endonuclease or a vector carrying the coding sequence of a DNA-targeting endonuclease.

[24] A method for producing an isolated genetic engineered human cell having at least one genetic modification comprising contacting an isolated cell with an effective amount of a composition comprising a nucleic acid molecule of any one of sub-paragraphs 1-11 or a vector of any one of sub-paragraphs 12-20, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region), causing at least one genetic modification therein, wherein the human chromosome 2 is that according to UCSC Genome Browser hg 19 human genome assembly.

[25] The method of any one of sub-paragraphs 22-24, wherein the at least a DNA-targeting endonuclease is a Cas (CRISPR-associated) protein.

[26] The method of sub-paragraph 25, the Cas protein is Cas9.

[27] The method of any one of sub-paragraphs 21-26, wherein the isolated progenitor cell or isolated cell is a hematopoietic progenitor cell or a hematopoietic stem cell.

[28] The method of sub-paragraph 27, wherein the hematopoietic progenitor is a cell of the erythroid lineage.

[29] The method of any one of sub-paragraphs 21-26, wherein the isolated progenitor cell or isolated cell is an induced pluripotent stem cell.

[30] The method of any one of sub-paragraphs 21-29, wherein the isolated progenitor cell or isolated cell is contacted ex vivo or in vitro.

[31] The method of any one of sub-paragraphs 21-30, wherein the contacted progenitor cell or contacted cell acquires at least one genetic modification.

[32] The method of sub-paragraph 29, wherein the at least one genetic modification is a deletion, insertion or substitution of the nucleic acid sequence.

[33] The method of any one of sub-paragraphs 21-32, wherein the least one genetic modification is located between chromosome 2 location 60725424 to 60725688 (+55 functional region), and/or at location 60722238 to 60722466 (+58 functional region), and/or at location 60718042 to 60718186 (+62 functional region).

[34] The method of any one of sub-paragraphs 21-32, wherein the contacted progenitor cell or contacted cell acquires at least one epigenetic modification in the BCL11A enhancer functional region.

[35] The method of sub-paragraph 34, wherein the at least one epigenetic modification is selected from the group consisting of alteration of DNA methylation, histone tail modification, histone subunit composition and nucleosome positioning.

[36] The method of sub-paragraph 34 or 35, wherein the at least one epigenetic modification is located between chromosome 2 location 60725424 to 60725688 (+55 functional region), and/or at location 60722238 to 60722466 (+58 functional region), and/or at location 60718042 to 60718186 (+62 functional region).

[37] An isolated genetic engineered human cell having at least one genetic modification on chromosome 2 location 60725424 to 60725688 (+55 functional region), and/or at location 60722238 to 60722466 (+58 functional region), and/or at location 60718042 to 60718186 (+62 functional region) according to sub-paragraphs 21-36.

[38] A composition comprising isolated genetic engineered human cells of sub-paragraph 37.

[39] A method of increasing fetal hemoglobin levels in a cell, the method comprising the steps of: contacting an isolated cell with an effective amount of a composition comprising a nucleic acid molecule of any one of sub-paragraphs 1-11 or a vector of any one of sub-paragraphs 12-20, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region), causing at least one genetic modification therein, whereby fetal hemoglobin expression is increased in said cell, or its progeny, relative to said cell prior to said contacting, and wherein the human chromosome 2 is that according to UCSC Genome Browser hg 19 human genome assembly.

[40] The method of sub-paragraph 39, wherein the isolated cell is a hematopoietic progenitor cell or hematopoietic stem cell.

[41] The method of sub-paragraph 39 or 40, wherein the hematopoietic progenitor cell is a cell of the erythroid lineage.

[42] The method of sub-paragraph 39, wherein the isolated cell is an induced pluripotent stem cell.

[43] The method of any one of sub-paragraphs 39-42, wherein the isolated cell, hematopoietic progenitor cell, hematopoietic stem cell or induced pluripotent stem cell is contacted ex vivo or in vitro.

[44] The method of any one of sub-paragraphs 39-43, wherein the at least a DNA-targeting endonuclease is a Cas (CRISPR-associated) protein.

[45] The method of sub-paragraph 44, the Cas protein is Cas9.

[46] A method for increasing fetal hemoglobin levels in a mammal in need thereof, the method comprising the steps of contacting an isolated hematopoietic progenitor cell in said mammal with an effective amount of a composition comprising a nucleic acid molecule of any one of sub-paragraphs 1-11 or a vector of any one of sub-paragraphs 12-20, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region), causing at least one genetic modification therein, whereby fetal hemoglobin expression is increased in said mammal, relative to expression prior to said contacting, and wherein the human chromosome 2 is that according to UCSC Genome Browser hg 19 human genome assembly.

[47] A method for increasing fetal hemoglobin levels in a mammal in need thereof, the method comprising transplanting an isolated genetic engineered human cell of sub-paragraph 37 or a composition of sub-paragraph 38 into the mammal.

This invention is further illustrated by the following example which should not be construed as limiting. The contents of all references cited throughout this application, as well as the figures and table are incorporated herein by reference.

Example 1

The inventors have discovered and characterized regulatory elements of the BCL11A gene that are critical for its expression in erythroid lineage cells. Common genetic variants within these sequences are associated with fetal hemoglobin level and beta-globin disorder severity. These sequences comprise distal regulatory elements with an enhancer chromatin signature, possessing accessible chromatin, active histone marks, and occupancy by erythroid transcription factors. These elements interact with the BCL11A promoter and promote gene expression in erythroid cells but not other lineages that express BCL11A such as B-lymphocytes. These regulatory elements can be targeted for therapeutic purposes to achieve BCL11A inhibition and fetal hemoglobin reinduction. This can be achieved by mechanisms not limited to genome editing, nucleic acid or protein binding, and epigenetic modification. Advantages of this method include: disruption of a physiologic regulator of fetal hemoglobin level resulting in increased gamma-globin production and reduced beta-globin production; minimal effect on overall globin output or on red blood cell production or function; limitation of impact on cells outside of the erythroid lineage thus reducing potential toxicity.

Enhancers are classically described as distal genetic elements able to positively regulate gene expression in an orientation-independent manner in ectopic heterologous gain-of-function expression experiments[1]. These elements coordinate when, where, and how genes are expressed. Enhancer sequences bind transcription factors and chromatin regulators and are correlated with specific chromatin features including reduced DNA methylation, characteristic histone modifications, heightened chromatin accessibility, long-range promoter interactions, and bidirectional transcription. Recent chromatin mapping has demonstrated the abundance of distal regulatory elements bearing an enhancer chromatin signature[2-8].

The biologic importance of enhancers is underscored by gene expression studies showing the predictive power of enhancer profile on lineage-specific programs[9-12]. Highly marked and clustered enhancers (e.g. so-called strong enhancers, stretch enhancers, or super-enhancers) are particularly indicative of cellular identity and may help to infer lineage-specific regulatory factors[13-15]. Genome-wide association studies reveal enrichment of trait-associated variants in sequences bearing lineage-restricted enhancer signatures[7,13,6-19]. Enhancers display signs of evolutionary constraint as well as heightened turnover with evidence of positive selection[20-25].

Despite their importance, enhancers are typically defined by criteria unrelated to in situ functional requirement. Advances in putative enhancer mapping, as well as of large-scale oligonucleotide synthesis, facilitate enhancer reporter assays on a massively parallel scale, allowing a systematic evaluation of the functional significance of enhancer sequences[26-30]. Nonetheless, ectopic heterologous enhancer assays cannot address the necessity of an element in its native chromatin environment. The growing appreciation of the nonrandom distribution of distal elements both with respect to the linear genome (for example, into super-enhancer clusters) and within the three-dimensional nuclear environment emphasizes the importance of studying enhancers by perturbing their endogenous condition[15,31].

Insightful observations have been made by mutagenizing enhancers using traditional molecular genetic approaches[32,33]. However the low throughput of these classical methods constrains their widespread application. Furthermore the elevated turnover of many enhancer sequences between species may limit the ability to derive conclusions from nonhuman organisms regarding human gene regulation. Advances in genome editing technology make practical the facile modification of the human genome[34,35]. High-throughput clustered regularly interspaced palindromic repeat (CRISPR)-Cas9 studies have revealed novel genes required for various biologic processes[36-41]. Genome editing is likewise suitable for the study of non-coding genetic elements such as enhancers, although these experiments have previously been conducted at low-throughput[42-44].

Materials and Methods

Design and Synthesis of Human and Mouse Lentiviral sgRNA Libraries.

Every 20-mer sequence upstream of an NGG or NAG PAM sequence on the sense or anti-sense strand was identified for both the human and mouse orthologous +55, +58, and +62 DNase hypersensitive site (DHS) as well as BCL11A/Bcl11a exon 2 (FIGS. 6-11). Relative to the human hg19 reference genome, a reference was used with the following substitutions to approximate a common low-HbF associated haplotype: rs1427407-G, rs1896293-T, rs6706648-T, rs6738440-G, rs7606173-C. Each of the sgRNA oligos were synthesized as previously described 37,41,64 and cloned using a Gibson Assembly master mix (New England Biolabs) into lentiGuide-Puro (Addgene plasmid ID 52963) BsmBI digested, PCR purified, and dephosphorylated. Gibson Assembly products were transformed to electrocompetent E. Cloni® cells (Lucigen). Sufficient colonies were isolated to ensure ~90× library coverage for both human and mouse libraries. Plasmid libraries were deep sequenced (described below) to confirm representation.

To make lentivirus, HEK293T cells were cultured with Dulbecco's Modified Eagle's Medium (DMEM) (Life Technologies) supplemented with 10% fetal bovine serum (FBS) (Omega Scientific) and 2% penicillin-streptomycin (Life Technologies) in 15 cm tissue culture treated petri dishes. HEK293T were transfected at 80% confluence in 12 mL of media with 13.3 µg psPAX2, 6.7 µg VSV-G, and 20 µg of the lentiviral construct plasmid of interest using 180 µg of branched polyethylenimine (Sigma). Medium was changed 16-24 hours after transfection. Lentiviral supernatant was collected at 48 and 72 hours post-transfection and subsequently concentrated by ultracentrifugation (24,000 rpm for 2 hours at 4° C. with Beckman Coulter SW 32 Ti rotor).

Tiled Pooled CRISPR-Cas9 Screen for In Situ Functional Mapping the Human BCL11A Erythroid Enhancer.

HUDEP clone 2 (HUDEP-2) was utilized as previously described by from Nakamura and colleagues[49]. HUDEP-2 cells were expanded in StemSpan SFEM (Stem Cell Technologies) supplemented with $10^{-6}$ M dexamethasone (Sigma), 100 ng/mL human stem cell factor (SCF) (R&D), 3 IU/mL erythropoietin (Amgen), 1% L-glutamine (Life Technologies), and 2% penicillin/streptomycin (Life Technologies). 1 µg/mL doxycycline (Sigma) was included in the culture to induce expression of the human papilloma virus type 16 E6/E7 genes[49]. HUDEP-2 cells were differentiated in Iscove's Modified Dulbecco's Medium (IMDM) supplemented with 330 µg/mL holo-transferrin (Sigma), 10 µg/mL recombinant human insulin (Sigma), 2 IU/mL heparin (Sigma), 5% human solvent detergent pooled plasma AB (Rhode Island Blood Center), 3 IU/mL erythropoietin (Amgen), 100 ng/mL human stem cell factor (SCF) (R&D), 1 µg/mL doxycycline (Sigma), 1% L-glutamine (Life Technologies), and 2% penicillin/streptomycin (Life Technologies).

HUDEP-2 cells with stable Cas9 expression were transduced at low multiplicity with the human sgRNA library lentivirus pool while in expansion medium. Control transductions were performed to ensure transduction rate did not exceed 50%. Cell numbers were maintained throughout the experiment at levels adequate to exceed 1000× representation of the library. 10 µg/mL blasticidin (Sigma) and 1 µg/mL puromycin (Sigma) were added 24 hours after transduction to select for lentiviral library integrants in cells with Cas9. Cells were cultured in expansion media for one week followed by differentiation media for an additional week.

Intracellular staining was performed by fixing cells with 0.05% glutaraldehyde (grade II) (Sigma) for 10 minutes at room temperature. Cells were centrifuged for 5 minutes at 350 g and then resuspended in 0.1% Triton-X 100 (Life Technologies) for 5 minutes at room temperature for permeabilization. Triton X-100 was diluted with phosphate buffered saline (PBS) and then centrifuged at 350 g for 15 minutes. Cells were stained with anti-human antibodies for HbF (clone HbF-1 with FITC or APC conjugation; Life Technologies) and β-hemoglobin antibody (clone 37-8 with PerCP-Cy5 or PE conjugation; Santa Cruz) for 20 minutes in the dark. Cells were washed to remove unbound antibody prior to FACS analysis. 0.2 µg HbF and 2 µg of HbA (β-hemoglobin) antibodies were used per 5 million cells. Control cells exposed to a non-targeting sgRNA sample and BCL11A exon 2 were used as negative and positive controls respectively to establish flow cytometry conditions. Populations of cells with the top and bottom 10% of expression of HbF were sorted by FACS.

After sorting the HbF-high and HbF-low pools, library preparation and deep sequencing was performed as previously described[37]. Briefly, genomic DNA was extracted using the Qiagen Blood and Tissue kit. Herculase PCR reaction (Agilent) using lentiGuide-Puro specific primers including a handle sequence was performed as follows: Herculase II reaction buffer (1×), forward and reverse primers (0.5 µM each), dimethyl sulfoxide (DMSO) (8%), deoxynucleotide triphosphates (dNTPs) (0.25 mM each), Herculase II Fusion DNA Polymerase (0.5 reactions) using the following cycling conditions: 95° C. for 2 minutes; 20 cycles of 95° C. for 15 seconds, 60° C. for 20 seconds, 72° C. for 30 seconds; 72° C. for 5 minutes. Multiple reactions of no more than 200 ng each were used to amplify from 6.6 ug gDNA (~10e6 cell genomes) per pool. Samples were subjected to a second PCR using handle-specific primers to add adaptors and indexes to each sample using the following conditions: Herculase II reaction buffer (1×), forward and reverse primers (0.5 µM each), deoxynucleotide triphosphates (dNTPs) (0.25 mM each), Herculase II Fusion DNA Polymerase (0.5 reactions) with the following cycling conditions: 95° C. for 2 minutes; 25 cycles of 95° C. for 15 seconds, 60° C. for 20 seconds, 72° C. for 30 seconds; 72° C. for 5 minutes. PCR products were run on an agarose gel and the band of expected size was gel purified. Illumina MiSeq 150 bp paired end sequencing was performed.

sgRNA sequences present in the plasmid pool as well as in the HbF-high and HbF-low pools were enumerated. Reads were normalized to sequencing depth per library. Dropout score was determined by calculating (1) the ratio of normalized reads in the HbF-high compared to HbF-low pools; (2) $\log_2$ transformation; and (3) median of biological replicates. HbF enrichment score was determined by calculating (1) the ratio of normalized reads in the HbF-high compared to HbF-low pools; (2) $\log_2$ transformation; and (3) median of biological replicates. After exclusion of sgRNAs with dropout scores $<2^{-3}$ and NAG PAM sgRNAs, a Q-Q plot was made with a line fitted through the first and third quantiles using R software. sgRNA sequences were mapped to the human genome (hg19) with cleavage positions set to between positions 17 and 18 given PAM positions[21-23]. For visual comparisons to targeting sgRNAs, non-targeting sgRNAs were pseudomapped each separated by 5 bp.

Validation in Primary Human CD34+ Hematopoietic Stem and Progenitor Cells (IISPCs).

Primary human CD34+ HSPCs from G-CSF mobilized healthy adult donors were obtained from the Center of Excellence in Molecular Hematology at the Fred Hutchinson Cancer Research Center, Seattle, Wash. CD34+ HSPCs were subject to erythroid differentiation liquid culture as previously described[65]. Briefly, HSPCs were thawed on day 0 into erythroid differentiation medium (EDM) consisting of IMDM supplemented with 330 µg/mL holo-human transferrin (Sigma), 10 µg/mL recombinant human insulin (Sigma), 2 IU/mL heparin (Sigma), 5% human solvent detergent pooled plasma AB (Rhode Island Blood Center), 3 IU/mL erythropoietin (Amgen), 1% L-glutamine (Life Technologies), and 2% penicillin/streptomycin (Life Technologies). During days 0-7 of culture, EDM was further supplemented with $10^{-6}$ M hydrocortisone (Sigma), 100 ng/mL human SCF (R&D), and human IL-3 (R&D). During days 7-11 of culture, EDM was supplemented with 100 ng/mL SCF only. During days 11-18 of culture, EDM had no additional supplements.

HSPCs were transduced with LentiCas9-Blast (Addgene plasmid ID 52962) 24 hours after thawing in the presence of 10 µM prostaglandin E2 (PGE2) (Cayman Chemical). At 48 hours after thawing, medium was changed and cells were transduced with LentiGuide-Puro or LentiGuide-Crimson cloned with relevant sgRNA sequence in the presence of 10 µM PGE2. At 72 hours after thawing, medium was changed and HSPCs were selected with 10 µg/mL blasticidin (Sigma) and 1 µg/mL puromycin (Sigma) or 10 µg/mL blasticidin followed by sorting for LentiGuide-Crimson+ cells on day 16 of culture. Blasticidin and/or puromycin selection occurred from days 3 to 8 of culture.

Differentiation was assessed on day 18 of culture using anti-human antibodies against the transferrin receptor (CD71) [Clone OKT9 with FITC conjugation; eBioscience] and glycophorin A (CD235a) [Clone HIR2 with PE conjugation; eBioscience]. Enucleation was assessed using 2 µg/mL of the cell-permeable DNA dye Hoescht 33342 (Life Technologies). CD235a+ Hoescht 33342-cells were determined to be enucleated erythroid cells. Cells were intracellularly stained for HbF and HbA on day 18 of culture as described above. 50,000-100,000 cells were centrifuged onto microscope slides at 350 rpm for 4 minutes. Slides were stained with Harleco May-Grünwald stain (Millipore) for two minutes, Giemsa stain (Sigma) for 12 minutes, and two water washes for 30 seconds each. Slides were air dried and then cover-slipped using Fisher Chemical Permount Mounting Medium (Fisher).

PCR primers were designed to amplify the genomic cleavage site for a given sgRNA. Resulting PCR products were subjected to Sanger sequencing. Sequencing traces were used for editing quantification using a previously described publically available tool[66].

Generation of Genomic Deletions in HUDEP-2 Cells.

Tandem sgRNA lentiviruses were transduced into HUDEP-2 with stable Cas9 expression (Table 1). Bulk cultures were incubated for 7-10 days with 10 µg/mL blasticidin (Sigma) and 1 µg/mL puromycin (Sigma) selection to allow for editing. Then bulk cultures were plated clonally at limiting dilution. 96 well plates with greater than 30 clones per plate were excluded to avoid mixed clones. After approximately 14 days of clonal expansion, genomic DNA was extracted using 50 µL QuickExtract DNA Extraction Solution per well (Epicentre). Clones were screened for deletion by conventional PCR with one PCR reaction internal to segment to be deleted ('non-deletion band') and one gap-PCR reaction across the deletion junction ('deletion band') that would only amplify in the presence of deletion[50,67]. Biallelic deletion clones were identified as the absence of the non-deletion PCR band and the presence of the deletion PCR band. Inversion clones were identified as previously described by PCR[50,67] (Table 3). Briefly inversion clones had one inverted allele and one deleted allele without the presence of non-deletion alleles. In our experience biallelic inversion clones are very rare events68. PCR was performed using the Qiagen HotStarTaq 2× master mix and the following cycling conditions: 95° C. for 15 minutes; 35 cycles of 95° C. for 15 seconds, 60° C. for 1 minute, 72° C. for 1 minute; 72° C. for 10 minutes. Alternatively, PCR was also performed using 2× Accuprime Supermix II (Life Technologies) with the following cycling conditions: 94° C. for 2 minutes; 35 cycles of 94° C. for 20 seconds, 60° C. for 20 seconds, 68° C. for 1 min/kb of PCR product; 68° C. for 5 minutes. RNA was extracted from each positive clone using a kit (Qiagen) and quantitative real-time PCR was performed using iQ SYBR Green Supermix (Bio-Rad). Primers used are found in Table 5.

Pooled CRISPR/Cas9 Screen for High Resolution Functional Mapping of Mouse BCL11A Enhancer.

Murine erythroleukemia (MEL) cells were cultured in DMEM supplemented with 10% FBS (Omega Scientific), 1% L-glutamine (Life Technologies), and 2% penicillin-streptomycin (Life Technologies). εy:mCherry reporter MEL cells with stable Cas9 expression were transduced at low multiplicity with the mouse sgRNA library lentivirus pool. Control transductions were performed to ensure transduction rate did not exceed 50%. Cell numbers were maintained throughout the experiment at levels adequate to exceed 1000× representation of the library. 10 μg/mL blasticidin (Sigma) and 1 μg/mL puromycin (Sigma) were added 24 hours after transduction to select for lentiviral library integrants in cells with Cas9. Subsequently cells were cultured for two weeks. The top and bottom 5% of εy-mCherry-expressing cells exposed to the library were sorted by FACS. A non-targeting sgRNA sample was used as a negative control and Bcl11a exon 2 as a positive control to establish flow cytometry conditions. After sorting, library preparation and deep sequencing were performed as described for the human library[37].

sgRNA sequences present in the Hbb-εy:mCherry-high and Hbb-εy:mCherry-low pools were enumerated. Dropout and enrichment scores were calculated as described for the human screen. sgRNA sequences were then mapped to the mouse genome (mm9).

Generation of Genomic Deletions in MEL Cells.

Deletions in MEL cells were generated using two sgRNA as previously described[50,67]. Briefly, sgRNA sequences were cloned into pX330 (Addgene plasmid ID 42230) using a Golden Gate assembly cloning strategy (Table 1 and 4). MEL cells were electroporated with 5 μg of each pX330-sgRNA plasmid and 0.5 μg pmax-GFP (Lonza) in BTX electroporation buffer using a BTX electroporator (Harvard Apparatus). Approximately 48 hours post-electroporation, the top 1-3% of GFP+ cells were sorted and plated clonally at limiting dilution. Clones were allowed to grow for 7-10 days. Clones were screened for deletion by conventional PCR using the same strategy as with the HUDEP-2 cells[50,67] (Table 2). Inversion clones were identified by PCR as previously described[50,67] (Table 3).

Generation of Genomic Deletions in β-YAC Mouse Embryonic Stem Cells (mESCs).

mESCs were maintained on irradiated mouse embryonic fibroblasts (GlobalStem) and cultured with high glucose DMEM (Life Technologies) supplemented with 20% fetal bovine serum (Omega Scientific), L-glutamine (Life Technologies), penicillin/streptomycin (Life Technologies), non-essential amino acids (Life Technologies), nucleosides, β-mercaptoethanol (Sigma), and leukemia inhibitory factor (Millipore). Cells were passaged using 0.25% trypsin (Life Technologies).

The β-YAC mouse line (A20), previously described as containing a transgene encompassing ~150 kb of the human β-globin locus[55], was used to analyze human globin expression. The mouse line was maintained in a hemizygous state and either used for creation of a β-YAC mESC line or bred with Bcl11a+62 deletion mice. The Bcl11a+62 deletion mice were derived from CRISPR/Cas9 modified CJ9 ES cells. Using Amaxa ES Cell transfection reagent (Lonza), two million CJ9 cells were electroporated with 2 μg of each pX330 plasmid vector containing individual target sequences flanking the +62 site along with 0.5 μg of a GFP plasmid. After 48 hours, the top 5% of GFP expressing cells were sorted, plated on irradiated fibroblasts and maintained. Individual ES cell colonies were then picked and screened for biallelic deletion using the same strategy as HUDEP-2 and MEL cells[50,67]. DNA for screening CRISPR/Cas9 modified clones was obtained from gelatin adapted ES cell clones to avoid genomic contamination from the fibroblasts.

Correctly targeted clones with greater than 80% normal karyotype were used to generate mice. Clones were injected into 2.5 day C57B16 blastocysts and implanted into pseudo-pregnant females. At specified days of development, embryos were taken and analyzed for chimerism and human globin expression by qPCR. Analysis of fetal liver human globin gene expression in the developing chimeric embryos demonstrated a two day delay in globin switching patterns as compared to non-chimeric β-YAC embryos with the earliest time point for robust γ-globin repression at embryonic day 16.5 $(E16.5)_{55}$. Additionally, flow cytometry was used to analyze both fetal liver and spleen from E18.5 embryos. Single cell suspensions were made by mechanical dissociation and cells were stained with IgM-FITC (Clone Il-41; eBioscience), CD19-PerCP-Cy5.5 (Clone 1D3; eBioscience), CD43-PE (Clone S7; eBioscience), AA4.1-PE-Cy7 (Clone AA4.1; BD Biosciences), B220-APC (RA3-6B2; Biolegend), and DAPI (Invitrogen).

Adult Mouse Hematopoietic Assays.

Peripheral blood was obtained from the tail vein of 4 week-old mice. Blood was collected in heparin coated tubes, red cells lysed with 2% dextran (Sigma), and stained with the following anti-mouse antibodies: CD3e-FITC (Clone 145-2C11; Biolegend), CD19-PerCP-Cy5.5 (Clone 1D3; eBioscience), CD71-PE (Clone C2; BD Biosciences), NK1.1-PE-Cy5 (Clone PK136; Biolegend), Ter119-APC (Clone TER-119; Biolegend), Gr-1-eF450 (Clone RB6-8C5; eBioscience), B220-BV605 (RA3-6B2; Biolegend), Mac-1-BV510 (Clone M1/70; Biolegend), and 7-AAD (BD Biosciences).

Computational Analysis.

Human H3K27ac ChIP-seq was obtained from Xu et al.[12] and mouse H3K27ac ChIP-seq was obtained from Kowalczyk et al[69]. Super enhancer analysis was performed using the publically available ROSE algorithm[15].

Hidden Markov Model (HMM) segmentation was performed to automatically segment the enrichment score signals into enhancer regions with Active, Repressive and Neutral effect. We designed a HMM with 3 states using the GHMM package obtained from the website of sourceforge. The emission probability for each state was modeled as a Gaussian distribution and all the possible transitions between states were allowed. Since the signal was not obtained with a constant genomic resolution, we interpolated and smoothed the signal using a Gaussian kernel over 12 bp. To set the initial parameters, we used the 1%, 50% and 99% percentile of the smoothed signal for the prior of the means of the Repressive, Neutral and Active states respectively, while the prior for the standard deviation was set to 0.001 for all the three states.

Motif analysis was performed to evaluate the human and mouse enhancer regions for potential binding sites for known transcription factors. We used the FIMO software with a P-value threshold of <$10^{-4}$ [70]. For each region we extracted sequences using the hg19 and mm9 assemblies respectively for human and mouse. The motif database was the latest version of the JASPAR database[39].

Deep sequencing paired-end reads of genomic amplicons from genome editing target sites were first filtered for reads with PHRED quality score <30, merged with the FLASH (Fast Length Adjustment of SHort reads) software, and subsequently aligned to a reference amplicon using the needle aligner from the EMBOSS suite, obtained from the website of sourceforge, to quantify insertions and deletions. Per nucleotide frequency of deletion of a position, insertion directly adjacent to the position, or no mutation at the position was quantitated using CRISPResso, obtained from the website of github, under lucapinello and CRISPResso.

Cloning lentiCas9-Venus.

Venus template[71] was PCR amplified to add BamHI-HF (5') and EcoRI-HF (3') restriction sites for cloning purposes using the following conditions: KOD buffer (1×), MgSO4 (1.5 mM), dNTPs (0.2 mM each), forward primer (0.3 µM; GGCCGGCCG-GATCCGGCGCAACAAACTTCTCTCTGCT-GAAACAAGCCGGAGATGTCGAAGA GAATCCTGGACCGATGGTGAGCAAGGGCGAGGA; SEQ. ID. NO: 145), reverse primer (0.3 µM; GGCCGGCCgaattcTTACTTGTACAGCTCGTCCA, SEQ. ID. NO: 146), and KOD Hot Start DNA Polymerase (0.02 U/µL) (Millipore). KOD PCR reaction used the following cycling conditions: 95° C. for 2 minutes; 50 cycles of 95° C. for 20 seconds, 60° C. for 20 seconds, and 70° C. for 30 seconds; 60° C. for 5 minutes. PCR products were purified (QIAquick PCR Purification Kit, Qiagen) and blunt ended cloned with Zero Blunt PCR cloning kit (Invitrogen). PCR-blunt cloned products and lentiCas9-Blast (Addgene plasmid ID 52962) were separately digested with BamHI-HF and EcoRI-HF in 1× Buffer CutSmart at 37° C. (New England Biolabs). Digest of lentiCas9-Blast was performed to remove the blasticidin cassette. Then digested PCR product was ligated into the lentiCas9 backbone.

Cloning lentiGuide-Crimson.

E2-Crimson template (Clontech) was PCR amplified to add BsiWI (5') and MluI (3') restriction sites for cloning purposes using the following conditions: KOD buffer (1×), MgSO$_4$ (1.5 mM), dNTPs (0.2 mM each), forward primer (0.3 µM; GGCCGGCCCGTACGCGTACGGCCACCATG-GATAGCACTGAGAACGTCATCAAGCCCTT, SEQ. ID. NO: 147), reverse primer (0.3 µM; GGCCGGC-CACGCGTCTACTGGAACAGGTGGTGGCGGGCCT, SEQ. ID. NO: 148), and KOD Hot Start DNA Polymerase (0.02 U/µL) (Millipore). KOD PCR reaction used the following cycling conditions: 95° C. for 2 minutes; 50 cycles of 95° C. for 20 seconds, 60° C. for 20 seconds, and 70° C. for 30 seconds; 60° C. for 5 minutes. PCR products were purified (QIAquick PCR Purification Kit, Qiagen) and cloned with Zero Blunt PCR cloning kit (Invitrogen). Cloned products and lentiGuide-puro were separately digested with BsiWI and MluI in 1× Buffer 3.1 at 37° C. (New England Biolabs). Digest of lentiGuide-Puro (Addgene plasmid ID 52963) was performed to remove the puromycin cassette. Then digested PCR product was ligated into the lentiGuide backbone.

Cloning sgRNAs.

lentiGuide-Puro (Addgene plasmid ID 52963) was digested with BsmBI in 1× Buffer 3.1 at 37° C. (New England Biolabs) for linearization. One unit of TSAP thermosensitive Alkaline Phosphatase (Promega) was added for 1 hour at 37° C. to dephosphorylate the linearized lentiGuide and then TSAP was heat inactivated at 74° C. for 15 minutes. Linearized and dephosphorylated lentiGuide was run on an agarose gel and gel purified. sgRNA-specifying oligos were phosphorylated and annealed using the following conditions: sgRNA sequence oligo (10 µM); sgRNA sequence reverse complement oligo (10 µM); T4 ligation buffer (1×) (New England Biolabs); and T4 polynucleotide kinase (5 units) (New England Biolabs) with the following temperature conditions: 37° C. for 30 min; 95° C. for 5 min; and then ramp down to 25° C. at 5° C./min. Annealed oligos were ligated into lentiGuide in a 1:3 ratio (vector:insert) using T4 ligation buffer (1×) and T4 DNA Ligase (750 Units) (New England Biolabs. Plasmids were verified by sequencing using a U6F promoter forward primer CGTAACTT-GAAAGTATTTCGATTTCTTGGC (SEQ. ID. NO: 149).

sgRNA-specifying oligos using sgRNA sequences from the screen library (Extended Data) were obtained and cloned as described into either lentiGuide-Puro or lentiGuide-Crimson. sgRNA constructs were used to produce lentivirus and transduce HUDEP-2 with stable Cas9 expression. Bulk cultures were incubated for 7-10 days with 10 µg/mL blasticidin (Sigma) and 1 µg/mL puromycin (Sigma) selection to allow for editing. Then bulk cultures were plated clonally at limiting dilution without antibiotic selection. Clones were allowed to grow for approximately 14 days and then were genomic DNA was extracted using 50 µL QuickExtract DNA Extraction Solution per well (Epicentre).

lentiTandemGuide Cloning.

lentiGuide-sgRNA1 was digested with PspXI and XmaI at 37° C. for four hours (New England Biolabs). Digests were run on an agarose gel and gel purified. lentiGuide-sgRNA2 was linearized using NotI (New England Biolabs). The hU6 promoter and sgRNA chimeric backbone for lentiGuide-sgRNA2 was PCR amplified using the following conditions: KOD buffer (1×), MgSO4 (1.5 mM), dNTPs (0.2 mM each), forward primer (0.3 µM; GGCCGGCCgctcgagg-GAGGGCCTATTTCC, SEQ. ID. NO: 150), reverse primer (0.3 µM; CCGGCCGGcccgggTTGTGGATGAATACTGC-CATTT, SEQ. ID. NO: 151), and KOD Hot Start DNA Polymerase (0.02 U/µL) (Millipore). KOD PCR reaction used the following cycling conditions: 95° C. for 2 minutes; 50 cycles of 95° C. for 20 seconds, 60° C. for 20 seconds, and 70° C. for 30 seconds; 60° C. for 5 minutes. PCR products were purified (QIAquick PCR Purification Kit, Qiagen) and blunt ended cloned with Zero Blunt PCR cloning kit (Invitrogen) and transformed and plated. Colonies were screened by digesting minipreps with EcoRI. Mini-preps were then digested with PspXI and XmaI as described above followed by PCR purification. Following PCR purification, sgRNA2 was ligated into digested lenti-Guide-sgRNA1. Sequence verified with following primers: GGAGGCTTGGTAGGTTTAAGAA (SEQ. ID. NO: 152) and CCAATTCCCACTCCTTTCAA (SEQ. ID. NO: 153).

Generation of HUDEP-2 with Stable Cas9.

LentiCas9-Blast (Addgene plasmid ID 52962) or Lenti-Cas9-Venus were produced as described above and used to transduce HUDEP-2 cells. Transduced cells were selected with 10 µg/mL blasticidin (Sigma) or Venus+ cells were sorted. Functional Cas9 was confirmed using the pXPR-011 (Addgene plasmid ID 59702) GFP reporter assay as previously described[72].

Generation of Hbb-εy:mCherry Reporter MEL Cells.

Figure 9D:
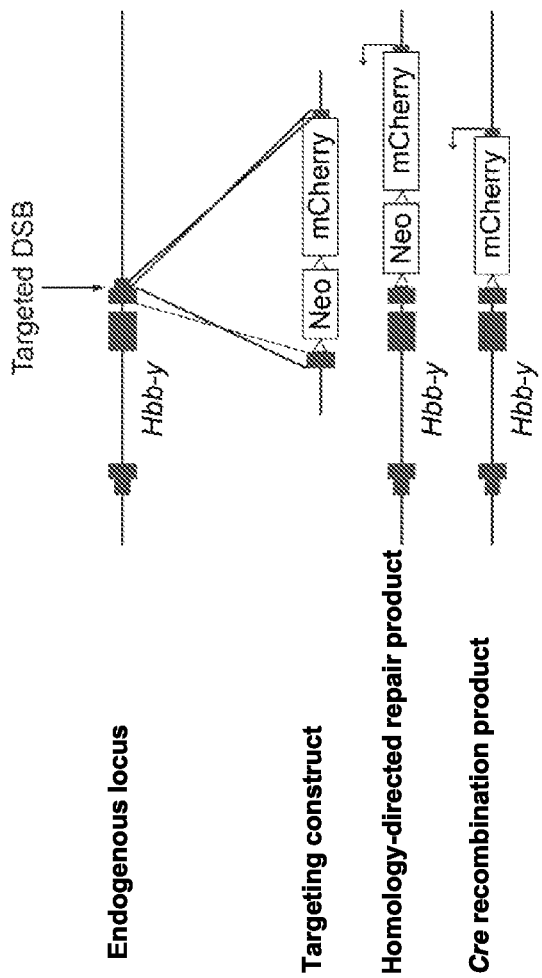

A reporter MEL line in which mCherry has been knocked into the Hbb-y locus was created (see FIG. 9D). Briefly, a TALEN-induced DSB was created adjacent to the Hbb-y transcriptional start site. A targeting vector with mCherry and a neomycin cassette were introduced through homology directed repair. Cre-mediated recombination was utilized to remove the neomycin cassette. Long-range PCR spanning each homology arm was utilized to ensure appropriate targeted integration. Cells were tested upon Bcl11a disruption by RT-qPCR and flow cytometry to confirm expected effects on εy:mCherry derepression. Subsequently CRISPR-Cas9 was used as described above to produce cells with monoallelic composite enhancer deletion to maximize screening sensitivity.

Generation of MEL Cells with Stable Cas9 Expression.

LentiCas9-Blast (Addgene plasmid ID 52962) lentivirus were produced as described above and used to transduce MEL cells. Transduced cells were selected with 10 μg/mL blasticidin (Sigma). Functional Cas9 was confirmed using the pXPR-011 (Addgene plasmid ID 59702) GFP reporter assay as previously described[72].

Results

Human Composite Enhancer

Recently we observed that common genetic variants associated with HbF (α2γ2) level and β-hemoglobin disorder clinical severity mark an adult developmental stage- and erythroid-lineage specific intronic enhancer of BCL11A[42], a validated repressor of HbF and therapeutic target for β-hemoglobin disorders[42,45-47]. This composite enhancer is composed of three DNase I hypersensitive sites (DHSs), termed +55, +58, and +62 based on distance in kilobases from the transcriptional start site (TSS)[42]. The most highly trait-associated haplotype is defined by two SNPs, rs1427407 within +62 and rs7606173 within +55 (FIG. 1A). In fact, based on H3K27ac ChIP-seq in primary human adult erythroid precursors, the composite BCL11A enhancer ranks as the #100 most intensely decorated of 503 total human erythroid super-enhancers (FIGS. 1A and 1B). Previously we showed that this enhancer possessed ectopic erythroid-restricted, adult-stage-specific enhancer activity[42]. Moreover, the mouse ortholog of the composite enhancer, defined by primary sequence homology, shared erythroid enhancer chromatin signature, and syntenic position relative to coding sequences, was shown to be required for BCL11A expression and embryonic globin gene repression in a mouse erythroid cell line but dispensable in a mouse B-lymphoid cell line[42]. These results recommend disruption of the BCL11A erythroid enhancer as a promising therapeutic strategy for HbF reinduction for the β-hemoglobin disorders[48].

Figure 6A:
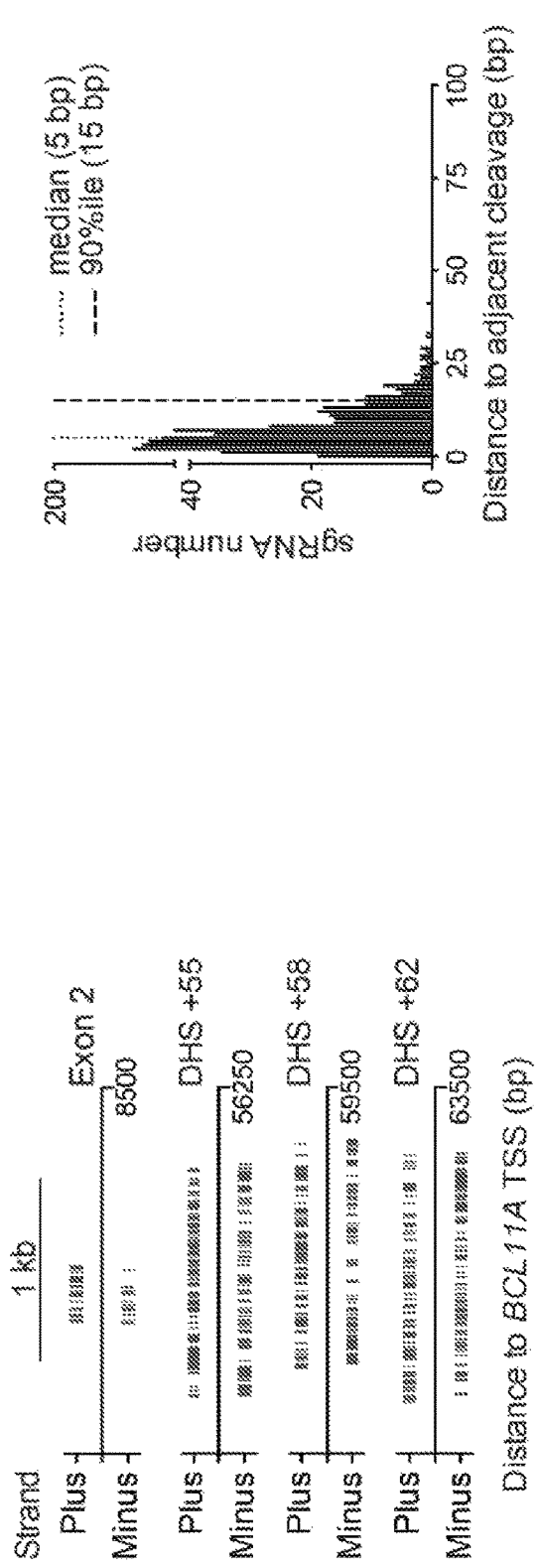
Figure 6B:
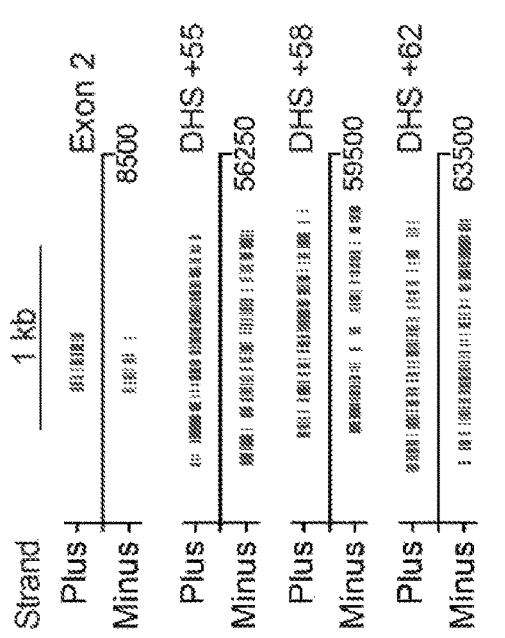
Figures 6C, 6D, 6E:
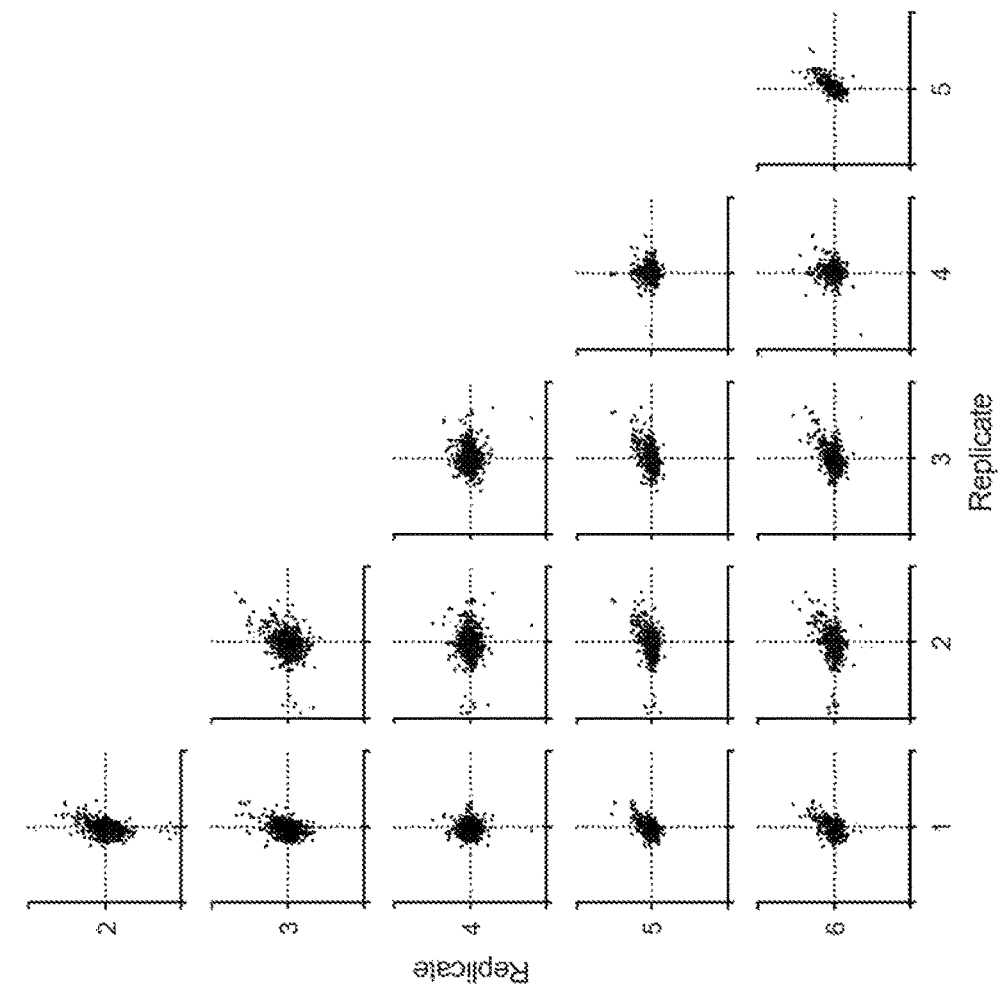

To evaluate the requirement for human BCL11A enhancer sequences, we utilized HUDEP-2 cells, an immortalized human CD34+ hematopoietic stem and progenitor cell (HSPC)-derived erythroid precursor cell line that expresses BCL11A and predominantly β- rather than γ-globin[49]. We used the CRISPR-Cas9 nuclease system to generate a clone of HUDEP-2 cells null for BCL11A by targeting coding sequences (FIG. 1C). These cells demonstrated elevated levels of γ-globin mRNA and HbF protein, consistent with the functional requirement of BCL11A for HbF repression (FIGS. 1D, 1E, and 6). Deletion of the 12-kb BCL11A composite enhancer with a pair of sgRNAs resulted in near complete loss of BCL11A expression and induction of γ-globin and HbF protein to similar levels as cells with BCL11A knockout (FIGS. 1C-1E, and 6), analogous to the requirement of the orthologous mouse composite enhancer for erythroid BCL11A expression[42]. Significant HbF induction resulting from deletion of the human BCL11A erythroid composite enhancer encourages targeting these sequences for therapeutic genome editing of the β-hemoglobinopathies[48]. Although targeted deletions by paired double strand breaks (DSBs) may be achieved by genome editing, competing genomic outcomes include local insertion/deletion (indel) production at each cleavage site as well as inversion of the intervening segment[34,35,50-52].

Tiled Pooled Enhancer Editing In Situ

We hypothesized that composite enhancers may be composed of a functional hierarchy with essential and dispensable constituent components. A functional hierarchy might enable enhancer disruption by a single DSB at a critical region followed by non-homologous end joining (NHEJ) repair with indels. In fact, the hypothesis that a prevalent mechanism of trait associations is enhancer variation rests on the premise that single nucleotide changes themselves may substantively modulate enhancer function. Therefore we reasoned that a tiling set of sgRNAs could uncover critical enhancer regions by disruption of essentially all sequences within an enhancer given the typical indel spectrum of each sgRNA of at least 10 bp[34,35,50,52,53].

Figures 7B, 8A:
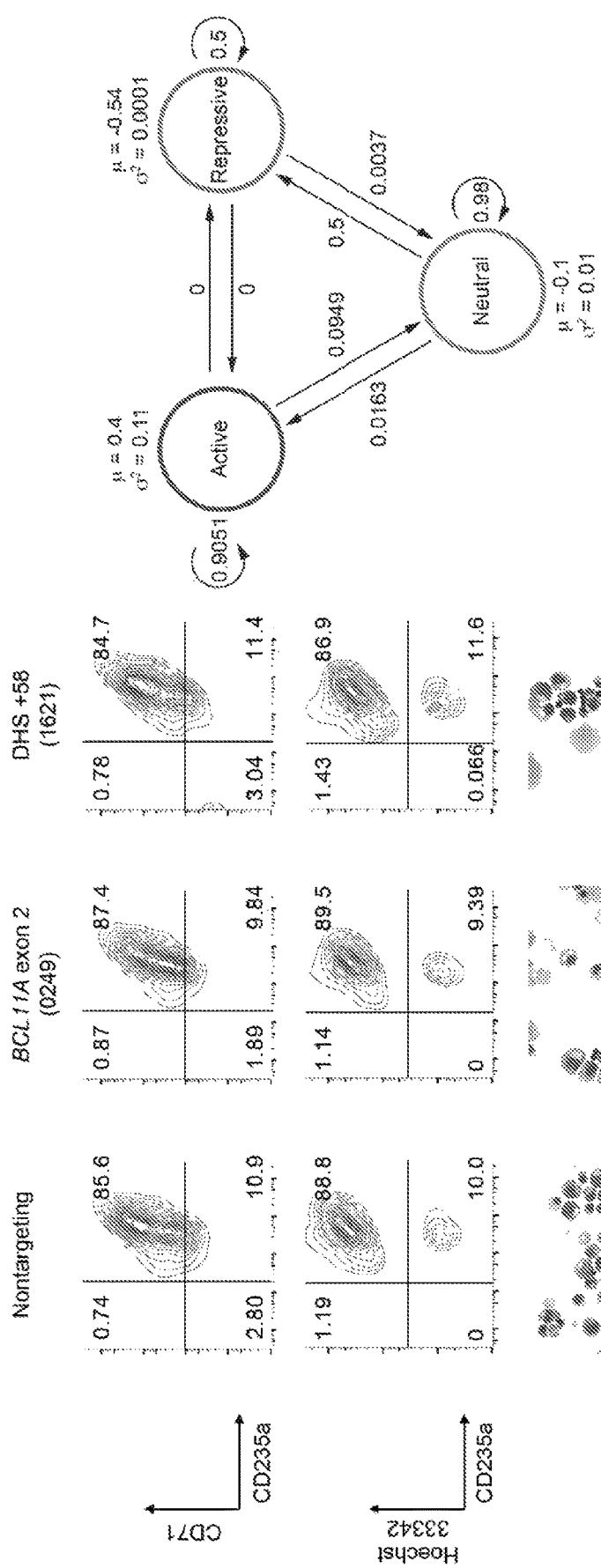
Figure 8B:
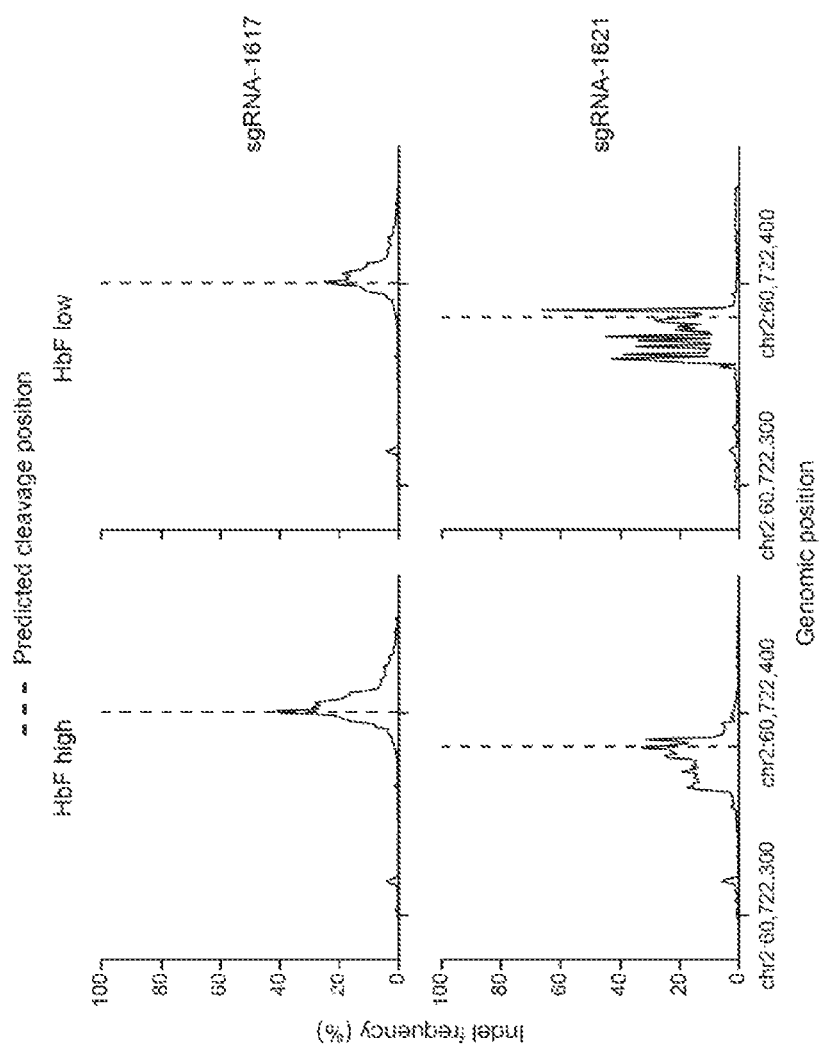

We designed all possible sgRNAs within the human BCL11A composite enhancer DHSs (FIGS. 2A-2D) as restricted only by the presence of the SpCas9 NGG protospacer adjacent motif (PAM), which restricts cleavage at an average 1/8 frequency at each genomic position (considering presence on plus and minus strands)[34,53]. The NGG PAM restricted sgRNAs had a median adjacent genomic cleavage distance of 4 bp and 90th percentile of 18 bp (FIG. 2D), which indicated that this strategy could approach saturation mutagenesis in situ. NAG may act as an alternate PAM for SpCas9, albeit with lower efficiency[53]. We also designed sgRNAs restricted by the NAG PAM (FIGS. 2B, and 7). We included 120 non-targeting sgRNAs as negative controls as well as 88 sgRNAs tiling exon-2 of BCL11A as positive controls. The total library included 1,338 sgRNAs.

Figure 2G:
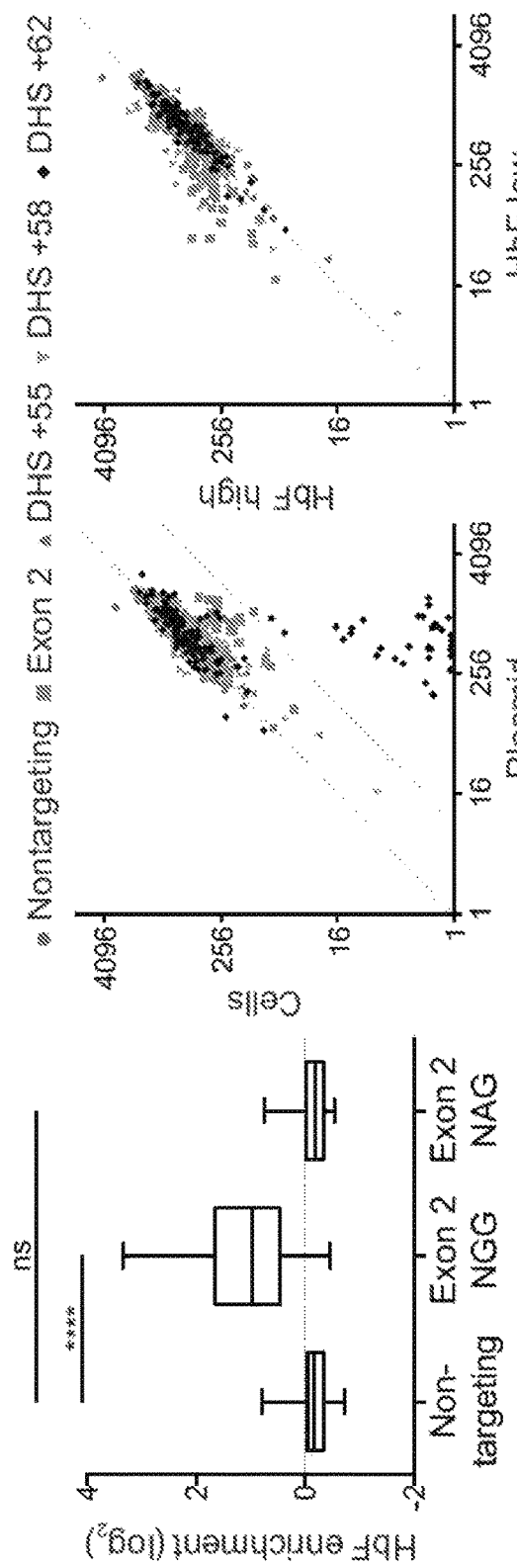

We synthesized oligonucleotides for the sgRNAs on a microarray and cloned the sgRNAs as a pool to a lentiviral vector[37]. Deep sequencing of the lentiviral plasmid library demonstrated that 1,337 of 1,338 sgRNAs (99.9%) were successfully cloned. The representation of sgRNAs within the library showed a relatively narrow distribution, with a median of 718 and the 10% and 90% percentile ranging from 337 to 1,205 normalized reads. The basic experimental schema was to transduce cells with the lentiviral library at low multiplicity such that nearly all selected cells contained a single integrant (FIG. 2A). Introduction of Cas9 and an individual sgRNA targeting BCL11A exon-2 produced cells with elevated HbF expression, indicating loss of BCL11A function and resultant derepression of BCL11A's target γ-globin. Therefore, we transduced HUDEP-2 cells stably expressing SpCas9 with the pooled library of BCL11A enhancer targeting sgRNAs. We initially expanded the cells for one week, and subsequently transferred them to erythroid differentiation conditions, for a total of two weeks of culture. Then we performed intracellular staining for HbF. Fluorescence activated cell sorting (FACS) was employed to isolate HbF-high and HbF-low pools (consistent with high and low BCL11A activity respectively; FIGS. 2A and 2E). We enumerated the representation of the library in each pool by deep sequencing. The enrichment of each sgRNA in the HbF-high compared to HbF-low pools was calculated as the log$_e$-ratio of normalized reads. We compared the HbF enrichment of the 120 non-targeting negative control sgRNAs and 88 coding sequence targeted positive controls for both NGG and NAG PAM restricted sgRNAs. We observed equivalent representation of the non-targeting sgRNAs in the high-HbF and low-HbF pools but highly significant enrichment of the NGG sgRNA targeting exon-2 of BCL11A in the HbF-high pool, consistent with a reduction of BCL11A activity (FIGS. 2F and 2G). One non-targeting sgRNA (#0548) had an enrichment score of 0.803, while the remaining 119/120 non-targeting sgRNAs (99.2%) showed enrichment scores below 0.259. In contrast 40/48 sgRNAs targeting BCL11A exon 2 (83.3%) showed enrichment scores above 0.259. These results indicate that the large majority of sgRNAs in the library were competent to produce indels. However, exon-2 targeting sgRNAs with NAG PAM restriction did not show significant enrichment so all the NAG restricted sgRNAs were excluded from further analysis (FIG. 2F).

Figure 10A:
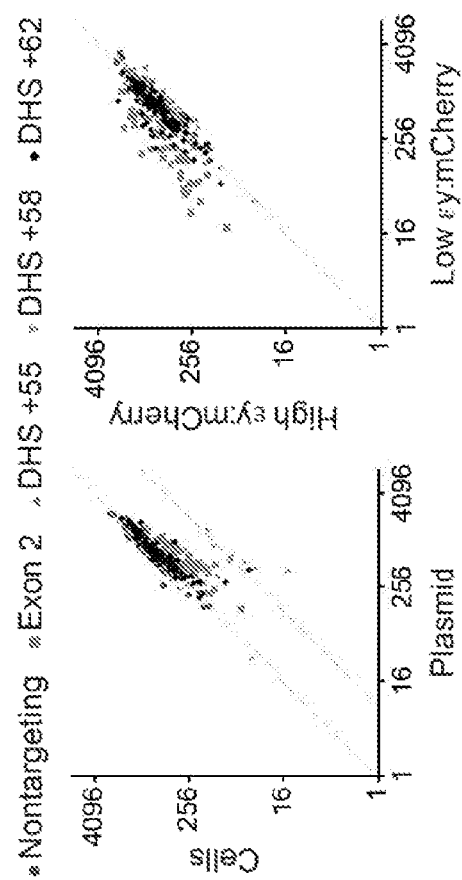

We compared the representation of sgRNAs in the initial plasmid pool to the representation of sgRNAs in the cells at the end of in vitro culture. While the majority of the library maintained neutral representation throughout the experiment, we observed a fraction of sgRNAs that were depleted, mainly among the +62 sgRNAs (FIGS. 2G, and 10A). We observed that these dropout sgRNAs mapped to repetitive elements within the genome, in particular to a SINE AluSq element that appears in the genome nearly 100,000 times 54. Initial design of sgRNAs did not include prediction of off-target cleavage to maximize the resolution of target mutagenesis. We removed from subsequent analysis 35 of 582 (6.0%) NGG PAM sgRNAs with final representation <$2^{-3}$ since these indicated likely BCL11A-independent effects of genomic disruption (FIG. 2G).

Figure 2H:
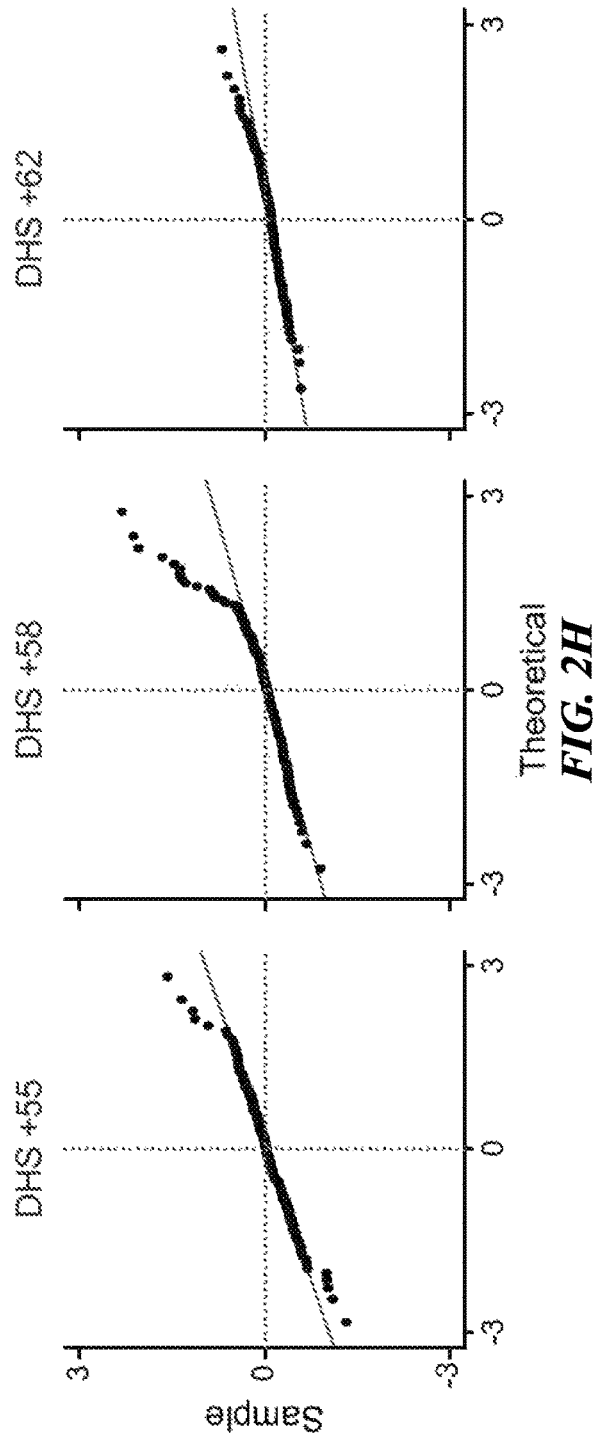

The majority of enhancer targeting sgRNAs showed no significant enrichment or depletion from the HbF-high pool (FIGS. 2G and 2H). We observed a number of sgRNAs with HbF enrichment at each of the DHSs as well as some with HbF depletion at +55 (FIG. 2H). We mapped the enrichment score of each sgRNA to its predicted position of genomic cleavage (FIG. 3A). The enriching sgRNAs colocalize to discrete genomic positions. For example, we observed a cluster of sgRNAs at +62 with modest enrichment, a cluster at +55 with moderate enrichment (as well as adjacent clusters with depletion), and a cluster at +58 with marked enrichment. Of note, we observed 10 sgRNAs at +58 with cleavage positions within 42 bp each with enrichment scores exceeding 0.99, the median enrichment score of BCL11A exon-2 targeting sgRNAs.

Exon-2 targeted sgRNAs showed a linear correlation between enrichment and dropout from the screen, indicating sgRNAs that result in complete knockout of BCL11A lead to a reduced rate of cellular accumulation inseparable from magnitude of HbF derepression (FIG. 3B). For example, we did not observe any exon-2 targeting sgRNAs with potent HbF enrichment that lacked substantial dropout. In contrast, the sgRNAs at +58 associated with marked HbF enrichment showed blunted impact on dropout (FIG. 3B). This finding could be consistent with a low residual level of BCL11A adequate to promote cellular accumulation but inadequate to suppress HbF.

To validate these findings, we generated cells with deletion of each individual DHS, +55, +58, and +62. Deletion of +58 phenocopied deletion of the composite enhancer, while deletion of +55 and +62 had moderate and modest effects respectively, consistent with the magnitude of top-scoring and colocalizing sgRNAs from the screen (FIGS. 3A, 3C-3E). Inversion of the +58 or +55 sites had no significant effect on gene expression, demonstrating that the BCL11A enhancer functions in an orientation-independent manner in situ, consistent with the classic enhancer definition[1] (FIGS. 3C-3E). In arrayed format we tested 24 sgRNAs with enrichment scores ranging from the highest to the lowest in the screen, and representing sgRNAs from all 5 mapping categories. We observed a strong correlation between the HbF enrichment score from the screen and the fraction of HbF+ cells in arrayed format (r=0.816, p<0.0001; FIG. 3F). These results demonstrate that a single enhancer-targeting sgRNA may mediate robust HbF induction (FIG. 8).

To validate the findings from the HUDEP-2 cells, the top-scoring enhancer targeting sgRNA from the screen (#1621 at +58) was tested in primary human erythroblasts by lentiviral transduction of CD34+ HSPCs exposed to ex vivo erythroid culture conditions. Consistent with the screen results, sgRNA-1621 resulted in down regulation of BCL11A expression and corresponding upregulation of γ-globin expression and increase in HbF+ cells (FIGS. 3G-3I, and 8B). Notably, sgRNA-1621 did not alter surface marker profile, enucleation frequency, or cellular morphology. Together these results indicate proof-of-principle of an individual sgRNA targeting a noncoding element for therapeutic genome editing of β-hemoglobin disorders.

Primate-Specific Enhancer Sequences

Figure 4A:
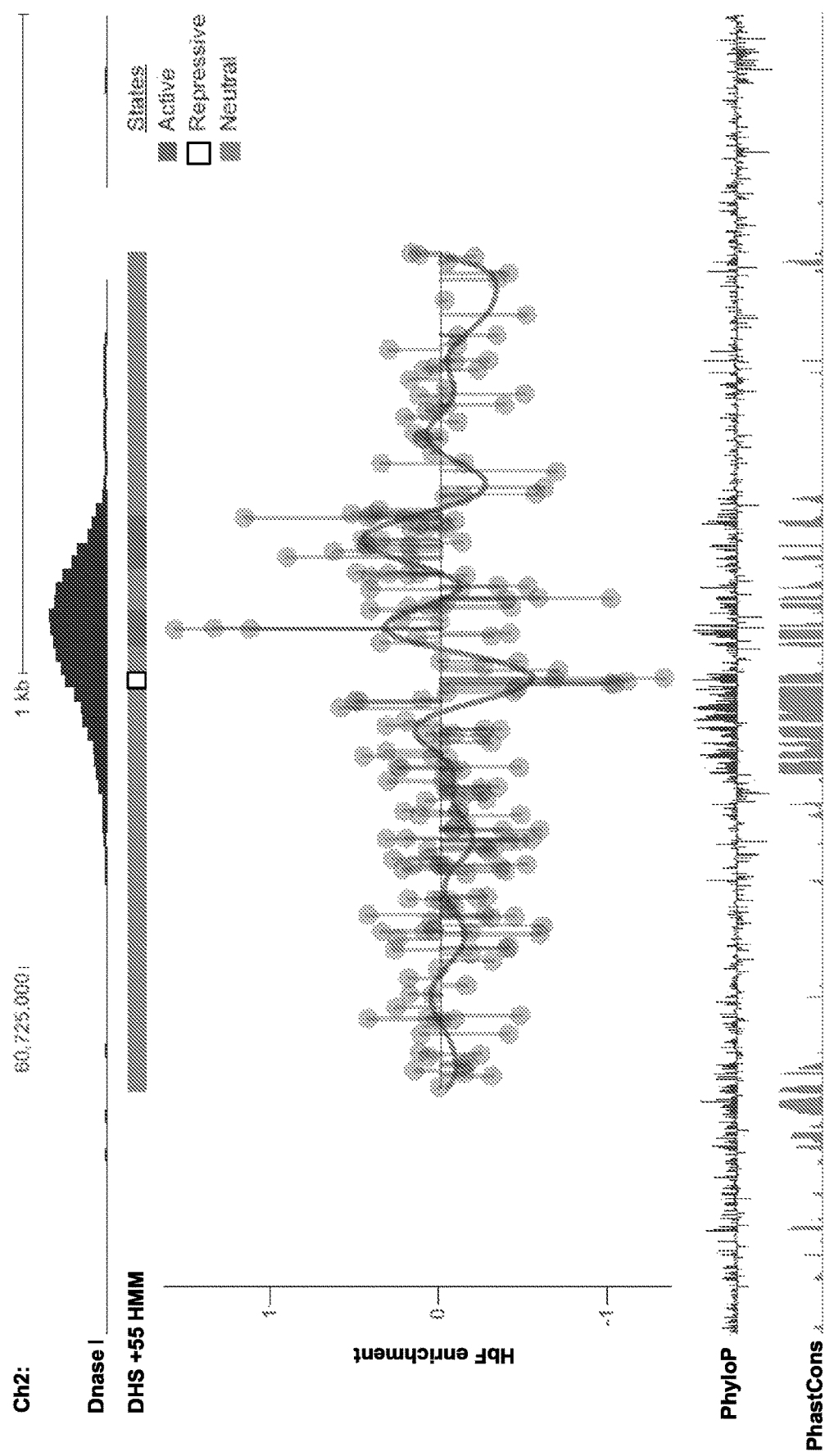
FIGS. 4A-4C show the inferred functional enhancer states relative to genomic features. Hidden Markov model (HMM) segmentation of functional enhancer states. HbF enrichment scores shown throughout DHSs +55, +58, +62 by gray lines and circles with curve graph line representing smoothed enrichment score. DNase I sequencing from primary human erythroblasts[42]. PhyloP (scale from −4.5 to 4.88) and PhastCons (from 0 to 1) estimates of evolutionary conservation among 100 vertebrates.
Figure 4B:
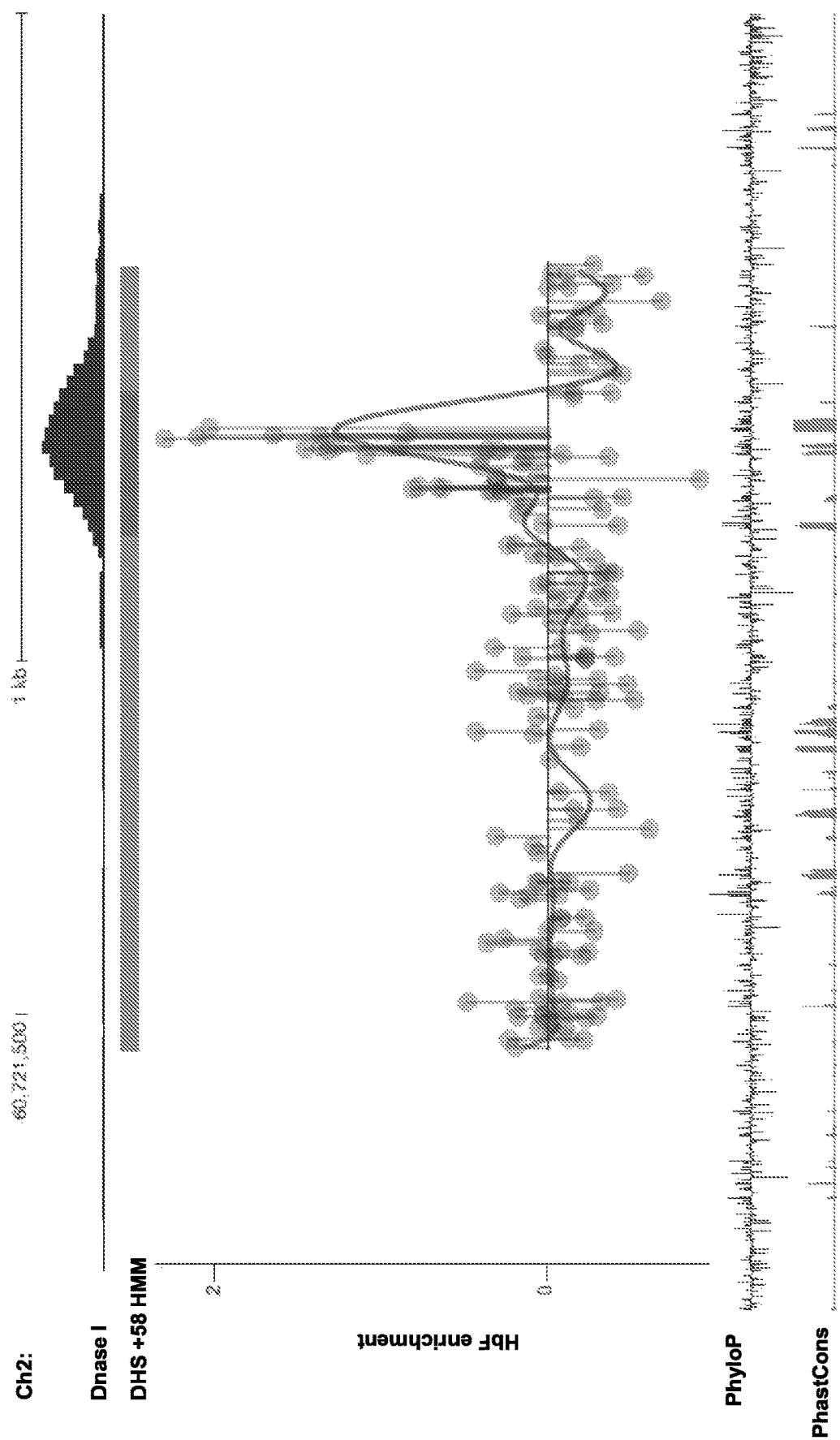
Figure 4C:
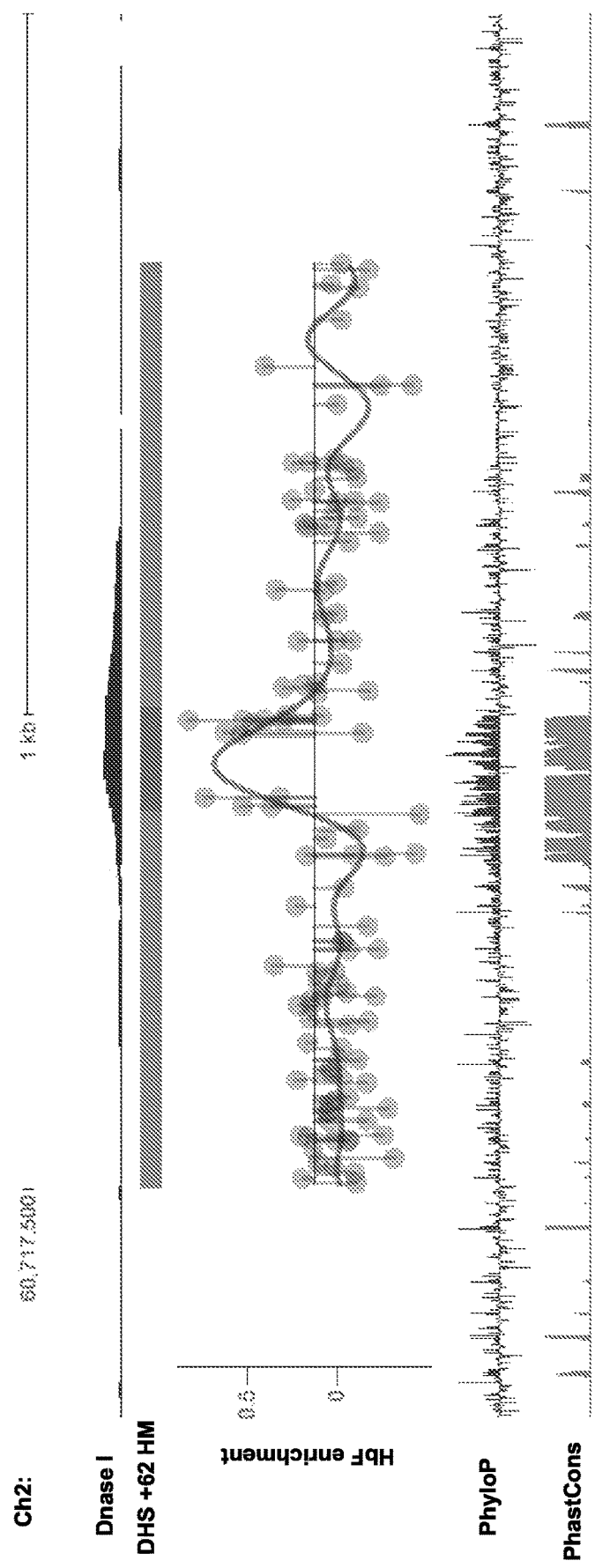

We applied a hidden Markov model (HMM) to the sgRNA enrichment score data to infer functionally important sequences within each DHS. This model defined three functional states, Active, Repressive, and Neutral, based on likelihood to encompass sequences that positively, negatively, and neutrally regulate target gene expression, respectively. The model identified functional states within each DHS (FIG. 4A-4C). At each of the three DHSs, the Active states were precisely located at regions with the highest degree of DNase I sensitivity.

The +62 Active region contains only one common SNP (MAF>1%), the variant rs1427407, which was previously identified by fine-mapping as the most highly trait-associated SNP[42]. The high-HbF T-allele is disruptive of an apparent half E-box/GATA composite motif (P=9.74×10$^{-4}$ for T-allele, P=1.69×10$^{-4}$ for G-allele, though neither met our predefined threshold for significance of P<10$^{-4}$ and associated with reduced GATA1 and TAL1 occupancy in primary human erythroid chromatin[42]. Multiple sgRNAs with cleavages mapping directly to the motif demonstrated positive enrichment scores (FIG. 4C). Of note, there was a gap of 88 nucleotides between sgRNA cleavages at the core of the Active region due to lack of NGG PAM motifs. Despite this uncommon limitation of functional resolution by SpCas9 and NGG PAM restricted sgRNAs (FIG. 2D), the HMM model was still able to identify the region. Substantial interspecies conservation as evaluated by both PhyloP and PhastCons (which model individual nucleotide and multi-base element conservation, respectively) was observed at this +62 Active state region as compared to flanking regions (FIG. 4C).

DHS +55 encompasses the SNP rs7606173, which along with rs1427407 defines the most highly trait-associated haplotype. Previous fine-mapping was unable to find additional SNPs at BCL11A with predictive power for the trait association beyond the rs1427407-rs7606173 haplotype based on conditional or rare-variant analyses. No common SNPs were found directly within the Active or Repressive state regions of +55, however rs7606173 resides merely 3 bp from the Repressive region and 34 bp from the Active region The next closest common SNP to an Active or Repressive state within +55 is rs62142646, which is 739 bp from an Active state. The major, ancestral G allele at rs7606163 is associated with high-HbF. The HUDEP-2 cells used in this screen are homozygous for this G variant. Given a model in which high-HbF trait is due to disruption of TF binding sequences at the BCL11A enhancer, sgRNA-mediated disruption of the high-HbF rs7606173-G allele might not be expected to lead to further functional impact. We did observe six motifs predicted ($P<10^4$) to be differentially impacted by the rs7606173 genotype. The top-scoring sgRNAs in +55 cluster 56-58 bp from rs7606173, at a site with a predicted TAL1::GATA1 motif ($P<10-4$). This sequence element possesses high vertebrate conservation. The entire region encompassing the Active/Repressive +55 states appears to have elevated sequence conservation as compared to flanking sequences (FIG. 4A).

The overall sequence conservation at the +58 Active region appears both less intense and less distinct from flanking sequences as compared to those of +62 and +55 (FIG. 4A-C). The top-scoring sgRNAs in the screen colocalize to 42 bp within +58 (FIG. 4B). The third-highest scoring enhancer-targeted sgRNA (sgRNA-1617) mapped directly onto an apparent GATA motif (data not shown). This motif was below a genome-scale significance threshold ($P=3.74\times10^4$). Of note, there is a 144 bp insertion in the mouse genome relative to the human reference directly adjacent to the orthologous position. The mouse orthologous sequence has a GATA1 motif P-value only modestly higher than the human ($p=4.33\times10^4$). This GATA1 motif appears to have relatively high vertebrate conservation, with exact human identity in rabbits, pigs, dogs, and elephants.

The top-scoring sgRNA (sgRNA-1621) mapped to a position 15 bp from this GATA1 motif (data not shown). An additional four sgRNAs mapping between sgRNA-1621 and 1617, including the second-highest scoring sgRNA in the screen, each had substantially elevated HbF enrichment scores. Underlying these sgRNAs were additional predicted motifs (i.e. Rxra, EHF, ELF1, and STAT1). Although these sequences showed a high level of conservation among primates, they showed high degeneracy among non-primate vertebrates (data not shown).

We tested the pattern of mutations observed upon treatment of cells with either sgRNA-1621 or sgRNA-1617 by deep sequencing. Each of these sgRNAs is sufficient to substantially induce HbF in human erythroid cells (FIG. 3F-3I). We sorted cells exposed to Cas9 and these sgRNAs into HbF-high and HbF-low pools. We determined the indel spectrum in each population by deep sequencing. As expected we observed indels clustering around the predicted cleavage positions. By comparing the per nucleotide indel ratio between cells from the HbF-high and HbF-low pools, we were able to calculate a relative enrichment across the amplicon used for deep sequencing. Notably both sgRNAs yielded maximal HbF enriching indels not precisely at the expected cleavage position but offset by about 10 bp. In the case of 1621, the positions of maximal HbF indel enrichment were towards the 1617 cleavage site. In the case of 1617, the positions of maximal HbF indel enrichment were towards the 1621 cleavage site. These results indicate that the sequences intervening these two cleavages are particularly required for BCL11A expression. These sites of maximal HbF mutation enrichment mapped to 7 bp directly overlapping the predicted motifs intervening the sgRNA cleavages (data not shown). Taken together, these data indicate that a conserved GATA1 motif scoring below the prediction threshold surrounded by primate-specific sequences form the core of an enhancer essential for human erythroid BCL11A expression and HbF repression.

Mouse Enhancer Dissection

To test functional conservation of the BCL11A enhancer, we examined the orthologous mouse Bcl11a enhancer in greater detail. Although moderately marked by H3K27ac, mouse Bcl11a does not meet the criteria for a super-enhancer element (FIGS. 9A and 9B). Erythroid DNase I sensitivity is only observed at those sequences homologous to +55 and +62 and not at +58 (FIG. 9A), consistent with the reduced sequence homology within the +58 Active region (FIG. 4A-4C). We previously observed that deletion of the entire composite enhancer (encompassing the homologous sequences to DHS +55, +58, and +62) in mouse erythroleukemia (MEL) cells resulted in dramatic reduction of BCL11A expression[42]. We generated a MEL cell reporter line with the mCherry fluorescent reporter knocked-in to the embryonic globin Hbb-y locus (FIG. 9C). Introduction of Cas9 and sgRNA targeting Bcl11a exon-2 resulted in the appearance of cells with elevated εy:mCherry expression, indicating derepression of the BCL11A target εy-globin (FIG. 9D). We designed a pooled CRISPR enhancer saturation mutagenesis screen in these εy:mCherry reporter cells, similar to the human screen described above (FIGS. 9E-9K).

Figure 10B:
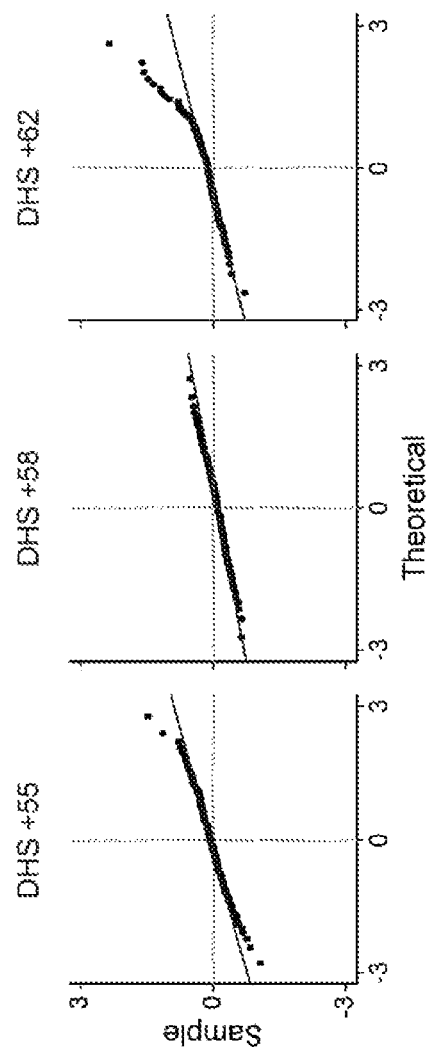

We determined enrichment score as the $\log_e$-ratio between representation in the high-as compared to low-εy:mCherry pools (FIG. 10A). We noted almost all exon-2 targeting sgRNAs demonstrated both positive enrichment scores and negative dropout scores with high correlation (FIGS. 10A, 10C, and 10D). The majority of enhancer targeting sgRNAs showed no significant enrichment (FIG. 10B). We detected sgRNAs with both modest enrichment and depletion from high-εy:mCherry at the +55 ortholog, similar to as seen at human +55. We detected a set of sgRNAs with marked enrichment at the +62 ortholog, exceeding the potency of those enriching at human +62. At the +58 ortholog we did not observe any evidence of enriching or depleting sgRNAs (FIG. 10B).

Figure 5A:
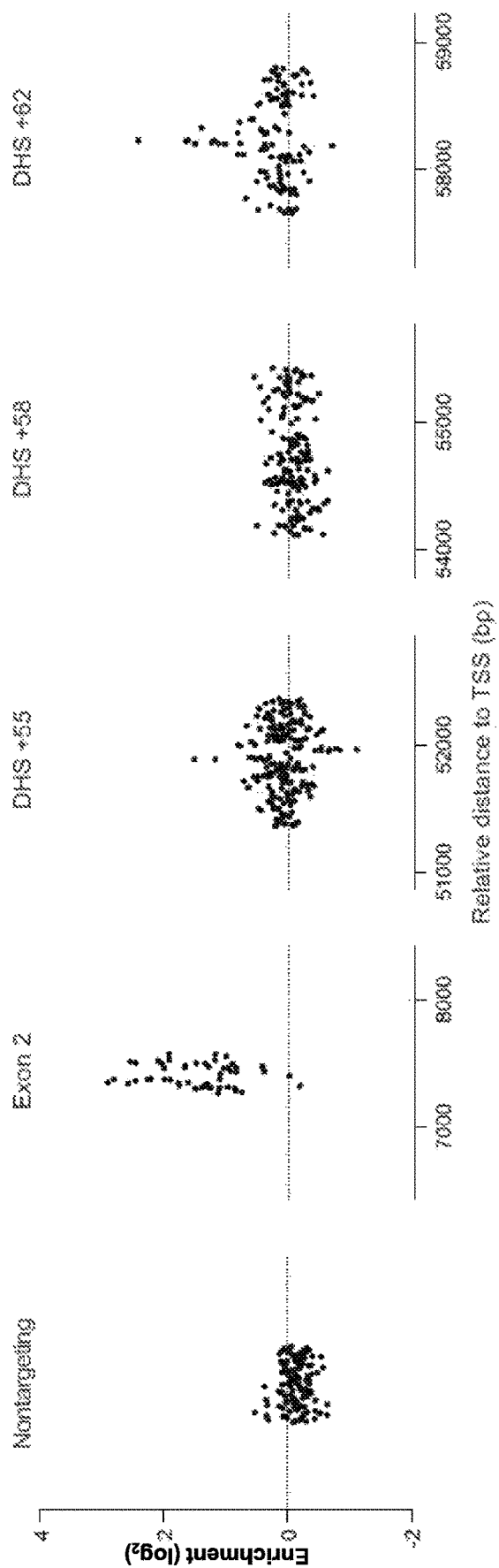

Upon mapping the sgRNA cleavage positions to the genome, we again observed colocalization of sets of sgRNAs (FIG. 5A). There was a similar complex pattern at the +55 ortholog as at human +55, with adjacent regions with enriching and depleting sgRNAs from the high-εy:mCherry pool at the DHS core. At the +62 ortholog there was a marked peak, with five sgRNA with enrichment scores exceeding 1.30, the median enrichment score of Bcl11a exon-2 targeting sgRNAs (FIG. 5A). This potent impact of the +62 ortholog was in contrast to the modest impact of individual sgRNAs or DHS deletion at human +62.

We used pairs of sgRNAs in the presence of Cas9 to produce MEL clones with deletions of various substituent elements at the BCL11A enhancer. We compared the expression of clones with deletions of the +55, +58, and +62 orthologs (FIG. 5B). Deletion of the DNase-insensitive +58 ortholog had no apparent effect on BCL11A expression consistent with the pooled screen result. Deletion of the +55 ortholog led to an approximately two-fold reduction in BCL11A expression (mean residual level 49%, p<0.0001), whereas deletion of the +62 ortholog mimicked deletion of the entire composite enhancer in terms of reduction in BCL11A expression (mean residual levels of 8% (p<0.0001) and 6% (p<0.0001) respectively, FIG. 5B). In addition, clones were isolated in which the +62 ortholog was inverted in which there was no change in BCL11A expression, indicating that the mouse, like the human, enhancer functions independent of orientation in situ (FIGS. 3C-3E; 5B).

We applied the same HMM model to infer Active, Repressive, and Neutral states at the mouse BCL11A enhancer orthologs (FIG. 5C). We identified an Active state at the +62 ortholog and Active and Repressive states at the +55 ortholog. Only the Neutral state was identified at the +58 ortholog. The regions of the +55 and +62 DHSs with peak DNase I sensitivity were inferred as possessing Active states (FIG. 5C).

We analyzed 108 clones in which the entire composite enhancer was first monoallelically deleted and subsequent mutations were produced by individual or pairs of sgRNAs targeting the +62 ortholog on the remaining allele. We measured BCL11A expression by RT-qPCR in each of these 108 clones normalized to 25 control clones not exposed to +62 targeting sgRNAs. This clonal analysis identified a core region of the +62 ortholog containing functional sequences required for BCL11A expression and embryonic 6γ-globin repression (FIG. 5C). The region is rich with TF-binding motifs, particularly those of key factors involved in erythropoiesis and globin gene regulation, including Gata1, Klf1, and Myb. Of note, despite the presence of relatively high vertebrate conservation throughout the mouse and human +62 Active state regions (FIGS. 4C, 5C), the potent impact of the mouse +62 ortholog on BCL11A and globin gene regulation greatly exceeded that of human +62 (FIGS. 3A,C-E, 5A-C).

Enhancer Function In Vivo

To substantiate the importance of the mouse +62 ortholog in BCL11A expression as well as to validate BCL11A enhancer disruption as a therapeutic strategy, we generated mouse Bcl11a+62 ortholog deficient animals. We generated mouse embryonic stem cells (mESCs) transgenic for the human β-globin cluster (β-YAC mESCs) to model the role of BCL11A in hemoglobin switching[55]. The +62 ortholog was deleted from these mESCs with the same Cas9 and paired sgRNA strategy. To determine the role of the +62 ortholog in developmental regulation of globin gene expression in vivo, two unique +62 ortholog biallelic deletion β-YAC mESC clones were injected into E3.5 non-β-YAC blastocysts and implanted into pseudo-pregnant females (FIG. 11). At E16.5, analysis revealed a 9.4-fold ($p<0.0001$) and 11.4-fold ($p<0.0001$) increase in γ-globin gene expression of +62 deletion chimeras with contributions from clones 1 and 2, respectively (FIG. 5D). These results indicated that murine erythroid cells have a cell-intrinsic functional requirement of the Bcl11a+62 ortholog for appropriate globin gene regulation in vivo.

Figure 5E:
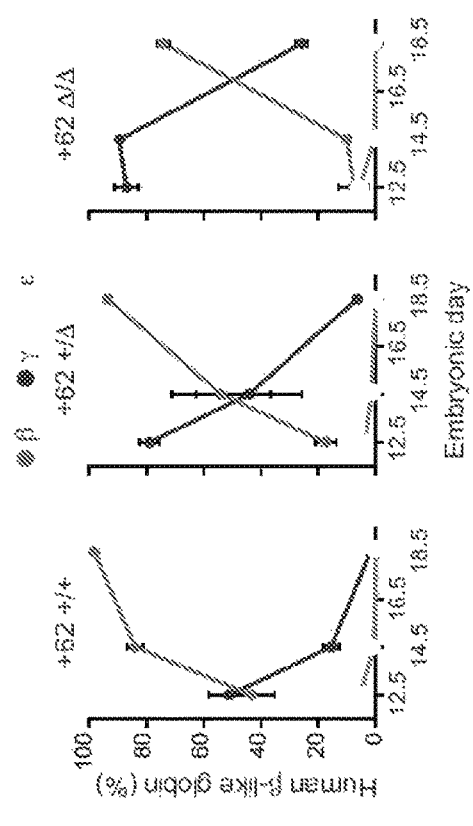
Figure 5F:
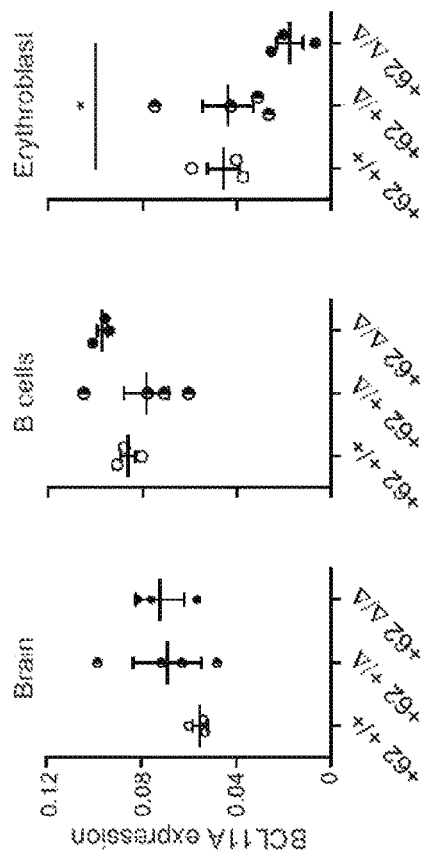

Germline+62 deletion mice were derived from CJ9 mESCs and bred with β-YAC mice. Previous studies have demonstrated an essential role for Bcl11a in structural development of the central nervous system as well as in B-lymphocyte ontogeny[56,57]. BCL11A expression was unperturbed in the brain or sorted B cell precursors from E16.5 embryos (FIGS. 5E AND 11D). In contrast, there was substantial reduction in BCL11A levels in sorted E16.5 erythroid precursors (FIG. 5E). Strikingly, unlike conventional Bcl11a knockouts that die a few hours after birth, +62 ortholog deletion mice were born healthy at expected Mendelian ratios (FIG. 10C). Bcl11a is required for the production of B-lymphocyte progenitors during both embryogenesis and adulthood[56,58]. The mice with biallelic deletion of the +62 ortholog appear to have normal numbers of B-cell progenitors in the fetal liver (FIG. 11). Furthermore, at four weeks of age these mutant animals demonstrated circulating peripheral blood B-lymphocyte frequencies comparable to wild-type littermates (FIG. 5F). Other hematopoietic lineages also appeared present at similar frequencies as wild-type littermates. Developmental regulation of transgenic human globin genes occurs in the mid-gestation mouse fetal liver. Fetal livers were evaluated every two days between E12.5 and E18.5 to monitor hemoglobin switching. Repression of human γ-globin and activation of human β-globin was markedly delayed in the +62 ortholog deleted mice. These results indicate that disrupting the erythroid enhancer of BCL11A in vivo results in erythroid-specific disruption of BCL11A expression and relaxed repression of γ-globin, unaccompanied by the obvious neurologic or immunologic toxicities seen in the BCL11A conventional knockout context.

We have employed a novel application of CRISPR-Cas9 genome editing, saturating mutagenesis of noncoding elements in situ, to provide important insight into the organization and function of the BCL11A erythroid enhancer. Traditional tests of enhancer function rely on ectopic heterologous reporter assays and/or correlative biochemical features such as the pattern of chromatin decoration. Genome editing allows facile evaluation of the requirement of enhancer sequences within their endogenous chromatin context for appropriate gene regulation. As shown here, high-resolution high-throughput pooled tiling sgRNA reveals underlying enhancer sequence requirements approaching nucleotide resolution. Although enhancers are composed of transcription factor binding motifs, the presence of motifs alone is inadequate to predict enhancers. Motif predictions can be overly sensitive, in that only a small fraction of predicted motifs tend to be corroborated by ChIP-seq occupancy studies. On the other hand, motif prediction can also be insensitive; for example, a recent report highlights the importance of low-affinity motifs for achieving specificity of enhancer function[59]. Previously we showed that GATA1 occupies +58 in primary erythroid precursors[42]. However this region possesses neither DNase sensitivity nor functional requirement in mouse erythroid cells. Despite this divergence, the human core GATA1 motif has a similar P-value in the nonfunctional mouse ortholog. These results are consistent with a model in which the motif context is critically important in enhancer activity. The sequences immediately adjacent to the GATA1 motif, where both HbF-associated sgRNAs and mutations enrich, are candidates to fulfill this contextual requirement.

Enhancers paradoxically demonstrate both evolutionary conservation and heightened turnover. Common trait-associated enhancer variation indicates the frequent occurrence of intraspecies polymorphic sequences sufficient to modulate enhancer function and thereby produce novel phenotypes. At BCL11A, we previously described a trait-associated enhancer haplotype defined by two SNPs[42]. Our pooled CRISPR screening revealed that each of these SNPs reside near functional enhancer states consistent with their roles as causal variants. The most potent enhancer region, within +58, has no common variants near its functional core. This example demonstrates how fine-mapping GWAS associations to individual SNPs can substantially underestimate the biologic importance of the underlying elements to the associated trait. In addition, these data demonstrate that apparent sequence conservation at the BCL11A enhancer masks underlying functional divergence. The mouse and human BCL11A erythroid composite enhancers share primary sequence homology, an erythroid enhancer chromatin signature, and syntenic intronic position relative to coding sequences. Moreover, both are required for erythroid expression of BCL11A and repression of embryonic/fetal globin genes. However, our high-resolution CRISPR mutagenesis analysis reveals divergence in the architecture of these enhancers. The mouse enhancer is composed of two DHSs, of which +62 has functional dominance, as validated in vivo. In contrast, the human enhancer has three DHSs, of which +62 is of the least and +58 of the greatest functional importance. Of note, human BCL11A enforces the γ- to β-globin developmental switch around the time of birth. The timing and nature of these switches and the globin genes themselves are distinct in primates as compared to non-primate vertebrates that only exhibit a mid-gestation embryonic to adult switch[60-62]. Therefore it would seem plausible that critical regulatory mechanisms at BCL11A might differ between species.

Recent appreciation for the wide variation in intensity of biochemical features associated with enhancer elements has led to a renewed interest in clustered enhancer elements and so-called super-enhancers. Here we show that one such super-enhancer is organized as a hierarchy of constituent DHSs, with some critical and others minimally required for gene expression. Moreover even within a critical DHS such as BCL11A +58, there are many dispensable and only a few critical sequences. These experiments show how a super-enhancer may be vulnerable to single DSBs.

The hemoglobin disorders represent the most common Mendelian inherited human conditions. The level of HbF is a key modifier of clinical severity of these diseases and BCL11A is the chief regulator of HbF level[63]. Natural occurring genetic variation at the BCL11A enhancer is well-tolerated and associated with HbF level and β-hemoglobin disorder clinical severity. The work presented here offers a framework for therapeutic genome editing of the BCL11A enhancer for β-hemoglobin disorders. Enhancer disruption by individual sgRNAs in primary erythroid precursors results in substantial HbF induction. This approach may mitigate erythroid-specific growth disadvantages of complete BCL11A loss. Furthermore it may spare BCL11A expression in non-erythroid contexts. For example we observed normal B-lymphopoiesis in mice deficient for the +62 ortholog. A challenge for the field is that it is not yet possible to accurately model HbF repression experimentally. However, individuals haploinsufficient for BCL11A due to microdeletions exhibit marked neurologic deficits, and elevated HbF, well beyond that seen in homozygotes for high-HbF common enhancer haplotypes (Basak et al, JCI, in press). Taken together, these data indicate that perturbation of the critical sequences within the BCL11A enhancer defined here may result in HbF levels exceeding a clinical threshold required to ameliorate the β-hemoglobin disorders.

Common SNP in human DHS +58. The only common SNP within the Active region is rs6738440 at the edge of state region (chr2:60722241), 118 to 160 bp from the cluster of top-scoring sgRNAs (chr2:60722359-60722401); the next closest common SNP was rs62142615 (chr2:60722120), 119 bp away. Neither sgRNAs with significant adjacent enrichment nor overlying genome-scale significant motifs with either the major A- or minor G-allele were observed at rs6738440. Previous conditional analysis of the rs1427407-rs7606173 haplotype was unable to demonstrate residual significant trait association for this variant[42].

Human and mouse DHS sequence homology. Sequence homology is detectable at an approximately similar intronic position with respect to the TSS for each of the mouse sequences homologous to the three human DHSs: human +55 (length 1283 bp) has 402 positions of nucleotide identity (31.3%) to the mouse +55 ortholog (length 1046 bp), human +58 (1264 bp) has 367 positions of nucleotide identity (28.6%) to the mouse +58 ortholog (length 1341 bp), and human +62 (length 1369 bp) has 281 positions of nucleotide identity (20.5%) to the mouse +62 ortholog (length 1216 bp). By comparison, of the 2508 bp in human BCL11A coding sequence, 2424 nucleotides demonstrate identity (96.7%) to mouse Bcl11a coding sequence.

Pooled CRISPR enhancer saturation mutagenesis screen in these MEL εy:mCherry reporter cells. The mouse sgRNA library was comprised of both NGG and NAG PAM restricted sgRNAs. Similar to the human enhancer screen, the sgRNAs were distributed throughout the target sites, with a median distance to adjacent cleavage site of 4 bp and 90% of adjacent cleavage sites falling within 18 bp for NGG PAM restricted sgRNAs (FIG. 9F). We successfully cloned into lentiviral plasmids all 1271 members of the library with a relatively narrow distribution of representation (median 735, 10% ile 393, 90% ile 1240 normalized reads (FIG. 9G).

Although there was slight enrichment that reached statistical significance, the NAG PAM restricted sgRNAs showed substantially reduced overrepresentation relative to the potent NGG restricted sgRNAs, so further analysis was restricted to the NGG PAM restricted sgRNAs (FIG. 9I).

Figure 9E:
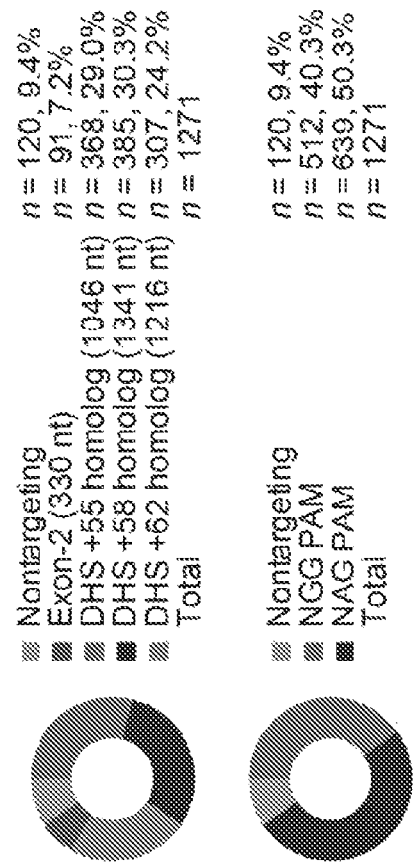
Figures 9F, 9G:
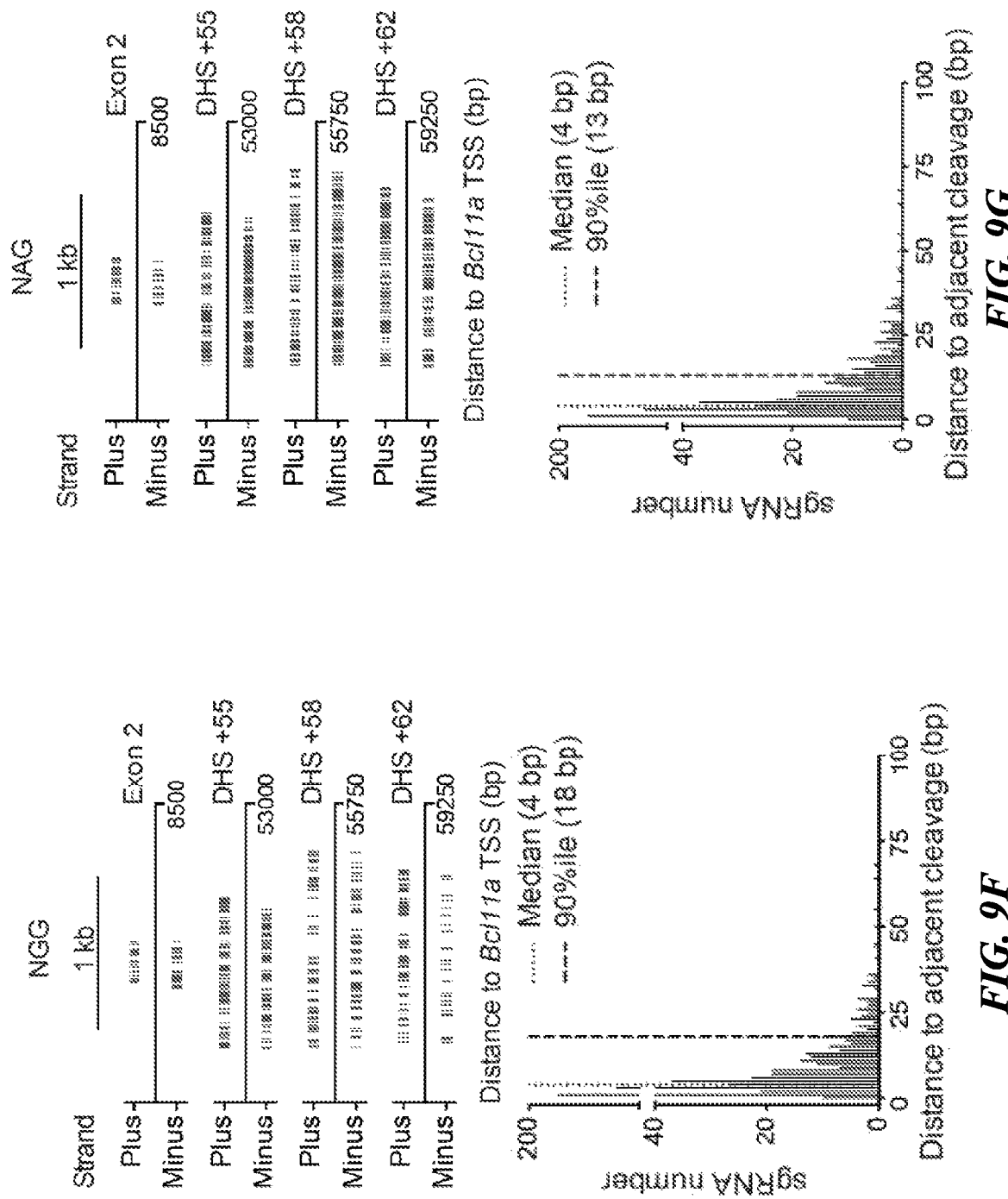

The library included sgRNA sets tiling the mouse DHS +55, +58, and +62 orthologs, as well as 120 non-targeting negative controls and 91 Bcl11a exon-2 targeting positive controls (FIG. 9E).

Figure 9H:
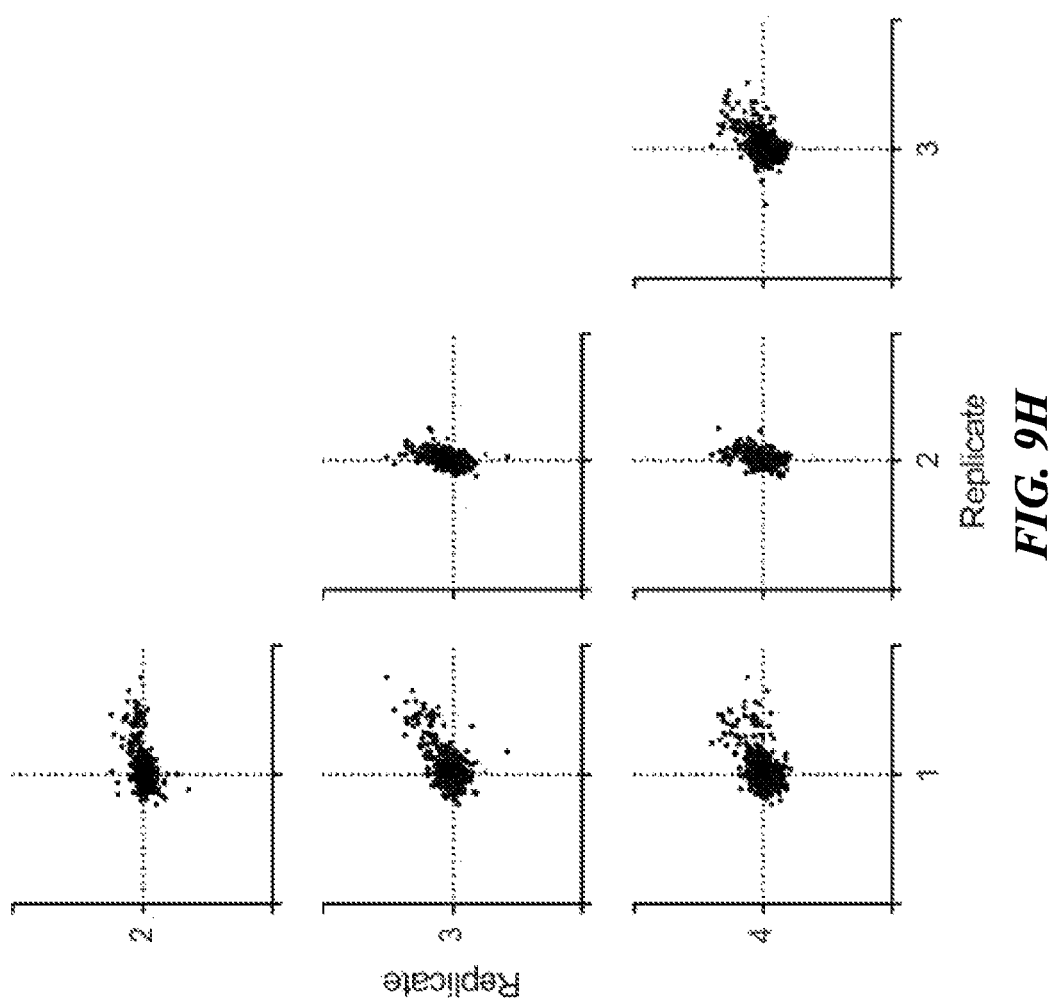

Following transduction at low multiplicity by the lentiviral library, and in vitro culture for two weeks, cells were sorted into high- and low-εy:mCherry pools (FIG. 9H). Deep sequencing was performed of the genomic DNA to evaluate the representation of sgRNA libraries in the pools. The non-targeting negative control sgRNAs were evenly represented in the high-as compared to low-εy:mCherry pools whereas the positive control Bcl11a exon-2 targeting sgRNAs with NGG PAM were significantly overrepresented in the εy:mCherry-high pool (FIG. 9I). We observed a strong correlation of enrichment scores for individual sgRNAs between the four biological replicates of the screen (FIG. 9J).

We analyzed the representation of the library in cells that had completed two weeks of in vitro culture (sum of the high- and low-εy:mCherry pools) as compared to the initial lentiviral plasmid pool. The large majority of sgRNAs showed equivalent representation in the initial plasmid pool and as integrants in cells at the completion of the experiment (FIG. 10A). A small number of sgRNAs (n=8) showed substantial dropout >2$^{-3}$ and were removed from subsequent enrichment analysis. Similar to the human screen, these mapped to repetitive elements (FIG. 10C).

Example 2

Genome Editing with NGA Restricted sgRNAs

In our initial studies we used SpCas9 for genome editing of the BCL11A erythroid enhancer. This nuclease is typically utilized along with sgRNAs restricted by the protospacer motif (PAM) sequence NGG. We subsequently tested the ability of an alternate Cas9 nuclease in conjunction with additional sgRNAs targeting the BCL11A erythroid enhancer +58 sequences to result in disruption of BCL11A expression and subsequent induction of fetal hemoglobin (HbF). We stably transduced HUDEP-2 cells with SpCas9-VQR[74], which unlike SpCas9, is restricted by the protospacer adjacent motif (PAM) sequence NGA rather than NGG. We tested a lentiviral library of sgRNAs restricted by the NGA PAM targeting the BCL11A +58 enhancer. Cells were transduced with the lentiviral library at low multiplicity, so that each transduced cell carried a single sgRNA integrant. Each sgRNA was represented 1000 times per cell. Cells were expanded, differentiated, and stained for HbF. Populations with high HbF and low HbF were sorted by FACS. Genomic DNA was isolated, and sgRNAs were deeply sequenced to determine enrichment in the high HbF pool. We identified 5 NGA restricted sgRNAs targeting BCL11A +58 that were associated with significant HbF enrichment (see Table 9). The top-scoring NGA restricted sgRNA, BCL_NGA_00069, specifies a cleavage position at hg19 chr2:60,722,388 which is only 4 bp from the cleavage position of BCL_01621, the top-scoring sgRNA from the NGG-restricted sgRNA screen. These results indicate that genome editing with SpCas9-VQR variant and NGA restricted sgRNAs at critical BCL11A +58 enhancer sequences is sufficient to disrupt BCL11A expression and result in elevated HbF level.

CRISPR Interference with dCas9-KRAB

Figure 12:
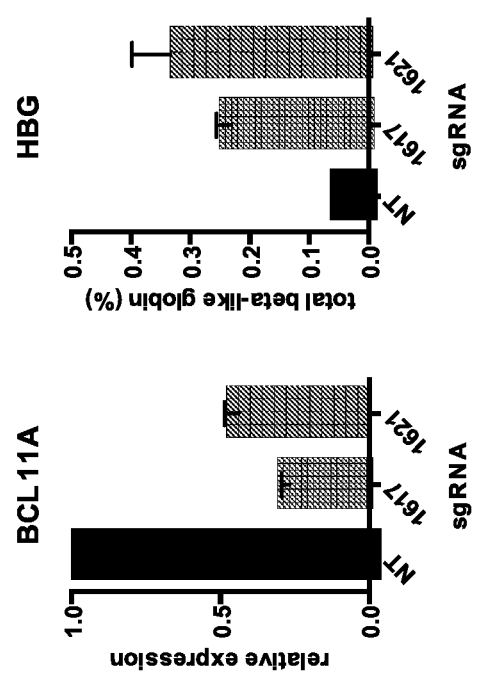
FIG. 12 shows that HUDEP-2 cells expressing dCas9-KRAB plus indicated sgRNA were analyzed for gene expression. BCL11A is plotted relative to GAPDH. HBG is plotted relative to total beta-like globin. Two different sgRNAs targeting BCL11A +58 (BCL_01617 and BCL_01621) lead to transcriptional repression of BCL11A and derepression of HBG (gamma-globin). NT, non-targeting control.

In addition to uses of CRISPR genome editing by the production of targeted double strand breaks, Cas9 may be repurposed to regulate gene expression by epigenome editing. One method is to use a catalytic inactive version of Cas9 (dCas9) coupled to a transcriptional repression domain such as the Kruppel associated box (KRAB) domain[73]. In this mode, sgRNAs may target the transcriptional repressor dCas9-KRAB to specific genomic loci to result in gene repression. We tested the ability of dCas9-KRAB with BCL11A enhancer targeting sgRNAs to mediate BCL11A gene repression and subsequent HbF induction. We observed reduction of BCL11A expression and induction of gamma-globin expression with two BCL11A +58 targeting sgRNAs (BCL_01617 and BCL_01621, see Table 7) as compared to a nontargeting control (see FIG. 12). These results indicate that epigenome editing targeting critical sequences at the BCL11A enhancer is sufficient to disrupt BCL11A expression and result in elevated HbF level.

REFERENCES

1. Banerji, J., Rusconi, S. & Schaffner, W. Expression of a beta-globin gene is enhanced by remote SV40 DNA sequences. Cell 27, 299-308 (1981).
2. Visel, A. et al. ChIP-seq accurately predicts tissue-specific activity of enhancers. Nature 457, 854-858 (2009).
3. Thurman, R. E. et al. The accessible chromatin landscape of the human genome. Nature 489, 75-82 (2012).
4. Dunham, I. et al. An integrated encyclopedia of DNA elements in the human genome. Nature 489, 57-74 (2012).
5. Johnson, D. S., Mortazavi, A. & Myers, R. M. Genome-Wide Mapping of in Vivo Protein-DNA Interactions. Science, 316, 1497-1503 (2007).
6. Barski, A. et al. High-Resolution Profiling of Histone Methylations in the Human Genome.
Cell 129, 823-837 (2007).
7. Andersson, R. et al. An atlas of active enhancers across human cell types and tissues. Nature 507, 455-61 (2014).
8. Consortium, R. E. et al. Integrative analysis of 111 reference human epigenomes. Nature 518, 7539 (2015).
9. Heintzman, N. D. et al. Histone modifications at human enhancers reflect global cell-type-specific gene expression. Nature 459, 108-112 (2009).
10. Creyghton, M. P. et al. Histone H3K27ac separates active from poised enhancers and predicts developmental state. Proc. Natl. Acad. Sci. U.S.A. 107, 21931-21936 (2010).
11. Rada-Iglesias, A. et al. A unique chromatin signature uncovers early developmental enhancers in humans. Nature 470, 279-283 (2011).
12. Xu, J. et al. Combinatorial assembly of developmental stage-specific enhancers controls gene expression programs during human erythropoiesis. Dev. Cell 23, 796-811 (2012).
13. Ernst, J. et al. Mapping and analysis of chromatin state dynamics in nine human cell types.
Nature 473, 43-49 (2011).
14. Parker, S. C. J. et al. Chromatin stretch enhancer states drive cell-specific gene regulation and harbor human disease risk variants. Proc. Natl. Acad. Sci. U.S.A 110, 17921-6 (2013).
15. Whyte, W. A. et al. Master transcription factors and mediator establish super-enhancers at key cell identity genes. Cell 153, 307-319 (2013).
16. Paul, D. S. et al. Maps of open chromatin guide the functional follow-up of genome-wide association signals: Application to hematological traits. PLoS Genet. 7, (2011).
17. Maurano, M. T. et al. Systematic localization of common disease-associated variation in regulatory DNA. Science, 337, 1190-1195 (2012).
18. Hnisz, D. et al. Super-enhancers in the control of cell identity and disease. Cell 155, 934-47 (2013).
19. Farh, K. K.-H. et al. Genetic and epigenetic fine mapping of causal autoimmune disease variants. Nature (2014). doi:10.1038/nature13835
20. Hardison, R. C. Variable evolutionary signatures at the heart of enhancers. Nat. Genet. 42, 734-735 (2010).
21. Blow, M. J. et al. ChIP-Seq identification of weakly conserved heart enhancers. Nat. Genet.
42, 806-810 (2010).
22. May, D. et al. Large-scale discovery of enhancers from human heart tissue. Nat. Genet. 44, 89-93 (2011).
23. Vierstra, J. et al. Mouse regulatory DNA landscapes reveal global principles of cis-regulatory evolution. Science 346, 1007-1012 (2014).
24. Villar, D. et al. Enhancer Evolution across 20 Mammalian Species. Cell 160, 554-566 (2015).
25. Pennacchio, L. et al. In vivo enhancer analysis of human conserved non-coding sequences.
Nature 444, 499-502 (2006).
26. Melnikov, A. et al. Systematic dissection and optimization of inducible enhancers in human cells using a massively parallel reporter assay. Nat. Biotechnol. 30, 271-277 (2012).
27. Patwardhan, R. P. et al. Massively parallel functional dissection of mammalian enhancers in vivo. Nat. Biotechnol. 30, 265-270 (2012).
28. Lieberman-Aiden, E. et al. Comprehensive Mapping of Long-Range Interactions Reveals Folding Principles of the Human Genome. Science (80-.). 326, 289-294 (2009).
29. Dixon, J. R. et al. Topological domains in mammalian genomes identified by analysis of chromatin interactions. Nature 485, 376-380 (2012).
30. Nord, A. S. et al. Rapid and pervasive changes in genome-wide enhancer usage during mammalian development. Cell 155, 1521-1531 (2013).
31. Sexton, T. & Cavalli, G. Review The Role of Chromosome Domains in Shaping the Functional Genome. Cell 160, 1049-1059 (2015).
32. Bender, M., Bulger, M., Close, J. & Groudine, M. Beta-globin gene switching and DNase I sensitivity of the endogenous beta-globin locus in mice do not require the locus control region. Mol. Cell 5, 387-393 (2000).

33. Johnson, K. D. et al. Cis-element mutated in GATA2-dependent immunodeficiency governs hematopoiesis and vascular integrity. J. Clin. Invest. 122, 3692-3704 (2012).
34. Cong, L. et al. Multiplex genome engineering using CRISPR/Cas systems. Science, 339, 819-23 (2013).
35. Mali, P. et al. RNA-guided human genome engineering via Cas9. Science, 339, 823-6 (2013).
36. Wang, T., Wei, J. J., Sabatini, D. M. & Lander, E. S. Genetic screens in human cells using the CRISPR-Cas9 system. Science, 343, 80-4 (2014).
37. Shalem, O. et al. Genome-scale CRISPR-Cas9 knockout screening in human cells. Science, 343, 84-7 (2014).
38. Koike-Yusa, H., Li, Y., Tan, E.-P., Del Castillo Velasco-Herrera, M. & Yusa, K. Genome-wide recessive genetic screening in mammalian cells with a lentiviral CRISPR-guide RNA library. Nat. Biotechnol. 1-10 (1AD).
39. Mathelier, A. et al. JASPAR 2014: An extensively expanded and updated open-access database of transcription factor binding profiles. Nucleic Acids Res. 42, 142-147 (2014).
40. Zhou, Y. et al. High-throughput screening of a CRISPR/Cas9 library for functional genomics in human cells. Nature (2014).
41. Chen, S. et al. Genome-wide CRISPR Screen in a Mouse Model of Tumor Growth and Metastasis Resource Genome-wide CRISPR Screen in a Mouse Model of Tumor Growth and Metastasis. Cell 160, 1-15 (2015).
42. Bauer, D. E. et al. An Erythroid Enhancer of BCL11A Subject to Genetic Variation Determines Fetal Hemoglobin Level. Science, 342, 253-257 (2013).
43. Gröschel, S. et al. A single oncogenic enhancer rearrangement causes concomitant EVI1 and GATA2 deregulation in Leukemia. Cell 157, 369-381 (2014).
44. Mansour, M. R. et al. An oncogenic super-enhancer formed through somatic mutation of a noncoding intergenic element. Science, 10-15 (2014).
45. Sankaran, V. G. et al. Human fetal hemoglobin expression is regulated by the developmental stage-specific repressor BCL11A. Science, 322, 1839-1842 (2008).
46. Sankaran, V. G. et al. Developmental and species-divergent globin switching are driven by BCL11A. Nature 460, 1093-1097 (2009).
47. Xu, J. et al. Correction of sickle cell disease in adult mice by interference with fetal hemoglobin silencing. Science, 334, 993-996 (2011).
48. Hardison, R. C. & Blobel, G. A. GWAS to therapy by genome edits? Science, 342, 206-7 (2013).
49. Kurita, R. et al. Establishment of Immortalized Human Erythroid Progenitor Cell Lines Able to Produce Enucleated Red Blood Cells. PLoS One 8, e59890 (2013).
50. Canver, M. C. et al. Characterization of Genomic Deletion Efficiency Mediated by Clusted Regularly Interspaced Palindromic Repeats (CRISPR)/Cas9 Nuclease System in Mammalian Cells. J. Biol. Chem. 289, 21312-21324 (2014).
51. Mandal, P. K. et al. Efficient Ablation of Genes in Human Hematopoietic Stem and Effector Cells using CRISPR/Cas9. Cell Stem Cell 15, 643-652 (2014).
52. Ran, F. A. et al. Double nicking by RNA-guided CRISPR Cas9 for enhanced genome editing specificity. Cell 154, 1380-9 (2013).
53. Hsu, P. D. et al. DNA targeting specificity of RNA-guided Cas9 nucleases. Nat. Biotechnol. 31, 827-32 (2013).
54. Cui, F., Sirotin, M. V & Zhurkin, V. B. Impact of Alu repeats on the evolution of human p53 binding sites. Biol. Direct 6, 2 (2011).
55. Porcu, B. S. et al. The human β globin locus introduced by YAC transfer exhibits a specific and reproducible pattern of developmental regulation in transgenic mice. Blood 90, 4602-4609 (1997).
56. Liu, P. et al. Bcl11a is essential for normal lymphoid development. Nat. Immunol. 4, 525-532 (2003).
57. John, A. et al. Bcl11a is required for neuronal morphogenesis and sensory circuit formation in dorsal spinal cord development. Development 139, 1831-41 (2012).
58. Yu, Y. et al. Bcl11a is essential for lymphoid development and negatively regulates p53. J. Exp. Med. 209, 2467-83 (2012).
59. Crocker, J. et al. Low Affinity Binding Site Clusters Confer Hox Specificity and Regulatory Robustness. Cell 191-203 (2015).
60. Bauer, D. E. & Orkin, S. H. Update on fetal hemoglobin gene regulation in hemoglobinopathies. Curr. Opin. Pediatr. 23, 1-8 (2011).
61. Bauer, D. E., Kamran, S. C. & Orkin, S. H. Reawakening fetal hemoglobin: Prospects for new therapies for the beta-globin disorders. Blood 120, 2945-2953 (2012).
62. Sankaran, V. G. & Orkin, S. H. The switch from fetal to adult hemoglobin. Cold Spring Harb. Perspect. Med. 3, 1-14 (2013).
63. Bauer, D. E. E., Kamran, S. C. C. & Orkin, S. H. H. Reawakening fetal hemoglobin: prospects for new therapies for the β-globin disorders. Blood 120, 2945-2953 (2012).
64. Sanjana, N. E., Shalem, O. & Zhang, F. Improved vectors and genome-wide libraries for CRISPR screening. Nat. Methods 11, 783-784 (2014).
65. Giarratana, M. et al. Proof of principle for transfusion of in vitro generated red blood cells. Blood 118, 5071-5079 (2011).
66. Brinkman, E. K., Chen, T., Amendola, M. & van Steensel, B. Easy quantitative assessment of genome editing by sequence trace decomposition. Nucleic Acids Res. 1-8 (2014).
67. Bauer, D. E., Canver, M. C. & Orkin, S. H. Generation of Genomic Deletions in Mammalian Cell Lines via CRISPR/Cas9. J. Vis. Exp. 1-10 (2014).
68. Canver, M. C. et al. Characterization of Genomic Deletion Efficiency Mediated by CRISPR/Cas9 in Mammalian Cells. J. Biol. Chem. 289, 21312-21324 (2014).
69. Kowalczyk, M. S. et al. Intragenic Enhancers Act as Alternative Promoters. Mol. Cell 45, 447-458 (2012).
70. Grant, C. E., Bailey, T. L. & Noble, W. S. FIMO: Scanning for occurrences of a given motif. Bioinformatics 27, 1017-1018 (2011).
71. Weber, K., Bartsch, U., Stocking, C. & Fehse, B. A multicolor panel of novel lentiviral 'gene ontology' (LeGO) vectors for functional gene analysis. Mol. Ther. 16, 698-706 (2008).
72. Doench, J. G. et al. Rational design of highly active sgRNAs for CRISPR-Cas9-mediated gene inactivation. Nat Biotechnol 32, (2014).
73. Gilbert, L. A, et al. CRISPR-Mediated Modular RNA-Guided Regulation of Transcription in Eukaryotes. Cell 154(2): 442-451, (2013).
74. Kleinstiver, B. P., et al. Engineered CRISPR-Cas9 Nucleases with Altered PAM Specificities. Nature 523 (7561): 481-85. (2015).

TABLE 1 sgRNA Sequences

| SEQ. ID. NO: | sgRNA Target Gene or Region | Species | Sequence |
|---|---|---|---|
| 154 | Composite Enhancer 5' Target 1 | Human | TGGAAAGGAGAACGGCCCGG |
| 155 | Composite Enhancer 5' Target 2 | Human | TGAACACCCTCGTTAAAGGC |
| 156 | Composite Enhancer 5' Target 3 | Human | AACACTAGCCCACATGCCAA |
| 157 | Composite Enhancer 3' Target 1 | Human | GCCCACAGAGGCACGGTTAA |
| 158 | Composite Enhancer 3' Target 2 | Human | AGGCACGGTTAATGGTGGCG |
| 159 | Composite Enhancer 3' Target 3 | Human | CACAGGAAGCCATGGTCCTT |
| 160 | +55 5' Target 1 | Human | GCACTGACGTAGGTAGTGAC |
| 161 | +55 5' Target 2 | Human | ATAGGATATGGCACTGACGT |
| 162 | +55 3' Target 1 | Human | CATTATCTTCTCTGGTCTCG |
| 163 | +55 3' Target 2 | Human | ATACTGGGGAACACATTGTA |
| 164 | +58 5' Target 1 | Human | TGAGCACATTCTTACGCCTA |
| 165 | +58 5' Target 2 | Human | CTAGGCGTAAGAATGTGCTC |
| 166 | +58 3' Target 1 | Human | GAACCCCCTATAAACTAGTC |
| 167 | +58 3' Target 2 | Human | GGCAAACCAGACTAGTTTAT |
| 168 | +62 5' Target 1 | Human | CAGGGGAGAACTCGGCATGA |
| 169 | +62 5' Target 2 | Human | GATGGAGTTGGTTGACCGTA |
| 170 | +62 3' Target 1 | Human | GGTAGGACCCAACACTACGC |
| 171 | +62 3' Target 2 | Human | ATGCCTAGGGTGTTTTGACG |
| 172 | BCL11A Exon 2 Target 2 | Human | TGAACCAGACCACGGCCCGT |
| 173 | BCL11A Exon 2 Target 3 | Human | GCATCCAATCCCGTGGAGGT |
| 174 | +55 5' Target | Mouse | CACTGGCTTCCTGTTCTTGT |
| 175 | +55 3' Target | Mouse | AAGGTTTTCAAGGCAAATAA |
| 176 | +58 5' Target | Mouse | GTAATGGAGCCCGCATGCTG |
| 177 | +58 3' Target | Mouse | GCCAGTGTACAGGCAAGTAC |
| 178 | +62 5' Target | Mouse | TCGCTGCCTTCAGTTCTGCT |
| 179 | +62 3' Target | Mouse | TTATGGAACTCAGGAACTGC |
| 180 | Bcl11a Exon 2 Target | Mouse | GATGCCTTTTTCATCTCGAT |
| 181 | +62 Heat Map Target 1 | Mouse | ATTCCTTGAGTGTCATATAT |
| 182 | +62 Heat Map Target 2 | Mouse | TCTGGAATCACTATGTATAT |

TABLE 2

Oligonucleotide primers for Deletion Clone Screening

| SEQ. ID. NO: | Gene or Region | Species | Non-Deletion (ND) or Deletion (D) | CRISPR Pair | Orientation | Sequence |
|---|---|---|---|---|---|---|
| 183 | Composite Enhancer | Human | ND | 5' Target 3 | Forward | TGCTCCGAGCTTGTGAACTA |
| 184 | | | | 3' Target 1 | Reverse | TATCACAGGCTCCAGGAAGG |
| 185 | Composite Enhancer | Human | D | 5' Target 3 | Forward | TAGTTTGCTTCCCCCAATGA |
| 186 | | | | 3' Target 1 | Reverse | GCCAGGAAATTGGTGGTAGA |
| 187 | Composite Enhancer | Human | ND | 5' Target 2 | Forward | TGCTCCGAGCTTGTGAACTA |
| 188 | | | | 3' Target 2 | Reverse | TATCACAGGCTCCAGGAAGG |
| 189 | Composite Enhancer | Human | D | 5' Target 2 | Forward | GTGGGCAGTTACGTTTTCGT |
| 190 | | | | 3' Target 2 | Reverse | GCCAGGAAATTGGTGGTAGA |
| 191 | +55 | Human | ND | 5' Target 1 or 2 | Forward | GGTCAGGGTGTTGCAGAGAT |
| 192 | | | | 3' Target 1 or 2 | Reverse | CACACCCTGTGATCTTGTGG |
| 193 | +55 | Human | D | 5' Target 1 or 2 | Forward | GACTTAAACTGCCGCTCCTG |
| 194 | | | | 3' Target 1 or 2 | Reverse | GGGCCTCAGGCTCTTTATCT |

TABLE 2-continued

Oligonucleotide primers for Deletion Clone Screening

| SEQ. ID. NO: | Gene or Region | Species | Non-Deletion (ND) or Deletion (D) | CRISPR Pair | Orientation | Sequence |
|---|---|---|---|---|---|---|
| 195 | +58 | Human | ND | 5' Target 1 or 2 | Forward | CCCAGAGCTCAGTGAGATGA |
| 196 | | | | 3' Target 1 or 2 | Reverse | GGGAAAGGGCCTGATAACTT |
| 197 | +58 | Human | D | 5' Target 1 or 2 | Forward | GAACAGAGACCACTACTGGCAAT |
| 198 | | | | 3' Target 1 or 2 | Reverse | CTCAGAAAAATGACAGCACCA |
| 199 | +62 | Human | ND | 5' Target 1 or 2 | Forward | TTTGAAAGTACCAGCACAGCA |
| 200 | | | | 3' Target 1 or 2 | Reverse | CCCTCTGGCATCAAAATGAG |
| 201 | +62 | Human | D | 5' Target 1 or 2 | Forward | AACAGACCCATGTGCTAGGC |
| 202 | | | | 3' Target 1 or 2 | Reverse | TGCTGAATTCCTGTAAAGTGAGG |
| 203 | +55 | Mouse | ND | 5' Target | Forward | GAGGTGACCAGGGTGTGAGT |
| 204 | | | | 3' Target | Reverse | AAGAAGAGGCCCTGGACATT |
| 205 | +55 | Mouse | D | 5' Target | Forward | CATCTTAAGGCAAGAATCACT |
| 206 | | | | 3' Target | Reverse | CCAGTCAATCCAAACCCTGT |
| 207 | +58 | Mouse | ND | 5' Target | Forward | TATTAATGCCCAGCCAGCTC |
| 208 | | | | 3' Target | Reverse | GTGGTCCAGACCTAGCCAAG |
| 209 | +58 | Mouse | D | 5' Target | Forward | TTTGAGCAGGAGGGAATTTG |
| 210 | | | | 3' Target | Reverse | ATAGGTGGTTGGGCTTCTCC |
| 211 | +62 | Mouse | ND | 5' Target | Forward | GGAGTGGCTGTTGAAAGAGG |
| 212 | | | | 3' Target | Reverse | CACTCAAGGAATGCAAGCAA |
| 213 | +62 | Mouse | D | 5' Target | Forward | TACTTGGTGGCTTTCCCAAC |
| 214 | | | | 3' Target | Reverse | AGATGGTCCTCTGCATCCAC |

TABLE 3

Oligonucleotide primers for Inversion Clone Screening

| SEQ. ID. NO: | Inverted Region | Species | CRISPR Pair | Orientation | Sequence |
|---|---|---|---|---|---|
| 215 | +55 | Human | 5' Target 1 or 2 | Forward | GACTTAAACTGCCGCTCCTG |
| 216 | | | 3' Target 1 or 2 | Forward | AGGCATCCAAAGGGAAGAAT |
| 217 | +55 | Human | 5' Target 1 or 2 | Reverse | ACTTCAGCCTCCAGCACTGT |
| 218 | | | 3' Target 1 or 2 | Reverse | CCACTGGAGTGGAACCAAGT |
| 219 | +58 | Human | 5' Target 1 or 2 | Forward | GGGATCAGAGGTGAACAGGA |
| 220 | | | 3' Target 1 or 2 | Forward | TGGACTTTGCACTGGAATCA |
| 221 | +58 | Human | 5' Target 1 or 2 | Reverse | TTGTTTACAGAGGGGCAACC |
| 222 | | | 3' Target 1 or 2 | Reverse | GGGGAAGGGGTATTGAATTG |
| 223 | +62 | Mouse | 5' Target 1 or 2 | Forward | AACAGACCCATGTGCTAGGC |
| 224 | | | 3' Target 1 or 2 | Forward | GAACCTGGGAGGCAGAAGAT |
| 225 | +62 | Mouse | 5' Target 1 or 2 | Reverse | TGTGTGGACTGCCTTTTCTG |
| 226 | | | 3' Target 1 or 2 | Reverse | TGTGGAGCTCTGGAATGATG |

TABLE 4

Oligonucleotide primers for Mouse +62 Deletion Analysis

| SEQ. ID. NO: | Region | Species | CRISPR Pair | Orientation | Sequence |
|---|---|---|---|---|---|
| 227 | +62 | Mouse | Screen 0484 | Forward | GGTAGTGTGGGGGTGGAGT |
| 228 | | | Screen 0475 | Reverse | TCAGCCTGTTCCCTCAGTG |
| 229 | +62 | Mouse | Screen 0484 | Forward | GGTAGTGTGGGGGTGGAGT |
| 230 | | | Screen 2456 | Reverse | TCAGCCTGTTCCCTCAGTG |
| 231 | +62 | Mouse | Screen 0475 | Forward | GGTAGTGTGGGGGTGGAGT |
| 232 | | | Screen 0490 | Reverse | TCAGCCTGTTCCCTCAGTG |
| 233 | +62 | Mouse | Screen 0490 | Forward | GGTAGTGTGGGGGTGGAGT |
| 234 | | | +62 3' Target | Reverse | AGATGGTCCTCTGCATCCAC |
| 235 | +62 | Mouse | Screen 0490 | Forward | GGTAGTGTGGGGGTGGAGT |
| 236 | | | +62 Heat Map Target 1 | Reverse | TCAGCCTGTTCCCTCAGTG |
| 237 | +62 | Mouse | +62 5' Target | Forward | TACTTGGTGGCTTTCCCAAC |
| 238 | | | Screen 0475 | Reverse | TCAGCCTGTTCCCTCAGTG |
| 239 | +62 | Mouse | +62 Heat Map Target 2 | Forward | ATGCTTGGTTGTCGCCTTAT |
| 240 | | | Screen 0475 | Reverse | CACTCAAGGAATGCAAGCAA |

TABLE 5

RT qPCR Oligonucleotides

| SEQ. ID. NO: | Gene | Species | Orientation | Sequence |
|---|---|---|---|---|
| 241 | GAPDH | Human | Forward | ACCCAGAAGACTGTGGATGG |
| 242 | | | Reverse | TTCAGCTCAGGGATGACCTT |
| 243 | HBB | Human | Forward | CTGAGGAGAAGTCTGCCGTTA |
| 244 | | | Reverse | AGCATCAGGAGTGGACAGAT |
| 245 | HBG | Human | Forward | TGGATGATCTCAAGGGCAC |
| 246 | | | Reverse | TCAGTGGTATCTGGAGGACA |
| 247 | HBE | Human | Forward | GCAAGAAGGTGCTGACTTCC |
| 248 | | | Reverse | ACCATCACGTTACCCAGGAG |
| 249 | HBD | Human | Forward | GAGGAGAAGACTGCTGTCAATG |
| 250 | | | Reverse | AGGGTAGACCACCAGTAATCTG |
| 251 | BCL11A | Human | Forward | AACCCCAGCACTTAAGCAAA |
| 252 | | | Reverse | GGAGGTCATGATCCCCTTCT |
| 253 | Gapdh | Mouse | Forward | TGGTGAAGGTCGGTGTGAAC |
| 254 | | | Reverse | CCATGTAGTTGAGGTCAATGAAGG |
| 255 | β-Major | Mouse | Forward | TTTAACGATGGCCTGAATCACTT |
| 256 | | | Reverse | CAGCACAATCACGATCATATTGC |
| 257 | Hbb-εγ | Mouse | Forward | TGGCCTGTGGAGTAAGGTCA |

TABLE 5-continued

RT qPCR Oligonucleotides

| SEQ. ID. NO: | Gene | Species | Orientation | Sequence |
|---|---|---|---|---|
| 258 | | | Reverse | GAAGCAGAGGACAAGTTCCCA |
| 259 | Hbb-βh1 | Mouse | Forward | TGGACAACCTCAAGGAGACC |
| 260 | | | Reverse | ACCTCTGGGGTGAATTCCTT |
| 261 | Bcl11a | Mouse | Forward | AACCCCAGCACTTAAGCAAA |
| 262 | | | Reverse | ACAGGTGAGAAGGTCGTGGT |

TABLE 6

Location of BCL11A enhancer region for targeting to achieve BCL11A knockdown

| chromosome | coordinate start (hg19) | coordinate end (hg19) | name |
|---|---|---|---|
| chr2 | 60725424 | 60725688 | +55 functional region |
| chr2 | 60722238 | 60722466 | +58 functional region |
| chr2 | 60718042 | 60718186 | +62 functional region |

TABLE 7 sgRNA targeting sequences that produced HbF enrichment over 0.259

| SEQ ID NO: | Identifer | sgRNA Sequence | PAM | Targeted Site | Coordinate Relative to TSS | Chr2 Genomic Coordinate (hg19) | Enrichment Score | Dropout Score |
|---|---|---|---|---|---|---|---|---|
| 1 | BCL_00108_H_D55 | TCTGAGGAGCTAGAGACTTG | NGG | DHS_55 | 54701 | 60725932 | 0.3065268 | -0.64986 |
| 2 | BCL_00096_H_D55 | AGCAAATAGGCTTAGTGTGC | NGG | DHS_55 | 54874 | 60725759 | 0.35208854 | -0.23956 |
| 3 | BCL_01427_H_D55 | GGCTAAATAATGAATGTCCC | NGG RC | DHS_55 | 54944 | 60725689 | 0.36697304 | -0.27163 |
| 4 | BCL_00093_H_D55 | TCCCTTCCTAGAATTGGCCT | NGG | DHS_55 | 54950 | 60725683 | 0.52834198 | -0.56164 |
| 5 | BCL_00092_H_D55 | TTCCCTTCCTAGAATTGGCC | NGG | DHS_55 | 54951 | 60725682 | 0.40353821 | -0.43691 |
| 6 | BCL_01428_H_D55 | GAATGTCCCAGGCCAATTCT | NGG RC | DHS_55 | 54955 | 60725678 | 0.4298807 | -0.54353 |
| 7 | BCL_00091_H_D55 | CCCACTTCCCTTCCTAGAAT | NGG | DHS_55 | 54956 | 60725677 | 1.16779598 | -0.50425 |
| 8 | BCL_00090_H_D55 | CCTGGTACCAGGAAGGCAAT | NGG | DHS_55 | 54989 | 60725644 | 0.46505933 | -0.52917 |
| 9 | BCL_00089_H_D55 | TCCTGGTACCAGGAAGGCAA | NGG | DHS_55 | 54990 | 60725643 | 0.35594471 | -0.78622 |
| 10 | BCL_00088_H_D55 | GCATCATCCTGGTACCAGGA | NGG | DHS_55 | 54996 | 60725637 | 0.43864112 | -0.37134 |
| 11 | BCL_00087_H_D55 | CATTGCATCATCCTGGTACC | NGG | DHS_55 | 55000 | 60725633 | 0.43801718 | -0.22534 |
| 12 | BCL_00086_H_D55 | CTCCAAGCATTGCATCATCC | NGG | DHS_55 | 55007 | 60725626 | 0.63433419 | -0.27033 |
| 13 | BCL_01438_H_D55 | TACCAGGATGATGCAATGCT | NGG RC | DHS_55 | 55016 | 60725617 | 0.91292075 | -0.34122 |
| 14 | BCL_00085_H_D55 | GGGTGTGCCCTGAGAAGGTG | NGG | DHS_55 | 55040 | 60725593 | 0.50114706 | -0.6263 |
| 15 | BCL_00084_H_D55 | AGGGTGTGCCCTGAGAAGGT | NGG | DHS_55 | 55041 | 60725592 | 0.31100243 | -0.36912 |
| 16 | BCL_00082_H_D55 | TCACAGGGTGTGCCCTGAGA | NGG | DHS_55 | 55045 | 60725588 | 0.41742767 | -1.08709 |
| 17 | BCL_01443_H_D55 | GGCACACCCTGTGATCTTGT | NGG RC | DHS_55 | 55065 | 60725568 | 0.41807361 | 0.257924 |
| 18 | BCL_00073_H_D55 | AGCACACAAGATGCACACCC | NGG | DHS_55 | 55096 | 60725537 | 0.41986965 | -0.83722 |
| 19 | BCL_01448_H_D55 | TGTGCTTGGTCGGCACTGAT | NGG RC | DHS_55 | 55124 | 60725509 | 1.34772811 | -0.49527 |
| 20 | BCL_01449_H_D55 | GTGCTTGGTCGGCACTGATA | NGG RC | DHS_55 | 55125 | 60725508 | 1.13392025 | -0.61013 |
| 21 | BCL_01450_H_D55 | TGCTTGGTCGGCACTGATAG | NGG RC | DHS_55 | 55126 | 60725507 | 1.5783257 | -0.31949 |
| 22 | BCL_01454_H_D55 | GGGTCGCGGTAGGGAGTTGT | NGG RC | DHS_55 | 55146 | 60725487 | 0.35789318 | -0.55774 |
| 23 | BCL_00065_H_D55 | GCCAACAGTGATAACCAGCA | NGG | DHS_55 | 55235 | 60725398 | 0.48864454 | -0.54147 |
| 24 | BCL_00064_H_D55 | TGCCAACAGTGATAACCAGC | NGG | DHS_55 | 55236 | 60725397 | 0.51080164 | -0.35814 |
| 25 | BCL_01461_H_D55 | GCCCTGCTGGTTATCACTGT | NGG RC | DHS_55 | 55245 | 60725388 | 0.59624098 | -0.51154 |
| 26 | BCL_00062_H_D55 | AGCAGCCCTGGGCACAGAAG | NGG | DHS_55 | 55272 | 60725361 | 0.32514466 | -0.64013 |
| 27 | BCL_00058_H_D55 | CCTCTATGTAGACGGGTGTG | NGG | DHS_55 | 55311 | 60725322 | 0.32368336 | -0.4848 |
| 28 | BCL_00057_H_D55 | GGAAGGGCCTCTATGTAGAC | NGG | DHS_55 | 55318 | 60725315 | 0.45996809 | -0.44507 |
| 29 | BCL_00051_H_D55 | GGAGGTGTGGAGGGGATAAC | NGG | DHS_55 | 55356 | 60725277 | 0.31408916 | -0.16554 |
| 30 | BCL_00031_H_D55 | CTGGCAGACCCTCAAGAGCA | NGG | DHS_55 | 55444 | 60725189 | 0.32158621 | -1.35414 |
| 31 | BCL_00027_H_D55 | CCCATGGAGGTGGGGAGATG | NGG | DHS_55 | 55474 | 60725159 | 0.28225491 | -0.45625 |
| 32 | BCL_01483_H_D55 | GTCATCCTCGGCCAATGAAG | NGG RC | DHS_55 | 55559 | 60725074 | 0.43184473 | -0.40557 |
| 33 | BCL_00012_H_D55 | AAGTGAGCCAGGTGATAGAA | NGG | DHS_55 | 55585 | 60725048 | 0.35107033 | -0.01983 |
| 34 | BCL_00008_H_D55 | TGAAACCAAGCTTCCTCTGC | NGG | DHS_55 | 55612 | 60725021 | 0.27412127 | -0.23029 |
| 35 | BCL_01495_H_D55 | AGGGAGAAATGAGACAAAAG | NGG RC | DHS_55 | 55700 | 60724933 | 0.26434414 | -0.49318 |
| 36 | BCL_01497_H_D55 | AAGAGGCCACTGAGTCCTTT | NGG RC | DHS_55 | 55717 | 60724916 | 0.43002762 | 0.456237 |

TABLE 7-continued sgRNA targeting sequences that produced HbF enrichment over 0.259

| SEQ ID NO: | Identifer | sgRNA Sequence | PAM | Targeted Site | Coordinate Relative to TSS | Chr2 Genomic Coordinate (hg19) | Enrichment Score | Dropout Score |
|---|---|---|---|---|---|---|---|---|
| 37 | BCL_01617_H_D58 | CTAACAGTTGCTTTTATCAC | NGG RC | DHS_58 | 58232 | 60722401 | 2.04948208 | -0.71934 |
| 38 | BCL_01618_H_D58 | TTGCTTTTATCACAGGCTCC | NGG RC | DHS_58 | 58239 | 60722394 | 0.85613918 | -0.81273 |
| 39 | BCL_01619_H_D58 | TTTTATCACAGGCTCCAGGA | NGG RC | DHS_58 | 58243 | 60722390 | 1.66244771 | -0.31469 |
| 40 | BCL_01620_H_D58 | TTTATCACAGGCTCCAGGAA | NGG RC | DHS_58 | 58244 | 60722389 | 1.38026011 | -0.94808 |
| 41 | BCL_00187_H_D58 | ATCAGAGGCCAAACCCTTCC | NGG | DHS_58 | 58246 | 60722387 | 2.12232899 | -0.74438 |
| 42 | BCL_01621_H_D58 | CACAGGCTCCAGGAAGGGTT | NGG RC | DHS_58 | 58249 | 60722384 | 2.31905068 | -0.60048 |
| 43 | BCL_00186_H_D58 | CACGCCCCCACCCTAATCAG | NGG | DHS_58 | 58261 | 60722372 | 0.89714161 | -0.79647 |
| 44 | BCL_01622_H_D58 | GAAGGGTTTGGCCTCTGATT | NGG RC | DHS_58 | 58261 | 60722372 | 1.37845184 | -0.66954 |
| 45 | BCL_01623_H_D58 | AAGGGTTTGGCCTCTGATTA | NGG RC | DHS_58 | 58262 | 60722371 | 1.28521056 | -0.26686 |
| 46 | BCL_01624_H_D58 | GGTTTGGCCTCTGATTAGGG | NGG RC | DHS_58 | 58265 | 60722368 | 1.47218462 | -0.77128 |
| 47 | BCL_01625_H_D58 | GTTTGGCCTCTGATTAGGGT | NGG RC | DHS_58 | 58266 | 60722367 | 0.37182118 | -0.94511 |
| 48 | BCL_01626_H_D58 | TTTGGCCTCTGATTAGGGTG | NGG RC | DHS_58 | 58267 | 60722366 | 1.33557005 | -0.27239 |
| 49 | BCL_01627_H_D58 | TTGGCCTCTGATTAGGGTGG | NGG RC | DHS_58 | 58268 | 60722365 | 0.30537167 | -0.2564 |
| 50 | BCL_01629_H_D58 | TCTGATTAGGGTGGGGCGT | NGG RC | DHS_58 | 58274 | 60722359 | 1.10417515 | 0.18067 |
| 51 | BCL_01631_H_D58 | ATTAGGGTGGGGCGTGGGT | NGG RC | DHS_58 | 58278 | 60722355 | 0.40981324 | -0.16153 |
| 52 | BCL_01634_H_D58 | TGGGTGGGGTAGAAGAGGAC | NGG RC | DHS_58 | 58293 | 60722340 | 0.41467523 | -1.07834 |
| 53 | BCL_00185_H_D58 | GCAAACGGCCACCGATGGAG | NGG | DHS_58 | 58309 | 60722324 | 0.3196407 | -0.51601 |
| 54 | BCL_00184_H_D58 | CCTGGGCAAACGGCCACCGA | NGG | DHS_58 | 58314 | 60722319 | 0.31547607 | -0.54143 |
| 55 | BCL_00183_H_D58 | AAGAGGCCCCCTGGGCAAA | NGG | DHS_58 | 58324 | 60722309 | 0.78527241 | -0.59129 |
| 56 | BCL_01637_H_D58 | CCATCGGTGGCCGTTTGCCC | NGG RC | DHS_58 | 58325 | 60722308 | 0.66904064 | -0.50156 |
| 57 | BCL_01638_H_D58 | CATCGGTGGCCGTTTGCCCA | NGG RC | DHS_58 | 58326 | 60722307 | 0.63502753 | -0.59285 |
| 58 | BCL_01639_H_D58 | ATCGGTGGCCGTTTGCCCAG | NGG RC | DHS_58 | 58327 | 60722306 | 0.82185918 | -0.89805 |
| 59 | BCL_01640_H_D58 | TCGGTGGCCGTTTGCCCAGG | NGG RC | DHS_58 | 58328 | 60722305 | 0.36580154 | -1.01297 |
| 60 | BCL_01641_H_D58 | CGGTGGCCGTTTGCCCAGGG | NGG RC | DHS_58 | 58329 | 60722304 | 0.28196886 | -0.46328 |
| 61 | BCL_00182_H_D58 | CTTCCGAAAGAGGCCCCCCT | NGG | DHS_58 | 58331 | 60722302 | 0.29420004 | 0.023956 |
| 62 | BCL_00181_H_D58 | CCTTCCGAAAGAGGCCCCCC | NGG | DHS_58 | 58332 | 60722301 | 0.33994629 | 0.262073 |
| 63 | BCL_00160_H_D58 | TCAGGGGAGGCAAGTCAGT | NGG | DHS_58 | 58575 | 60722058 | 0.32935479 | -0.31801 |
| 64 | BCL_00154_H_D58 | AGGGAAAGGGAGAGGAAAA | NGG | DHS_58 | 58612 | 60722021 | 0.4446489 | -0.39917 |
| 65 | BCL_01665_H_D58 | TGTAACTAATAAATACCAGG | NGG RC | DHS_58 | 58706 | 60721927 | 0.44183247 | -0.65165 |
| 66 | BCL_01669_H_D58 | CCAGCTGAAGAAAGAACATT | NGG RC | DHS_58 | 58870 | 60721763 | 0.31959971 | -0.00075 |
| 67 | BCL_00135_H_D58 | CCATCTCCCTAATCTCCAAT | NGG | DHS_58 | 58958 | 60721675 | 0.29845544 | -0.04502 |
| 68 | BCL_00131_H_D58 | TGGGGAGAGAAGAGTGGAAA | NGG | DHS_58 | 59030 | 60721603 | 0.26979883 | -0.3654 |
| 69 | BCL_00130_H_D58 | GGAGTATGGGGAGAAGAG | NGG | DHS_58 | 59036 | 60721597 | 0.37521645 | -2.21246 |
| 70 | BCL_01684_H_D58 | ACAACCTCCTTGTTTACAGA | NGG | DHS_58 | 59129 | 60721504 | 0.49451625 | 0.36739 |
| 71 | BCL_01788_H_D62 | GAGATTTACTCTTGTTGCCC | NGG RC | DHS_62 | 61848 | 60718785 | 1.29003182 | -5.46287 |
| 72 | BCL_01790_H_D62 | TTGCCCGGGCTGGAATGCAA | NGG RC | DHS_62 | 61862 | 60718771 | 0.46730546 | -8.12292 |

TABLE 7-continued sgRNA targeting sequences that produced HbF enrichment over 0.259

| SEQ ID NO: | Identifer | sgRNA Sequence | PAM | Targeted Site | Coordinate Relative to TSS | Chr2 Genomic Coordinate (hg19) | Enrichment Score | Dropout Score |
|---|---|---|---|---|---|---|---|---|
| 73 | BCL_00245_H_D62 | GGAGATCGCTTGAACCTGGG | NGG | DHS_62 | 61901 | 60718732 | 0.47622708 | -5.06663 |
| 74 | BCL_00241_H_D62 | CTCAGCTACTCGGGAGGCTG | NGG | DHS_62 | 61926 | 60718707 | 0.6113192 | -9.05154 |
| 75 | BCL_00240_H_D62 | TGTAATCTCAGCTACTCGGG | NGG | DHS_62 | 61932 | 60718701 | 0.79003182 | -8.69099 |
| 76 | BCL_00239_H_D62 | GCCTGTAATCTCAGCTACTC | NGG | DHS_62 | 61935 | 60718698 | 1.91594174 | -6.03102 |
| 77 | BCL_00238_H_D62 | TGCCTGTAATCTCAGCTACT | NGG | DHS_62 | 61936 | 60718697 | 0.6113192 | -8.92274 |
| 78 | BCL_01794_H_D62 | CAGGCATGTATTACCATGCC | NGG RC | DHS_62 | 61964 | 60718669 | 0.28012743 | -1.01079 |
| 79 | BCL_00233_H_D62 | CAGGAGGATCACCTGAGGTC | NGG | DHS_62 | 62037 | 60718596 | 0.6113192 | -9.20231 |
| 80 | BCL_01799_H_D62 | CTCAGGTGATCCTCCTGCCC | NGG RC | DHS_62 | 62054 | 60718579 | 0.91082485 | -9.47845 |
| 81 | BCL_00229_H_D62 | CCCAGCACTTTGGGAGGCCG | NGG | DHS_62 | 62060 | 60718573 | 0.6113192 | -8.71688 |
| 82 | BCL_00228_H_D62 | TCCCAGCACTTTGGGAGGCC | NGG | DHS_62 | 62061 | 60718572 | 0.76104471 | -5.65759 |
| 83 | BCL_00227_H_D62 | ATCCCAGCACTTTGGGAGGC | NGG | DHS_62 | 62062 | 60718571 | 0.79003182 | -8.09896 |
| 84 | BCL_00225_H_D62 | ACCTGTAATCCCAGCACTTT | NGG | DHS_62 | 62069 | 60718564 | 0.33277348 | -8.82052 |
| 85 | BCL_01800_H_D62 | GCCCCGGCCTCCCAAAGTGC | NGG RC | DHS_62 | 62070 | 60718563 | 0.6113192 | -7.64956 |
| 86 | BCL_01801_H_D62 | CCCCGGCCTCCCAAAGTGCT | NGG RC | DHS_62 | 62071 | 60718562 | 0.6113192 | -8.0566 |
| 87 | BCL_01825_H_D62 | ATTTGCTCTTCTCCAGGGTG | NGG RC | DHS_62 | 62469 | 60718164 | 0.28180883 | -0.39453 |
| 88 | BCL_00210_H_D62 | TAAACAGCCACCCCACACCC | NGG | DHS_62 | 62470 | 60718163 | 0.70263344 | -0.87051 |
| 89 | BCL_01826_H_D62 | TTTGCTCTTCTCCAGGGTGT | NGG RC | DHS_62 | 62470 | 60718163 | 0.40028858 | -0.33863 |
| 90 | BCL_01828_H_D62 | CTCTTCTCCAGGGTGTGGGG | NGG RC | DHS_62 | 62474 | 60718159 | 0.34846068 | -0.39104 |
| 91 | BCL_01829_H_D62 | TGTGGGGTGGCTGTTTAAAG | NGG RC | DHS_62 | 62487 | 60718146 | 0.49598477 | -0.14693 |
| 92 | BCL_01831_H_D62 | GGGTGGCTGTTTAAAGAGGG | NGG RC | DHS_62 | 62491 | 60718142 | 0.41044562 | -0.14856 |
| 93 | BCL_01833_H_D62 | AGTTCAAGTAGATATCAGAA | NGG RC | DHS_62 | 62580 | 60718053 | 0.61158376 | 0.228869 |
| 94 | BCL_01834_H_D62 | TATCAGAAGGGAACTGTTTG | NGG RC | DHS_62 | 62592 | 60718041 | 0.40286685 | 0.023271 |
| 95 | BCL_02015_H_exon2 | AAGAATGGCTTCAAGAGGCT | NGG RC | exon2 | 7218 | 60773415 | 1.06436679 | -1.34908 |
| 96 | BCL_02014_H_exon2 | TCTGTAAGAATGGCTTCAAG | NGG RC | exon2 | 7223 | 60773410 | 0.99011778 | -0.7711 |
| 97 | BCL_00248_H_exon2 | ACAGATGATGAACCAGACCA | NGG | exon2 | 7224 | 60773409 | 1.60874074 | -2.53181 |
| 98 | BCL_00249_H_exon2 | TGAACCAGACCACGGCCCGT | NGG | exon2 | 7232 | 60773401 | 1.1752178 | -0.82211 |
| 99 | BCL_00250_H_exon2 | GAACCAGACCACGGCCCGTT | NGG | exon2 | 7233 | 60773400 | 1.58125311 | -0.68474 |
| 100 | BCL_00251_H_exon2 | GGCCCGTTGGGAGCTCCAGA | NGG | exon2 | 7245 | 60773388 | 1.91082485 | -1.23576 |
| 101 | BCL_00252_H_exon2 | GCCCGTTGGGAGCTCCAGAA | NGG | exon2 | 7246 | 60773387 | 0.54529072 | 0.092119 |
| 102 | BCL_00253_H_exon2 | CCCGTTGGGAGCTCCAGAAG | NGG | exon2 | 7247 | 60773386 | 1.20485173 | -1.96839 |
| 103 | BCL_02011_H_exon2 | CTGGAGCTCCCAACGGGCCG | NGG RC | exon2 | 7258 | 60773375 | 0.6044195 | 0.791184 |
| 104 | BCL_02010_H_exon2 | CCCCTTCTGGAGCTCCCAAC | NGG RC | exon2 | 7264 | 60773369 | 0.50032578 | -0.14628 |
| 105 | BCL_02009_H_exon2 | TCCCCTTCTGGAGCTCCCAA | NGG RC | exon2 | 7265 | 60773368 | 2.10774428 | -1.69298 |
| 106 | BCL_00254_H_exon2 | GATCATGACCTCCTCACCTG | NGG | exon2 | 7269 | 60773364 | 2.19780485 | -2.25564 |
| 107 | BCL_00255_H_exon2 | ATCATGACCTCCTCACCTGT | NGG | exon2 | 7270 | 60773363 | 1.70330708 | -2.49715 |
| 108 | BCL_02008_H_exon2 | AGGAGGTCATGATCCCCTTC | NGG RC | exon2 | 7277 | 60773356 | 0.34947658 | -0.44825 |

TABLE 7-continued sgRNA targeting sequences that produced HbF enrichment over 0.259

| SEQ ID NO: | Identifer | sgRNA Sequence | PAM | Targeted Site | Coordinate Relative to TSS | Chr2 Genomic Coordinate (hg19) | Enrichment Score | Dropout Score |
|---|---|---|---|---|---|---|---|---|
| 109 | BCL_02007_H_exon2 | GGCACTGCCCACAGGTGAGG | NGG RC | exon2 | 7294 | 60773339 | 3.35094127 | -1.66199 |
| 110 | BCL_00256_H_exon2 | GTGCCAGATGAACTTCCCAT | NGG | exon2 | 7295 | 60773338 | 1.89017832 | -1.76407 |
| 111 | BCL_00257_H_exon2 | TGCCAGATGAACTTCCCATT | NGG | exon2 | 7296 | 60773337 | 1.94508027 | -1.9609 |
| 112 | BCL_00258_H_exon2 | GCCAGATGAACTTCCCATTG | NGG | exon2 | 7297 | 60773336 | 1.59275545 | -1.89857 |
| 113 | BCL_02006_H_exon2 | TCTGGCACTGCCCACAGGTG | NGG RC | exon2 | 7297 | 60773336 | 1.48917633 | -2.02947 |
| 114 | BCL_00259_H_exon2 | CCAGATGAACTTCCCATTGG | NGG | exon2 | 7298 | 60773335 | 3.26617426 | -3.32127 |
| 115 | BCL_02005_H_exon2 | GTTCATCTGGCACTGCCCAC | NGG RC | exon2 | 7302 | 60773331 | 3.20226887 | -1.83694 |
| 116 | BCL_02004_H_exon2 | CCCCCAATGGGAAGTTCATC | NGG RC | exon2 | 7315 | 60773318 | 0.46854155 | -0.11887 |
| 117 | BCL_02003_H_exon2 | AAATAAGAATGTCCCCCAAT | NGG RC | exon2 | 7327 | 60773306 | 1.08475851 | -0.09695 |
| 118 | BCL_02002_H_exon2 | AAAATAAGAATGTCCCCCAA | NGG RC | exon2 | 7328 | 60773305 | 0.50500271 | -0.4259 |
| 119 | BCL_00261_H_exon2 | CACAAACGGAAACAATGCAA | NGG | exon2 | 7341 | 60773292 | 3.32908014 | -2.54324 |
| 120 | BCL_00262_H_exon2 | CCTCTGCTTAGAAAAAGCTG | NGG | exon2 | 7367 | 60773266 | 1.00055405 | -1.35239 |
| 121 | BCL_02001_H_exon2 | CCACAGCTTTTTCTAAGCAG | NGG RC | exon2 | 7384 | 60773249 | 0.49127532 | -0.24954 |
| 122 | BCL_02000_H_exon2 | TCGATTGGTGAAGGGGAAGG | NGG RC | exon2 | 7412 | 60773221 | 0.46242001 | -1.36477 |
| 123 | BCL_01999_H_exon2 | ATCTCGATTGGTGAAGGGGA | NGG RC | exon2 | 7415 | 60773218 | 0.62036667 | -0.76015 |
| 124 | BCL_01998_H_exon2 | TTTCATCTCGATTGGTGAAG | NGG RC | exon2 | 7419 | 60773214 | 0.34887409 | -0.14262 |
| 125 | BCL_00263_H_exon2 | GAAAAAGCATCCAATCCCG | NGG | exon2 | 7421 | 60773212 | 0.6213377 | -2.11505 |
| 126 | BCL_00264_H_exon2 | AAAGCATCCAATCCCGTGG | NGG | exon2 | 7424 | 60773209 | 0.55781702 | -1.37569 |
| 127 | BCL_00265_H_exon2 | GCATCCAATCCCGTGGAGGT | NGG | exon2 | 7428 | 60773205 | 1.290845 | -0.88953 |
| 128 | BCL_00266_H_exon2 | TCCCGTGGAGGTTGGCATCC | NGG | exon2 | 7436 | 60773197 | 0.58892468 | -0.18023 |
| 129 | BCL_00267_H_exon2 | TGGCATCCAGGTCACGCCAG | NGG | exon2 | 7448 | 60773185 | 2.04934363 | -2.00635 |
| 130 | BCL_01994_H_exon2 | GATGCCAACCTCCACGGGAT | NGG RC | exon2 | 7449 | 60773184 | 1.10977009 | -0.99042 |
| 131 | BCL_01993_H_exon2 | ACCTGGATGCCAACCTCCAC | NGG RC | exon2 | 7454 | 60773179 | 1.97417272 | -1.73599 |
| 132 | BCL_01992_H_exon2 | GACCTGGATGCCAACCTCCA | NGG RC | exon2 | 7455 | 60773178 | 1.23389832 | -0.6955 |
| 133 | BCL_01991_H_exon2 | CGTCATCCTCTGGCGTGACC | NGG RC | exon2 | 7471 | 60773162 | 0.85232011 | -0.71662 |
| 134 | BCL_01990_H_exon2 | GATAAACAATCGTCATCCTC | NGG RC | exon2 | 7481 | 60773152 | 0.84221705 | -0.61283 |
| 135 | BCL_01989_H_exon2 | CTGCTATGTGTTCCTGTTTG | NGG RC | exon2 | 7525 | 60773108 | 0.62008756 | 0.033203 |

TABLE 8

Sequences of the BCL11A enhancer +62, +58, and +55 functional regions

| SEQ ID NO: | chromosome | coordinate start (hg19) | coordinate end (hg19) | name | sequence |
|---|---|---|---|---|---|
| 136 | chr2 | 60725424 | 60725688 | +55 functional region | GACACTGAAGGCTGGGCACAGCCTTGGGGACCGCTCACAGGACATG CAGCAGTGTGTGCCGACAACTCCCTACCGCGACCCCTATCAGTGCC GACCAAGCACACAAGATGCACACCCAGGCTGGGCTGGACAGAGGGG TCCCACAAGATACAGGGTGTGCCCTGAGAAGGTGGGGAGCTCACA GCCTCCAAGCATTGCATCATCCTGGTACCAGGAAGGCAATGGGCTG CCCCATACCCCACTTCCCTTCCTAGAATTGGCCTGG |

TABLE 8-continued

Sequences of the BCL11A enhancer +62, +58, and +55 functional regions

| SEQ ID NO: | chromosome | coordinate start (hg19) | coordinate end (hg19) | name | sequence |
|---|---|---|---|---|---|
| 137 | chr2 | 60722238 | 60722466 | +58 functional region | TTCATTCCCATTGAGAAATAAAATCCAATTCTCCATCACCAAGAGA GCCTTCCGAAAGAGGCCCCCCTGGGCAAACGGCCACCGATGGAGAG GTCTGCCAGTCCTCTTCTACCCCACCCACGCCCCCACCCTAATCAG AGGCCAAACCCTTCCTGGAGCCTGTGATAAAAGCAACTGTTAGCTT GCACTAGACTAGCTTCAAAGTTGTATTGACCCTGGTGTGTTATGT |
| 138 | chr2 | 60718042 | 60718186 | +62 functional region | ATTTCCCTTCTGATATCTACTTGAACTTTCAGATAAAAAAAAAAA GCAAGTTGCAGTAACATGTTATGCTACACAAGATTAGCATGAATA TCCACCCTCTTTAAACAGCCACCCCACACCCTGGAGAAGAGCAAAT GTGAAGT |

TABLE 9

NGA restricted sgRNA sequences that produced HbF enrichment over 0.259

| SEQ ID NO: | Identifier | sgRNA sequence | PAM | Targeted Site | Coordinate Relative to TSS | Chr2 Genomic Coordinate (hg19) | Enrichment Score | Dropout Score |
|---|---|---|---|---|---|---|---|---|
| 139 | BCL_NGA_00066 | GGCGTGGGTG GGGTAGAAGA | GGA | DHS_58 | 58288 | 60722345 | 2.05370263 | 0.338399 |
| 140 | BCL_NGA_00067 | GGGGGCGTGG GTGGGGTAGA | AGA | DHS_58 | 58285 | 60722348 | 1.243740753 | 2.374513 |
| 141 | BCL_NGA_00069 | TCAGAGGCCA AACCCTTCCT | GGA | DHS_58 | 58245 | 60722388 | 2.585165023 | 0.387305 |
| 142 | BCL_NGA_00062 | CAAACCCTTC CTGGAGCCTG | TGA | DHS_58 | 58237 | 60722396 | 1.591649789 | 0.133042 |
| 143 | BCL_NGA_00063 | CACCAGGGTC AATACAACTT | TGA | DHS_58 | 58191 | 60722442 | 0.507770464 | 0.322734 |

What is claimed:

1. A vector for gene editing comprising:
   a) a protospacer adjacent motif (PAM) sequence;
   b) a trans-activating CRISPR RNA (tracrRNA) sequence; and
   c) a nucleic acid sequence selected from the group consisting of SEQ ID NOS: 1-94.

2. The vector of claim 1, wherein the vector is a virus.

3. The virus of claim 2, wherein the viral vector is a lentivirus, a retrovirus, an adenovirus, or adeno-associated virus.

4. The vector of claim 1, wherein the vector further comprises a nucleic acid encoding a Cas9 enzyme.

5. A population of vectors, wherein the population comprises a first and a second vector, wherein the first vector is the vector of claim 1, and the second vector comprises a nucleic acid encoding a Cas9 enzyme.

6. A host cell comprising the vector of claim 1.

7. The host cell of claim 6, wherein (a) the cell is an embryonic stem cell, a somatic stem cell, a progenitor cell, a bone marrow cell, a hematopoietic progenitor cell or a hematopoietic stem cell, or (b) the cell is an erythrocyte.

* * * * *